United States Patent [19]

Croce et al.

[11] Patent Number: 6,040,140
[45] Date of Patent: Mar. 21, 2000

[54] METHODS FOR SCREENING AND TREATING LEUKEMIAS RESULTING FROM ALL-1 REGION CHROMOSOME ABNORMALITIES

[75] Inventors: Carlo Croce, Philadelphia; Eli Canaani, Glenside, both of Pa.

[73] Assignee: Thomas Jefferson University, Philadelphia, Pa.

[21] Appl. No.: 08/545,860

[22] Filed: Mar. 7, 1996

Related U.S. Application Data

[63] Continuation-in-part of application No. 08/062,443, May 14, 1993, abandoned, which is a continuation-in-part of application No. 07/971,094, Oct. 30, 1992, abandoned, which is a continuation-in-part of application No. 07/888,839, May 27, 1992, abandoned, which is a continuation-in-part of application No. 07/805,093, Dec. 11, 1991, abandoned.

[51] Int. Cl.$^7$ .............................. C12Q 1/68; C12P 19/34; C07H 21/04; C07H 21/02
[52] U.S. Cl. ........................ 435/6; 435/91.2; 536/24.31
[58] Field of Search ................... 435/6, 92.1; 536/24.31; 935/77, 78

[56] References Cited

U.S. PATENT DOCUMENTS

5,487,970   1/1996   Rowley et al. ............................... 435/6

FOREIGN PATENT DOCUMENTS

WO 93/12136   6/1993   WIPO.
WO 94/26930   11/1993   WIPO.

OTHER PUBLICATIONS

Chomczynski, P. and Sacchi, "Single–Step Method of RNA Isolation by Acid Guanidinum Thiocyanate–Phenol–Chloroform Extraction", *Analytical Biochem.* 1987, 162, 156–159.

Haluska, F. et al., "Localization of the Human JUN Protooncogene to Chromosome Region 1p31–32", *PNAS USA* 1988, 85, 2215–2218.

Herlyn, M. et al., "Characteristics of Cultured Human Melanocytes Isolated from Different Stages of Tumor Progression", *Cancer Research* 1985, 45, 5670–5676.

Huebner, K. et al., "Twenty–seven Nonoverlapping Zinc Finger cDNAs from Human T Cells Map to Nine Different Chromosomes with Apparent Clustering", *Am. J. Hum. Genet.* 1991, 48, 726–740.

Kobayashi, H. et al., "Analysis of Deletions of the Long Arm of Chromosome II in Hematologic Malignancies With Fluorescence In Situ Hybridization", *Genes, Chromosomes & Cancer* 1993, 8, 246–252.

Linnenbach, A. et al., "Structural Alteration in the MYB Protooncogene and Deletion Within the Gene Encoding α–type Protein Kinase C in Human Melanoma Cell Lines", *PNAS USA* 1988, 85, 74–78.

Morris, S. et al., "Reassignment of the Human ARH9 RAS–Related Gene to Chromosome 1p13–p21", *Genomics* 1993, 15, 677–679.

Schichman, S. et al., "ALL–1 Partial Duplication in Acute Leukemia", *PNAS USA* 1994, 91, 6236–6239.

Bowden et al., "Studies on Locus Expansion, Library Representation, and Chromosome Walking Using an Efficient Method to Screen Cosmid Libraries" Gene 71: 391–400 (1988).

Djabali et al, "A Trithroax–like Gene is Interrupted by Chromosome 11q23 Translocations in Acute Leukemias," Nature Genet 2: 113–118 (1992) (Abstract).

Domer et al., "Acute, Mixed–Lineage Leukemia t(4;11)(q21;q23) generates an MLL–AF4 Fusion Product", *PNAS USA* 90: 7884–7888 (1993).

Morrissey et al., "A Serine/Proline–Rich Protein is Fushed to HRX in t(4;11) Acute Leukemias" Blood 81: 1124–1131 (1993).

Morse et al., "Acute Non–Lymphoblastic Leukemia in Childhood" *Cancer 44*: 164–170 (1979).

Nadkarni et al., "Antisense RNA Therapy for CML—An Hypothesis", *Med. Hypotheses* 1991, 35, 307–310.

Nakamura et al., "Genes on Chromosomes 4, 9, and 19 involved in 11q23 Abnormalities in Acute Leukemia Share Sequence Homology and/or Common Motifs" PNAS USA 90: 4631–4635 (1993).

Schichman et al., "All–1 Tandem Duplication in Acute Myeloid Leukemia with a Normal Karyotype Involves Homologous Recombination Between Alu Elements", *Cancer Res.* 54: 4277–4280 (1994).

Trent et al., Report of the committee on Structural Chromosome Changes in Neoplasia, 10th International Workshop on Human Gene Mapping. *Cytogenet. Cell Genet. 51*: 533–562 (1989).

Yunis and Brunning, Prognostic Significance of Chromosomal Abnormalities in Acute Leukemias and Myelodysplastic Syndromes. *Clinics in Haemotology 15*: 597–620 (1986) (Gale and Hoffbrand, Eds.).

Adams et al., "Sequence Identification of 2,375 Human Brain Genes", *Nature 355*: 632–634, 1992.

Arad et al., "Use of Reconstituted Sendai Virus Envelopes for Fusion–Mediated Microinjection of Double–Stranded RNA: Inhibition of Protein Synthesis inInterferon–Treated Cells", *Biochem. Biophy. Acta. 859*: 88–94, 1986.

(List continued on next page.)

*Primary Examiner*—Stephanie Zitomer
*Attorney, Agent, or Firm*—Woodcock Washburn Kurtz Mackiewicz & Norris LLP

[57] ABSTRACT

The cDNA sequence of the ALL-1 gene on chromosome 11 is provided. A partial sequence of the AF-4 gene is also provided in the context of the sequences of two reciprocal endproducts of a translocation. Amino acid sequences corresponding to the cDNA sequences of the entire ALL-1 gene and the partial sequence of the AF-4 gene, and sequences relating to chimeric genes formed by chromosome translocations with chromosome 4, 9 and 19, respectively, are provided. Probes are provided for detecting chromosome abnormalities involving the ALL-1 gene on chromosome 11, including probes for detecting chimeric genes generated by translocations. Monoclonal antibodies for diagnosis and treatment and antisense oligonucleotides for treatment of acute leukemias are also described.

12 Claims, 43 Drawing Sheets

OTHER PUBLICATIONS

Capdevila and Garcia–Bellido, "Genes Involved in the Activation of the Bithorax Complex of Drosophila", *Roux's Arch. Dev. Biol. 190*: 339–350, 1981.

Chen et al., "Break point Clustering in t(4;11) (q21;q23) Acute Leukemia", *Blood 78*: 2498–2504, 1991.

Chu et al., "Mosaic Structure of Globular Domains in the Human Type VI Collagen α3 Chain: Similarity to Von Wilebrand Factor, Fibronectin, Actin, Salivary Proteins and Aprotinin Type Protease Inhibitors", *EMBO J. 9*: 385–393, 1990.

Cimino et al., "Cloning of ALL–1, the Locus involved in Leukemias with the t(4;11(q21;q23), t(9;11) (p22;q23), and t(11;9) (p22;q13) Chromosome Translocations", Cancer Res 51: 6712–6714 1991.

Cimino et al., "An Altered 11–Kilobase Transcript in Leukemic Cell Lines with the t(4;11) (q21;q23) Chromosome Translocation", *Cancer Research 52*: 3811–3813, 1992.

Cohen et al., "Constitutive Expression and Role in Growth Regulation of Interleukin–1 and Multiple Cytokine Receptors in a Biphenotypic Leukemic Cell Line", *Blood 78*: 94–102, 1991.

Cotter et al., "Gene Mapping by Microdissection and Enzymatic Amplification: Heterogeneity in Leukaemia Associated Breakpoints on Chromosome II", *Genes, Chromosomes & Cancer 3*: 8–15, 1991.

Croce, "Role of Chromosome Translocations in Human Neoplasia", *Cell 49*: 155–156, 1987.

de Thè et al., "The PLM–RARα Fusion mRNA Generated by the t(15;17) Translocation in Acute Promyelocytic Leukemia Encodes a Functionally Altered RAR", *Cell 66*: 675–684, 1991.

Erikson et al., "Heterogeneity of Chromosome 22 Breakpoint in Philadelphia–Positive (Ph+) Acute Lymphocytic Leukemia", *Proc. Natl. Acad. Sci. USA 83*: 1807–1811, 1986.

Gale and Canaani, "An 8–kilobase abl RNA Transcript in Chronic Myelogenous Leukemia", *Proc. Natl. Acad. Sci. USA 81*: 5648–5652, 1984.

Garvey et al., Methods in Immunology: A Laboratory Text for Instruction and Research, Third Ed., The Benjamin/Cummings Publishing Company, Chapter 22, 24–30.

Green et al., "Systematic Screening of Yeast Artificial–Chromosome Libraries by Use of the Polymerase Chain Reaction", *Proc. Natl. Acad. Sci. USA 87*: 1213–1217, 1990.

Gu et al., "The (4;11) (q21;q23) Chromosome Translocations in Acute Leukemias Involve the VDJ Recombinase", *Proc. Natl. Acad. Sci. USA 89*: 10464–10468 1992.

Gu et al., "The t(4;11) Chromosome Translocation of Human Acute Leukemias Fuses the ALL–1 Gene, Related to *Drosophila trithorax*, to the AF–4 Gene", *Cell 71*: 701–708, 1992.

Heim and Mitelman, *Cancer Cytogenetics*, Alan R. Liss, New York, (85–87 and 148–152) 1987.

Heisterkamp et al., "Structural Organization of the BCR Gene and its Role in the Ph' Translocation", *Nature 315*: 758–761, 1985.

Hoheisel et al., "Control of Partial Digestion Combining the Enzymes dam methylase and MboI", *Nuc. Acid Res. 17*: 9571–9582, 1989.

Ingham, "Genetic Control of the Spatial Pattern of Selector Gene Expression in Drosophilia", *Cold Spring Harbor Symp. Quant. Biol. 50*: 201–208, 1985.

Kakizuka et al., "Chromosomal Translocation t(15;17) in Human Acute Promyelocytic Leukemia Fuses RARα with a Novel Putative Transcription Factor, PLM", *Cell 66*: 663–674, 1991.

Kamps et al., "A New Homeobox Gene Contributes the DNA Binding Domain of the t(1;19) Translocation Protein in Pre–B ALL", *Cell 60* 547–555, 1990.

Kitazawa et al., "Immunocytochemical Evaluation of AB1–Gene Products in Leukemic Cell Lines", *Med. Oncol Tumor Pharmacother 7*: 35–41, 1990. (Abstract).

Kurzrock et al., "Identification of Molecular Variants of $p210^{bcr-abl}$ in Chron Myelogenous Leukemia", *Blood 70*: 233–236, 1987.

Lange et al., "Growth Factor Requirements of Childhood Acute Leukemia: Establishment of GM–CSF–Dependent Cell Lines", *Blood 70*:192–199, 1987.

Lozzio and Lozzio, "Human Chronic Myelogenous Leukemia Cell–Line With Positive Philadelphia Chromosome", *Blood 45*: 321–334, 1975.

Marcu et al., "Transcriptionally Active C–MYC Oncogene is Contained Within NIARD, a DNA Sequence Associated with Chromosome Translocations in B–cell Neoplasia", *Proc. Natl. Acad. Sci. USA 80*: 519–523 1983.

Mazo et al., "The Trithorax Gene, a Trans–Acting Regulator of the bithorax Complex in Drosophila, Encodes a protein with Zinc–Binding Domains", PNAS USA 87: 2112–2116 (1990).

McGinnis and Krumlauf, "Homeobox Genes and Axial Patterning", *Cell 68*: 283–302, 1992.

McKeon and Brock, "Interactions of the Polycomb Group of Genes with Homeotic Loci of Drosophila", *Roux's Arch. Dev. Biol. 199*: 387–396 1991.

Mellentin et al., "The Gene for Enhancer Bidning Proteins E12/E47 Lies at the t(1;19) Breakpoint in Acute Leukemias", Science 246: 379–382 (1989).

Mozer and David, "Cloning and Molecular Characterization of the Trithorax Locus of *Drosophila Melanogaster*", *Proc. Natl. Acad. Sci. USA 86*: 3738–3742 1989.

Nagasaka et al., "Four Cases of t(4;11) Acute Leukemia and Its Myelomonocytic Nature in Infants", *Blood 61*: 1174–1181, 1983.

Nourse et al., "Chromosomal Translocation t(1;19) Results in Synthesis of a Homeobox Fusion mRNA That Codes for a Potential Chimeric Transcription Factor", *Cell 60*: 535–545, 1990.

Pui et al., "Clinical Characteristics and Treatment Outcome of Childhood Acute Lumphoblastic Leukemia With the t(4;11) (q21;q23): A Collaborative Study of 40 Case" *Blood 77*: 440–447, 1991.

Rabbitts, "Translocations, Master Genes, and Differences Between the Origins of Acute and Chronic Leukemias", *Cell 67*, 641–644, 1991.

Rowley et al., "Mapping Chromosome Band 11q23 in Human Acute Leukemia with Biotinylated Probes: Identification of 11q23 Translocation Breakpoints with a Yeast Artificial Chromosome", *Proc. Natl. Acad. Sci. USA 87*: 9358–9362, 1990.

Sacchi et al., "Hu–ets–1 and Hu–ets–2 Genes are Transposed in Acute Leukemias with (4;11) and (8;21) Translocations", *Science 231*: 379–382, 1986.

Saito et al., "Activation of the C–MYC Gene by Translocation: A Model for Translational Control", *Proc. Natl. Acad. Sci. USA 80*: 7476–7480, 1983.

Savage et al., "Mapping Studies and Expression of Genes Located on Human Chromosome 11, Band q23", *Cytogenet. Cell Genet. 49*: 289–292, 1988.

Shtivelman et al., "Fused Transcript of abl and bcr Genes in Chronic Myelogenous Leukaemia", *Nature 315*: 550–554, 1985.

Siminovitch et al., "Immunoglobulin Gene Rearrangements and Expression in Diffuse Histiocytic Lymphomas Reveal Cellular Lineage, Molecular Defects, and Sites of Chromosomal Translocation", *Blood 67*: 391–397, 1986.

Solomon et al., "Chromosome Aberrations and Cancer", *Science 254*: 1153–1160, 1991.

Stong and Kersey, "In Vitro Culture of Leukemic Cells in t(4;11) Acute Leukemia" *Blood 66*: 439–443, 1985.

Tkachuk et al., "Involvement of a Homolog of *Drosophila Trithorax* by 11q23 Chromosomal Translocations in Acute Leukemias", *Cell 71*: 691–700, 1992.

Tsujimoto et al., "Molecular Cloning of the Chromosomal Breakpoint of B–Cell Lymphomas and Leukemias with the t(11;14) Chromosome Translocation", *Science 224*: 1403–1406, 1984.

Tsujimoto et al., "Cloning of the Chromosome Breakpoint of Neoplastic B Cells with the t(14;18) Chromosome Translocation", *Science 226*: 1097–1099, 1984.

van Den Elsen et al., "Exon/Intron Organization of the Genes Coding for the δ Chains of the Human and Murine T–Cell Receptor/T3 Complex", *Proc. Natl. Acad. Sci. USA 83*: 2944–2948, 1986.

von Lindern et al., "The (6,9) Chtomosome Translocation, Associated with a Specific Subtype of Acute Nonlymphocytic Leukemia, Leads to Aberrant Transciption of a Target Gene on 9q34," *Mol. Cell. Biol.* 10:4016–4026, 1990.

von Lindern et al., "The Translocation (6;9), Associated with a Specific Subtype of Acute Myeloid Leukemia, Results in the Fusion of Two Genes, dek and can, and the Expression of a Chimeric, Leukemia–Specific dek–can mRNA," *Mol. Cell. Biol.* 12:1687–1697, 1992.

Watson et al., "Mammalian ets–1 and ets–2 Genes Encode Highly Conserved Proteins", *Proc. Natl. Acad. Sci. USA 85*: 7862–7866, 1988.

Watson et al., "The ets Sequence from the Transforming Gene of Avian Erythroblastosis Virus, E26, has Unique Domains on Human Chromosomes 11 and 21: Both Loci are Transcriptionally Active,".

Wei et al., "Physical Mapping of the Human Chromosome 11q23 Region Containing the Ataxia–Telangiectasia Locus," *Cancer Genet. Cytogenet.* 46: 1–8, 1990.

Yunis et al., "Gene Order, Amplification, and Rearrangement of Chromosome Band 11q23 in Hematologic Malignancies," *Genomics 5*: 84–90, 1989.

Ziemin–van der Poel et al., "Identification of a Gene, MLL, That Spans the Break point in 11q23 Translocations Associated with Human Leukemias", *Proc. Natl. Acad. Sci.USA 88*: 10735–10739, 1991.

FIG. 8A

Figure shows a DNA sequence with corresponding amino acid translation. The sequence is presented in rows with nucleotide position numbers on the right side (90, 30, 180, 60, 270, 90, 360, 120, 450, 150, 540, 180, 630, 210, 720, 240, 810, 270, 900, 300, 990, 330, 1080, 360, 1170, 390, 1260, 420, 1350, 450, 1440, 480, 1530).

```
V  S  N  F  T  Q  T  V  D  A  P  N  S  M  G  L  E  Q  N  K  A  L  S  S  A  V  Q  A  S  P                           3450
ACTCTCCTGGGGTCTCCATCCTCTGACAGGGTCAGCAAGCCCTTCAGTGCCGGTCCCACTAAACCAAAA                                              10440
T  S  P  G  G  S  P  S  S  P  S  S  G  Q  R  S  A  S  P  S  V  P  G  P  T  K  P  K  P  K                           3480
ACCAAACGGTTTCAGCTGCCTGCCCTCTAGACAAAGGAATGCAAGAAGCACAATGTTCCCATTGCCGGACCAGTCTCTGAAGCACACATT                         10530
T  K  R  F  Q  L  P  L  D  K  G  N  G  K  K  H  N  V  S  H  L  R  T  S  S  E  A  H  I                              3510
CCAGACCAAGAAACGACATCCCTGACTTGACAAAGGAAATGGGAAGAAGCACAATGTTTCCCATTGCCGGACCAGTCTCTGAAGCACACATT                       10620
P  D  Q  E  T  T  S  L  T  S  G  T  G  T  P  G  A  E  A  E  Q  Q  D  T  A  S  V  E  Q  S                           3540
TCCCAGAAGGAGTGTGGGCAACCTGCAGGCAAGTCGCTGCTTCTTCCGAAGTTCAGTGACCAAAATCCAGCAAGTGTGGAGCAGTCC                            10710
S  Q  K  E  C  G  Q  P  A  G  Q  V  A  V  L  P  E  V  Q  V  T  Q  N  P  A  N  E  Q  E  S                           3570
GCAGAACCTAAAACAGTGGAAGAGGAAGAAAGTAATTTCAGCTCCCCACTGATGCTTTGGCTTCAAGAACAAAGCGGAAGGAAAGC                             10800
A  E  P  K  T  V  E  E  E  E  S  N  F  S  S  P  L  M  L  W  L  Q  E  Q  K  R  K  E  S                              3600
ATTACTGAGAAGAAAACCAAGAGTCAGATAAAGTCCAGGAAGCTCGTTTTGAAATTCAGCTGTCAGTCTGTTAACGGTTTGAGGATG                            10890
I  T  E  K  K  P  K  K  G  L  V  E  E  I  S  S  D  D  G  E  F  Q  I  C  A  E  S  I  E  D  A                        3630
TGGAAGTCATTGACACAGATAAAGTCCAGGAAGCTCAGGAAGTCCAGTGTGTTCCTCATTGCCAGTCTTGTAACGGTTTGAGGATG                             10980
W  K  S  L  T  D  K  V  Q  E  A  R  S  N  A  R  L  K  Q  L  S  F  A  G  V  N  G  L  R  M                           3660
CTGGGGATTCTCCATGATGCCAGTTGTGTTCCTCGAACCCCCTGAAACCCTGAACCTGTCGAAGTCCACCTGAAGCTCAGAATTACAAATTCCGTTCCACAAG          11070
L  G  I  L  H  D  A  V  V  F  L  I  E  Q  L  S  G  A  K  H  C  R  N  Y  K  F  R  F  H  K                           3690
CCAGAGAACCCTTCTAAACATCGCCAATGCCAATGCCCTGAATACAACCCCATGAAGAGAGGAGTACAGCTGAAGTCAGTCGGAGGCA                          11160
P  E  A  N  E  P  P  L  N  P  H  G  S  A  R  A  E  V  H  L  R  K  S  A  F  D  M  F  N                              3720
TTCCTGGCTTCTAAACATCGCCAATGCCAATGCCCTGAATACAACCCCATGAAGAGAGGAGTACAGCTGAAGTCAGTCGGAGGCA                             11250
F  L  A  S  K  H  R  Q  P  P  E  Y  N  P  N  D  E  E  E  E  E  V  Q  L  K  S  A  R  R  A                           3750
ACTAGCATGGATCTGCCAATGCCAATGCCCTAAGAACATTGATGCAGTGATTGAGATGTGAATTGATGAAGTATGCCGGCAACGTCATCCGCCTCATCCAGACTGAC    11340
T  S  M  D  L  P  M  P  M  R  E  R  H  L  K  T  S  K  E  A  V  G  V  Y  R  S  P  I  H                              3780
GGGCGGGTCTTTTCTGTAAGAGAAACATTGATGCAGTGATTGAGATGTGAATTGATGAAGTATGCCGGCAACGTCATCCGCCTCATCCAGACTGAC                  11430
G  R  G  L  F  C  K  R  N  I  D  A  G  E  M  V  I  E  Y  A  G  N  V  I  R  S  I  Q  T  D                           3810
AAGCGGGAAAAGTATTACGACAGCAAGGCATTGTTGTCTATATGTTCCGAATTGATGACTGAGGTAGTGATGCCACCATGCATGGA                            11520
K  R  E  K  Y  Y  D  S  K  G  I  G  C  Y  M  F  R  I  D  D  S  E  V  V  D  A  T  M  H  G                           3840
AATGCTGCACGCTTCATCAATCACTCTGTGAGCCTAACTCGTGAGCCTATTCTGTGAGCCTAACTGCTATTCTCGGGTCATCAATATTGATGGGCAGAAGCACATTGTCATCTTT  11610
N  A  R  F  I  N  H  S  C  E  P  N  C  Y  S  R  V  I  N  I  D  G  Q  K  H  I  V  I  F                              3870
GCCATGCGTAAGATCGTACGAGGAGAACTCACTTACGACTATAAGTTCCCCATTGAGGATGCCAGCAACAAGCTGCCCTGCAACTGT                           11700
A  M  R  K  I  Y  R  G  E  E  L  T  Y  D  Y  K  F  P  I  E  D  A  S  N  K  L  P  C  N  C                           3900
GGCGCCAAGAAATGCCAAGGTTCCTAAACTAAAGCTGCCTCTCCCCAGTGTTGGAGTGGAGTGGAGCAAGGAGGCCATCCAAAGCAACG                         11790
```

FIG. 8I

```
ALL-1    1021 RVVCFLCASSGHVEFVYCQVCCEPFHKFCLEEN....ERPLED.......
              |.:||||:|.|  .::::|..||||:|.:|::::  . .:||
D.TRX    1266 RALCFLCGSTGLDPLIFCACCCEPYHQYCVQDEYNLKHGSFEDTTLMGSL

................QLENWCCRRCKFCHVCGRQHQATKQLLECNKCRN
                              ||..:  : |. | ||    :  ..  :.|.||..
              LETTVNASTGPSSSLNQLTQRLNWLCPRCTVCYTCNMSSGSKVKCQKCQK

SYHPECLGPNYPTKPTKKKKVWICTKCVRCKSCGSTTPGKGWDAQWSHDF
              .||..|||.   ..:     .:.:||..|::||||:.|...:|    : ::
              NYHSTCLGT..SKRLLGADRPLICVNCLKCKSCSTTKVSK.....FVGNL

SLCHDCAKLFAKGNFCPLCDKCYDDDDYESKMMQCGKCDRWVHSKCENLS
              .:|  :|  ||   ||||||:|::||||:|::  |||:||.|.:.||||||.||
              PMCTGCFKLRKKGNFCPICQRCYDDNDFDLKMMECGDCGQWVHSKCEGLS

GTEDEMYEILSNLPESVAYTCVNCTERH 1221
              ||  |::||.||||:.:.|  .|. |:
              ...DEQYNLLSTLPESIEFICKKCARRN 1483

ALL-1    1462 DNRQCALCLTYGDDSANDAGRLLYIGQNEWTHVNCALWSAEVFEDDDGSL
              |.| |  :| .  |::  ...:.:||||.|:: |.|.|||:|||||||: ||||
D.TRX    1733 DTRMCLFCRKSGEGLSGEEARLLYCGHDCWVHTNCAMWSAEVFEEIDGSL

KNVHMAVIRGKQLRCEFCQKPGATVGCCLTSCTSNYHFMCSRAKNCVFLD
              .||| || ||  ::: |..|...|||||| : ||...:|| |.|. :|.||.
              QNVHSAVARGRMIKCTVCGNRGATVGCNVRSCGEHYHYPCARSIDCAFLT

DKKVYCQRH 1570
              ||.:||. |
              DKSMYCPAH 1841

ALL-1    3348 EPPLNPHGSARAEVHLRKSAFDMFNFLASKHRQPPEYNPNDEEEEEVQLK
              |  .  |:.::||.|..  .:|.:|||.:|||:||..|    :..::|:
D.TRX    3550 ELEENAYDCARCEPYSNRSEYDMFSWLASRHRKQPIQVFVQPSDNEL...

SARRATSMDLPMPMRFRHLKKTSKEAVGVYRSPIHGRGLFCKRNIDAGEM
              :||:|: :||||:|::|  ||.| |: |||:||.||||||:|..::||||
              VPRRGTGSNLPMAMKYRTLKETYKDYVGVFRSHIHGRGLYCTKDIEAGEM

VIEYAGNVIRSIQTDKREKYYDSKGIGCYMFRIDDSEVVDATMHGNAARF
              ||||||::|||. |||||:||||:|||||||. ||||||:|||||||
              VIEYAGELIRSTLTDKRERYYDSRGIGCYMFKIDDNLVVDATMRGNAARF

INHSCEPNCYSRVINIDGQKHIVIFAMRKIYRGEELTYDKFPIEDASNK
              |||:||||||||:|::|  |:|||:|||:|:|  .|||||||||||:||  :|
              INHCCEPNCYSKVVDILGHKHIIIFAVRRIVQGEELTYDKFPFED..EK

LPCNCGAKKCRKFLN 3562
              :||.||.|:|||:||
              IPCSCGSKRCRKYLN 3759
```

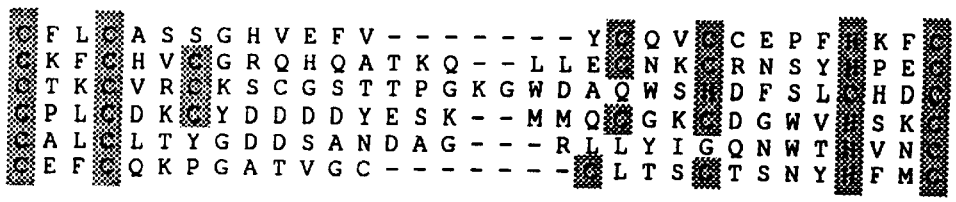

FIG. 9

TGAGGAGAGATTGTTTCTCTGCCATTTCTCAGGGATGTATTCTATTTTGTAGGGAAAAGCCCTTATCCTTGACTTCTATGTAGATGGCAGTGGAATTTCTTAAAATTAAGAAA Chr.11q23
||||||||||||||||||||||||||||||||||||||||||||||||||||||||||||||||||||||||||||||||||||||||||||||||||||||| |||||||
TTCCTCATAGGAAATAAAATCTTTTAAATTAGCTTGTTTAGTTCCAGGAAAAAGCCTTATCCTTGACTTCTATGTAGATGGCAGTGGAATTTCTTAAAATTAAGAAA der (6)
|||||||||||||||||||||||||||||||||||||||||||
TTCCTCATAGGAAATAAAATCTTTTAAATTAGCTTGTTTAGTTCCAGGAGAAAAAGAAAAAGAAAACCATTGTATTTTAGTTACTGTTTCTAAATTTATAAATTAA Chr. 6q27

FIG. 12C

1     MSAGGRDEERRKLADIIHHWNANRLDLFEISQPTEDLEFHGVMRFYFQDKAAGNFATKCIRVSSTATTQDVIETLAEKFRPDMRMLSSPKYSLYEVHVSG
101   ERRLDIDEKPLVVQLNWNKDDREGRFVLKNENDAIPPKAQSNGPEKQEKEGVIQNFKRTLSKKEKKKREKEALRQASDKDDRPFQGEDVENSRLAAE
201   VYKDMPETSFTRTISNPEVVMKRRQQKLEKRMQEFRSSDGRPDSGGTLRIYADSLKPNIPYKTILLSTTDPADFAVAEALEKYGLEKENPKDYCIARVM
301   LPPGAQHSDEKGAKEIILDDDECPLQIFREWPSDKGILVFQLKRRPPDHIPKKTKKHLEGKTPKGKERADGSVYGSTLPPEKLPYLVELSPDGSDRDKP
401   KLYRLQLSVTEVGTEKLDDNSIQLFGPGIQPHHCDLTNMDGVVTVTPRSMDAETYVEGQRISETTMLQSGMKVQFGASHVFKFVDPSQDHALAKRSVDGG
501   LMVKGPRHKPGIVQETTFDLGDIHSGTALPTSKSTTRLDSDRVSSASSTAERGMVKPMIRVEQQPDYRRQESRTQDASGPELILPASIEFRESSEDSFL
601   SAINYTNSSTVHFKLSPTYVLYMACRYVLSNQYRPDISPTERTHKVIAVVNKMVSMMEGVIQKQKNIAGALAFWMANASELLNFIKQDRDLSRITLDAQ
701   DVLAHLVQMAFKYLVHCLQSELNNYMPAFLDDPEENSLQRPKIDDVLHTLTGAMSLLRRCVNAALTIQLFSQLFHFINMWLFNRLVTDPDSGLCSHYWG
801   AIIRQQLGHIEAWAEKQGLELAADCHILSRIVQATTLLTMDKYAPDDIPNINSTCFKLNSLQLQALLQNYHCAPDEPFIPTDLIENVVTVAENTADELARS
901   DGREVQLEEDPDLQLPFLLPEDGYSCDVVRNIPNGLQEFLDPLCQRGFCRLIPHTRSPGTWTIYFEGADYESHLLRENTELAQPLRKEPEIITVTLKKQN
1001  GMGLSIVAAKGAGQDKLGIYVKSVVKGGAADVDGRLAAGDQLLSVDGRSLVGLSQERAAELMTRTSSVVTLEVAKQGAIYHGLATLLNQPSPMMQRISDR
1101  RGSGKPRPKSEGFELYNNSTQNGSPESPQLPWAEYSEPKKLPGDDRLMKNRADHRSSPNVANQPPSPGGKSAYASGTTAKITSVSTGNLCTEEQTPPPRP
1201  EAYPIPTQTYTREYFTFPASKSQDRMAPPQNQWPNYEEKPHMHTDSNHSSIAIQRVTRSQEELREDKAYQLERHRIEAAMDRKSDSDMWINQSSSLDSST
1301  SSQEHLNHSSKSVTPASTLTKSGPGRWKTPAAIPATPVAVSQPIRTDLPPPPPPPPVHYAGDFDGMSMDLPLPPPPSANQIGLPSAQVAAAERRKREEHQ
1401  RWYEKEKAPLEEERERKRREQERKLGQMRTQSLNPAPFSPLTAQQMKPEKPSTLQRPQETVIRELQPQQQPRTIERRDLQYITVSKEELSSGDSLSPDPW
1501  KRDAKEKLEKQQQMHIVDMLSKEIQELQSKPDRSAEESDRLRKLMLEWQFQKRLQESKQKDEDDEEEDDVDTMLIMQRLEAERRARVKGGVLWLCPSV
1601  VPILASACFPWG*  1612

FIG. I3B

```
AF-6     KKQNGMGLSIVAAKGAGQ..DKLGIYVKSVVKGGAADVDGRLAAGDQLLSVDGRSLVGLSQERAAELM..TRTSSVVTLEVAKQGAIY
ZO-1(3)  RKGDSVGLRL....AGG..NDVGIFVAGVLEDSPAAKEG.LEEGDQILRVNNVDFTNIIREEAVLFLLDLPKGEEVTILAQKKDVY
psd95(2) KGPKGLGFSIAGGVGNQHIPGDNSIYVTKIIEGGAAHKDGRLQIGDKILAVNSVGLEDVMHEDAVAAL..KNTYDVVYLKVAKPSNAY
dlg(3)   KGPQGLGFNIVG....GE..DGQGIYVSFILAGGPADLGSELKRGDQLLSVNNVNLTHATHEEAAQAL..KTSGGVVTLLAQYRPEEY
```

FIG. 14

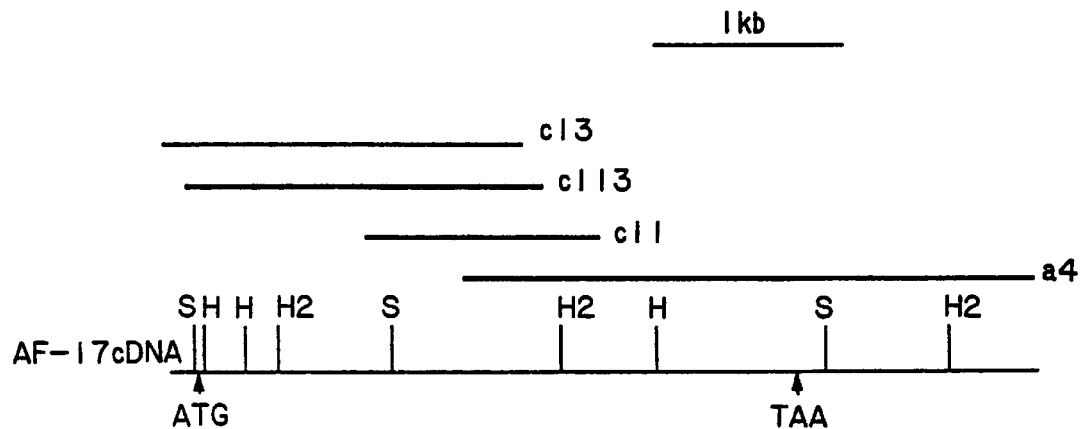

FIG. 17A

```
CCACCTACTACAGGACCGCCAAGAAAAGAAGTTCCCAAAACCACTCCTAGTGAGCCCAAG
 P  P  T  T  G  P  P  R  K  E  V  P  K  T  T  P  S  E  P  K
```

ALL-1 exon5 →|← AF-17 exon

```
AAAAAGCAGCCTCCACCACCAGAATCAGGCATCTACACCAGTAATAAGGACCCCATCTCC
 K  K  Q  P  P  P  P  E  S  G  I  Y  T  S  N  K  D  P  I  S

CACAGTGGCGGGATGCTGCGGGCTGTCTGCAGCACCCCTCTCTCCTCCAGCCTCCTGGGG
 H  S  G  G  M  L  R  A  V  C  S  T  P  L  S  S  S  L  L  G

CCCCCAGGGACCTCGGCCCTGCCCCGCCTCAGCCGCTCCCCGTTCACC
 P  P  G  T  S  A  L  P  R  L  S  R  S  P  F  T
```

FIG. 17C

1    MKEMVGGCCVCSDERGWAENPLVYCDGHACSVAVHQACYGIVQVPTGPWFCRKCESQERAARVRCELCPHKDGALKRTDNGGWAHVVCALYIPEVQFANV
101  LTMEPIVLQYVPHDRFNKTCYICEETGRESKAASGACMTCNRHGCRQAFHVTCAQMAGLLCEEEVLEVDNVKYCGYCKYHFSKMKTSRHSSGGGGAGG
201  GGGSMGGGGSGFISGRRSRSASPSTQQEKHPTHHERGQKKSRKDKERLKQKHKKRPESPPSILTPPVVPTADKVSSSASSSHHEASTQETSESSRESKG
301  KKSSSHSLSHKGKKLSSGKGVSSFTSASSSSSSSGGPFQPAVSSLQSSPDFSAFPKLEQPEEDKYSKPTAPAPSAPPSPSAPEPPKADLFEQKVVF
401  SGFGPIMRFSTTTSSSGRARAPSPGDYKSPHVTGSGASAGTHKRMPALSATPVPADETPETGLKEKKHKASKRSRHGPGRPKGSRNKEGTGPAAPSLPS
501  AQLAGFTATAASPFSGGSLVSSGLGGLSSRTFGPSGSLPSLSLESPLLGAGIYTSNKDPISHSGGMLRAVCSTPLSSSLLGPPGTSALPRLSRSPFTSTL
601  PSSSASISTTQVFSLAGSTFSLPSTHIFGTPMGAVNPLLSQAESSHTEPDLEDCSFRCRGTSPQESLSSMSPISSLPALFDQTASAPCGGQLDPAAPGT
701  TNMEQLLEKQGDEAGVNIVEMLKALHALQKENQRLQEQILSLTAKKERLQIINVQLSVPFPALPAALPAANGPVPGPYGLPPQAGSSDSLSTSKSPPGK
801  SSLGLDNSLSTSSEDPHSGCPSRSSSSLSFHSTPPLPLLQQSPATLPLALPGAPAPLPPQPQNGLGRAPGAAGLGAMPMAEGLLGGLAGSGGLPLNGLL
901  GGLNGAAAPNPASLSQAGGAPTLQLPGCLNSLTEQQRHLLQQQEQLQQLQQLLASPQLITPEHQTVVYQMIQQIQQKRELQRLQMAGGSQLPMASLLAGS
1001 STPLLSAGTPGLLPTASAPPLLPAGALVAPSLGNNTSLMAAAAAAAVAAAGGPPVLTAQTNPFLSLSGAEGSGGGPKGTADKGASANQEKG*   1093

FIG. 17B

```
AF-17       1 MKEMVGGCCVCSDERGWAENPLVYCDGHACSVAVHQACYGIVQVPTGPWF
              : :  :.||:|.|:  ...|.:::||   |.:.|||.|||:. :|.|.|:
Peregrin  278 LVDEDAVCCICNDGECQNSNVILFCD..MCNLEVHQECYGVPYIPEGQWL 51 CRKC.ESQERAARVACELCPHKDGALKRTDNGGWAHVVCALYIPEVQFAN
              ||:|  :|..||   | |.|||:|:||:|.||:|  ||||||||:|||  |||
          326 CRRCLQSPSRA..VDCALCPNKGGAFKQTDDGRWAHVVCALWIPEVCFAN 100 VLTMEPI.VLQYVPHDRFNKTCYICEETGRESKAASGACMTCNRHGCRQA
              .:  :|||  :::.:|..|:.  |||||.:  |   ||||: |:: .| |
          374 TVFLEPIDSIEHIPPARWKLTCYICKQRG......SGACIQCHKANCYTA 149 FHVTCAQMAGL.LCEEEVLEVD......NVKYCGYCKYHFSKMKTSR   188
              ||||||| |||  :  |.| |.:        .|:  .:||..|  .. ...|
          418 FHVTCAQQAGLYMKMEPVRETGANGTSFSVRKTAYCDIHTPPGSARR   464
```

CONSENSUS   C-X$_2$-C----------X$_{10-13}$-------------C--X$_{2-4}$--C

FIG. 18B

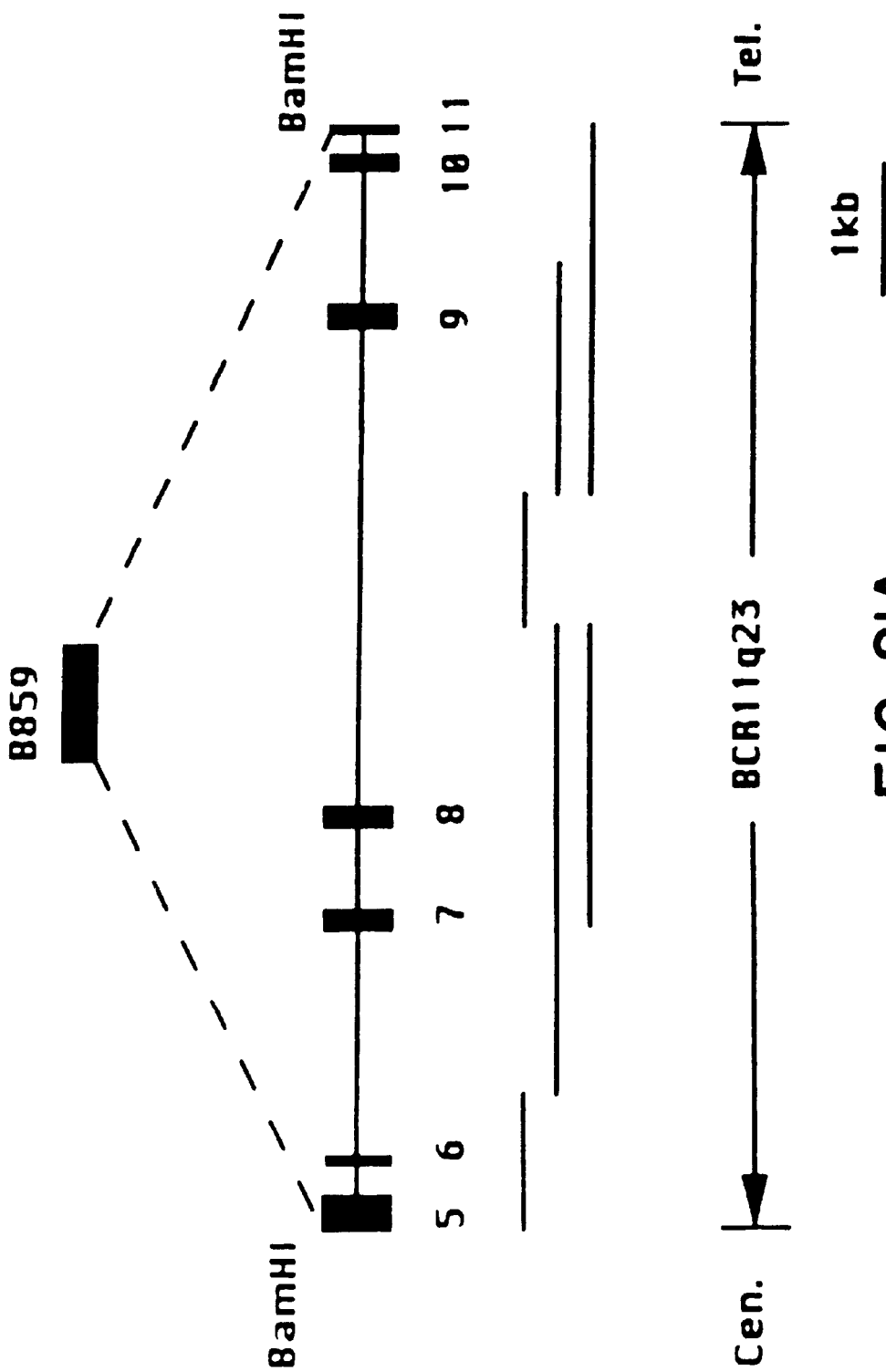

```
   1  GGATCCTGCCCCAAAGAAAAGCAGTAGTGAGCCTCCTCCACGAAAGCCCGTCGAGGAAAA    60
      D  P  A  P  K  K  S  S  S  E  P  P  P  R  K  P  V  E  E  K
  61  GAGTGAAGAAGGGAATGTCTCGGCCCCTGGGCCTGAATCCAAACAGGCCACCACTCCAGC   120
      S  E  E  G  N  V  S  A  P  G  P  E  S  K  Q  A  T  T  P  A
 121  TTCCAGGAAGTCAAGCAAGCAGGTCTCCCAGCCAGCACTGGTCATCCCGCCTCAGCCACC   180
      S  R  K  S  S  K  Q  V  S  Q  P  A  L  V  I  P  P  Q  P  P
 181  TACTACAGGACCGCCAAGAAAAGAAGTTCCCAAAACCACTCCTAGTGAGCCCAAGAAAAA   240
      T  T  G  P  P  R  K  E  V  P  K  T  T  P  S  E  P  K  K
 241  GCAGCCTCCACCACCAGAATCAGGTGAGTGAGGAGGGCAAGAAGGAATTGCTGACCCACA   300
      Q  P  P  P  P  E  S  G
 301  AGTACTAACAAAAAAGCACTGATGTCTCAAACAGCATTTGAAAGCAGGAAATGTATGATT   360
 361  TGAAGTCTTCAGTTCAAGAAAATCAGCTCTCTTTCTAACTATTATGTTTAATAATAAAGA   420
 421  AACAGAAACAAAAAAAACAGTTAAATTGGAGGTATTGTTTTAATTTCCTGTTCGAAGCCT   480
 481  AGAGTTTAAATAGTTTTTTTTTTTTTTTCTAATGGCCCTTTCTTCACAGGTCAGTCAGT   540
 541  ACTAAAGTAGTCGTTGCCAGCATCTGACTGCAATTTATTCTGAATTTTTTAGGTCCAGAG   600
                                                              P  E
 601  CAGAGCAAACAGAAAAAAGTGGCTCCCCGCCCAAGTATCCCTGTAAAACAAAAACCAAAA   660
      Q  S  K  Q  K  K  V  A  P  R  P  S  I  P  V  K  Q  K  P  K
 661  GAAAAGGTGAGGAGAGATTTGTTTCTCTGCCATTTCTCAGGGATGTATTCTATTTTGTAG   720
      E  K
 721  GGAAAAGCCTTATCCTTGACTTCTATGTAGATGGCAGTGGAATTTCTTAAAATTAAGAAA   780
 781  CTTCAAGTTTAGGCTTTTAGCTGGGCACGGTGGCTCACGCTGGTAATCCCAACACTTAGT   840
 841  GAGGCTGAGGTGGGAGGATTGCTTGAGGCCAGCAGTTCAAGACCAGCCTGGGCAACATAG   900
 901  CAAGACCCTGTCTTTATTTAAACCAAAAAAAAAAAAAGAAGAAGAAGAAGTTAGCCAGGC   960
 961  ATGGTGGCAGTTGCGTGTAGTCCCAGGTACTCAGGAGGCTGAGATAGAAGGATTGTCTTG  1020
1021  AGCCCAGGAATTCAAGGCTGTAGTGAGCTATGATTGTACCACTGCAGTCCAGCCTGGGTG  1080
1081  ACAAAGCAAAACACTGTCTCAAAAAAAAATTTAGGCTTGGCAAGGCGCAGCGGCTCACGC  1140
1141  CTGTGATCCCAGCACTTTGGGAAGCCGAAGCAGGCAGATCACTTGAGGTCAGGAGTTGGA  1200
1201  GACCAGCCTGGCCAACATGGTGAAACCCTGTCTCTACTGAAAATACAAAAATTAGCCGGT  1260
1261  TGTGGTAGTGGGTGCTTGGTAATCCTAGCTACTTGGGAGGCTGAGGCAGGGGGAATTGCC  1320
1321  TGAAACCTGCGAGGCGGAGGCTGCAGTGAGCCGAGATTGCATCATTGCACTCTAGCCTGG  1380
1381  ACAACAGAGCTAGACTCCATCCCAAAAAAAAAAAAAAAAGTAGCCGGGCACGGTGGCTC  1440
1441  ACGCCTGTAATCCCAGCACTTTGGGAGGCCGAGGCGGGCGGATCATGAGGGCAGGAGATC  1500
1501  GAGACCATCCTGGCTAACACGGTGAAACCCTGTCTCTACTAAAAATACAAAAAATTAGCC  1560
1561  CGGCGAGGTGGCGGGCGCCTGTAGTCCCAGCTACTCAGGAGAGTGAGCCAGGAGAATGGC  1620
1621  GTGAACCCGGGGGGCGGAGCCTGCAGTGAGCCGAGATCGCGCCACTGCACTCCAGCTTGG  1680
1681  GTGACACCGAGACTCCGTCTCAAAAAAAAATAAAAGTTTAGGCTTTAGCCTGTTCTTT  1740
1741  TTTGGTTTCTTCCTTGTTGCTTTTCCCTTCTTTGTGGCCCCACATGTTCTAGCCTAGGAA  1800
1801  TCTGCTTATTCTAAAGGCCATTTGGCGTAATTATTTTTGACCCCAACATCCTTTAGCAA  1860
1861  TTATTTGTCTGTAAAAATCACCCTTCCCTGTATTCACTATTTTTATTTATTATGGATAAA  1920
1921  GAGATAGTGTGGTGGCTCACATCTATAATCCCAGCACTTTGGGGGCCCAAGGCGGGAGGA  1980
1981  TCACTTGAGGGCAGGAGCTGGAGACCAGCCTGGGCAGCACAGTGACACACAGTTGCTATA  2040
2041  AAAAATTTAAAACCCAACTAGGCATGGTGGCATGCACCTGTAGTCCCAGCTACTCTTGAG  2100
2101  AAGCTGAGGCAGGAGGATCACGAGCCCACAAGGTCTAGGCTGCAGTGAGCTGTGACTGTG  2160
2161  CCACTGTATTGCAGCCTAGGCAACAAAGCAAGACCCAGTCTCTTTTAAAAAAAAATTCAA  2220
2221  AGATTATTGTTTATGTTGGAAACATGTTTTTAGATCTATTAATAAAATTTGTCATTTGC  2280
2281  ATTATTATCTGTTGCAAATGTGAAGGCAAATAGGGTGTGATTTTGTTCTATATTCATCTT  2340
2341  TTGTCTCCTTAGGAAAAACCACCTCCGGTCAATAAGCAGGAGAATGCAGGCACTTTGAAC  2400
      E  K  P  P  P  V  N  K  Q  E  N  A  G  T  L  N
2401  ATCCTCAGCACTCTCTCCAATGGCAATAGTTCTAAGCAAAAAATTCCAGCAGATGGAGTC  2460
      I  L  S  T  L  S  N  G  N  S  S  K  Q  I  P  A  D  G  V
2461  CACAGGATCAGAGTGGACTTTAAGGTAAAGGTGTTCAGTGATCATAAAGTATATTGAGTG  2520
      H  R  I  R  V  D  F  K
2521  TCAAAGACTTTAAATAAAGAAAATGCTACTACCAAAGGTGTTGAAAGAGGAAATCAGCAC  2580
```

FIG. 22A

```
2581 CAACTGGGGGAATGAATAAGAACTCCCATTAGCAGGTGGGTTTAGCGCTGGGAGAGCTTT 2640
2641 GGACAGTGTTGTTAGGTCACTGTTTGTGAACTGACTGCAGAACATACATAATGAAACATT 2700
2701 CCTATCCATCCTGAGGAGTATCAGAGGAAGTAATTCCTTCACATGGAAAGTATCAAACCA 2760
2761 TGATGATTCCTTGAGTCAGCAAAACTGTAAGAGAAATTCAATCCCAGTGTATTTTCGCAA 2820
2821 TATCTTCACTATGAATTGAACAACTAGGTGAGCCTTTTAATAGTCCGTGTCTGAGATTAA 2880
2881 AACTTTTTAAAGCAGCAGTTATTTTTGGACTCATTGAAATGAAATACTCTGACATTGTGA 2940
2941 TGTCACACTAATTTTATGCTTTTCATCCTTATTTTCCATCCAAAGTTGTGTAATTGTAAA 3000
3001 ACTTTCCTAAGTGACCTTTCTCTCTCCACAGGAGGATTGTGAAGCAGAAAATGTGTGGGA 3060
                                E  D  C  E  A  E  N  V  W  E
3061 GATGGGAGGCTTAGGAATCTTGACTTCTGTTCCTATAACACCCAGGGTGGTTTGCTTTCT 3120
      M  G  G  L  G  I  L  T  S  V  P  I  T  P  R  V  V  C  F  L
3121 CTGTGCCAGTAGTGGGCATGTAGAGGTAAGGCATCCTGCTTCTTTGTACCCCAGGAAGTA 3180
      C  A  S  S  G  H  V  E
3181 CATAAATGATTGATCTGGGGATGAGATTACTATAGTCTGTTTTGTTGGTATTTAGCAGGT 3240
3241 ACTATTCCCTGTTTAAACCAGCTAAAGAAATGTTTTGAAGTATTTTAGAGATTTTAGGAA 3300
3301 GGAATCTGCTATTAGAGTAGCAAAGTTATTGAGAGTGAAAAGATCAATAATCCCATCTCT 3360
3361 CTTAAATTCAGTCTTTATTAGAGTTCTGATCTTTCTGTTAGATGTCTAAATAAGAGAAAA 3420
3421 AATTATACAGTGGTCTATTAAAAGGGATGCTATTGATGGTTATTTTATATTGTATATCAA 3480
3481 AGCCTCTTCATCTATAAGGAGCTCTTACCAATTAATAAGAAAAAGGAATGACATCCAGAA 3540
3541 AAAAAAATAGGCAAAAGACAGAAATAGATAATTCACAAAATTAGAAATAAATACATGTTG 3600
3601 GGTGGCAGGGGGAGGTGAAGGGAGGGTGTCTGTTTTTAGCCCTCTAGTGACCAAAAACT 3660
3661 GGAAATTAAAGCATGATAAAAAAGAATCCTGAATAAATGGGGACTTTCTGTTGGTGGAA 3720
3721 AGAAATATAGATTAGTTACAATCTTTCTTTCTGAGGGAATTATTTGGAAATATATATATC 3780
3781 TATCTTTAAAATAGGTATATCCTCTAACATAGCAATTGCACTTCAAACACTTATGGATAT 3840
3841 AATTAGATAAATTGGCAAATCTGTAGATATAAAGAAGTGTTCATTTCAATATTGCTCATA 3900
3901 ATAATAAAAAACTGGAAACAACCCGAAAGTCCATCTATAGGAGCATGGGTTAAAATAAG 3960
3961 CATAGGGCATATAGCTGGGCACGGTGGCTCACGCCTGTAATCCCAGCACTTTGGGAGGCC 4020
4021 AAGGCAGGCGGATCACAAGGTCAGGAGATCCAGACCATCCTGGCTAACACAGTGAAACCC 4080
4081 CGTCTCTATTAAAAATACAAAAAAATTAGCCGGGTGTGGTGGCGGGCGCCTGTAGTCCCA 4140
4141 GCTACTCGAGAGGCTGAGGCAGGAGAACGGCATGAACCCGGGAGGTGGAGCTTGCAGTGA 4200
4201 GCCGAGATCGCCCCACTGCACTCCCGCCTGGGCGACAGAGCAAGACTCCGTCTCAAAAAA 4260
4261 AAATAAAAGTGTAGGGCATATATAATGCCAAATATGAAGTCCTAAAGATAATATATATTA 4320
4321 ATATTATTAGGTTGGTCCAAAAGTAATTGCAGTAATAACATGGAAAGATGTCCATGACAT 4380
4381 ATCACTGAGTGAAAAGAGCAGGTTACAAGATAATATATAAAGCACAATCCCATCTTAGTT 4440
4441 TGGAAAAGTGTTTTTAAAGTATATATCTAGAAAACAATCTGGAAGGATTCACACCAAAAT 4500
4501 ATTAAGAGTGTGGTTGGATTATGGGTGACCTTTATTTGTTTCTCTGGTTTTTTTTTTTTT 4560
4561 AATCTTTCTGAGTTTTTTGGAGTATGTACCACCTTTACAATGAGGAAGGAAAAAGTAGCA 4620
4621 CAATTTTAAATAGGAAGCAGTAGTTTGTCATTTATAAGGGACATATCCTACATCCTTTAC 4680
4681 AGTTCTTAAATTCCTGGCAGATACCTCTTTGGCTTATTACTTACCACATAAGATATGTAT 4740
4741 TCAAAGGTGGTAAAGAAAATCCACGTCGGGTGCAGTGGCTCACGCCTGTAATCCCAGTAC 4800
4801 TTTGGGAGGCTGACGCAGGAGGACCGCTTGAGCTCAGGAGTTCAAGACCAGCCTGAGCAC 4860
4861 CATAGTGAGACCTCATCTCTACTAAAAAAAAAATAAAATACCAGGCATGGTAGCATGTGC 4920
4921 CTGTAGTCCCAGCTACTCTAGTCCCAGCTACTTGGGAGGCTGAGGTGAGAGGATCACTTG 4980
4981 AGCCCAGGAGATCGAGGCTGCAGTGAGCCATTATCACGCCACTGCACTCCAGCCTGGGCA 5040
5041 ACTAAGCAAGACCCTGTCTCAAAAAAATTTTAAAAAATTTAAAAAATAAGAAAAATCCAAG 5100
5101 CTAGGTTGAAATCTGAATGTTGAGCAGTCAGTGAGACACAAACTAGCTAAGAAAGTCAAC 5160
5161 CCTGCCCACTTGCCATTTGAAGTTATTACTAGCAAAATTACAAATTATTGCCTACTATTC 5220
5221 ATTTACTAAGCAAATATTCTCTTAGTCCCTATTACGAACAACTTATTGTTCTAAGTGCAG 5280
5281 AAGTTCAGATATCATTGAGACTGAGAATATTCAGTCTACAAGTGCCAGGGGTCTACTGTA 5340
5341 TCCTCTTTTCCGTCTTAATACAGTGCTTTGCACCCATATATATGCCACCCACAGGAATAA 5400
5401 CTTTTTTTATAGCACCAGTCCTTCAACTTCTGGGATTAAACAGATTTTTTTTCAGGGTAT 5460
5461 AATTGTTCTGATCTAAATTCTTTATAGTTGTACATAGCAATCTCACAGGGTTCCTAAAAT 5520
5521 ATAAAATAGAGAATAGCATGCTGCCTGCACTGCACTCCTAAAGCATGACCAGTGCTTGAT 5580
5581 AAACTCTCCTCCATGCGAATTTTTTAAACTTTTTATGTTGACATGATTTCAGACTTACAA 5640
5641 AAAAACTATGAGTTGTACAGAGAATTCTAAGTACCCCTCACCCAAATTCCCTAAGTGTTA 5700
5701 ATATGTTTCTCTGTGTGTATATATTTTACAAAATAACAAATAAAATACATATACACATTT 5760
5761 TACCTGTAGATACACATGTATCTAAAAATTTGAGAACAAGTTGGAGACATAAACCATTTT 5820
5821 ACCTCTAAATATTTTAGTGTATATTTTTAAAAATCAAGGACGTTCTCGTATTTAACCATG 5880
```

FIG. 22B

```
5881 GTATAATTACCAAATCAGGAAATTAACACACTGGGACATTACTATTATCTGATCTATAGG 5940
5941 CCTTATTTAGGTTTGACCAATTGTCCCAATAATTCCTTTATGGCAAAAGAAAATTCTGGA 6000
6001 TTATCCTAGTTAGTATTTTGAAAATCCTATATCAATATGAAAATAACTTATTTCTAAAA 6060
6061 TTAGAAATGGAGGCTGGGCGTGGTGGCTCACGCCTATAATCCCAGCACTTTGGGAGGCCG 6120
6121 AGGCAGGCAGATCACAAGGTCAGGAGATTGAGACCATCCTCGCTAACACAGTGAAACCCC 6180
6181 ATCTCTACTAAAAATACAAAAAATTAGCCAGGTGTGGTGGGACGCGCCTGTGATCCCAGC 6240
6241 TACTCAGGAGACTGAGGCTGGAGAATCGCTTGAACCCAACAGGCGGAGGGTTGCAGTGAG 6300
6301 TCGAGATCGCACCACTGCACCCCAGCCTGGGCGACAGCGAGACTCCGTCTCAAAAAAATA 6360
6361 AATAAATAAAAATTAAAACAATTAAAAAAATAAAATTACAAATGGAAAGGACAAACCAGA 6420
6421 CCTTACAACTGTTTCGTATATTACAGAAAACGTTTAAACCCTCCCTATTTCCCCCACCCC 6480
6481 ACTCCTTTATATTCCCATAGCTCTTTGTTTATACCACTCTTAGGTCACTTAGCATGTTCT 6540
6541 GTTAAATCTTGTATTATATTTATTTTGTTACTTTCTATTTCCACTGGTATTACCACTTTA 6600
6601 GTACTCTGAATCTCCCGCAATGTCCAATACTGTACTTTTTACATAGTCATTGCTTAATG 6660
6661 AAATATGTATTGAATTAAATATATGCCAGTGGACTACTAAAACCCAAAGTATATAAGAAGG 6720
6721 GTATGGTTGATTATGTTTTCTACATATTATTTGACATACTTCTATCTTCCCATGTTCTT 6780
6781 ACTATAGTTTGTGTATTGCCAAGTCTGTTGTGAGCCCTTCCACAAGTTTTGTTTAGAGGA 6840
                 F  V  Y  C  Q  V  C  C  E  P  F  H  K  F  C  L  E  E
6841 GAACGAGCGCCCTCGGAGGACCAGCTGGAAAATTGGTGTTGTCGTCGCTGCAAATTCTG 6900
         N  E  R  P  L  E  D  Q  L  E  N  W  C  C  R  R  C  K  F  C
6901 TCACGTTTGTGGAGGGCAACATCAGGCTACAAAGGTACAAAACTTGGTAATAGAACTACA 6960
        H  V  C  G  G  Q  H  Q  A  T  K
6961 GCTGGGCCTCTGTATCAGTGGGTTCTGTATCCCTGGACTCAACCAACCTTGGATTGAATG 7020
7021 TATCTGGGAAAAAATGAGTAGTTGCCTCTGTACTCTATGTGAACAGACTTTTTCTTGTCA 7080
7081 TTATTTCCTAAACAATACAGTATAACAACTATTTACATTGTATTAGGTATGATAAGTAAT 7140
7141 CTAGAGATAATTTAAAGTATATGGTGGGCGGATCACTTGAAGCCAGGAGTTCGAGACCAG 7200
7201 CCTGAGCCAACATGGTGAAACCCCATCTCTACTAAAAATACAAAAAATTAGCCAGGTGTG 7260
7261 GTGGTGGGCACCTGTAGTCCCAGCTACTTGGGAGGCTGAGGCAGGAGAAAATCGCTTGAACT 7320
7321 TTGGAGGCAGAGGTTGCAGTGAGCCACTCCAGCCTGTGGTGCAGTCTGTCACTCCAGCCT 7380
7381 GGGTGACACAGTGAGACTCCATCTCAAAAAAAAAAAAAAAAAAAACTATATGGGAGGA 7440
7441 TGTGCATTTTGTTATATGCAAATGCTGCACCATTTTGTCTAGGGACTTGGGCATCCATGG 7500
7501 ACTTTGGTATCCTCTGGGGGTCCTGGAACCAATCCCCCATGGAAACCAAGGATGACTGTG 7560
7561 CTTAGAGTATTGCTTTCTTTCTTGATTTGTATTTCTGTCTTCCAGTTAAGATTTTGTATC 7620
7621 TATATTATTTCTCTTTTTACTTAGTCTGTCTTTAGCATTTAATTGGGTGTAATCAGTTGC 7680
7681 CTATTTTGTGTTTTAATTTTGGGACTATAGCAGAAAACATGATGTTGAATAAAATTCCAA 7740
7741 AAATAAGTCAAATCTACCTAATATGAATACTCATCACTGAGTGCCTTTGGCAGGAAATAA 7800
7801 ATCTATCTCAATGCGTTAATTGGGAGTAAATAATGCATGAGGAAATTTAAACTCATAATT 7860
7861 GTGTGCTGTACTTACTTGCCAGTAAATGTGAAATGGGGTACTAAGTAATAGGTGTTGGGT 7920
7921 GAAGGTAATATGATGCTTATCTTTTTGCCATTATATTTTCTTACAGCAGCTGCTGGAGTG 7980
                                                         Q  L  L  E  C
7981 TAATAAGTGCCGAAACAGCTATCACCCTGAGTGCCTGGGACCAAACTACCCCACCAAACC 8040
         N  K  C  R  N  S  Y  H  P  E  C  L  G  P  N  Y  P  T  K  P
8041 CACAAAGAAGAAGAAAGTCTGGGTGAGTTATACACATGATGCTCTTTTATAGAGAACCAC 8100
         T  K  K  K  V  W
8101 CATGTGACTATTGGACTTATGTAACTTGTATTACAAATATCTATGCATGAGGATGTCAGT 8160
8161 ATGACAATCTTTTTCCCTCATTACTAGGAAATCATCTCAGGAGAGAAATTAAATCTATAA 8220
8221 ATGGATGCATTTAAGATCTTTTTAGTTAAGTAAAGATATTAAAAACAAGAAATTCCTATT 8280
8281 GAATTTCTTTTCTTCTTTTCTAGATCTGTACCAAGTGTGTTCGCTGTAAGAGCTGTGGAT 8340
         I  C  T  K  C  V  R  C  K  S  C  G  S
8341 CC 8342
```

FIG. 22C

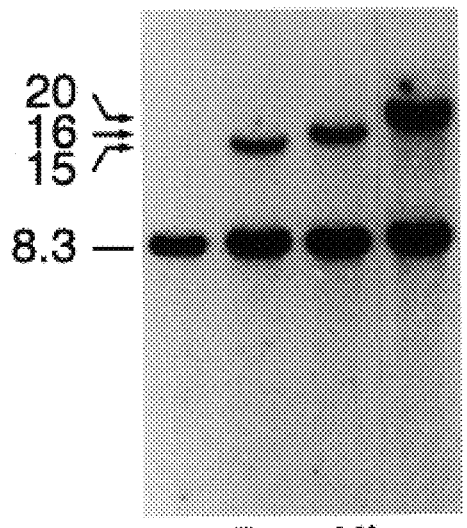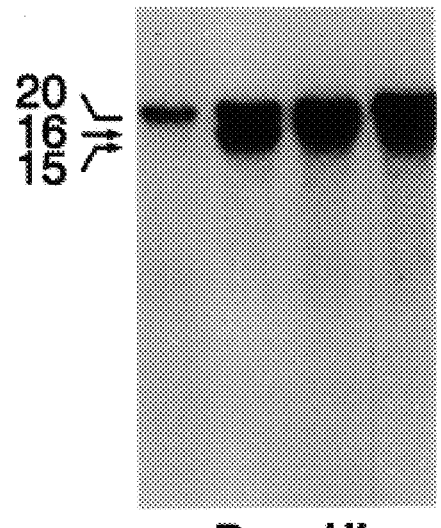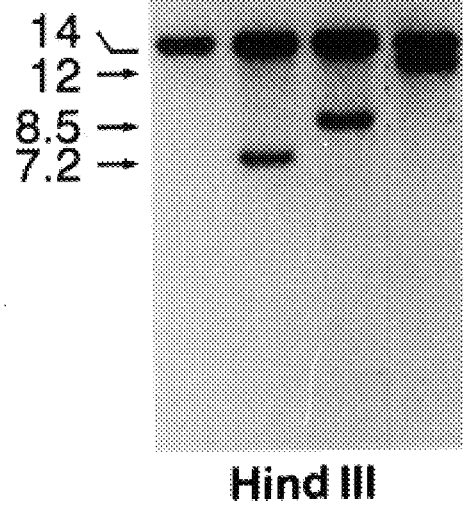
FIG. 24A    FIG. 24B

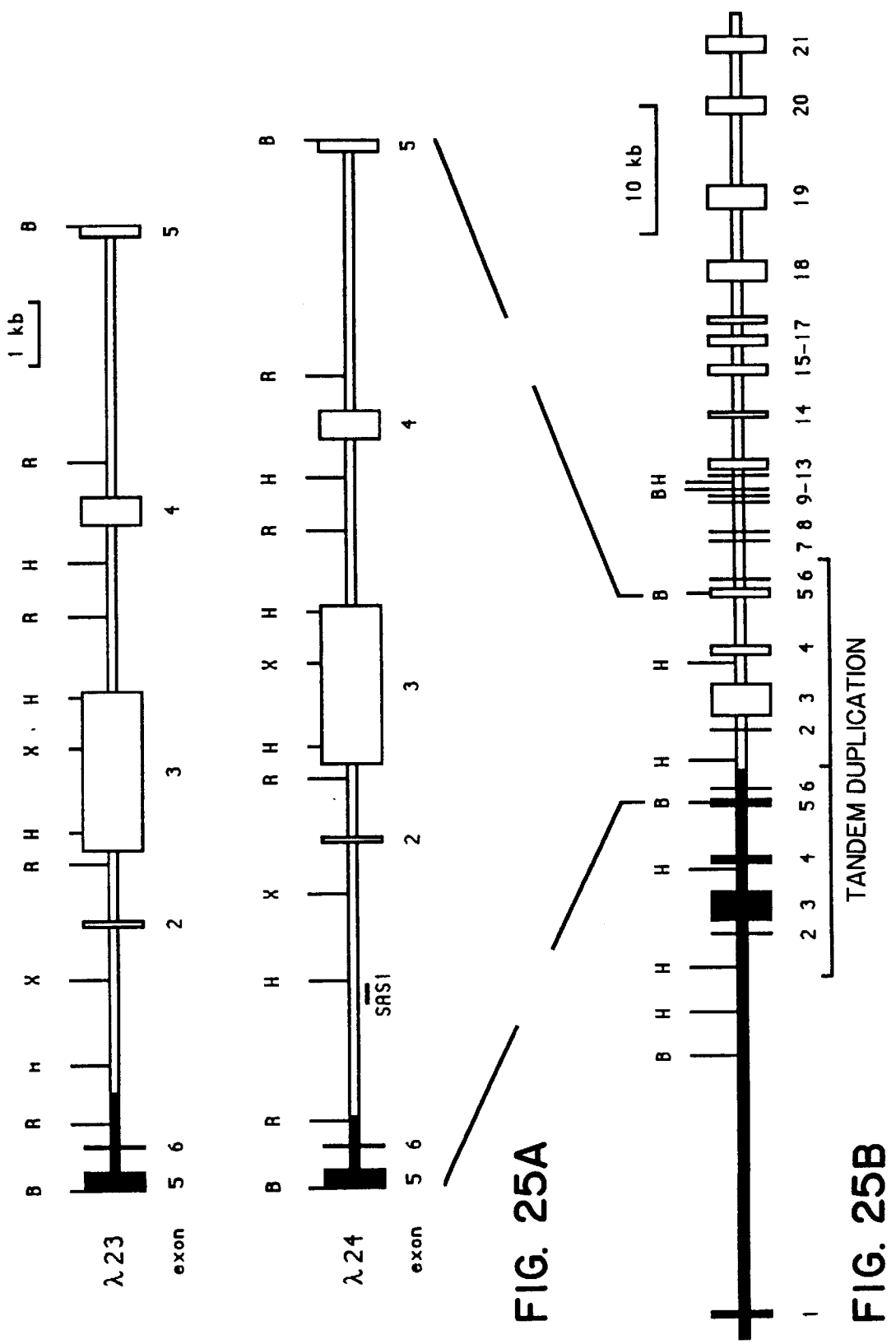

```
Intron 6   GCCTGTGTAGTCCCAGCTACTCAGGAGAGTGAGCCAGGAGAGAATGGCGTGAACCCGGGGGGCG
           ||||||||||||||||||||||||||||||||||||          |||||||||||||||||
λ23        GCCTGTGTAGTCCCAGCTACTCAGGAGAGTGAGTCCTAAAAGTTATATATGTCTTTTAATAT
                                             ||||||||||||||||||||||||||||
Intron 1                                    TTTAAATTTAAGAGATGAACCTGCTAATTTGTCCTAAAAGTTATATATGTCTTTTAATAT Intron 6   TTGTACCACTGCAGTCCAGTCCAGCCTGGGTGACAAAGCAAAACACTGTCTCCAAAAAAATTTA
           |||||||||||||||||||||||||||||||||||   ||||||||||||||||||||||
λ24        TTGTACCACTGCAGTCCAGTCCAGCCTGGGTGACTGCATCCAGCACTCTCCTCACTGGCATCACG
                                                ||||||||||||||||||||||||||||
Intron 1                                       CTGAGACCCCTAAACCAACCCTTCTCTCCCCACATCCAGCACTCTCCTCACTGGCATCACG
```

FIG. 25C

```
5'  AAA CCA AAA GAA AAG | GAT GAG CAA TTC TTA  3'
    Lys Pro Lys Glu Lys | Asp Glu Gln Phe Leu
              exon 6    | exon 2
```

METHODS FOR SCREENING AND TREATING LEUKEMIAS RESULTING FROM ALL-1 REGION CHROMOSOME ABNORMALITIES

CROSS REFERENCE TO RELATED APPLICATIONS

This application is a 371 of application PCT/US94/04496, filed Apr. 22, 1994, which was a continuation-in-part of application Ser. No. 08/062,443, filed May 14, 1993, now abandoned, which was a continuation-in-part of application Ser. No. 07/971,094, filed Oct. 30, 1992, now abandoned, which is a continuation-in-part of application Ser. No. 07/888,839, filed May 27, 1992, now abandoned, which was a continuation-in-part of application Ser. No. 07/805,093, filed Dec. 11, 1991, now abandoned, each of which is herein incorporated by reference.

ACKNOWLEDGMENT OF GOVERNMENT SUPPORT

Research for this invention was supported in part by an OIG grant CA39860 from the National Cancer Institute. The United States Government may have certain rights in this invention.

FIELD OF THE INVENTION

The present invention relates to the field of methods for diagnosis and treatment of human leukemias wherein hematopoietic cells of patients have translocations in a small region of chromosome 11 designated as ALL-1. Diagnostics and therapeutics based on nucleic acid and amino acid sequences are provided.

BACKGROUND OF THE INVENTION

Specific reciprocal chromosome translocations are very frequently found in human lymphomas and leukemias. These chromosomal abnormalities alter normal cellular genes leading to their deregulation. Chromosome translocations have been shown to play an important role in the pathogenesis of human leukemias and lymphomas by either activating cellular protooncogenes or by leading to the formation of chimeric genes capable of transforming hematopoietic cells. Erikson et al., Proc. Natl. Acad. Sci. USA 1983, 80, 519–523; Tsujimoto et al., Science 1984, 226, 1097–1099; Tsujimoto et al., Science 1984, 224, 1403–1406; Shtivelman et al., Nature 1985, 315, 35–354; Mellentin et al., Science 1989, 246, 379–382.

Translocations can lead to gene fusion resulting in a chimeric oncoprotein whose transforming activity is derived from both genes. The prototype of such events is the t(9;22) of chronic myelogenous leukemia (CML) which leads to a BCR-ABL fusion mRNA and protein (Shtivelman, supra). Translocations t(1;19), t(15;17), and t(6;9) are other examples of gene fusions, involving in the first two cases transcription factors (Nourse et al., Cell 1990, 60, 535–545; Kamps et al., Cell 1990, 60, 547–555; Kakizuka et al., Cell 1991, 66, 663–674; de The et al., Cell 1991, 66, 675–684; von Lindern et al., Mol. Cell. Biol. 1990, 10, 4016–4026).

The alternative molecular consequence of translocations is deregulation of protooncogenes by their juxtapositioning to an enhancer or promoter which is active in the type of cell from which the tumor arises. The immunoglobulin (Ig) and T cell receptor (TCR) enhancers participate in at least 15 different translocations associated with Burkitt lymphoma, chronic lymphocytic leukemia, follicular lymphoma, mantle cell lymphoma, and acute T or B cell leukemia. (Croce, C M, Cell 1987, 49, 155–156; Rabbitts, T H, Cell 1991, 67, 641–644; Solomon et al., Science 1991, 254, 1153–1160).

Chromosomal region 11q23 has been shown to be involved in different chromosomal translocations in human acute leukemias of different hematopoietic lineages. 11q23 chromosome abnormalities have been reported in acute lymphoblastic leukemia and in acute nonlymphoblastic leukemia (ANLL), most commonly of the M4 and M5A subtypes. Heim and Mitelman, Cancer Cytogenetics, Alan R. Liss, New York 1987. Chromosome 11 band q23 is frequently rearranged in acute lymphocytic (ALL), in acute myelomonocytic (AMMOL), acute monocytic (AMOL) and acute myeloid (AML) leukemias, mostly in reciprocal exchanges with various translocation partners. The t(4;11) (q21;q23), t(11;19) (q23;p13), and t(1;11) (p32;q23) are found in 10%, 2% and <1% of ALL, respectively. Reciprocal translocation between 11q23 and chromosomal regions 9p22, 6q27, 1p21, 2p21, 10p11, 17q25 and 19p13 are found in 5–6% of AML. Heim and Mitelman, supra. In addition, interstitial deletions in 11q23 have been detected both in ALL and AML.

The same segment on chromosome 11 is apparently involved in the t(11;19) (q23;p13) and t(1;11)(p32;q23) translocations in ALL as well as in translocations with the chromosomal regions 9p21, 2p21 6q27, 17q25 and 19p13 associated with 5–6% of acute myelogenous leukemias (AML). Heim and Mitelman, Cancer Cytogenetics, Alan R. Liss, New York 1987. Reciprocal translocations between chromosome region 11q23 and chromosomal regions 9p22, 6q27, 1p21, 2p21, 10p11, 17p25 and 19p13 are found in 5–6% of ANLL.

In clinical terms, rearrangements of 11q23, in particular the t(4;11) chromosome translocation, have some distinct features. The patients are often quite young; t(4;11) accounts for the vast majority of cytogenetically abnormal ALLs in infants. In the majority of patients, the leukemic cells show both B-cell and myeloid marker (Stong et al. Blood 1986, 67, 391–397) and the disease is consequently considered "biphenotypic."

Among children, most patients with the t(4;11) abnormality are less than one year of age and have a poor prognosis. The leukemic cells have a CD10−/CD19+ early B cell precursor phenotype and most of them express a myeloid associated antigen (CD15); Pui et al., Blood 1991, 77, 440–447. Myelomonocytic and biphenotypic leukemias carrying the t(4;1) aberration have also been reported; Nagasaka et al., Blood 1983, 61, 1174–1181.

There remains an unmet need for identification of the breakpoint cluster region and the genes involved in chromosome 11 aberrations associated with acute leukemias in order to provide diagnostics and therapeutics for these diseases.

SUMMARY OF THE INVENTION

The cDNA sequence of the ALL-1 gene on chromosome 11 is provided. A partial sequence of the AF-4 gene is also provided in the context of the sequences of two reciprocal endproducts of a translocation. Amino acid sequences corresponding to the cDNA sequences of the entire ALL-1 gene and the partial sequence of the AF-4 gene, and sequences relating to chimeric genes formed by chromosome translocations with chromosome 4, 9 and 19, respectively, are provided. Probes are provided for detecting chromosome abnormalities involving the ALL-1 gene on chromosome 11, including probes for detecting chimeric genes generated by translocations. Monoclonal antibodies for diagnosis and treatment and antisense oligonucleotides for treatment of acute leukemias are also described.

DESCRIPTION OF THE DRAWINGS

Figure 8B:
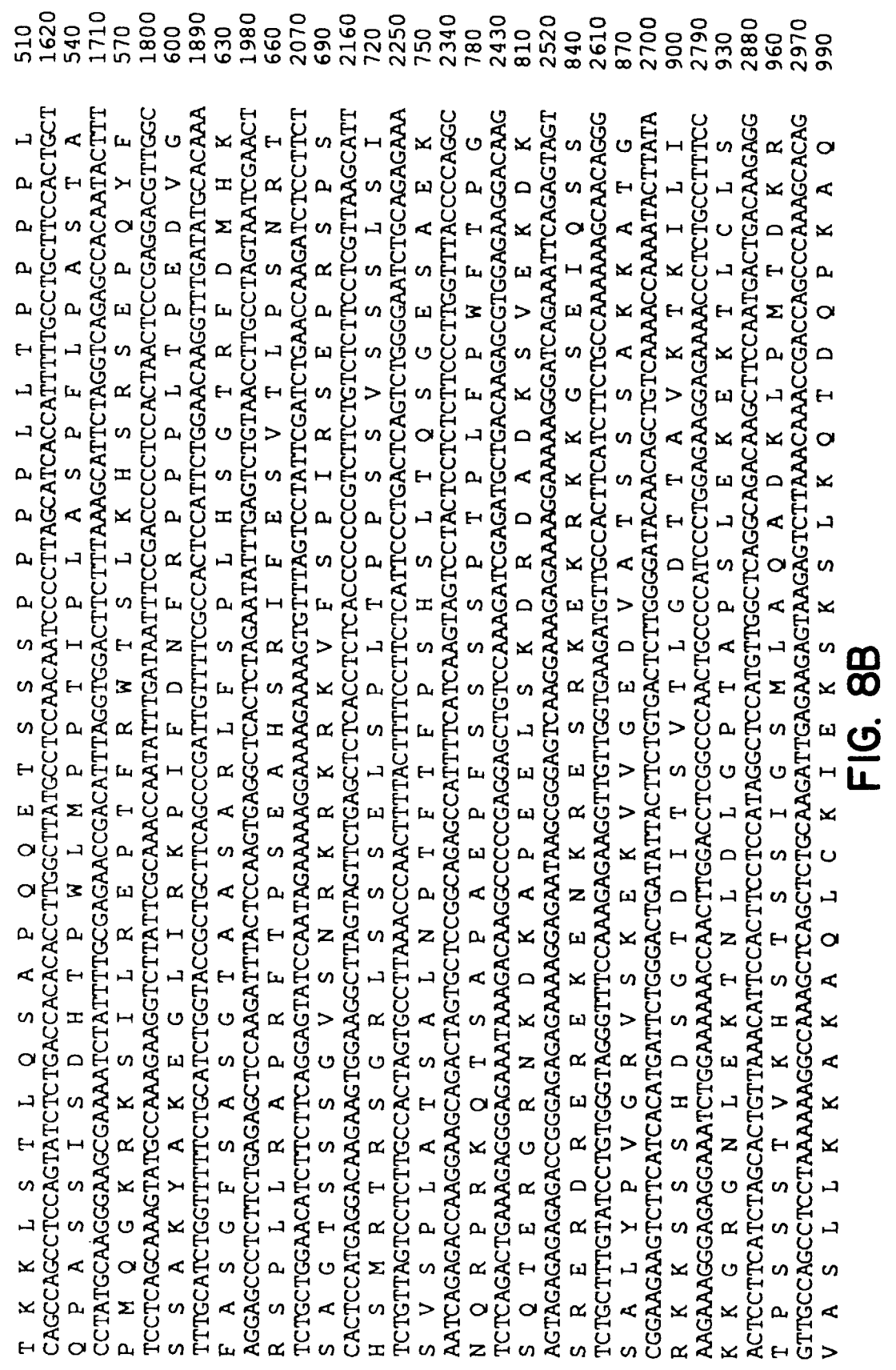
Figure 8C:
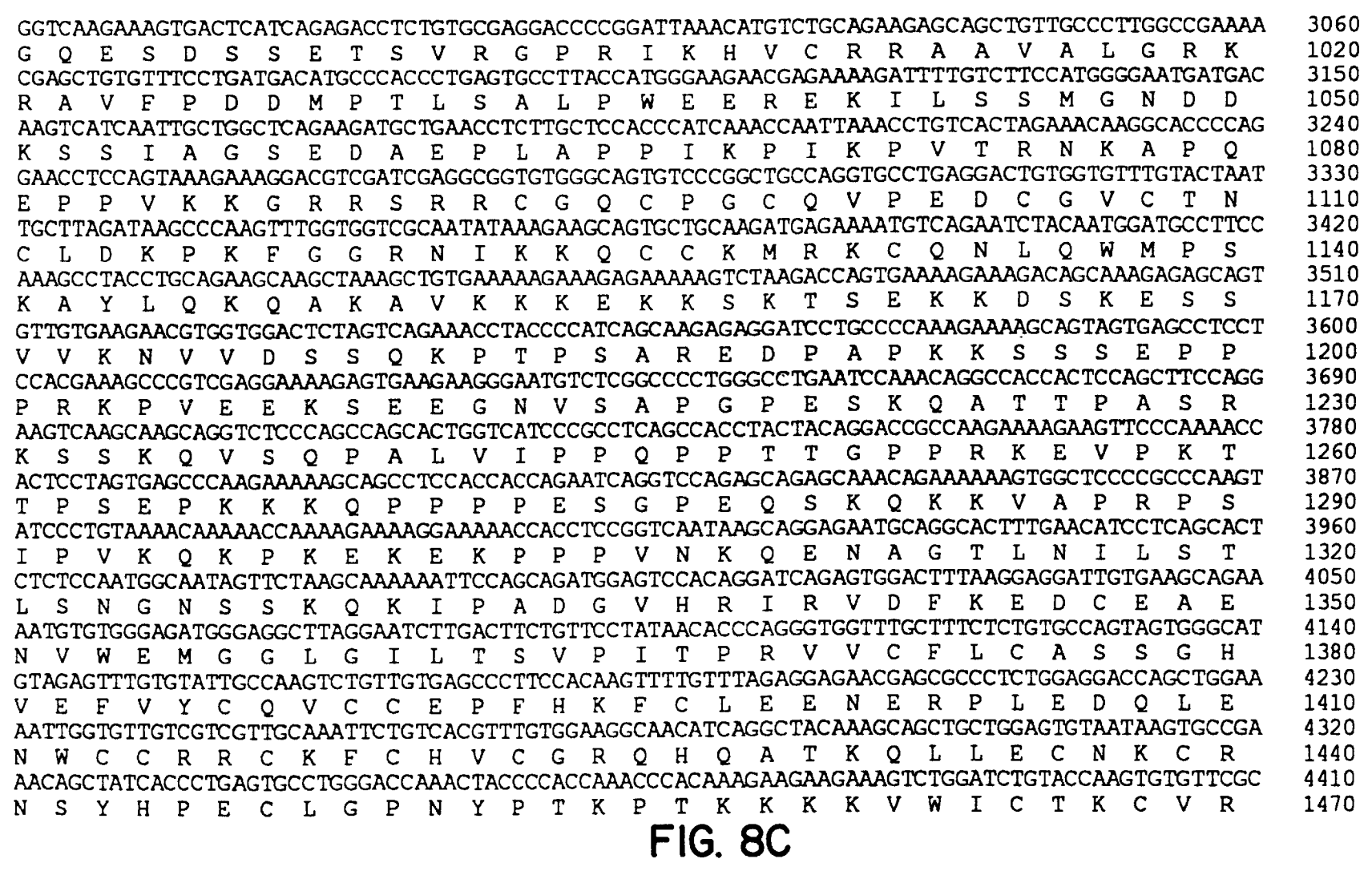
Figure 8D:
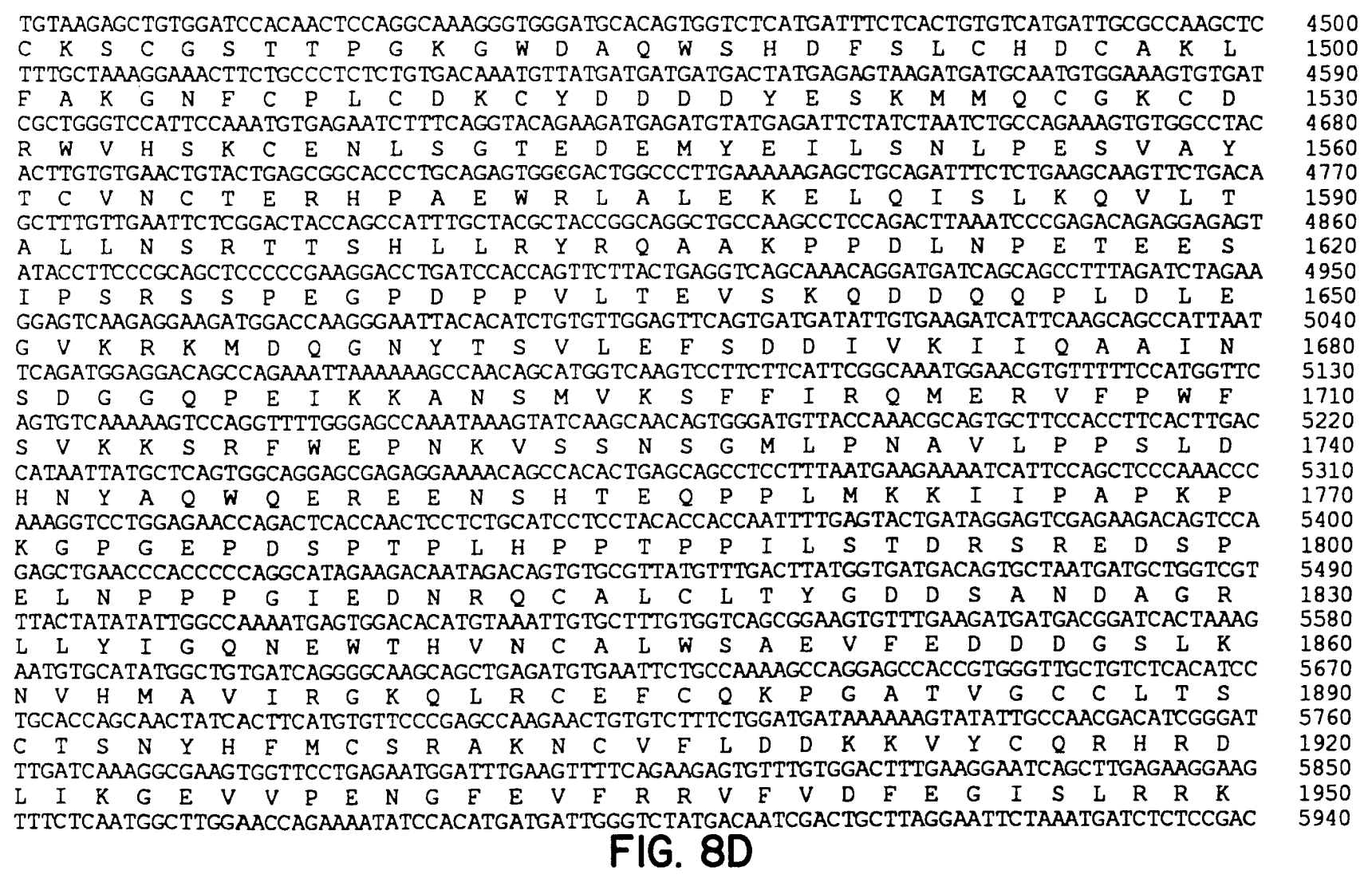
Figure 8E:
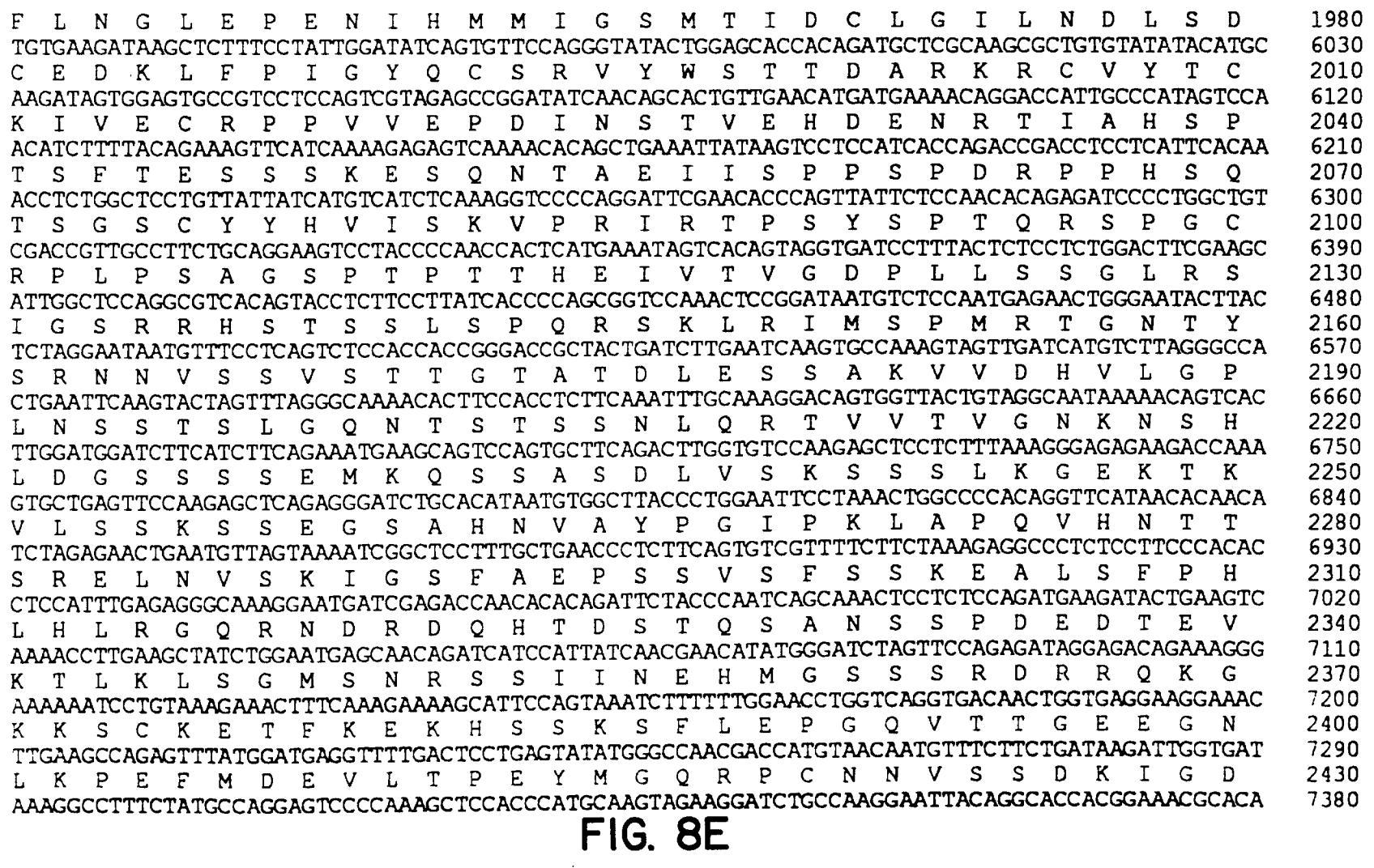
Figure 8F:
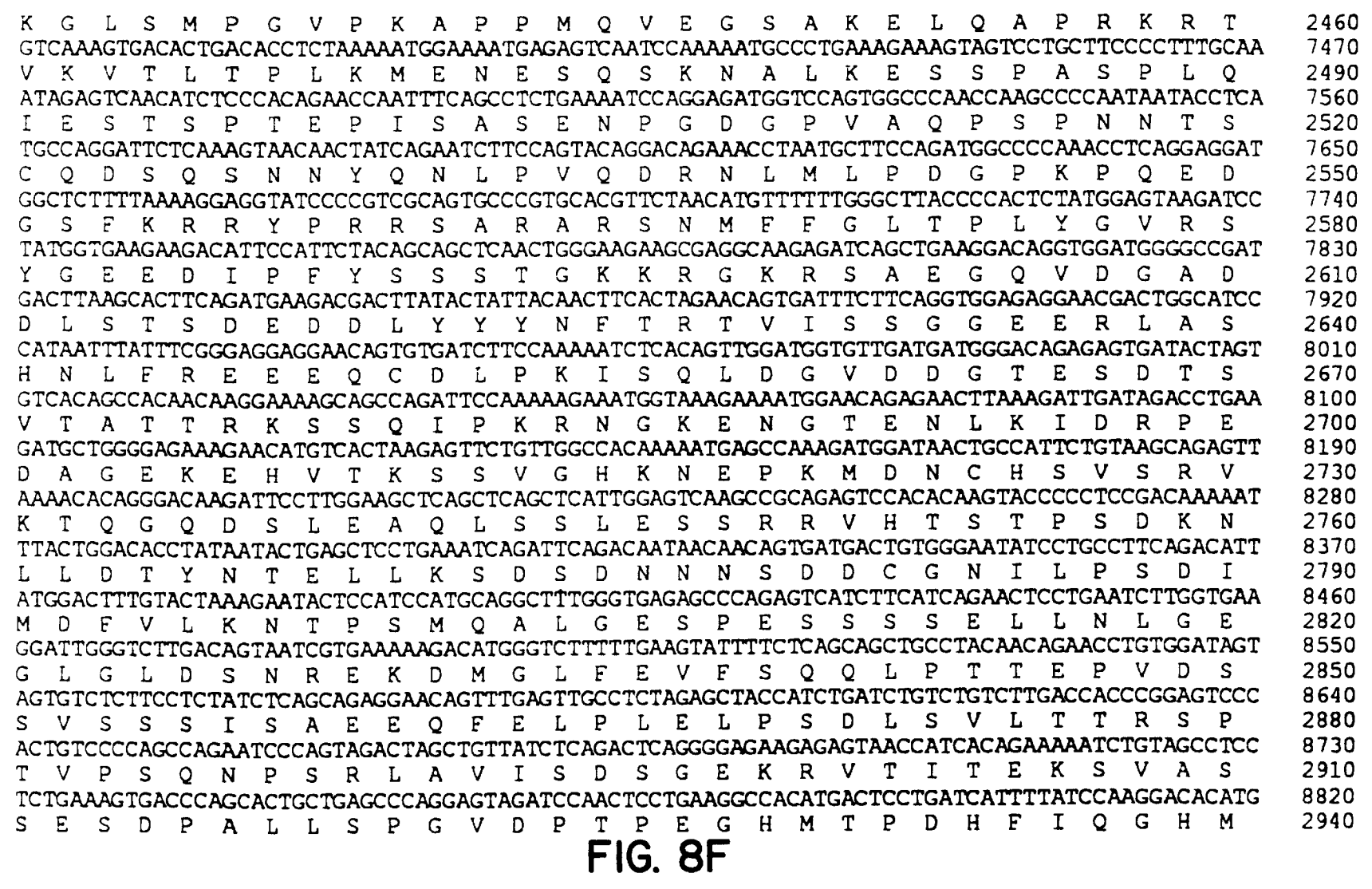
Figure 8G:
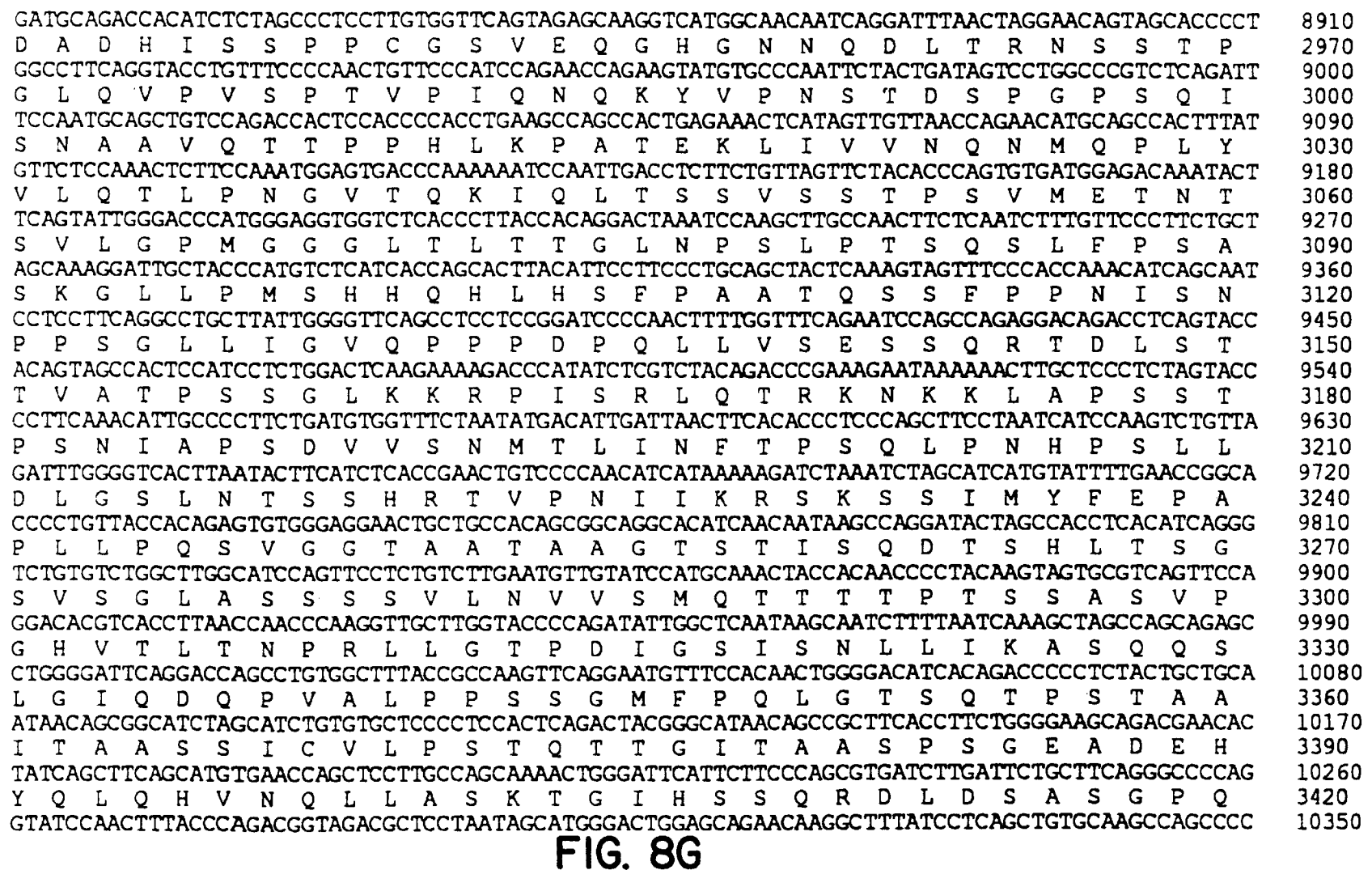
Figure 8I:
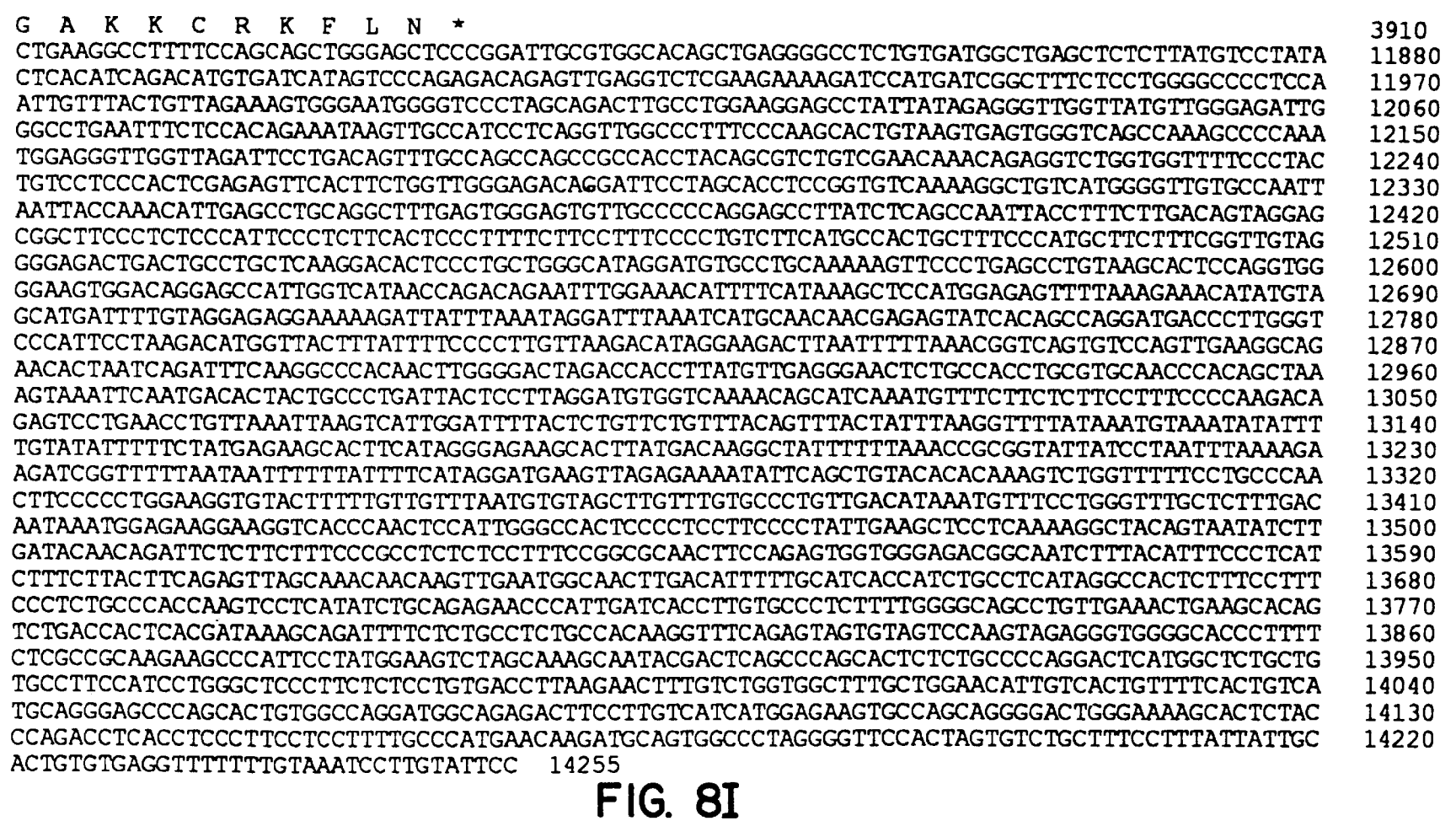

FIG. 8A shows nucleotide sequence and predicted amino acid sequence of ALL-1 cDNA (SEQ ID NO:1).

FIG. 9 depicts homology between ALL-1 (SEQ ID NO:1) and Drosophila trithorax (D. Trx) proteins (SEQ ID NOS:2, 3 and 4) (top and center), and the structure of ALL-1 zinc finger-like domains (bottom). Bars indicate identical residues. One dot and two dots indicate first and second degree conservative differences, respectively.

In FIG. 10A exons containing the zinc finger-like domains (8–12) are represented by cross-hatched boxes. Among the five t(4;11) breakpoints shown (arrowheads in FIG. 10A), included are those of the MV4;11 (MV), RS4;11 (RS), and B1 (B1) cell lines. C.L. and I.V. represent leukemic cells with t(4;11) from two patients. B, R, G, X, H correspond to sites for the enzymes BamHI, EcoRI, BglII, XbaI, and HindIII, respectively. In sequences within FIG. 10A, small and large letters represent introns and exons, respectively. Breakpoint cluster region around exon 6 is represented by SEQ ID NOS: 5 and 6. Breakpoint cluster region around exon 7 is represented by SEQ ID NOS: 7 and 8. Breakpoint cluster region around exon 8 is represented by SEQ ID NOS: 9 and 10. Breakpoint cluster region around exon 9 is represented by SEQ ID NOS: 11 and 12. Breakpoint cluster region around exon 10 is represented by SEQ ID NOS: 13 and 14. Breakpoint cluster region around exon 11 is represented by SEQ ID NOS: 15 and 16. Breakpoint cluster region around exon 12 is represented by SEQ ID NOS: 17 and 18. Partial AF-4 sequence (SEQ ID NO. 19) and ALL-1 exon 9 sequence (SEQ ID NO: 20) is illustrated in FIG. 10B. Cytosine in position 4141 of ALL-1 sequence (FIG. 2) is replaced by thymidine in clone 25, resulting in alteration of Leucine into Phenylalanine (FIG. 10C). FIG. 10C shows ALL-1 exon 7 sequence (SEQ ID NO: 21) and partial AF-4 sequence (SEQ ID NO: 22).

FIGS. 12A–C depicts the genomic analysis of the t(6:11) (q27:q23) chromosome translocation. FIG. 12A: Physical map of the t(6;11) junction, as well as of the corresponding regions from chromosomes 11 and 6. The RVP0.5 probe was used to isolate the corresponding normal DNA of 6q27 (FIG. 12B). Chromosome 6-specific probe XR0.5 detects DNA rearrangement in the bone marrow from a patient, whose karyotype showed 11q23 deletion; (FIG. 12C). FIG. 12C shows the sequence of Chr. 11q23 (SEQ ID NO: 45), der(6) (SEQ ID NO: 46), and Chr 6q27 (SEQ ID NO: 47). Sequence of the t(6;11) breakpoint region. Cen and Tel denote the direction of the telomeres and centromeres of the two chromosomes. Open vertical boxes represent defined exons. Restriction sites: B, BamHI, H., HindIII, G, BglII; Rm, EcoRI and X, XbaI.

FIGS. 13A–C shows the cloning and sequencing of AF-6 cDNA and of ALL-1/AG-6 fusion transcript. FIG. 13A: AF-6 cDNA clones. Dashed lines indicate different sequences possibly representing alternative non-coding exons. Restriction sites: A, ApaI; B, BamHI;, H, HindIII and S, SacI. FIG. 13B: Predicted amino acid sequence of AF-6 cDNA coding region (SEQ ID NO: 48). Arrow indicates the RNA fusion point. FIG. 13C: Fusion transcript of ALL-1 and AF-6 cloned from the RNAs of patients 01 and Ed. The nucleotide sequence (SEQ ID NO. 87) and amino acid sequence (SEQ ID NO. 88) of the chimeric ALL-1/AF-6 fusion transcript are described in FIG. 13C. ALL-1 exon 6 (SEQ ID NO. 89) and AF-6 exon (SEQ ID NO. 90) are also described in FIG. 13C.

FIG. 14 shows a comparison of the GLGF repeat within the AF-6 protein (SEQ ID NO: 51) to GLGF repeats of other patients. GLGF repeats are the third GLGF in human ZO-1 (ZO-1 3) (SEQ ID NO: 52); the second GLGF in rat PSD95 (PSD95 2) (SEQ ID NO: 53), and the third GLGF in Drosophila large disc tumor suppressor gene (dlg3) (SEQ ID NO: 54). Bold amino acids are consensus amino acids conserved among the four proteins.

FIG. 16A: Physical map of the genomic junction of patient GUS [der (17)] and a map of the corresponding normal region (chr. 11q23). Numbered open boxes in the top line represent ALL-1 exons. Darkened segment of der (17) correspond to chromosome 17 sequences, and open box therein represents an exon. Fragment R1.7 was used as a probe for the genomic Southern analysis as well as for cDNA screening. Cen and Tel show directions of the centromeres and telomeres, respectively. R, EcoRI; H, HindIII; B, BamHI; G, BglII, X, XbaI. FIG. 16B: Southern genomic analysis of a DNA from patient GE with AML and t(11;17), and a normal DNA (lanes b and a, respectively). DNAs were digested with EcoRV and hybridized with the R1.7 probe. Germline fragment is 18 kb.

FIGS. 17A–C shows cloning and sequencing of AF-17 cDNA and of the junction within ALL-1/AF-17 fusion transcript. FIG. 17A: Physical map of AF-17 cDNA clones. Restriction sites: S, SacI; H, HindIII; H2, HincII. Initiation (ATG) and termination (TAA) are shown by arrows. FIG. 17B: Predicted amino acid sequence of AF-17 protein (SEQ ID NO:55). Cysteines within the cysteine-rich region at the N-terminus are underlined. Also underlined is the leucine zipper at positions 729–764. Arrow indicates point of fusion with the ALL-1 protein. FIG. 17C: All-1 /AF-17 RNA junction cloned from the leukemic cells of patient GUS. The nucleotide sequence (SEQ ID NO.91) and amino acid sequence (SEQ ID NO. 92) of the chimeric ALL-1/AF-17 fusion transcript are described in FIG. 17C. ALL-1 exon 5 (SEQ ID NO. 93) and AF-17 exon (SEQ ID NO. 94) are also described in FIG. 17C.

FIGS. 18A and 18B depicts homology between the AF-17 protein (SEQ ID NO: 58) and the human Br140 (peregrin) protein (SEQ ID NO: 59). FIG. 18A: Alignment of AF-17 and Br140 cysteine-rich domains. Bars indicate identical residues; one dot and two dots indicate first and second degree conservative differences, respectively. FIG. 18B: Potential zinc fingers within the cysteine-rich domain of AF-17.

FIGS. 21A and 21B shows use of the B859 probe in detecting ALL-1 abnormalities. FIG. 21A: The B859 probe and the breakpoint cluster region of the ALL-1 gene (BCR11q23). Numbered boxes are the exons of the ALL-1 gene. Thin lines display the subclones used for sequencing. Cen. and Tel. denote the centromere and telomere. FIG. 21B: Southern analysis of the ALL-1 gene rearrangements in patients with acute leukemia. Patient's DNA samples were digested with BamHI and probed with the B859 probe. Numbers in each lane correspond to the case numbers in Table 2.

FIGS. 22A–C shows the nucleotide sequence of the breakpoint cluster region within the ALL-1 gene (SEQ ID NO: 63). The predicted amino acid sequences of each exon are shown under the corresponding nucleotide sequences. A consensus sequence for topoisomerase II recognition site is underlined.

FIGS. 24A and 24B shows Southern analysis of ALL-1 gene rearrangements in adult AML patients without cytogenetic evidence of 11q23 translocations. The label above each lane corresponds to a unique patient identification number taken from (Caligiuri et al., Cancer Res. 1994 54, 370–373). Patients nos. 23 and 24 had trisomy 11 as a sole cytogenetic abnormality whereas patient no. 1 had a normal karyotype. Arrows indicate rearranged bands. N, normal control. FIG. 24A: Blots examined with the B859 probe. B859 is a cDNA probe (Caligiuri et al., Cancer Res. 1994 54, 370–373) which spans the ALL-1 breakpoint cluster region defined by exons 5–11 of the ALL-1 gene (Gu et al., Cell 1992 71, 701–708). Germline 8.3 kb (BamHI) and 14 kb (HindIII) bands are indicated. FIG. 24B: Blots examined with the SAS1 probe. SAS1 is a 289 bp DNA probe from intron 1 of the ALL-1 gene (see FIG. 25A). Germline kb (BamHI) and 3.3 kb (HindIII) bands are indicated. The rearranged BamHI band for patient no. 1 is presumably coincident with the germline 20 kb band. Rearranged bands detected with the SAS1 probe comigrate with the rearranged bands detected by the B859 probe.

FIGS. 25A–C shows the structure of partial duplication of the ALL-1 gene. FIG. 25A: Restriction enzyme maps of lambda clones (λ23 and λ24) corresponding to rearranged BamHI fragments from two AML patients with trisomy 11. Boxes represent ALL-1 exon positions determined by subcloning and partial DNA sequence analysis. The junction point of the duplication is indicated by the juncture of the black and shaded bars. Position of the SAS1 probe is shown. B, BamHI; R, EcoRI; H, HindIII; X, XbaI. FIG. 25B: Proposed structure of the partially duplicated ALL-1 gene contains a direct tandem duplication spanning exons 2–6. Only the BamHI and HindIII sites giving rise to bands detected on Southern blot (FIG. 24) are indicated. FIG. 25C: DNA sequence across the junction points of clones λ23 and λ24 are aligned with sequences from introns 1 and 6 of the ALL-1 gene. λ24 has a 2 bp N-segment. Heptamer-like signal sequences (Akira et al., *Science* 1987 238, 1134–1138) near the junction points in both clones are underlined. Nonamer-like signal sequences are not present. FIG. 25C shows Intron 6 (upper) sequence (SEQ ID NO: 71), λ23 sequence (SEQ ID NO: 72), Intron 1 (upper) sequence (SEQ ID NO: 73), Intron 6 (lower) sequence (SEQ ID NO: 74), λ24 sequence (SEQ ID NO: 75) and Intron 1 (lower) sequence (SEQ ID NO: 76).

FIG. 26A: Agarose gel of RNA-PCR products (left-hand lanes) using oligonucleotide primers specific for the ALL-1 partial duplication. Right-hand lanes show the results of standard PCR amplification of an aliquot of the RNA-PCR product using nested oligonucleotide primers. Discrete bands of the size predicted from the ALL-1 cDNA sequence (Gu et al., *Cell* 1992 71, 701–708) were detected for both RNA-PCR (619 bp) and nested PCR (228 bp) products. Lanes are labeled with patient identification numbers (Caligiuri et al., *Cancer Res.* 1994 54, 370–373).

DETAILED DESCRIPTION OF THE INVENTION

Figure 1:
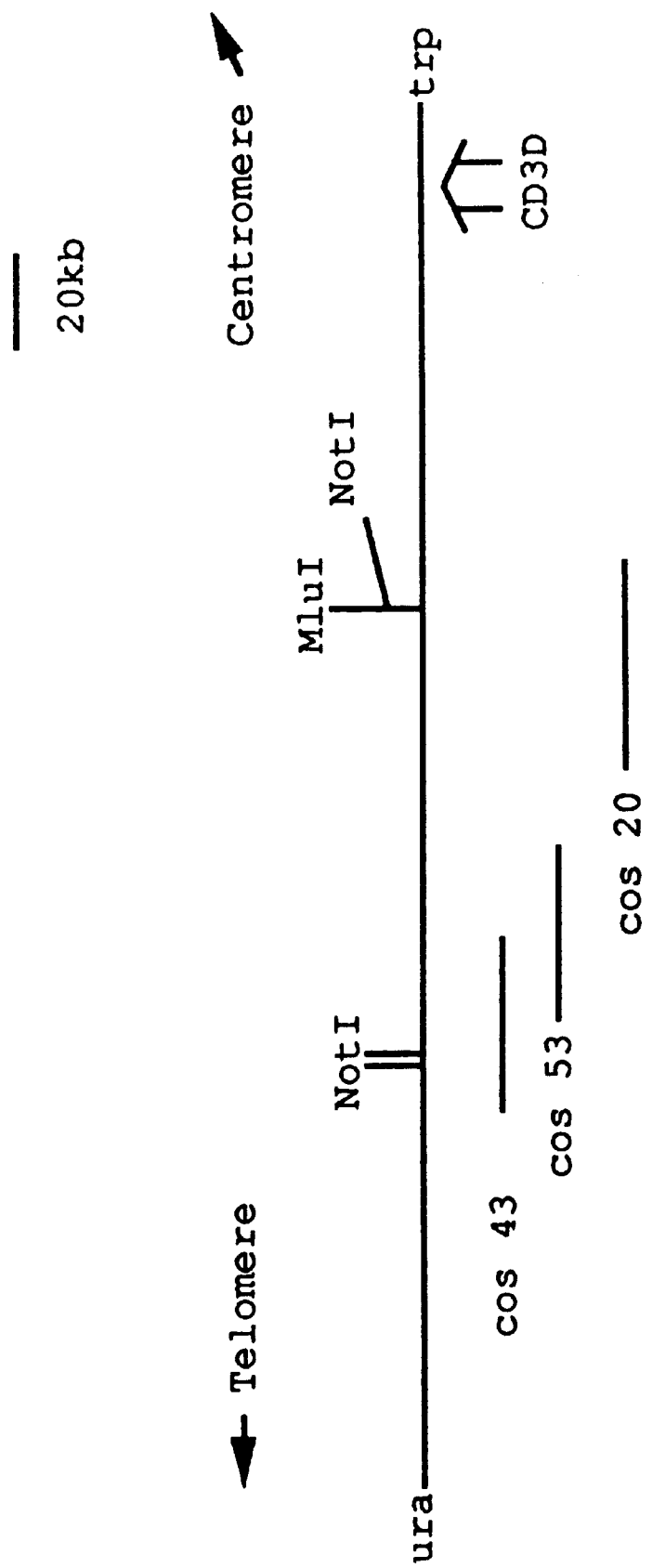
FIG. 1 is a drawing depicting a physical map of YAC B22B, which has been described in Rowley et al., *Proc. Natl. Acad. Sci. USA* 1990, 87, 9358–9362. ura and trp correspond to the termini of the vector. A 40 kb segment located towards the ura end and lacking NotI and MluI sites is not included in the map. Pulse field analysis indicates two or three SfiI sites located to the left of cosmid 43.

The ALL-1 gene located at human chromosome 11 band q23 is rearranged in acute leukemias with interstitial deletions or reciprocal translocations between this region and chromosomes 1, 2, 4, 6, 9, 10, 15, 17 or 19. The gene spans approximately 100 kb of DNA and contains at least 21 exons. It encodes a protein of approximately 4,000 amino acids containing three regions with homology to sequences within the Drosophila trithorax gene including cysteine-rich regions which can be folded into six zinc finger-like domains. The breakpoint cluster region within ALL-1 spans approximately 8 kb and encompasses several small exons (including exons 5–12), most of which begin in the same phase of the open reading frame.

It is to be understood from the description given below that each of the examples describing the practice of the invention are applicable to each of the now cloned and sequenced AF-4, AF-9, AF-6 and AF-17 genes and their respective ALL-1 fusion genes ALL-1/AF-4, ALL-1/AF-9, ALL-1/AF-6 and ALL-1/AF-17.

The t(4;11) chromosome translocation results in two reciprocal fusion products coding for chimeric proteins derived from ALL-1 and from a gene on chromosome 4. This gene on chromosome 4 is termed "AF-4" while the chimeric gene resulting from the t(4;11) translocation is termed "ALL-1/AF-4." It is believed that the 11q23 abnormality of translocation with 4q21 gives rise to one or two specific oncogenic fusion proteins.

The t(9;11) chromosome translocation results in two reciprocal fusion products coding for chimeric proteins derived from ALL-1 and from a gene on chromosome 9. This gene on chromosome 9 is termed "AF-9" while the chimeric gene resulting from the t(9;11) translocation is termed "ALL-1/AF-9." It is believed that the 11q23 abnormality of translocation with 9p22 gives rise to one or two specific oncogenic fusion proteins.

The t(11;19) chromosome translocation results in two reciprocal fusion products coding for chimeric proteins derived from ALL-1 and from a gene on chromosome 19. This gene on chromosome 19 is termed "ENL" while the chimeric gene resulting from the t(11;19) translocation is termed "ALL-1/ENL." It is believed that the t(11;19) translocation gives rise to one or two specific oncogenic fusion proteins.

In translocations involving the ALL-1 gene and chromosome 6, t(6;11), the gene on chromosome 6 is termed AF-6 and the chimeric gene resulting from the t(6;11) translocation is termed ALL-1/AF-6. Similarly, in translocations involving the ALL-1 gene and chromosome 17, t(11;17), the gene on chromosome 17 is termed AF-17 and the chimeric gene resulting from the t(11:17) translocation is termed ALL-1/AF-17.

A DNA fragment which detects DNA rearrangements by Southern analysis in the majority of patients with t(4;11), t(9;11) and t(11;19) chromosomal aberrations has been cloned from chromosome 11. This locus is referred to as ALL-1 for acute lymphocytic leukemia, although the same locus is also involved in acute myelomonocytic, myelogenous and monocytic leukemias carrying translocations involving 11q23.

DNAs and RNAs were extracted from cell lines and primary tumors by conventional methods. Southern and Northern analysis were performed as described in Shtivelman et al., *Nature* 1985, 315, 550–554). To obtain unique (repeat free) probes, cosmids were digested with a variety of restriction enzymes, and analyzed by Southern blotting for fragments which do not react with radiolabeled total human DNA. End fragments of cosmids were identified by hybridizing cosmids' digests to radiolabeled oligonucleotides corresponding to the recognition sequences for T7 and T3 RNA polymerases. If the end fragments contained human repeats, they were isolated, digested with frequent cutters and analyzed as described above. The 0.7 kb DdeI probe was thus obtained from a terminal 3.5 kb EcoRV fragment of cosmid 53. A portion of the Washington University's human DNA-containing YAC library (Green et al., *Proc. Natl. Acad. Sci. USA* 1990, 87, 9358–9362) was screened for CD3 DNA sequences (van Den Elsen et al., *Proc. Natl. Acad. Sci. USA* 1986, 83, 2944–2948) by a polymerase chain reaction (PCR)-based screening protocol (Green et al., supra). The YAC clone obtained appeared to be identical to the one described by Rowley et al., *Proc. Natl. Acad. Sci. USA* 1990, 87, 9358–9362, and spanned the translocation breakpoint in a t(4;11) cell line as evidenced by hybridization analysis. By pulse field electrophoretic analysis, the size of the insert was estimated as 350 kb. A 310 kb version of the insert, generated by spontaneous deletion at the left (telomeric) side, predominated in the population of DNA molecules and was mapped (FIG. 1).

To obtain specific segments of the insert, the YAC was purified by pulse field electrophoresis and shotgun cloned into the Supercos (Stratagene) cosmid vector. For this purpose the insert was partially digested by a combined application of dam methylase and the restriction endonuclease MboI, Hoheisel et al., *Nuc. Acid Res.* 1989, 17, 9571–9582. Both enzymes act on the sequence GATC, but MboI is unable to cut the methylated form. More than a hundred cosmid clones, detected with a probe for human repetitive sequences, were obtained. The cosmids were mapped by screening for those with sites for NotI and MluI enzymes, and for those hybridizing to CD3, trp and ura probes. Some cosmids were established using unique (repeat free) probes obtained from termini of cosmids. The positions of 3 cosmids mapped to the center of the YAC are shown in FIG. 1. Unique probes from these cosmids as well as from cosmids mapped to other regions of the YAC were used to screen Southern blots of DNAs from tumors exhibiting translocations.

Figure 2:
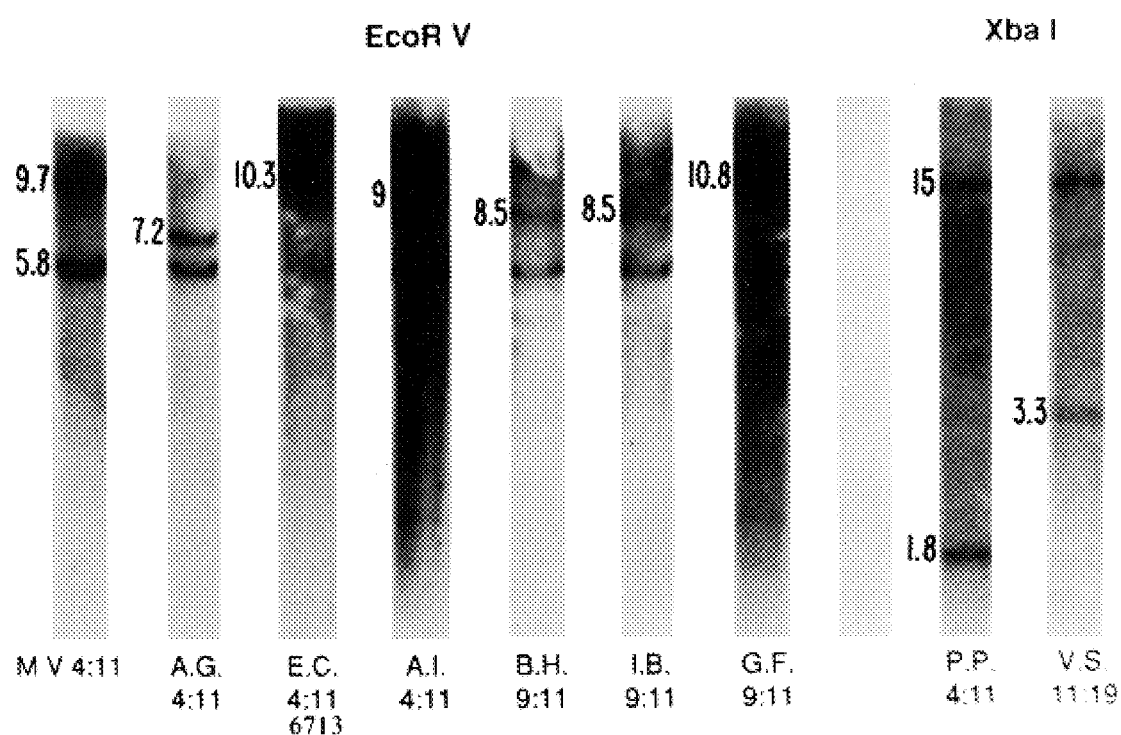
FIG. 2 is a photograph showing the results of Southern blot analysis of tumor DNAs. Blots were hybridized to the radiolabeled 0.7 kb DdeI fragment derived from the terminus of cosmid 53. Aliquots of 10 μg were analyzed.
Figure 3:
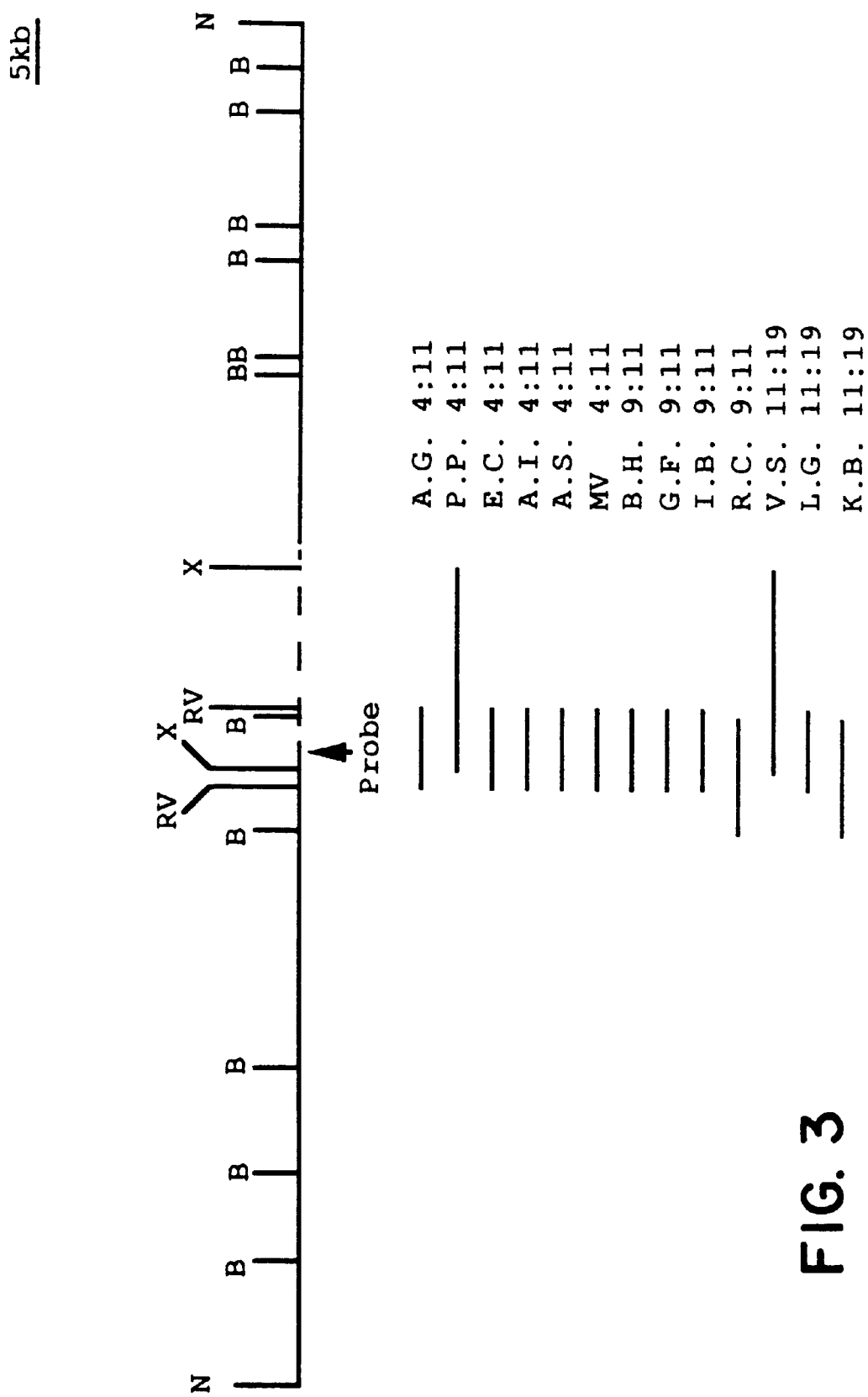
FIG. 3 is a drawing showing mapping of tumor breakpoints. The internal NotI fragment of YAC is shown in the same orientation as in FIG. 1. The dotted line represents a region not cloned in the cosmids. Restriction sites within this region are deduced from the size of the relevant germline fragments detected in genomic Southern blots using the indicated probe. Additional EcoRV and XbaI sites are not shown. Some of the samples were not analyzed with BamHI. Lines below the map correspond to the smallest genomic fragments found rearranged. N=NotI; B=BamHI; RV=EcoRV; X=XbaI. The breakpoint cluster region is believed to span approximately the region encompassed by the two nearest BamHI sites flanking the arrow; more specifically, the breakpoint cluster region is believed to span exons 6–12 illustrated in FIG. 10.

A 0.7 kb DdeI fragment derived from the terminus of cosmid 53 detected rearranged fragments in tumor DNAs digested with EcoRV, XbaI, or BamHI. Examples of these analyses are shown in FIG. 2. The leukemic cells from patients A. G., E. C., A. L., B. H., I. B., G. F., P. P., and V. S. contained novel EcoRV or XbaI fragments of various sizes. This probe detected rearrangements in 6/7, 4/5, and 3/4 patients with the t(4;11), t(9;11) and t(11;19) translocations, respectively. Upon determination of the smallest genomic fragment in which rearrangement could be identified, (FIG. 3) it became apparent that most or all breakpoints clustered within a small DNA region of approximately 8 kb. In three other patients two rearranged fragments (as well as a germline species) were detected, probably due to the presence of the breakpoint in these patients within the 0.7 kb DdeI segment corresponding to the probe. Finally, normal fibroblast DNAs from 7 additional individuals were used for comparison to show the germline fragments after digestions with EcoRV, XbaI or BamHI.

Figure 4:
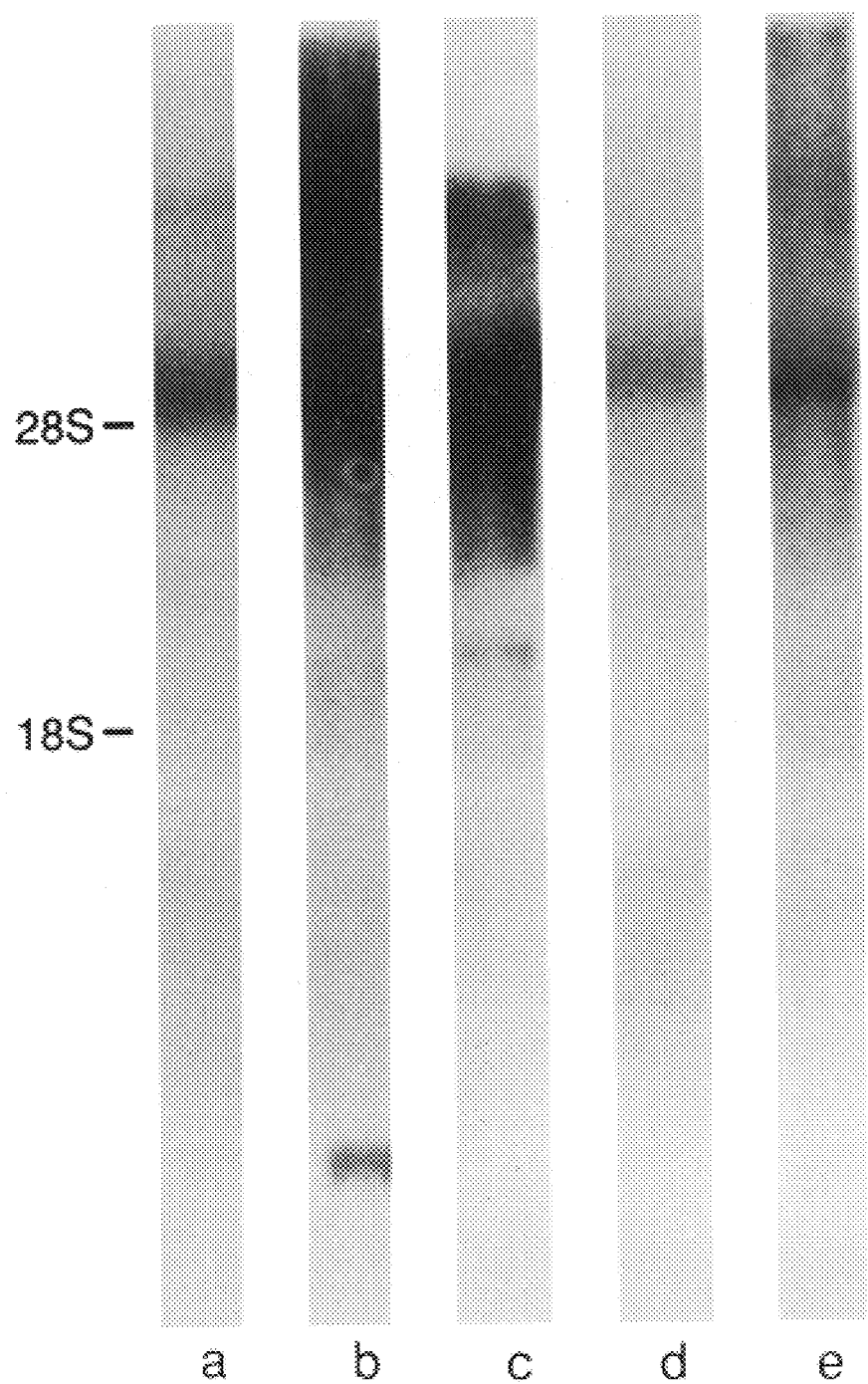
FIG. 4 is a photograph showing the results of Northern blot analysis of RNA from cell lines and a primary leukemia using pooled probes. 10–20 μg aliquots of total RNA were analyzed on a formaldehyde gel. Following hybridization, blots were washed in a solution containing 0.1% SSC and 0.1% SOS at 700. RNAs were obtained from: a) K562 cells; b) the glioblastoma T98G cell line; c) the SupB pre B ALL cell line; d) the MV4;11 cell line; and e) a patient with t(9;11).

As a first step toward identification of genes neighboring the breakpoint cluster region, pooled unique fragments from cosmid 20 were labeled, together with the terminal fragment of cosmid 53, and were used to probe RNAs from cell lines and patients with or without 11q23 translocations (FIG. 4). The pooled probe detected 5 kb and 10 kb RNA species in the K562, glioblastoma T986 and Sup B cell lines (lanes a, b, c). It also hybridized with a 5 kb RNA from patients with t(4;11), t(9;11), and t(11;19) (FIG. 4, lanes d, e,). In another patient with t(4;11) the probe detected the 10 kb RNA species alone.

It has been discovered that in leukemic cells of patients with the t(4;11), t(9;11) and t(11;19) translocations, the breakpoints on chromosome 11 cluster in a small region of approximately 8 kb. Other translocations in acute leukemias affecting 11q23 are believed to map to the same locus. This locus has been designated ALL-1 for acute lymphocytic leukemia, although the ALL-1 locus is also involved in translocations in acute myelomonocytic, monocytic and myelogenous leukemias. The tight clustering of breaks suggests that the gene involved is close to the breakpoints. The Northern analysis indicates that DNA sequences adjacent to the breakpoints are expressed. However, no new transcript was detected in the leukemic cells. Moreover, only one of the transcripts (usually the 5 kb species) found in cells without the translocation was detected in the patients.

Figure 5:
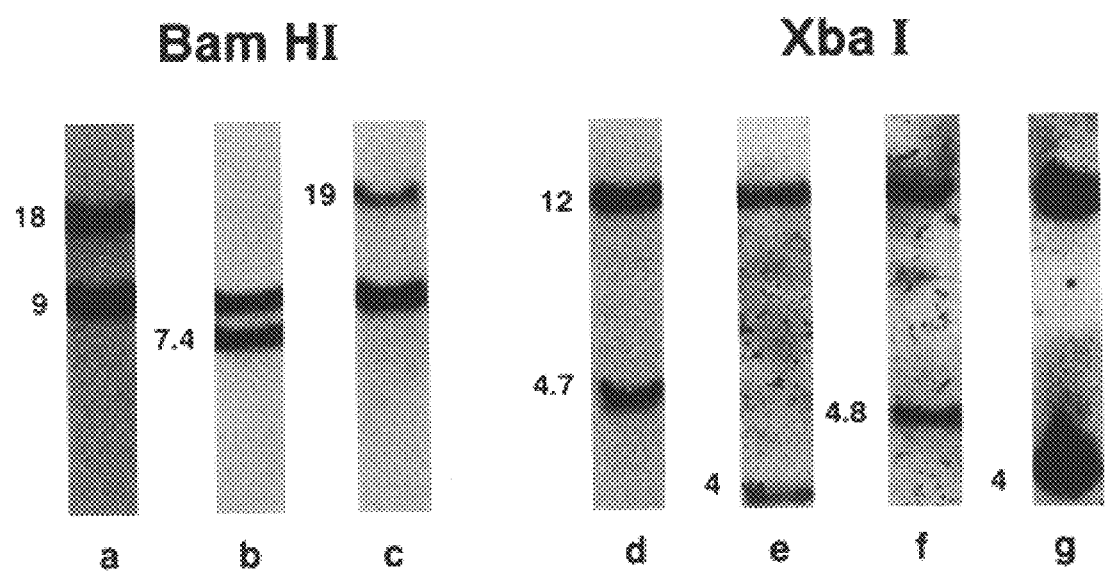
FIG. 5 is a photograph showing the results of Southern blot analysis of DNAs from primary tumors and cell lines with 11q23 abnormalities using a modified 0.5 kb DdeI probe. a) patient C. H. with t(6;11); b) the B1 cell line with t(4;11); c) the R S 4;11 cell line with t(4;11); d) patient J. B. with t(10;11); e) patient M. L. with t(1;11); f) patient S. O. with del(11)(q23); g) patient R. E. with del(11)(q23). Numbers indicate kilobases. The germline BamHI and XbaI fragments are of 9 and 12 kb, respectively.

The finding of tight clustering of the breakpoints on chromosome 11 in the three most common 11q23 abnormalities raised the possibility that the same region is rearranged in other chromosomal aberrations involving 11q23. To test this, tumor DNAs from the leukemic cells of patients with t(6;11) (q27;q23), t(1;11) (p34;q23), t(10;11) (p11–15;q23) and del (11) (q23) were digested with BamHI, XbaI, EcoRV and HindIII enzymes and subjected to Southern analysis using the modified 0.5 kb DdeI fragment as a probe. This probe was obtained from the 0.7 kb DdeI probe by digestion with AluI, which ultimately improved performance by removing a 0.24 kb internal fragment that had caused a higher background in Southern analyses. Following digestion with AluI, the internal fragment and the two end fragments were electrophoresed to isolate the two terminal fragments, which were then ligated to form a 0.5 kb fragment which was cloned into a plasmid vector. Results of Southern blotting are shown in FIG. 5. Rearranged fragments were found in the DNAs of patients with t(6;11), t(1;11) and t(10;11) (lanes a, d, e, respectively) and in two patients (lanes f, g) out of five with interstitial deletion in 11q23 (the 3 negative patients had del 11(q21;q23)). The patients with t(6;11) and t(10;11), as well as one of those with del(11)(q23) showing rearrangement had AML; the rest of the patients tested had ALL.

Figure 6:
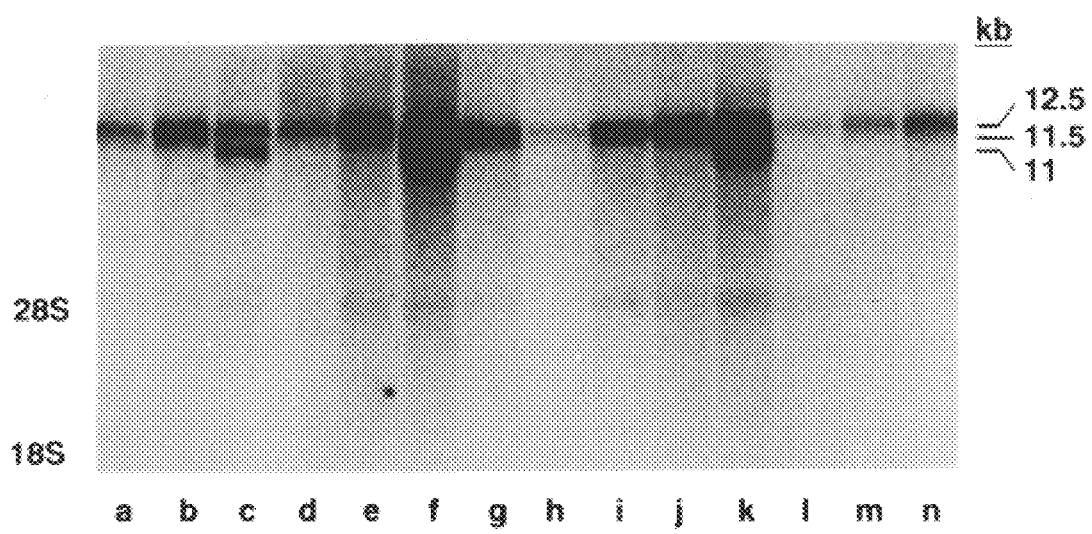
FIG. 6 is a photograph showing the results of Northern blot analysis of RNAs from cell lines using a 1.5 kb EcoRI probe generated from cosmid 20. Lanes included SK DHL (a); KCl22 (b); MV 4;11 (c); T98G (d); All-1 (e); B1 (f); K562 (g); Jurkat (h); GM607 (i); 697 (j); RS4;11 (k); GM1500 (l); LNCaPFGC (m); PC3 (n). 28S and 18S indicate migration of ribosomal RNA.

To further analyze transcription of the genomic DNA adjacent to the breakpoint cluster region, segments of cosmid 20 found fully or partially free of repetitive sequences were examined as probes to polyadenylated RNAs obtained from a variety of hematopoietic and non-hematopoietic cell lines. Three ALL cell lines, MV 4;11, RS 4;11 and Bi containing the t(4;11) chromosome translocation were included in the analysis. These three cell lines had rearrangements at the breakpoint cluster region, as shown in FIG. 5, lanes b and c. A 1.5 kb EcoRI DNA segment generated from cosmid 20 was used as a probe and identified a 12.5 kb RNA in all cell lines (FIG. 6). A minor species of 11.5 kb was detected in most of the samples without involvement of 11q23, but it was not possible to determine if this RNA was present in the cells with the t(4;11) translocation. A transcript of 11 kb was detected in the three cell lines with the t(4;11) chromosome translocation (FIG. 6; lanes c, f, k). The width of this band on the autoradiogram suggests that it corresponds to two comigrating RNA species. The 11 kb RNA was not detected in any of the cell lines lacking 11q23 aberrations (FIG. 6).

These results show that the same breakpoint cluster region is rearranged in at least seven different 11q23 abnormalities, including six types of translocations, as well as interstitial deletions. Three samples with 11(q21;q23) deletions, one sample with t(11;15) (q23;q22), and one sample with t(11;X) (q23;q26) did not show rearrangements within the locus. In addition, in 1 of 12, 1 of 9, and 2 of 9 patients with t(4;11), t(9;11), and t(11;19) chromosome translocations respectively, rearrangements were not detected using the DdeI probe. Finally, the breakpoint in the RC-K8 cell line containing the t(11;14) (q23;q32) is apparently telomeric to the locus discussed here. In all of these cases, other unidentified loci on chromosome 11 could be involved. Alternatively, the ALL-1 locus might also be affected in these patients, but this may occur at a different site.

Using a new probe, three polyadenylated transcripts were identified. Two of them, a 12.5 and an 11.5 kb species, are expressed as detected by Northern analysis in most or all cell lines, but the third, an 11 kb RNA, was detected solely in cell lines with the t(4;11) abnormality. RNA species of similar size have recently been reported by others. For example, Ziemin-van der Poel et al., *Proc. Natl. Acad. Sci. USA* 1991, 88, 10735–10739. However, while the instant probe which is located centromeric to the breakpoints, detects all three RNAs; Ziemin-van der Poel et al. reported that their probe (#1), which is derived from the same general location, detects predominantly the 12.5 kb species. While the instant probe detects 11 kb transcript solely in leukemic cells with the t(4;11) chromosome translocation, the Ziemin-van der Poel et al. study identifies an 11 kb mRNA in the RS4;11 cell line, as well as in small amounts in all cells tested. The results show, however, a clear qualitative alteration in expression of a region adjacent to the breakpoint cluster region on chromosome 11 in cells with the t(4;11) chromosome translocation.

Using either somatic cell hybrids (Savage et al., Cytogenet. Cell Genet. 1988, 49, 289–292; Wei et al., Cancer Genet. Cytogenet. 1990, 46, 1–8; Yunis et al., Genomics 1989, 5, 84–90), or the fluorescent in situ hybridization (FISH) technique (Rowley et al., Proc. Natl. Acad. Sci. USA 1990, 87, 9358–9362), it was possible to position the breakpoints on chromosome 11 to a region between the CD3 and PBGD genes. Rowley et al., supra, used a CD3-gamma probe to clone a 350 kb human DNA fragment from a yeast artificial chromosome (YAC) library. This YAC spanned the t(4;11), t(9;11), t(11;19), and t(6;11) breakpoints as indicated by FISH analysis. Using probes derived from both sides of the breakpoint cluster region, Rowley et al. identified a 12.5 kb RNA in cells with or without 11q23 abnormalities. Further, a probe located telomeric to the cluster region detected two additional transcripts of 11.5 and 11 kb in the RS 4;11 cell line, as well as in all hematopoietic and nonhematopoietic cells tested (Ziemin-van der Poel et al., Proc. Natl. Acad. Sci. USA 1991, 88, 10735–10739).

From a YAC clone similar to the one used by Rowley et al., a DNA segment was obtained which detected rearrangements in leukemic cells from patients with the t(1;11), t(4;11), t(6;11), t(9;11), t(10;11), t(11;19) or del (11q23) chromosome abnormalities on Southern blots (Cimino et al., Cancer Research 1991, 51, 6712–6714; Cimino et al., Cancer Research 1992, 52, 3811–3813). The breakpoints clustered within a small region of approximately 8 kb termed the ALL-1 locus. Translocation junction fragments were cloned from leukemic cells with t(4;11) and showed clustering of the breakpoints in an area of 7–8 kb on chromosome 4. Sequencing analysis indicated heptamer and nonamer-like sequences, associated with rearrangements of immunoglobulin and T cell receptor genes, near the breakpoints. These sequences suggested a direct involvement of the VDJ recombinase in the 11q23 translocations.

Transcription of the genomic DNA adjacent to the breakpoint cluster region was analyzed using segments of cloned DNAs as probes. Probes from both sides of the region identified a major transcript of 15–16 kb (previously estimated as 12.5 kb) (Cimino et al., Cancer Research 1991, 51, 6712–6714; Cimino et al., Cancer Research 1992, 52, 3811–3813) in cells with or without 11q23 abnormalities. The gene coding for these RNAs was termed ALL-1. Leukemic cells with the t(4;11) chromosome translocation contained, in addition to the normal species, shorter RNAs transcribed from the der (11) and der (4) chromosomes. These studies were extended to clone and sequence ALL-1 RNA, to further characterize the ALL-1 gene, and to identify chimeric transcripts produced in cells with the t(4;11) chromosome translocation.

Structure of the ALL-1 Gene and cDNA

Utilizing a repeat-free genomic DNA segment located 10 kb centromeric to the breakpoint cluster region on chromosome 11 (Cimino et al., Cancer Research 1992, 52, 3811–3813), a human fibroblast cDNA library and a K562 cDNA library were screened (Chu et al., EMBO J. 1990, 9, 985–993; Shtivelman et al., Nature 1985, 315, 550–554).

Figure 7:
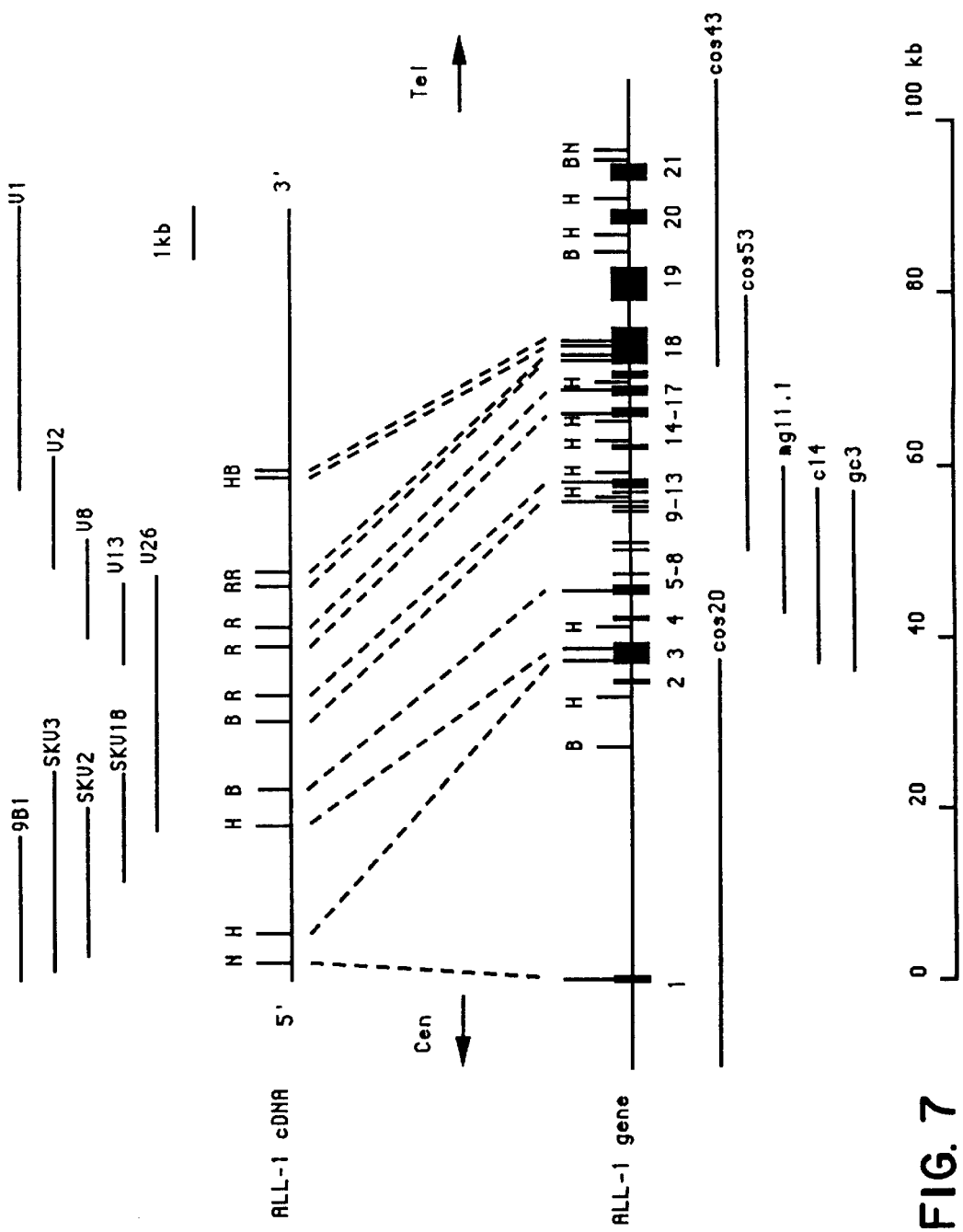
FIG. 7 shows physical maps of ALL-1 cDNA and gene. All NotI (N), HindIII (H), BamHI (B), and EcoRI (R) sites of the cDNA are shown; only some EcoRI sites are indicated within the gene and HindIII or BamHI sites within the 5' 25 kb of the first intron are not shown. Exons are depicted as rods or boxes extending above and below the line. Cen and Tel correspond to direction of the centromere and telomere, respectively. cDNA clones SKV2, SKV3, and SKV18 were obtained from K562 cDNA library. Clones V1–V26 were obtained from a normal fibroblast cDNA library. The 9B1 clone originated from a Burkitt lymphoma cDNA library.

Positive clones were used as probes for further screening. 5–10 µg aliquots of polyadenylated RNAs were electrophoresed on 1.1% agarose gels in formaldehyde, blotted onto nitrocellulose filters and analyzed by hybridization. (Gale, R P and Canaani, Proc. Natl. Acad. Sci. USA 1984, 81, 5648–5652). 20 µg aliquots of high molecular weight DNA were digested with BamHI and analyzed by the Southern technique. 3' and 5' ALL-1 probes were composed of phages V1 and SKV2 sequences, respectively (FIG. 7). Non ALL-1 probes were generated from clones 16 and 25 by PCR.

A series of overlapping clones spanning 14.7 kb (FIG. 7 top) was obtained. These cDNAs presumably originated from the major ALL-1 transcript. All cDNA sequences were found to hybridize to genomic DNA within the 95 kb internal Not I fragment of the YAC B22B (Cimino et al., Cancer Research 1991, 51, 6712–6714). This region was previously subcloned into cosmids 20, 43, and 53 and into phages gc3, c14, and mg 11.1 (FIG. 7). The cloning of cosmids 20, 43, and 53 from YAC B22B has been described (Cimino et al., Cancer Research 1991, 51, 6712–6714) and clones mg 11.1, c14, and gc3 were obtained from a genomic DNA library made in the EMBL-3 vector (Stratagene).

Restriction enzyme mapping of the cDNA and genomic clones and analysis of the hybridization pattern of cDNA fragments to genomic DNA indicated that the ALL-1 gene is composed of a minimum of 21 exons, some of them (6–12) very small (shorter than 150 bp). The first intron was found to be the largest, spanning approximately 35 kb of DNA.

The nucleotide sequence of ALL-1 cDNA was determined using an automatic sequencer (ABI). The sequence revealed a single long open reading frame predicting a protein of approximately 4,000 amino acids with molecular weight of approximately 400,000 Daltons (FIG. 8). To search for homologous nucleotide sequences and protein sequences the GenBank and SWISS data bases were screened by the FASTA program. Nucleotides 9353–9696 were found to be nearly identical to an anonymous sequence (EST00626) cloned from human fetal brain cDNA library (Adams et al., Nature 1992, 355, 632–634).

Three regions demonstrated homology to the trithorax gene of Drosophila (Mazo et al., Proc. Natl. Acad. Sci. USA 1990, 87, 2112–2116). Thus, predicted amino acids 1021–1221, 1462–1570, and 3348–3562 showed 64%, 66%, and 82% similarity, and 43%, 50%, and 61% identity, respectively, to the Drosophila gene (FIG. 9). The third region of homology constitutes the extreme C-terminus of the two proteins; both species end in an identical sequence. The first homology region is cysteine-rich and contains sequence motifs analogous to four zinc finger domains (3–6) within the trithorax gene (Mazo et al., supra). The second region of homology is also cysteine-rich and corresponds to zinc fingers 7 and 8 of the Drosophila gene. The human putative zinc finger structures are shown at the bottom of FIG. 9. The multiple conserved cysteines and histidines at the 3' end of the motifs allow two or three arrangements of the putative fingers. The structure of these cysteine-rich domains appears to be unique to the trithorax and ALL-1 genes.

Chimeric RNAs Resulting from the t(4;11) Chromosome Translocations

Figure 10A:
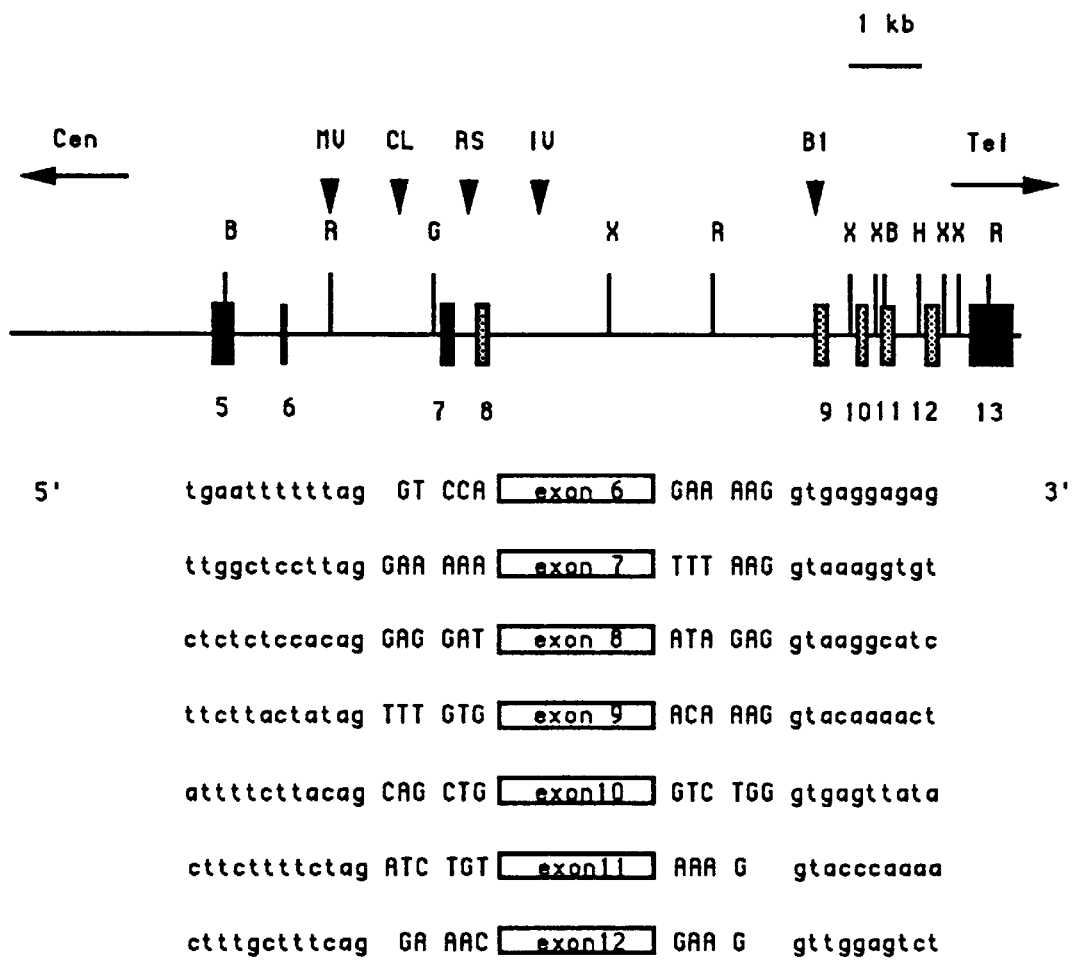
FIGS. 10A–C shows exon-intron structure of ALL-1 breakpoint cluster region FIG. 10A and partial sequence of the two reciprocal ALL-1/AF-4 fused transcripts (FIG. 10B and FIG. 10C).

Clustering of t(4;11) breakpoints has previously been found within a small segment of the ALL-1 locus (Cimino et al., Cancer Research 1991, 51, 6712–6714; Cimino et al., Cancer Research 1992, 52, 3811–3813). This region includes 7 coding exons (6–12) containing 74, 132, 114, 147, 96, 121, and 123 bp respectively. Exons 8–12 contain four zinc finger motifs. Exons 7–11 all begin in the first nucleotide of a codon. Precise mapping of five t(4;11) breakpoints localized them to introns between exons 6 and 7, 7 and 8, and 8 and 9 (FIG. 10A). These breaks in chromosome 11 result in removal of the N-terminal 996 amino acids from the ALL-1 protein, as well as in disjoining of the 5' noncoding region of the gene.

If the breaks on chromosome 4 occur within a gene positioned with its 5' terminus toward the centromere, t(4;11) translocations should result in fusion of the ALL-1 gene to the gene aforementioned and, consequently, in production of two reciprocal chimeric RNAs. To investigate this possibility, a cDNA library was constructed from RNA extracted from the RS4;11 leukemic cell line established from a patient with the t(4;11) chromosome translocation (Stong, R G, and Kersey, J H, *Blood* 1985, 66, 439–443). This RS4;11 cDNA library was constructed by treating polyadenylated RNA with 1 mM methyl mercury for 10 minutes at room temperature, followed by neutralization with 10 mM mercaptoethanol and alcohol precipitation. cDNA was prepared by using the Time Saver kit (Pharmacia) and was cloned into the lambda ZAP II vector (Stratagene).

The library ($2\times10^6$ clones) was screened with a probe composed of exons 3–13. Twenty positive clones were purified and mapped. Two clones varied from normal ALL-1 cDNA and were further analyzed by sequencing.

Figure 10B:
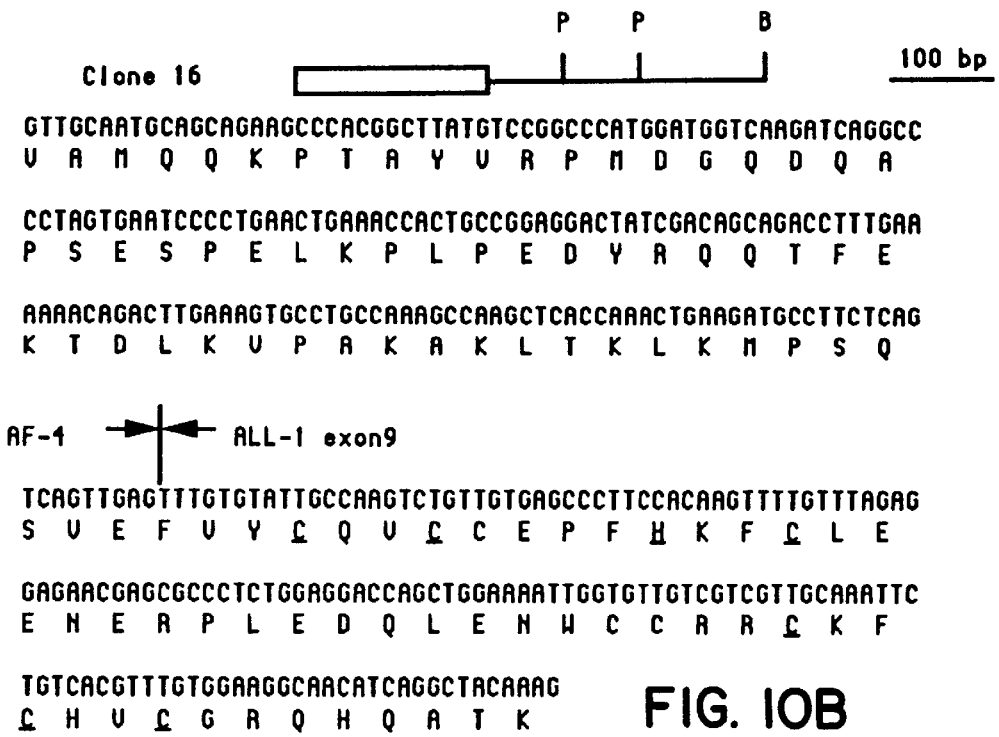
Figure 10C:
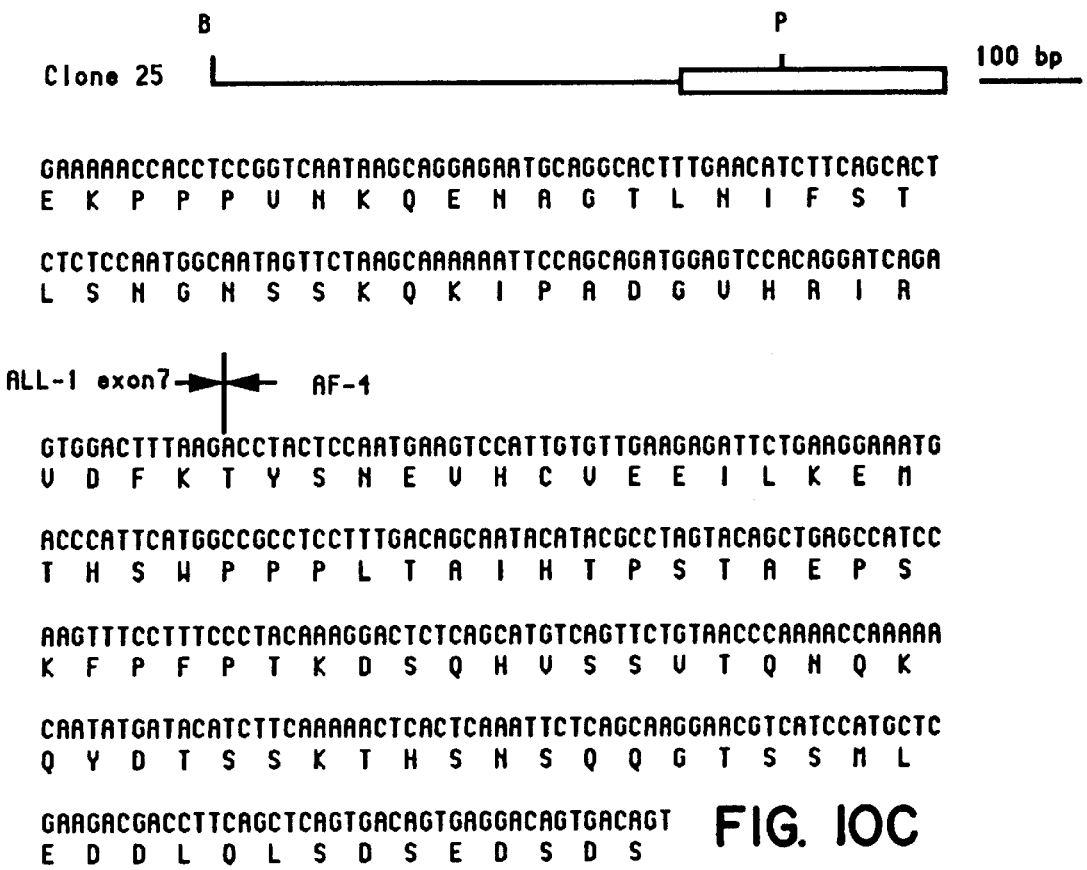

Clone 16 contained normal ALL-1 sequences 3' to the beginning of exon 9. 5' to this position, ALL-1 information was substituted with a new DNA fragment composed of an open reading frame (ORF) that joins in phase the rest of ALL-1 ORF (FIG. 10B). Clone 25 had a reciprocal configuration in which exon 7 of ALL-1 is linked to a new DNA segment containing an open reading frame. Here again, the two ORFs are joined in phase (FIG. 10C). Since, in the RS4;11 cell line, the breakpoint on chromosome 11 is within an intron located between ALL-1 exons 7 and 8 (FIG. 10A), it was expected that in the putative chimeric RNAs sequences of these exons will be directly linked to the new cDNA sequence. This is indeed the case in clone 25 but not in clone 16. In the latter, it was assumed that exon 8 was excluded from the fused transcript by a mechanism involving alternative splicing. Skipping this exon retains the fused ORFs in phase.

The identification of new sequences linked to ALL-1 cDNA in RS4;11 leukemic cells suggested that they originated from altered RNAs specific to cells with the t(4;11) chromosome translocation. Previously, two such transcripts were identified: a 14 kb RNA (previously estimated as 11.5 kb) containing 3' ALL-1 sequences and a 12.7 kb RNA (previously estimated as 11 kb) hybridizing to 5' ALL-1 probe. These RNAs were transcribed from chromosome derivatives 4 and 11, respectively.

A radiolabelled probe composed of non ALL-1 sequences of clone 16 was examined for hybridization to RNAs from cell lines with or without the t(4;11) chromosome translocation. As a control, the RNAs were first hybridized to 3' ALL-1 cDNA probe which detected the major normal transcript of 15–16 kb (previously estimated as 12.5 kb) in all cell lines and an altered 14 kb RNA (previously estimated as 11.5 kb) in the three cell lines with t(4;11) (FIG. 11A).

Figures 11A, 11B:
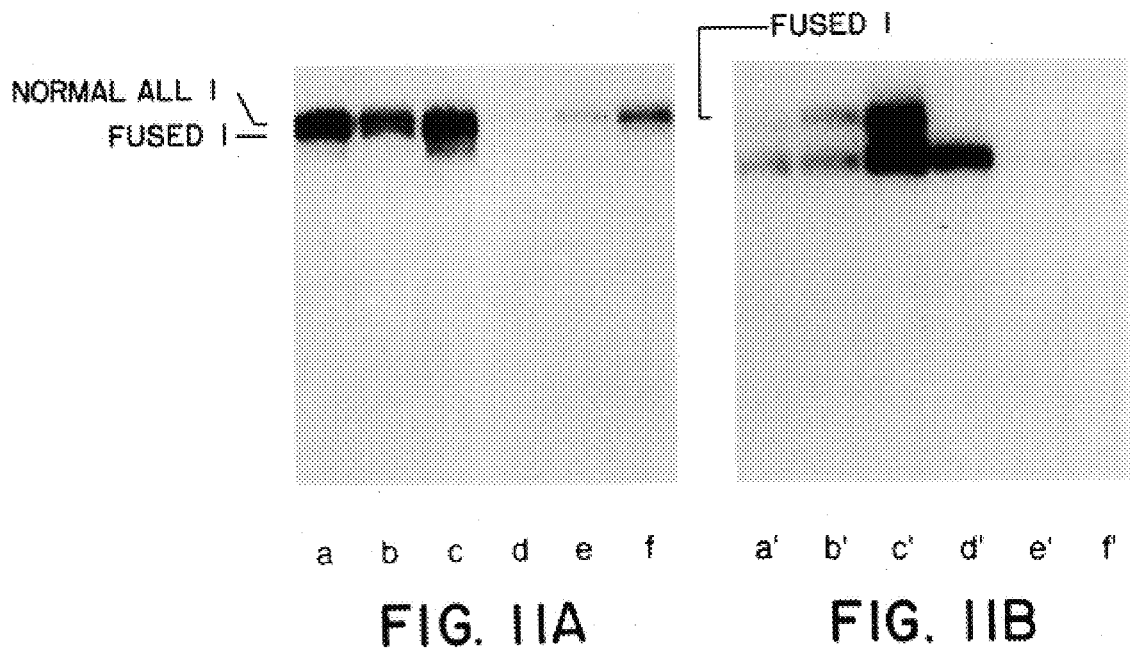
FIGS. 11A–E shows the non ALL-1 sequences within the fused RNAs unique to cells with t(4;11) chromosome translocations (FIGS. 11A–C) which originate from chromosome 4 (FIGS. 11D and 11E). Cell lines with t(4;11) chromosome translocations included: RS4;11 (Stong, R G, and Kersey, J H, *Blood* 1985, 66, 439–443), MV4;11 (Lange et al., *Blood* 1987, 70, 192–198) and B1 (Cohen et al., *Blood* 1991, 78, 94–102). Northern blots with RNAs from cell lines with translocations t(4;11)-B-1 (a, a'), MV4;11 (b, b') and RS4;11 (c, c', c"), and RNAs from control cell lines without the translocation: ALL-1 (d, d', d"), K562 (e, e'), SKDHL (f, f'), were hybridized to 5' ALL-1 cDNA probe (FIG. 11A), to non ALL-1 sequences from cDNA clone 16 (FIG. 11B), and to non ALL-1 sequences from cDNA clone 25 (FIG. 11C). ALL-1 is a Philadelphia-chromosome positive cell line (B cell leukemia) lacking 11q23 aberrations (Erikson et al., *Proc Natl. Acad. Sci. USA* 1986, 83, 1807–1811). K562 originated from chronic myelogenous leukemia (Lozzio, C B and Lozzio, B B, *Blood* 1975, 45, 321–324). SKDHL is a B cell lymphoma cell line (Saito et al., *Proc. Natl. Acad. Sci. USA* 1983, 80, 7476–7480). The second and third probes were also used in hybridization to Southern blots (FIG. 11D and 11E, respectively) with DNAs from Chinese hamster ovary (CHO cells and CHO cells containing chromosome 4 (CHO/4) "Fused 1" and "fused 2" correspond to the altered ALL-1 RNAs of 14 kb and 12.7 kb, respectively.

Clone 16 probe identified a 9.5 kb RNA in all cells examined and a 14 kb transcript in RS4;11, MV4;11 and B-1 cells (FIG. 11B). It was concluded that clone 16 originated from the 14 kb altered ALL-1 transcript and that the non-ALL-1 sequence within this RNA is expressed in human cells as a 9.5 kb transcript, which corresponds to the normal AF-4 transcript on a non-rearranged chromosome 4.

Figures 11C, 11D, 11E:
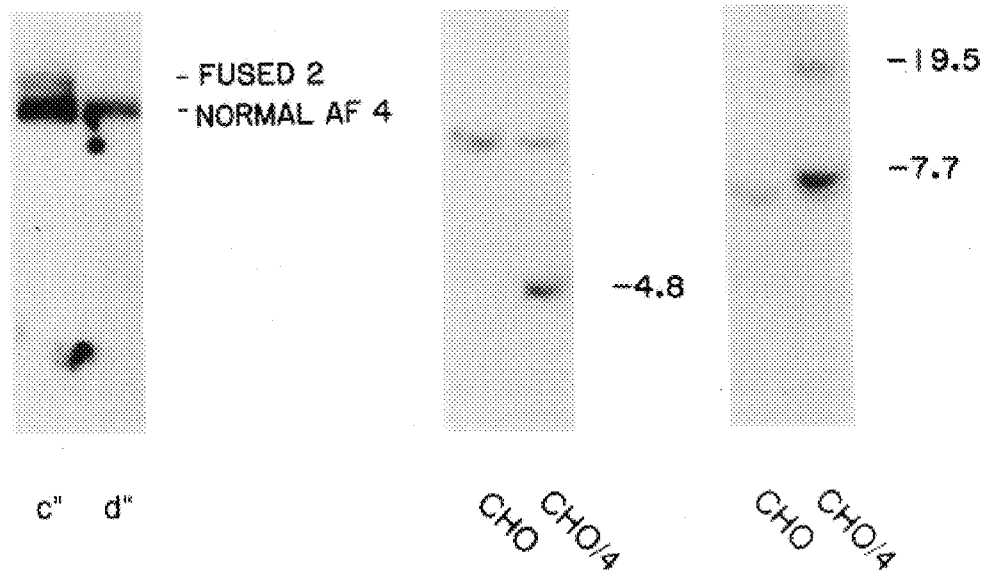

In an analogous experiment, a probe composed of non-ALL-1 sequences in clone 25 hybridized to the 12.7 kb altered RNA present in the RS4;11 cell line and to a 9.5 kb RNA species present in RS4;11 cells and in control cells (FIG. 11C). Thus, clone 25 originated from the second altered 12.7 kb ALL-1 RNA unique to cells with the t(4;11) chromosome translocation.

The chromosome from which the new sequences of clones 16 and 25 originated was then identified. High molecular weight DNAs from lines of Chinese hamster ovary (CHO) cells with or without human chromosome 4 were digested with BamHI enzyme and analyzed by Southern blotting for hybridization to the non ALL-1 sequence in clone 16 (FIG. 11D) and clone 25 (FIG. 11E). The cell lines showed an 11 kb or a 6.6 kb band representing CHO cell DNA cross-reacting with the probes. A fragment of 4.8 kb and fragments of 7.7 and 19.5 kb were detected in the somatic cell hybrid line containing human chromosome 4 (CHO/4) after hybridization with non ALL-1 sequences of clones 16 and 25, respectively (FIGS. 11D and E). The non-ALL-1 sequences in clone 25 hybridized to a specific segment within cloned chromosome 4 DNA spanning the RS4;11 breakpoint. Thus, clones 16 and 25 correspond to the two reciprocal fused transcripts of the ALL-1 gene and a gene on chromosome 4. The latter is denominated "AF-4" for ALL-1 fused gene from chromosome 4.

Cloning and sequence analysis of the ALL-1 gene indicates that it encodes an unusually large protein of 4,000 amino acids with a mass of approximately 400 kD. The striking feature of the protein is its homology to the Drosophila trithorax gene. The homology is reflected in three ways. First, the transcripts and proteins have a similar size; the Drosophila gene is transcribed into a 15 kb RNA encoding a protein of 3759 amino acids (Mozer, B A, and David, I B, *Proc. Natl. Acad. Sci. USA* 1989, 86, 3738–3742; Mazo et al., *Proc. Natl. Acad. Sci. USA* 1990, 87, 2112–2116).

Second, there is strong sequence homology in three regions, two of which contain zinc finger-like domains unique to the trithorax gene and presumably utilized in interaction with target DNA. The third region shows 82% similarity and 61% identity across 220 amino acids which end both proteins at their C-terminus.

Finally, there is colinearity of the homologous sequences in the two proteins. Although the sequence homology does not extend to other parts of the protein, the two genes very possibly evolved from a common ancestor and may carry out similar function(s). In this context, it has been previously noted that structural homology between Drosophila and mammalian genes such as the Antennapedia class homeobox genes, is frequently limited to the functional domains, e.g., the homeodomain (McGinnis, W, and Krumlauf, R., *Cell* 1992, 68, 283–302).

The trithorax gene in Drosophila acts to maintain spatially-restricted expression patterns of the Antennapedia and Bithorax complexes during fruit fly development (Ingham, P W, *Cold Spring Harbor Symp. Quant. Biol.* 1985, 50, 201–208). Trithorax activates transcription of multiple genes of the two complexes and, as such, counteracts the activity of Polycomb group genes which act as repressors of transcription for the same genes (McKeon, J and Brock, H W, *Roux's Arch. Dev. Biol.* 1991, 199, 387–396). Thus, mutations in the trithorax gene frequently result in homeotic transformations (Capdevila, M P and Garcia-Bellido, A., *Roux's Arch. Dev. Biol.* 1981, 190, 339–350). The discovery of zinc finger-like domains in the predicted amino acid sequence strongly suggested that the trithorax protein is a transcription factor which binds to DNA (Mazo et al., *Proc. Natl. Acad. Sci. USA* 1990, 87, 2112–2116). Indeed, antibodies to the protein react with specific regions of the chromatin in the salivary glands of Drosophila.

Based on what is known about the Drosophila gene, it is very likely that the ALL-1 gene is a transcription factor and that it is involved in regulation of genes controlling human development and/or differentiation. While expression of ALL-1 during embryonic development has not yet been investigated, the isolation of ALL-1 sequences from a human fetal cDNA library indicates transcription of the gene during fetal development. Previous studies (Cimino et al., *Cancer Research* 1992, 52, 3811–3813) demonstrated ALL-1 RNA in a variety of hematopoietic cell lines, as well as in tumors originating from precursors of epithelial and glial cells.

It was also found that the t(4;11) chromosome translocation cleaves the ALL-1 gene within the coding region and results in fusion of the open reading frames of ALL-1 and a gene on chromosome 4 (termed AF-4) in phase. The breakpoints on chromosome 11 cluster in a region containing several small exons, 5 of them (exons 7–11) begin in the first letter of a codon. Splicing from the same exon on chromosome 4, adjacent to the breakpoint in RS4;11, to each one of the five exons on chromosome 11 will retain the two open reading frames fused in phase. This situation is similar to the situation in the t(9;22) chromosome translocations where the breakpoints cluster near two BCR exons whose splicing to ABL exon 11 maintain the fused open reading frames in phase (Shtivelman et al., *Nature* 1985, 315, 550–554; Heisterkamp et al., *Nature* 1985, 315, 758–761). The clustering of breakpoints must also reflect the specific biological properties of the fused proteins and probably is also due to the presence of recombination signals in this region.

Two chimeric proteins from the 12.7 and 14 kb RNAs are predicted for cells with the t(4;11) chromosome translocation. The lack of information about the normal AF-4 protein precludes at this time the determination if it is also a transcription factor that exchanges functional domains with ALL-1 to give a chimeric transcription factor. This occurs in the t(1;19) and t(15;17) chromosome translocations (Kamps et al., *Cell* 1990, 60, 547–555; Nourse et al., *Cell* 1990, 60, 535–545; Kakizuka et al., *Cell* 1991, 66, 663–674; de The et al., *Cell* 1991, 66, 675–684).

Both the 12.7 and the 14 kb fused RNAs are found ln the three cell lines with t(4;11), therefore it is not possible at this time to establish which of the two products is oncogenic. However, the presence of the three trithorax homologous domains within the 14 kb transcript makes it an attractive candidate. The substitution of the N-terminus 996 amino acids of ALL-1 with an AF-4 polypeptide could result in at least two scenarios, both based on the assumption that ALL-1 and ALL-1/AF-4 activate transcription of the same gene(s). First, the substitution could place ALL-1 DNA binding domain under the control of a new effector domain activated by either ubiquitous or tissue specific factors. This will result in transcription of the target genes in the wrong cells. Second, the fusion product may function as a dominant negative inhibitor of ALL-1 by forming inactive heterodimers or by occupying target DNA sites.

The present invention provides methods of diagnosis for human leukemia by providing a tissue sample from a person suspected of having acute lymphocytic, myelomonocytic, monocytic or myelogenous leukemia, and determining if there are breakpoints on chromosome 11 in the ALL-1 locus. The sequence of the ALL-1 cDNA can be used to generate probes to detect chromosome abnormalities in the ALL-1 breakpoint cluster region. These probes may be generated from both the sense and antisense strands of double-stranded DNA. The term "ALL-1 probe" refers to both genomic and cDNA probes derived from the ALL-1 gene.

It is believed from the data described above and those data described below that genomic probes capable of detecting chromosomal translocations involving the ALL-1 breakpoint cluster region span sequences from at least 10 kb centromeric to at least 10 kb telomeric to the breakpoint cluster region, which has been shown to span at least exons 6–9, and may span exons 5–12 of the ALL-1 gene. It is believed that cDNA probes capable of detecting chromosomal translocations involving the ALL-1 breakpoint cluster region span sequences ranging from 2 kb centromeric to 2 kb telomeric to the breakpoint cluster region. Thus, preferred embodiments of the present invention for detecting chromosomal abnormalities involving ALL-1 provide genomic and cDNA probes spanning the chromosome 11 regions described above. cDNA probes are more preferred, and probes comprising the exons included in the breakpoint cluster region are most preferred.

Part or all of the ALL-1 cDNA sequence may be used to create a probe capable of detecting aberrant transcripts resulting from chromosome 11 translocations. The EcoRI probe, for example, was derived from a genomic clone but its location lies within an exon. Thus, preferred embodiments of the present invention for detecting aberrant transcripts provide cDNA probes spanning the ALL-1 gene.

The ALL-1 /AF-4 sequences provided in SEQ ID NO:23 and SEQ ID NO:24 can be used to create probes to detect t(4;11) chromosome abnormalities and aberrant transcripts corresponding to t(4;11) translocations. Additional sequences (see below) include those specific for the ALL-1 /AF-6, ALL-1 /AF-9 and ALL-1/AF-17 chimeric genes. Also included in the invention and described below are specific ALL-1 probes capable of detecting chromosomal abnormalities in the ALL-1 gene irrespective of the nature of the fusion partner gene.

Using the probes of the present invention, several methods are available for detecting chromosome abnormalities in the ALL-1 gene on chromosome 11. Such methods include, for example, Polymerase Chain Reaction (PCR) technology, restriction fragment length analysis, and oligonucleotide hybridization using, for example, Southern and Northern blotting and in situ hybridization.

PCR technology is practiced routinely by those having ordinary skill in the art and its uses in diagnostics are well known and accepted. Methods for practicing PCR technology are disclosed in *PCR Protocols: A Guide to Methods and Applications*, Innis, M. A. et al., Eds., Academic Press, San Diego, Calif. 1990, and RT-PCR, Clontech Laboratories (1991), which are incorporated herein by reference. Applications of PCR technology are disclosed in *Polymerase Chain Reaction*, Erlich, H A. et al., Eds., Cold Spring Harbor Press, Cold Spring Harbor, N.Y. 1989, which is incorporated herein by reference.

PCR technology allows for the rapid generation of multiple copies of DNA sequences by providing 5' and 3' primers that hybridize to sequences present in a DNA molecule, and further providing free nucleotides and an enzyme which fills in the complementary bases to the DNA sequence between the primers with the free nucleotides to produce a complementary strand of DNA. The enzyme will fill in the complementary sequences between probes only if both the 5' primer and 3' primer hybridize to DNA sequences on the same strand of DNA.

To detect rearrangements involving for example, chromosomes 11 and 4, one of the two probes can be generated from the ALL-1 cDNA and one probe from the AF-4 gene. RNA is isolated from hematopoietic cells of a person suspected of having acute lymphoblastic or nonlymphoblastic leukemia, and cDNA is generated from the MRNA. If the cDNA of the chimeric ALL-1/AF-4 gene is present, both primers will hybridize to the cDNA and the intervening sequence will be amplified. The PCR technology therefore provides a straightforward and reliable method of detecting the chimeric gene.

The preferred primers for PCR are selected, one from a portion of SEQ ID NO: 1, corresponding to the ALL-1 cDNA, and one from a portion of either SEQ ID NO: 19 or SEQ ID NO: 22, corresponding to AF-4 gene sequences. Preferably, the sequences chosen from SEQ ID NO: 1 comprise at least a portion of SEQ ID NO: 20, which corresponds to exon 9, or SEQ ID NO: 21, which corresponds to exon 7.

According to the invention, diagnostic kits can be assembled which are useful to practice oligonucleotide hybridization methods of distinguishing chromosome 11 abnormalities from non-rearranged chromosomes 11. Such diagnostic kits comprise a labelled oligonucleotide which hybridizes, for example, to the chimeric transcript that results from t(4;11) translocations but which does not hybridize to nucleic acid transcripts not associated with aberrations. Accordingly, diagnostic kits of the present invention comprise, for example, a labelled probe that includes ALL-1 and AF-4 sequences which make up the chimeric transcript associated with t(4;11) translocations. Such probes comprise oligonucleotides having at least a portion of the sequence of the ALL-1/AF-4 gene of SEQ ID NO: 23 or SEQ ID NO: 24.

It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

Probes useful as diagnostics can be used not only to diagnose the onset of illness in a patient, but may also be used to assess the status of a patient who may or may not be in remission. It is believed that emergence of a patient from remission is characterized by the presence of cells containing chromosome abnormalities. Thus, patients believed to be in remission may be monitored using the probes of the invention to determine their status regarding progression or remission from disease. Use of such probes will thus provide a highly sensitive assay the results of which may be used by physicians in their overall assessment and management of the patient's illness.

Antisense oligonucleotides which hybridize to at least a portion of an aberrant transcript resulting from chromosome 11 abnormalities involving the ALL-1 gene are also contemplated by the present invention. The oligonucleotide may match the target region exactly or may contain several mismatches. Thus, molecules which bind competitively to RNA coded by, for example, the chimeric ALL-1/AF-4 gene, for example, are envisioned for therapeutics. Preferred embodiments include antisense oligonucleotides capable of binding to at least a portion of SEQ ID NO: 23 and SEQ ID NO: 24.

Preferred embodiments of the present invention include antisense oligonucleotides capable of binding to a region of the ALL-1/AF-4 mRNA corresponding to the ALL-1 sequences which encode a peptide having homology with the Drosophila trithorax protein and antisense oligonucleotides capable of binding to a region of the mRNA encoding a zinc finger-like domain in the ALL-1 protein.

While any length oligonucleotide may be utilized, sequences shorter than 15 bases may be less specific in hybridizing to the target and may be more easily destroyed by enzymatic degradation. Hence, oligonucleotides having at least 15 nucleotides are preferred. Sequences longer than 21 nucleotides may be somewhat less effective in interfering with ALL-1 expression because of decreased uptake by the target cell. Therefore, oligonucleotides of 15–21 nucleotides are most preferred.

The term "oligonucleotide" as used herein includes both ribonucleotides and deoxyribonucleotides, and includes molecules which may be long enough to be termed "polynucleotides." Oligodeoxyribonucleotides are preferred since oligoribonucleotides are more susceptible to enzymatic attack by ribonucleotides than deoxyribonucleotides. It will also be understood that the bases, sugars or internucleotide linkages may be chemically modified by methods known in the art. Modifications may be made, for example, to improve stability and/or lipid solubility. For instance, it is known that enhanced lipid solubility and/or resistance to nuclease digestion results by substituting a methyl group or sulfur atom for a phosphate oxygen in the internucleotide phosphodiester linkage. The phosphorothioates, in particular, are stable to nuclease cleavage and soluble in lipid. Modified oligonucleotides are termed "derivatives."

The oligonucleotides of the present invention may be synthesized by any of the known chemical oligonucleotide synthesis methods. See for example, Gait, M. J., ed. (1984), *Oligonucleotide Synthesis* (IRL, Oxford). Since the entire sequence of the ALL-1 gene has been provided along with partial sequences of the AF-4 gene, antisense oligonucleotides hybridizable with any portion of these sequences may be prepared by the synthetic methods known by those skilled in the art.

It is generally preferred to apply the therapeutic agent in accordance with this invention internally such as intravenously, transdermally or intramuscularly. Other forms of administration such as topically or interlesionally may also be useful. Inclusion in suppositories is presently believed to be likely to be highly useful. Use of pharmacologically acceptable carriers is also preferred for some embodiments.

For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solution of dextrose, and the like. In addition to administration with conventional carriers, the antisense oligonucleotides may be administered by a variety of specialized oligonucleotide delivery techniques. For example, oligonucleotides have been successfully encapsulated in unilameller liposomes. Reconstituted Sendai virus envelopes have been successfully used to deliver RNA and DNA to cells (Arad et al., *Biochem. Biophy. Acta.* 1986, 859, 88–94).

For in vivo use, the antisense oligonucleotides may be administered in an amount effective to result in extracellular concentrations approximating in vitro concentrations described below. The actual dosage administered may take into account the size and weight of the patient, whether the nature of the treatment is prophylactic or therapeutic in nature, the age, weight, health and sex of the patient, the route of administration, and other factors. The daily dosage may range from about 0.1 to 1,000 mg oligonucleotide per day, preferably from about 10 to about 1,000 mg per day. Greater or lesser amounts of oligonucleotide may be administered, as required.

It is also possible to administer the antisense oligonucleotides ex vivo by isolating white blood cells from peripheral blood, treating them with the antisense oligonucleotides, then returning the cells to the donor's blood. Ex vivo techniques have been used in the treatment of cancer patients with interleukin-2 activated lymphocytes.

For ex vivo application, for example, in bone marrow purging, the antisense oligonucleotides may be administered in amounts effective to kill leukemic cells while maintaining the viability of normal hematologic cells. Such amounts may vary depending on the nature and extent of the leukemia, the particular oligonucleotide utilized, the relative sensitivity of the leukemia to the oligonucleotide, and other factors. Concentrations from about 10 to 100 $\mu$g/ml per $10^5$ cells may be employed, preferably from about 40 to about 60 $\mu$g/ml per $10^5$ cells. Supplemental dosing of the same or lesser amounts of oligonucleotide are advantageous to optimize the treatment. Thus, for purging bone marrow containing $2\times10^7$ per ml of marrow volume, dosages from about 2 to about 20 mg antisense per ml of marrow may be effectively utilized, preferably from about 8 to 12 mg/ml. Greater or lesser amounts of oligonucleotide may be employed.

The present invention is also directed to monoclonal antibodies capable of binding to chimeric ALL-1/AF proteins including ALL-1/AF-4, ALL-1/AF-6, ALL-1/AF-9 and ALL-1/AF-17, and includes monoclonal antibodies capable of binding to a region of the protein having homology with the Drosophila trithorax protein and monoclonal antibodies capable of binding to a zinc finger-like domain. Such monoclonal antibodies are useful as diagnostic and therapeutic agents for leukemias characterized by t(4;11), (t(6;11), t(9;11) and t(11;17) translocations. Thus, the present invention encompasses immunoassays for detecting at least portions of either the ALL-1/AF-4, ALL-1/AF-6, ALL-1/AF-9 and ALL-1/AF-17 proteins. In addition, the instant invention contemplates diagnostic kits comprising a monoclonal antibody to at least a portion of the ALL-1 fusion proteins listed above in combination with conventional diagnostic kit components.

The present invention is also directed to pharmaceutical compositions comprising monoclonal antibodies and a suitable pharmaceutical carrier, which are well known in the pharmaceutical art, and are described, for example, in *Remington's Pharmaceutical Sciences*, Gennaro, A. R., ed., Mack Publishing Co., Easton, Pa. 1985. The useful dosage will vary depending upon the age, weight, and particular patient treated.

Polyclonal antibodies to the instant polypeptides are also within the ambit of the invention. Such polyclonal antibodies may be produced using standard techniques, for example, by immunizing a rabbit or a rat with a protein or peptide of the invention, removing serum from the rabbit, and harvesting the resultant polyclonal antibodies from the serum. If desired, the polyclonal antibodies may be used as an IgG fraction or may be further purified in varying degrees. Procedures for preparing, harvesting and purifying polyclonal antibodies are well known in the art, and are described, for example, in *Methods in Immunology: A Laboratory Text for Instruction and Research*, Garvey et al., Ed., W. A. Benjamin, Reading Mass., 1977, 3rd ed., chapter 22, 24–30.

Experiments reported in Example 1 provide further data for designing methods of diagnosing and treating acute lymphoblastic or nonlymphoblastic leukemia, particularly those involving a chimeric gene in t(4;11) translocations. The information provided in example 1 includes complete cDNA sequences encoding AF-4. These sequences may be used design probes of at least 15 nucleotides which are capable of identifying chromosome abnormalities within the ALL-1 gene of chromosome 11. Examples of such probes comprise an oligonucleotide sequence or derivatives thereof comprising at least a portion of SEQ ID NO:25 or SEQ ID NO:27. The procedures for using such probes are described above.

Experiments reported in Example 2 provide further data for designing methods of diagnosing and treating acute lymphoblastic or nonlymphoblastic leukemia, particularly those involving a chimeric gene in t(9;11) translocations. The information provided in example 2 may be used design probes of at least 15 nucleotides which is capable of identifying chromosome abnormalities within the ALL-1 gene of chromosome 11. Examples of such probes may comprise at least a portion of SEQ ID NO:32, SEQ ID NO:33 or SEQ ID NO:34. Further, probes capable of identifying chromosome abnormalities within the AF-9 gene of chromosome 9 may be designed. Examples of such probes comprise an oligonucleotide sequence or derivatives thereof comprising at least a portion of SEQ ID NO:29, SEQ ID NO:32, SEQ ID NO:33 or SEQ ID NO:34. The procedures for using such probes are described above.

The experiments reported in Examples 3 and 4 describe the cloning and sequencing of ALL-1 /AF-6 and ALL-1/ AF-17 genes, respectively. The experiments reported in Example 5 describe a probe capable of detecting abnormalities in the ALL-1 region irrespective of the nature of the fusion gene, and the experiments reported in Example 6 describe duplications of the ALL-1 region in cells of some patients with leukemia. Thus, the invention must be construed to include each of these genes, their products and probes derived therefrom as being useful for the diagnosis and treatment of patients with these types of leukemias. Although specific examples are given, each example must be construed to include the other named fusion genes as being useful in the methods and compositins of the invention.

A method of diagnosing acute lymphoblastic or nonlymphoblastic leukemia involving a chimeric gene in t(9;11) translocations may be performed by first providing a tissue sample containing hematopoietic cells from a person suspected of having acute lymphoblastic or nonlymphoblastic leukemia; then isolating RNA from the sample followed by generating cDNA from said RNA and amplifying a chimeric gene sequence in said cDNA which is generated by said translocation using a set of PCR primers if said chimeric gene is present such that detecting the presence of amplified DNA indicates the tissue sample is derived from an individual suffering from lymphoblastic or nonlymphoblastic leukemia involving a chimeric gene in t(9;11) translocations. The method, which is generally described in detail above, may be performed using sets of primers which can be used to amplify a chimeric gene generated by the translocation. Examples of such primers can be designed, for example, using the sequence information in SEQ ID NO:32, SEQ ID NO:33 or SEQ ID NO:34. Examples of primers include SEQ ID NO:39 and SEQ ID NO:40; SEQ ID NO:41 and SEQ ID NO:42; and SEQ ID NO:43 and SEQ ID NO:44.

Monoclonal antibody capable of binding to at least a portion of for example, the chimeric ALL-1/AF-9 protein may be produced by standard techniques. Examples of such a monoclonal antibodies, which can bind specifically to at least a portion of the amino acid sequences encoded by SEQ ID NO:9, SEQ ID NO:11 or SEQ ID NO:13, may be produced using peptides which comprise at least a portion of SEQ ID NO:9, SEQ ID NO:11 or SEQ ID NO:13.

In one method of diagnosing acute lymphoblastic or nonlymphoblastic leukemia, tissue sample containing hematopoietic cells from a person suspected of having acute lymphocytic or nonlymphoblastic leukemia is examined to detect the ALL-1/AF-9 chimeric protein or a portion of the chimeric ALL-1/AF-9 protein. In one embodiment of such a method, a monoclonal antibody capable of binding to at least a portion of the chimeric ALL-1/AF-9 protein is used.

The present invention provides antisense oligonucleotides capable of binding to at least a portion of the chimeric ALL-1/AF-9 mRNA. Such antisense oligonucleotides include those capable of binding to at least a portion of SEQ ID NO:32, SEQ ID NO:33 or SEQ ID NO:34.

Method of treating acute lymphoblastic or nonlymphoblastic leukemia are provide which comprise administering an antisense oligonucleotide capable of binding to at least a portion of the chimeric ALL-1/AF-9 mRNA or, alternatively, administering a monoclonal antibody capable of binding to at least a portion of the chimeric ALL-1/AF-9 protein. The formulation and administration of therapeutics are outlined above.

EXAMPLE 1

Experiments were performed to determine the cDNA sequence of AF-4 and study ALL-1/AF-4 chimeric genes.

Cloning and Sequencing-AF-4-cDNA cDNA clones containing the two reciprocal ALL-1/AF-4 RNA junctions were cloned from RNA of the RS4 11 cell line carrying the t(4:11) chromosome translocation. AF-4 specific probes obtained from these clones were used to screen cDNA libraries prepared from RNAs of the K562 and KCl22 hematopoietic cell lines. Positive clones were sequenced and utilized to prepare end probes for further screening. overlapping clones spanning most or all of the 9.5 kb AF-4 transcript were obtained. Analysis of the longest cDNA composite indicated an open reading frame initiated with a consensus ATG and coding for a protein of 1210 amino acids (SEQ ID NO:25 and SEQ ID NO:27; and SEQ ID NO:26 and SEQ ID NO:28, respectively).

cDNA clone k 12, SEQ ID NO:25, diverged from cDNA clone kcl 6, SEQ ID NO:27, at nucleotide 435 of the latter. 5' of this position the two sequences completely varied. The open reading frames of clones kcl 6 and k 12 started 5 and 12 codons, respectively 5' of the divergence point. This suggests an alternative first exon for AF-4. A third cDNA clone, k 1.1, represents another RNA variant probably resulting from alternative splicing; an in frame termination codon is present in this clone immediately 3' to the divergence point. Thus, AF-4 encodes 2 or more proteins varying at their termini. AF-4 contains an unusually long 3' untranslated region of 5 3 kb. This region includes multiple AATAAA sequences located 20 nucleotides 5' of the poly A, as well as in several upstream positions; it also contains several stretches of T.

Using the Swiss, Prosite and Profilescan data bases, the complete AF-4 protein sequence was searched for homology to other proteins and for the presence of motifs. The sequence AKKRK at positions 811–815 matched the consensus nuclear targeting sequence -(RKTA) KK (RQNTSG) K-. AF-4 was relatively rich in serine (16%) and proline (11) compared to the average frequency of these amino acids (7.1% and 4.6%, respectively).

Inspection of AF-4 sequence at the fusion point to ALL-1 RNA in the RS4:11 cell line indicates that three nucleotides (1959–1961) of AF-4 RNA are missing from cDNA clone 25 corresponding to ALL-1/AF-4 fused RNA; these nucleotides might have been excluded through an error in the splicing process where an Ag at positions 1960–1961 was mistaken to the 3' end of an intron.

We have previously shown that in leukemic cells with t(4:11) abnormalities the breakpoints cluster in a region of approximately 8 kb on chromosome 4. This region corresponds to a single intron flanked by an exon located within a 1 kb BamHI-EcoRI fragment, and an exon positioned >20 kb away towards the telomere.

EXAMPLE 2

Cloning of AF-9/ALL-1 Genomic Junctions

The nonavailability of cell lines with the t(9;11) abnormality made it impossible to obtain intact mRNA in amounts sufficient for preparation of a cDNA library and cloning from it fused ALL-1/AF-9 cDNA. To circumvent this problem, we first cloned (clone C19) to genomic junction fragment from the leukemic cells of patient Co with acute myeloid leukemia (AML) and t(9;11). We also cloned (clone F2) the genomic junction fragment from tumor cells of patient FI with acute lymphocytic leukemia (ALL) and t(9;11). The cloned genomic fragments were derived from the der 9 chromosomes of the patients. Mapping and hybridization analysis of the non-ALL-1 segments within the two phage clones indicated no homology between them.

A 1 kb HindIII fragment from non-ALL-1 region in clone F2 was used to clone the corresponding normal DNA. A 0.4 kb HindIII fragment from clone 3 and 0.4 kb HindIII-AvaII probe from clone C19 hybridized to human DNA within Chinese hamster cell hybrids containing human chromosome 9. This established that in both patients' DNAs the ALL-1 gene is linked to chromosome 9 sequences. Subsequent work showed that both sequences are included in a single gene which we term AF-9, for ALL-1 fused gene from chromosome 9.

The same repeat-free fragments were used as probes for detecting rearrangements in DNAs from leukemic cells with t(9;11) chromosome translocations. Samples from three patients with ALL and from five patients with AML were studied. The 0.4 kb HindIII fragment detected rearrangement in DNA of the ALL patient CU. The HindIII-AvaII probe showed rearrangements in patients TA, SU and AG, all with AML. This indicated that at least two regions in the AF-9 gene are involved in recurrent t(9;11) aberrations. Presently, it is not known whether one region is preferentially rearranged in AML and the second in ALL; it is also not clear whether the AF-9 gene is involved in all t(9;11) abnormalities.

Characterization of Normal and Chimeric cDNAs of AF-9

Repeat-free fragments from AF-9 DNA for hybridization to cDNA libraries were examined. The lkb HindIII fragment reacted with several overlapping cDNAs spanning 3.4 kb. These cDNAs reacted in northern analysis with a major 5 kb transcript expressed in several hematopoietic cell lines.

Nucleotide sequence analysis of AF-9 cDNA revealed an open reading frame beginning in a consensus initiation codon (SEQ ID NO:29) and coding for a protein of 568 amino acids (SEQ ID NO:30). The protein encloses a nuclear targeting sequence AKKQK at positions 297–301. AF-9 protein is serine rich (20%) and includes a remarkable uninterrupted stretch of 42 serines at positions 149–190; it also contains proline at a frequency of 7% which is above the average frequency of 4.1%.

A homology search showed, unexpectedly, that the predicted protein shared high similarity with the ENL protein SEQ ID NO:31. The latter is located on chromosome 19 and is fused to the ALL-1/HRX gene in t(11;19) chromosome translocations. The two proteins show 56% identity and 68% similarly. The homology is highest within the 140 amino acids at the N terminus where the proteins are 82% identical, and 92% similar, and within the 67 amino acids at the C terminus where the corresponding values are 82% and 91%.

To demonstrate chimeric ALL-1/AF-9 RNAs, we designed primers supposed to flank the RNA junction points in the two genes and used them in RT-PCR reactions with RNA from patient FI. Two reciprocal cDNA products were amplified SEQ ID NO:32 and SEQ ID NO:34 (encoding protein products SEQ ID NO:33 and SEQ ID NO:35 respectively). Close examination of sequences at the RNA junctions showed a stretch of 11 nucleotides of AF-9 (ATTCTTGAAGT; SEQ ID NO:38) at both RNA junctions. In an attempt to understand this, we sequenced the genomic junction in clone F2 and determined exon-intron boundaries of AF-9 exons in this region. This analysis suggested that the two derivative chromosomes of patient FI were formed by staggered breaks in the DNAs of chromosomes 9 and 11 resulting in a small overlapping AF-9 genomic DNA segment and consequently in the overlapping of 11 nucleotides of AF-9 at the RNA junction points. The der 9 chromosome resulted from a break within exon 7 of ALL-1 and a break within an exon of AF-9 (11 nucleotides 3' of the intron-exon boundary). The hybrid exon spans the fusion point in cDNA clone EN (ALL-1 exon 8 was skipped during splicing). The der 11 chromosome was due to a break in the other ALL-1 DNA strands within the intron flanked by exons 6 and 7, and to a breakage of the second AF-9 DNA strand within an intron located 5' of the AF-9 exon mentioned above. The der 11 is transcribed into an RNA corresponding to cDNA clone E2.

A BamHI-StuI cDNA probe detected some normal genomic fragments, which were also detected by the 0.4 kb HindIII-AvaII probe-derived from the genomic junction cloned from DNA of patient CO. This enabled designing primers predicted to flank the RNA fusion point of patient CO and use them in a RT-PCR reaction to amplify AF-9/ALL-1 RNA SEQ ID NO:36 (encoding protein SEQ ID NO:37). In this patient the AF-9 protein is linked at position 375 to the ALL-1 moiety, while in patient FI the junction point is at amino acids 444 or 477 of AF-9. In the three junctions examined the reading frames of the two genes are joined in phase.

Perhaps the most unusual feature of 11q23 abnormalities is the multitude of chromosome partners participating in translocations with the ALL-1 locus. Using a probe containing sequences of ALL-1 exons 5 and 11, which flank the breakpoint cluster region, we have been able to detect rearrangements in 10 types of 11q23 chromosome translocations. This promiscuity in partners for rearrangement and fusion could suggest that the only critical event in all these different translocations is the separation of a DNA binding domain (either the zinc fingers or the AT hooks in the ALL-1 gene) from a positive or negative regulatory element, and that the proteins encoded by the partner genes solely provide initiation or termination codons.

Our sequence analysis of AF-4 and AF-9 proteins and a comparison to the sequence of the ENL protein is not consistent with such interpretation. The finding that AF-9 and ENL share extensive sequence homology indicates that the two proteins have similar biological function and that presumably they contribute an identical activity to the chimeric proteins. Possibly, other genes participating in 11q23 aberrations have also sequence homology with AF-9 and ENL. Moreover, these two proteins share with AF-4 several common motifs: 1) a nuclear targeting sequence (NTS) (suggesting that the three proteins are nuclear), 2) serine-rich domains, the most prominent being an uninterrupted stretch of 42 serines in AF-9, 3) stretches rich in proline or in basic amino acids reaching frequency of ~30% in some regions. While serine-rich regions have not yet been implicated in function of transcription factors, domains with abundant prolines were shown to act as transcription activators, and domains rich in positively charged amino acids were found to bind DNA. These common structural motifs suggest that AF-4, AF-9, and ENL are involved in transcription regulation, possibly representing a new class of transcription factors. Proteins coded by the other genes involved in 11q23 chromosome translocations might belong to this class.

Inspection of the position of the elements discussed above in relation to the fusion point(s) with the ALL-1 protein shows that the NTS of AF-4 is linked to the N-terminus of ALL-1 containing the AT hooks, while AF-4 domains rich in serine, proline, or basic amino acids are fused to both reciprocal products of ALL-1 cleavage. In patient FI with t(9;11), the NTS and most of AF-9 domains rich in specific amino acids are linked to the C-terminus of ALL-1 which contains the zinc tingers. In leukemic cells with t(11;19) all landmarks observed in the ENL protein will be linked to the N-termininus of ALL-1; this may suggest that N-ALL-1/ENL-C is the oncogenic product of the t(11;19) abnormality. The opposite distribution of the common elements in AF-9 fusion products in patients such as FI raises the possibility that in these cases N-AF-9/ALL-1-C is the oncogenic species. Determination of which one (or both) of the fusion products of 11q23 translocations induce malignancy should be resolved by biological assays in cells in culture and in transgenic mice. Transcription assays utilizing elements of AF-4, AF-9 and ENL should help in understanding the normal function of these elements, as well as their role in the fused proteins.

DNA and Sequencing Analysis

Aliquots (20 micrograms) of high molecular weight DNAs were digested with excess of restriction enzymes and analyzed by the Southern technique using the Probe Tech™2 system (ONCOR). Sequencing was done with an automatic sequencer (ABI).

Genomic and cDNA Libraries

High molecular weight DNAs from patients with t(9;11) chromosome translocation were partially digested with MboI enzyme and cloned into the EMBL-3 phage vector (Promega). To reduce the frequency of rearrangements during propagation in bacteria, the libraries were plated into the host bacteria CES200 (Wyman et al., 1986). The libraries were screened with an ALL-1 specific probe (Cimino et al., 1992) and positive clones were mapped with restriction enzymes. To construct a cDNA library from RNA of the KCl22 cell line, cytoplasmic RNA was extracted by standard techniques (Berger & Chirgwin, 1989) and polyadenylated RNA purified on an oligo dT column. cDNA was prepared using the Timesaver kit of Pharmacia and cloned into the lambda ZAPII vector (Stratagene). Construction of cDNA libraries from K562 or fibroblasts RNA was described (Shtivelman et al., 1985; Chu et al., 1990). AF-4 cDNA clones k1.1, k1.2, k11 and k12 originated from the K562 library and the clones kcl 6, kcl 10, and kcl 12 were cloned from the KC122 library. AF-9 cDNA clones v4 and v7 were obtained from the fibroblasts library, and k 16 was cloned from the K562 library.

RT PCR

Two micrograms of RNA from a patient FI were reverse transcribed in a reaction utilizing the AF-9 oligonucleotide TCCTCAGGATGTTCCAGATGT (SEQ ID NO:39) or the ALL-1 oligonucleotide GGCTCACAACAGACTTGGCAA (SEQ ID NO:40) as primers. The cDNAs were amplified with Taq 1 polymerase (Boeringer) using the same primers together with the ALL-1 primer ACCTACTACAGGAC-CGCCAAG (SEQ ID NO:41), and the AF-9 primer CAGATGAAGTGGAGGATAACG (SEQ ID NO:42), respectively. The reaction products were purified by gel electrophoresis and cloned into the SK plasmid vector (Stratagene). Recombinants with AF-9/ALL-1 or ALL-1/AF-9 DNA were identified by colony hybridization and were subsequently sequenced. The AF-9/ALL-1 RNA function of patient Co was obtained in a similar way using the ALL-1 primer CAGCGAACACACTTGGTACAG (SEQ ID NO:43) for synthesis of cDNA and the same primer together with the AF-9 primer CAACGTTACCGCCATTTGAT (SEQ ID NO:44) for PCR amplification.

EXAMPLE 3

Cloning and Sequencing of AF-6 cDNA

The patient 01 was a 47 year old female, diagnosed as AML(M4). Her karyotype was 46XX, t(6;11) (q27;q23) in 20/20 of bone marrow cells. Patient Ed was a male diagnosed as AML(M5) with a karyotype of 46 XY del(11q23). The cell lines used for RNA analysis included K562 and KC122 (erythroid and myeloid acute phase of chronic myeloid leukemia) (Lozzio et al., Blood 1975 45, 321–324; and Kubonishi et al., Int. J. Cell Cloning 1 1983 1, 105–117), B-1 and MV4:11—ALL with the t(4;11) abnormality (Cohen et al., Blood 1991 78, 93–102; and Lange et al., Blood 1987, 70, 192–198), SKDHL (B-cell lymphoma) Saito et al., Proc. Natl. Acad. Sci. USA 1983 80, 7476–7480, T98G (glioblastoma) (Stein, J. Cell Physiol. 1979 99, 43–54) and the 293 cell line derived from kidney (Graham et al., Virology 1978 86, 10–21).

The rearranged genomic fragments of ALL-1 patients 01 and Ed were cloned into the EMBL-3 phage vector (Promega) after partial digestion of the DNAs with the Mbol enzyme and size selection. Phage libraries were screened using a 0.86 kb Bam HI fragment derived from ALL-1 cDNA and spanning exons 5–11. Normal genomic library was constructed in a similar way from normal white blood cell DNA. cDNA library was constructed utilizing a kit from Pharmacia. Cytoplasmic poly A-selected RNA was prepared from KC122 cells. For RT-PCR reactions, aliquots of 2 μg of patients' RNAs were reverse transcribed utilizing the AF-6 oligonucleotide 5' ATC TGA ATT CTC CGC TGA CAT GCA CTT CAT AG 3' [SEQ ID NO:79]. The cDNA was amplified using the same AF-6 primer together with the All-1 primer 5' ATC TGA ATT CTC CGC TGA CAT GCA CTT CAT AG 3' [SEQ ID NO:80]. Both primers contained cloning sites at their 5' termini. The amplified products were cloned into the SK plasmid vector and sequenced.

cDNAs and genomic DNAs were excised from the phage vectors and recloned into the SK plasmid vector. Sequencing was performed using the ABI automatic sequencer. Sequence was analyzed using the FASTA, TFASTA and motifs programs.

Figures 12A, 12B:
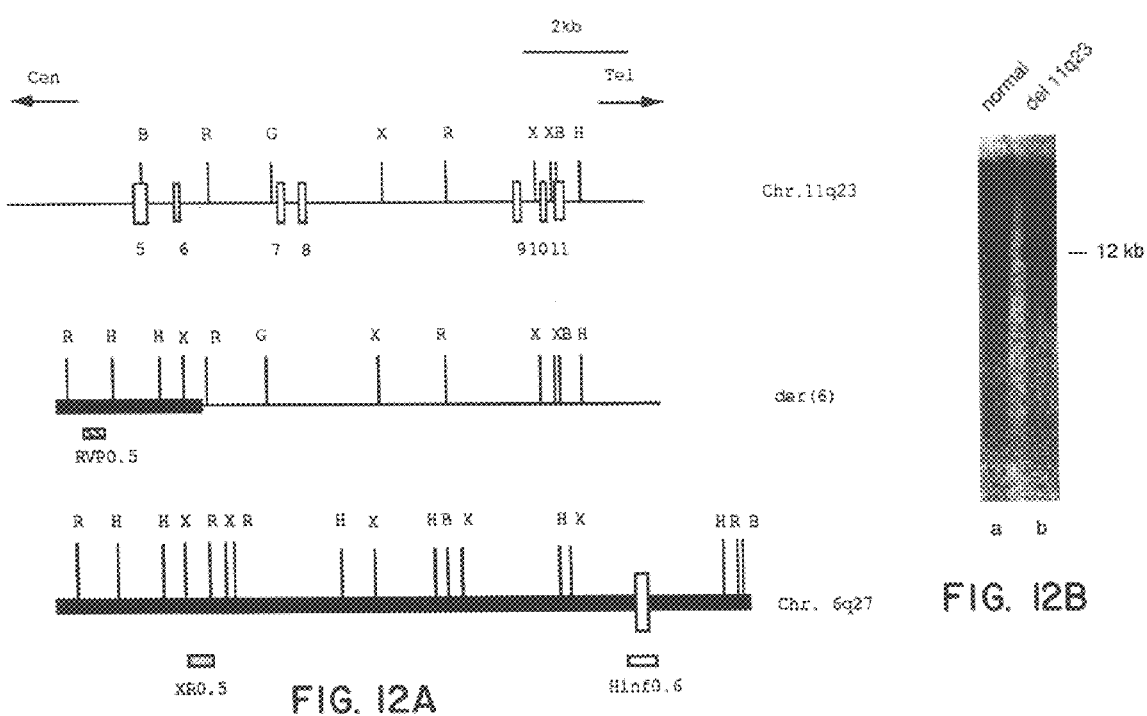

A rearranged ALL-1 segment was cloned from the genomic DNA of leukemic cells of patient 01. Mapping of this segment indicated that it originated from the der (6) chromosome (FIG. 12A). Sequencing of the junction region (FIG. 12C) showed neither extra neucleotides nor haptamer-like signal at the junction point. Therefore, unlike two t(4;11) and one (9;11) translocation points that we previously studied (Gu et al., Proc. Natl. Acad. Sci. USA 1992 89, 10464–10468), here the VDJ recombinase was probably not involved in the recombination process.

We used now a repeat free EcoRV-PstI 0.5 kb fragment (RVP 0.5) as a probe to clone the corresponding region from normal DNA (FIG. 12A bottom). To examine whether this region of chromosome 6 is altered in other patients with 11q23 abnormalities and rearranged ALL-1, we probed genomic blots of patients' DNAs with the 0.5 kb Xbal-EcoRI (XRO.5) radiolabelled fragment. While the DNA of another patient with AML and t(6;11) showed only germ line configuration of this region, the DNA of the patient Ed with AML and the del(11q23) aberration contained a rearranged BamHI fragment of 12 kb (FIG. 12B). The XRO-5 probe hybridized to human DNA within Chinese hamster cell hybrids containing human chromosome 6. This indicated that the cloned DNA spanned a breakpoint cluster region and that a cytogenetic pattern of del(11q23) could correspond to a t(6;11) translocation.

Figure 13A:
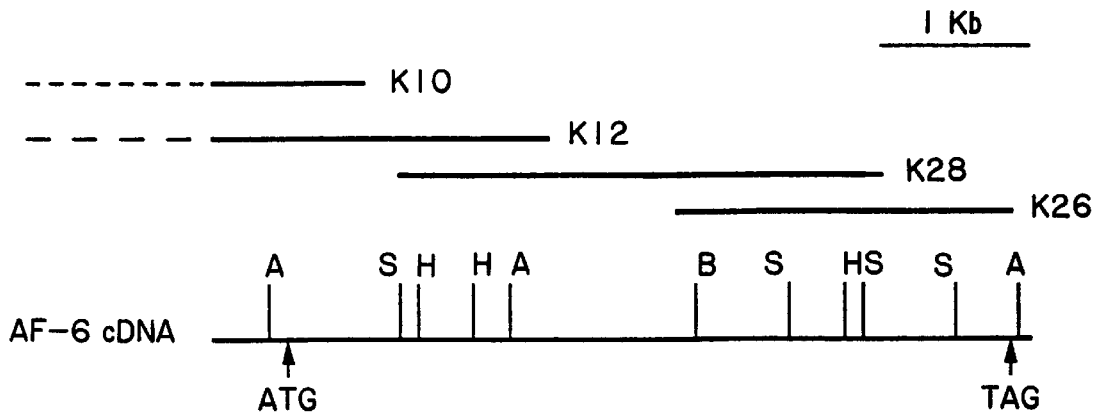
Figure 13C:

The entire area of 30 kb cloned from 6q27 was searched for segments reacting with clones from a normal cDNA library. A 0.6 kb HinfI DNA reacted with the K12 cDNA clone (FIG. 13A). The overlapping cDNA clones which spanned the complete coding region of the gene were cloned. We named the latter AF-6 for ALL-1 fused gene from chromosome 6. AF-6 encodes a protein of 1612 amino acids. In cDNA clone K10 we find two additional amino acids—glutamic acid at position 101, and a lysine in position 139; both are probably due to alteration in splicing similar to those which we previously detected in ALL-1 (Nakamura et al., Proc. Natl. Acad. Sci. USA 1993 90, 4631–4635; and Ma et al., Proc. Natl. Acad. Sci. USA 1993 90, 6350–6354). To directly demonstrate a fused transcript we performed RT-PCR reactions on RNAs from patients 01 and Ed using ALL-1 and AF-6 primers flanking the expected junction region. Products of the reactions were cloned, screened for hybridization to ALL-1 and AF-6 probes and sequenced. The RT-PCR products of both patients showed identical chimeric ALL-1/AF-6 RNAs transcribed from the der(11) chromosome (FIG. 13C). The two open reading frames were linked in phase.

The nucleotide and the amino acid sequences of AF-6 were examined for motifs and homology to other genes. Beginning around amino acid 1290 up to the C-terminus of the protein there exist several small domains rich in prolines, serines, acidic amino acids, or glutamines. AF-6 protein, residue 745–925, shows 23.2% identity over 181 amino acids with the C-terminus of yeast myosin-1 isoform (Johnston et al., J. Cell Biol. 1991 113, 539–551). AF-6 protein also shows high similarity, though low identity, (66% similarity plus identity) over amino acids 1000–1–594 to amino acids 1400–1980 of the myosin heavy chain from Dictyostelium discoideum (Warrick et al., Proc. Natl. Acad. Sci. USA 1986 83, 9433–9437). In the latter protein this region is part of the tail domain which assumes, due to a high α helical potential, a rod structure. A striking homology was detected in the polypeptide spanning amino acids 997–1080. A series of amino acids in this domain are conserved (FIG.

14) in three other proteins—in the human tight junction protein ZO-1 (Willott et al., *Proc. Natl. Acad. Sci. USA* 1993 90, 7834–7838), in the rat PSD-92 protein present in brain synapses Cho et al., *Neuron* 1992 9, 929–942), and in a tumor suppressor gene of Drosophila (dlg) located at septate junctions, which are thought to be the invertebrate equivalent of tight junctions (Woods et al., *Cell* 1991 66, 451–464). In this domain, termed the GLGF repeat (Cho et al., *Neuron* 1992 9, 929–942), AF-6 shows identity of 28%, 36% and 42%, and similarity of 57%, 59%, and 67% to the human, rat and Drosophila proteins, respectively.

Figure 15:
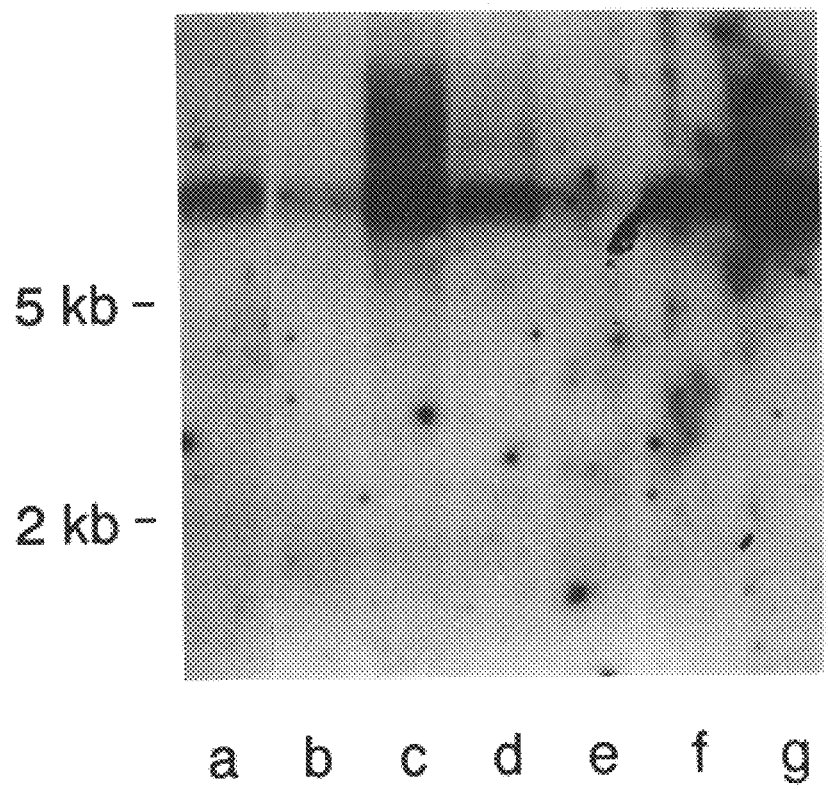
FIG. 15 depicts a Northern analysis of AF-6 RNA in human cell lines. 5–10 μg of polyadenylated RNA were analyzed on agarose gel containing formaldehyde. RNAs were obtained from the lines KCl22, K562, B-1, MV4;11, SKDHL, T98G, 293 (a–g, respectively).

To examine the expression of AF-6 in different cell types, we performed a Northern analysis on RNAs extracted from several cell lines (FIG. 15). An 8 kb transcript was detected in cell lines of myeloid (a), erythroid (b), lymphoid (c–e), glia (f) and epithelial (g) origin. Thus, it appears that AF-6 is expressed in a variety of hematopoietic and nonhematopoietic cells.

The t(6;11) (q27;q23) translocation is one of the most frequent translocations involving 11q23. Cloning of the AF-6 gene involved in this abnormality would enable now the use of Southern blotting and the RT-PCR technique to identify relevant patients whose karyotype was different, complex, or not clear In addition it is possible now to examine residual disease in patients in remission. The analysis reported here of the patient Ed illustrates the first point. This patient showed a typical del(11q23) abnormality. Using the molecular approaches we found here that he had the ALL-1/AF-6 fusion product. Presumably, del (11q23) and t(6;11) are difficult to distinguish cytogenetically. Using chromosome 6-specific probes and FISH analysis, others have -recently concluded that some patients with del(11q23) in fact carry the t(6;11) chromosome translocation (Shannon et al., *Genes, Chromosomes & Cancer* 1993 7, 204–208).

One of the main reasons for cloning AF-6 was to see if it is related to the partner genes AF-4, AF-9, and ENL. Among these, AF-9 and ENL are highly related. However, AF-6 showed no sequence homology to any of the three partner genes. Short domains rich in prolines, serines and acidic amino acids were the only motifs shared by the four genes. The C-terminus AF-6 showed homology to the tail domain of myosin-1 isoform from yeast and myosin heavy chain from *Dictyostelium discoideum*; this domain presumably confers the rod structure to the myosin protein. Within this region AF-6 displays a remarkable homology to the GLGF repeat found in the ZO-1, PSD-95 and dlg proteins from human, rat, and Drosophila respectively. The first and the third proteins are presumably homologous and are thought to play a role in signal transduction on the cytoplasmic surface of intracellular junctions (Willott et al., *Proc. Natl. Acad. Sci. USA* 1993 90, 7834–7838; Woods et al., *Cell* 1991 66, 451–464). The second protein localizes to synaptic junctions and is thought to be involved in synaptic signalling or organization (Willott et al., *Proc. Natl. Acad. Sci. USA* 1993 90, 7834–7838). The three proteins are cytoplasmic or associated with membranes. The presence of this domain in AF-6 raises the possibility that AF-6 is not a nuclear protein. Indeed, unlike AF-4, AF-9 and ENL, AF-6 does not contain a nuclear targeting sequence.

Probes comprising oligonucleotide sequences which identify chromosomal abnormalities within the AF-6 gene of chromosome 6 include SEQ ID NOS. 45, 46, 47, 49 and 90. The nucleotide sequence of the chimeric ALL-1/AF-6 gene (SEQ ID NO. 87) is described in FIG. 13C.

EXAMPLE 4

Cloning and Sequencing of AF-17 cDNA

AML patients GUS and GE showed the chromosome translocation t(11;17) (q23;q21) in their leukemic cells. The cell lines used for RNA analysis included K562 and KCl-22 (erythroid and myeloid acute phase of chronic myeloid leukemia), MV4:11 and B-1 (ALLs with the 4:11 translocation), 380, ALL-1, 697, GM607, (ALLs), GM1500 (EBV transformed lymphoblastoid cell line), T98G (glioblastoma), PC3 (prostate carcinoma), (Prasad et al., *Cancer* 1993 53, 5624–5628; Licht et al., *Nature* 1990, 346, 76–79)

The junction fragment of patient GUS was cloned from a library prepared from a partial digest of genomic DNA clones into the EMBL-3 phage vector. The library was screened with a 0.86 kb BamH1 cDNA probe spanning ALL-1 exons 5–11. cDNA libraries were prepared from ALL-1 and KCl-22 cytoplasmic RNAs utilizing a kit manufactured by Pharmacia, and the lambda ZAPII vector of Stratagene. RT-PCR reaction was performed as described (Nakamura et al., *Proc. Natl. Acad. Sci. USA* 1993 90, 4631–4635) utilizing as primers an ALL-1 oligonucleotide with BamH1 site attached at the 5' end CGGGATCCCGAC-CTACTACAGGACCGCCAAG [SEQ ID NO:81] and AF-17 oligonucleotide with EcoRI site at the 5' end -ATCTGAATTCTGGTGGAGATAGAAGCAGAA [SEQ ID NO:82]. Sequencing was performed in the ABI automatic sequencer with cDNAs and genomic fragments excised from phase vectors and cloned into the SK plasmid vector. The sequence was analyzed using the FASTA, TFASTA and motifs program.

Figure 16A:
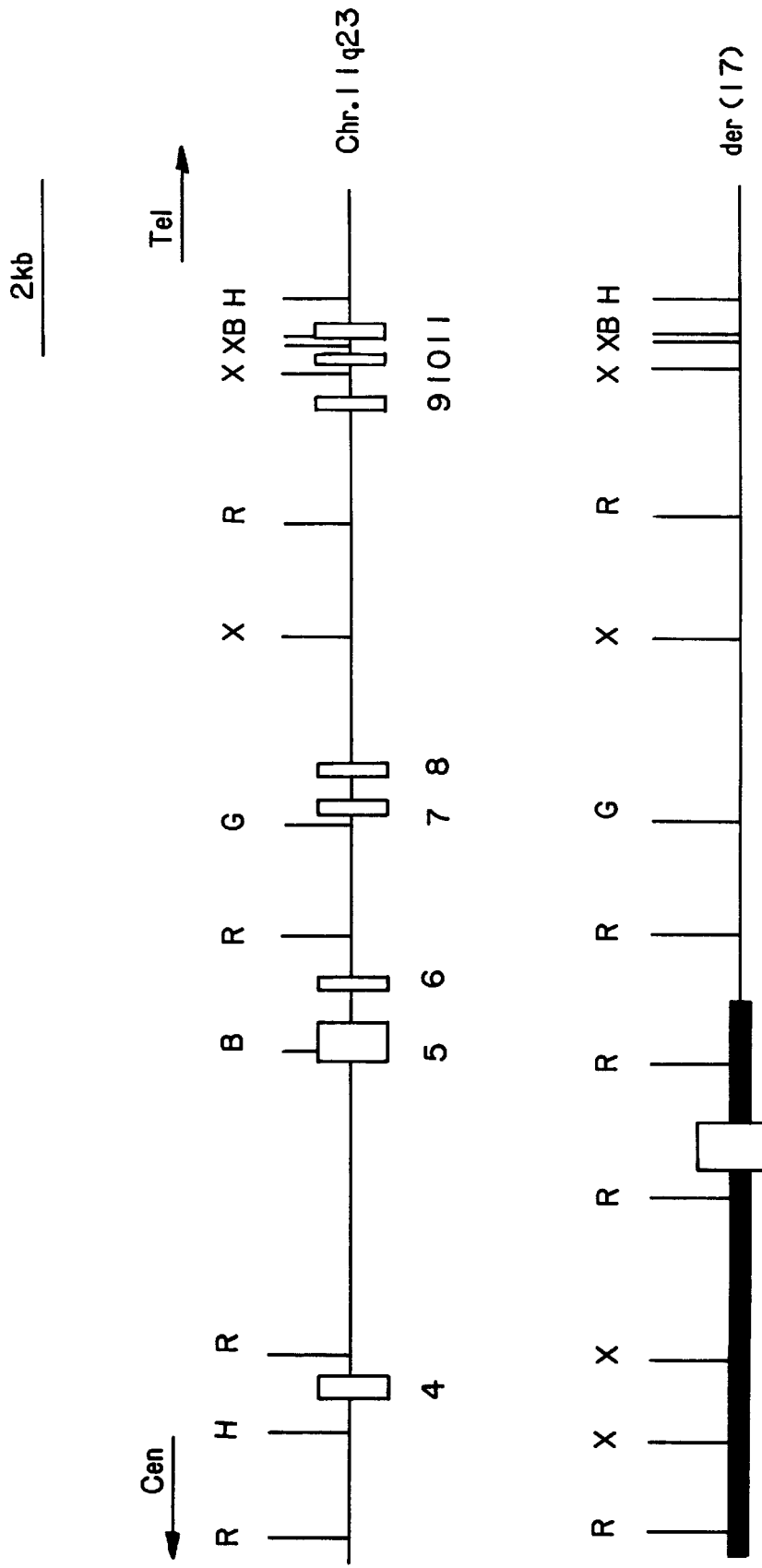
FIGS. 16A and 16B shows genomic analysis of the t(11;17) chromosome translocation.
Figure 16B:
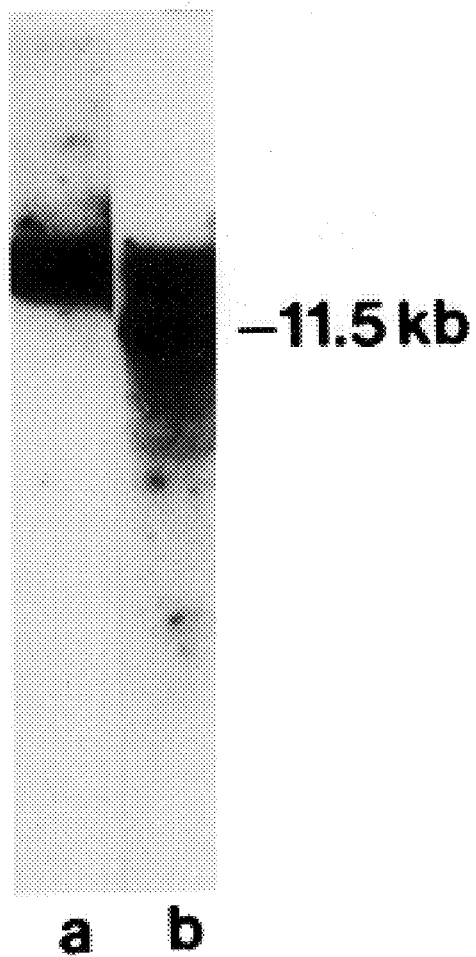

DNA from patient GUS with AML and t(11;17) was partially digested with Mbol enzyme, and following size selection was cloned into the EMBL-3 phage vector. The library was screened with a cDNA probe spanning the breakpoint cluster region. A clone composed of a rearranged ALL-1 segment was identified among positive clones. Comparison between the physical maps of this clone and the corresponding normal ALL-1 DNA (FIG. 16A) indicated that ALL-1 sequences upstream of exon 6 were substituted with new DNA; the latter was subsequently found to be derived from chromosome 17. Within the non-ALL-1 segment of the junction clone, a 1.7 kb EcoRI fragment (R1.7) was found to be devoid of repetitive sequences. This fragment was used as a probe to analyze by the Southern technique DNA from a second patient (GE) with AML and the t(11;17) aberration. In that DNA we detected an 11.6 kb rearranged EcoRV fragment (FIG. 16B, lane b). This indicated that in both patients the breaks occurred in the same region on chromosome 17.

Fragment R1.7 was next used as a probe on cDNA libraries derived from RNAs of the cell lines KCl-22 and ALL-1. Inserts from positive clones were subcloned into the SK plasmid vector and mapped. Clones 1, 3, 13, and a4 (FIG. 17A) were subjected to sequencing analysis. AF-17 cDNA contains an open reading frame spanning 3279 nucleotides. The first ATG shows a good fit to a Kozak consensus sequence and is preceded by an in-frame termination codon. The predicted protein spans 1093 amino acids. It contains relatively high concentrations of serines, glycines, alanines, leucines and prolines (15%, 11%, 10%, 10%, 10%, respectively) often concentrated in short stretches. In addition, it has a glutamine-rich region (41%) between amino acids 935 and 984 (FIG. 17B). The same region shows high concentration of hydrophobic amino acids, in particular leucines. It should be noted that domains rich in alanines (Licht et al., *Nature* 1990, 346, 76–79], glycines (Shi et al., *Cell* 1991 67, 377–388), glutamines and prolines (Madden et al., *Science* 1991 253, 1550–1553) were implicated in transcriptional repression. Also, regions with high concentration of serines and prolines (Gill et al., *Proc. Natl.*

*Acad. Sci. USA* 1993 91, 192–196) or glutamines intercalated with hydrophobic amino acids (Theill et al., *Nature* 1989 342, 945–948) were found to be involved in transcriptional activation.

Homology search in GenBank indicated 90% identity over amino acids 45–139 between AF-17 and an anonymous human cDNA sequence (Accession No. T06113). Furthermore, over 118 residues (FIG. 18A) AF-17 showed 48% identity and 67% similarity to a region within the protein Br140, previously named peregrin (Accession No. M91585). This domain is cysteine-rich in both proteins and can be arranged into three zinc fingers according to the consensus $C-X_2-C-X_{10-13}\ C-X_{2-4}-C$ (FIG. 18B). Related consensus sequences are present in the adenovirus E1A protein and in the steroid receptor superfamily. The human Br140 protein has a second cysteine-rich domain and is located in the nucleus; the function of this protein is unknown. Inspection of AF-17 predicted protein sequence revealed a leucine zipper dimerization motif between amino acids 729 and 764 (FIG. 17B). Unlike many leucine zippers, the one in AF-17 is not preceded by a basic region.

To prove that ALL-1/AF-17 fused gene is transcribed into a chimeric RNA, we used cDNA and genomic DNA sequence information to design primers for amplification by RT-PCR of a putative ALL-1/AF-17 RNA junction from the leukemic cells of patient GUS. An amplification product was indeed found to contain the RNA junction (FIG. 17C). Within the fused RNA the open reading frames of the two genes were found to be linked in phase. Thus, the t(11;17) abnormality results in production of an RNA encoding a chimeric ALL-1/AF-17 protein. Probes comprising oligonucleotide sequences which identify chromosomal abnormalities within the AF-17 gene of chromosome 6 include SEQ ID NOS. 56, 82, and 94. The nucleotide sequence of the chimeric ALL-1/AF-17 gene (SEQ ID NO. 91) is described in FIG. 17C.

Figure 19:
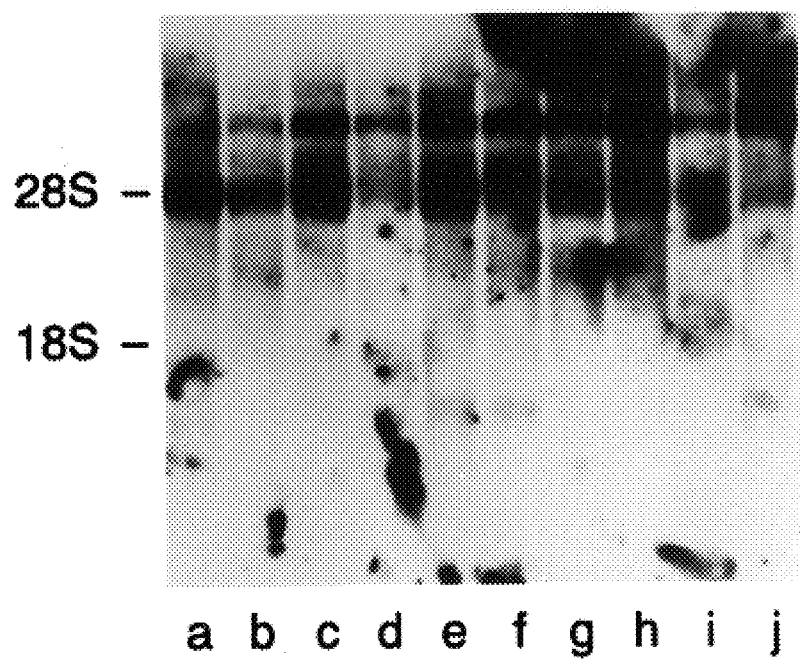
FIG. 19 shows Northern analysis of AF-17 RNA in human cell lines. 5–10 μg of polyadenylated RNA were analyzed on agarose gel containing formaldehyde. RNAs were obtained from the cell lines KCl-122, MV4;11, ALL-1, GM-607, B 1, 380, PC3, GM 1500, K562, T93G, 679 (a to j, respectively).

To examine the expression of the normal AF-17 gene we performed a Northern blot analysis. A major transcript of 7.5 kb and a minor diffuse species of 5 kb were detected in a variety of hematopoietic and non-hematopoietic cell lines (FIG. 19).

The cloning and sequence analysis of the partner genes which recombine with ALL-1 in 11q23 translocations provides information and reagents which can be used in the diagnosis, prognosis and monitoring of human acute leukemias. In addition, this cloning enables construction of biologically active molecules, and might provide insights into the mechanism of leukemogenesis. The most notable feature of AF-17 protein is the leucine zipper protein dimerization motif. Following the t(11;17) chromosome translocation, this motif will be included in the ALL-1/AF-17 chimeric protein which is presumed to be the critical product of the aberration. Since the leucine zipper of AF-17 is not preceded by a basic region required for interaction with DNA, and because leucine zippers are found not only in transcription factors but also in other proteins with diverse functions, it is concurrently not clear whether AF-17 is a transcription factor. The presence at the N-terminus of AF-17 of a cysteine-rich domain, with high homology to the nuclear protein Br140 suggests that AF-17 is also located within the nucleus.

Figure 20:
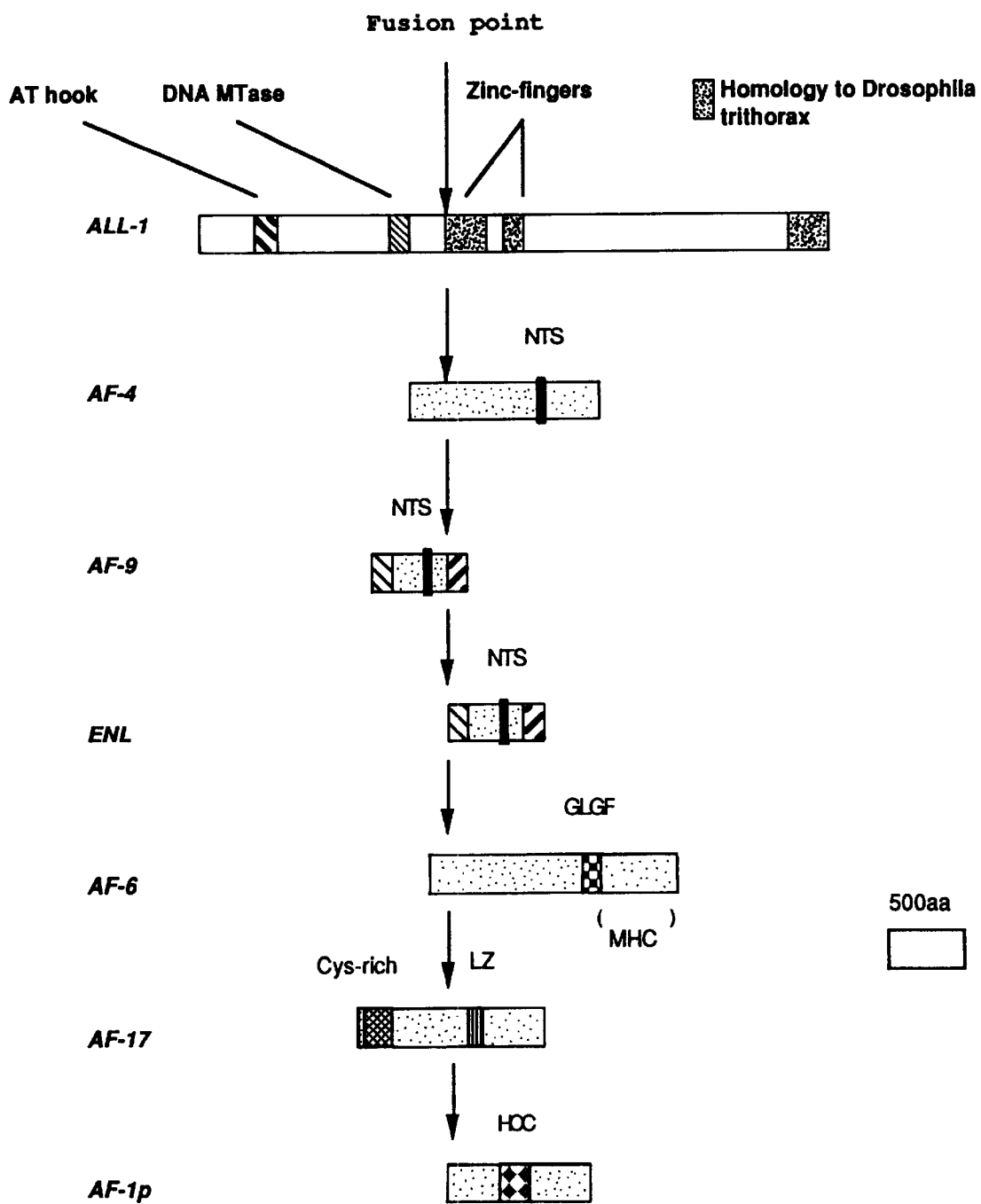
FIG. 20 depicts landmarks, common motifs and homologous sequences within the partner proteins AF-4, AF-9, ENL, AF-6 and AF-17, and within the ALL-1 protein. Arrows indicate fusion points between ALL-1 and the partner proteins. Striped regions in AF-9 and ENL indicate domains of highest homology between the two proteins. NTS, nuclear targeting sequence, LZ, leucine zipper, MTase, methyl transferase.

AF-17 is the fifth partner gene involved in 11q23 abnormalities to be cloned and characterized. Schematic representation of the proteins encoded by these genes and by ALL-1 is shown in FIG. 20. Inspection of the sequences within the segments of the partner proteins (right side of the arrows) linked to ALL-1 sequences (left side of the fusion point within the top scheme) in the chimeric proteins thought to be critical for leukemogenesis, does not reveal a common motif. AF-9 and ENL are the only partner genes which share sequence homology (Nakamura et al., *Proc. Natl. Acad. Sci. USA* 1993 90, 4631–4635). The highly homologous C-terminal polypeptides contributed by both genes to the chimeric proteins, do not contain obviously recognized motifs and are not particularly rich in serines or prolines (as do other regions of these two proteins). AF-9 and ENL proteins contain nuclear targeting sequences and are probably nuclear proteins. The AF-6 polypeptide linked to the N-terminus of ALL-1 contains the GLGF motif (Prasad et al., *Cancer* 1993 53, 5624–5628) whose function is not known, as well as short regions very rich in acidic amino acids, basic amino acids or prolines. The GLGF motif is found in cytoplasmic or membrane-associated proteins and this suggests that AF-6 is not located in the nucleus. The AF-4 polypeptide within the ALL-1 /AF-4 protein includes several segments with high concentration of serines or prolines (Nakamura et al., *Proc. Natl. Acad. Sci. USA* 1993 90, 4631–4635). The AF-4 protein includes a nuclear targeting sequence and therefore is probably associated with the nucleus. Finally, each of the normal five partner genes is expressed in all cell lines analyzed, both of hematopoietic and non hematopoietic lineages.

The high homology between AF-9 and ENL has previously prompted us to speculate (Nakamura et al., *Proc. Natl. Acad. Sci. USA* 1993 90, 4631–4635) that the partner polypeptides are related and possibly contribute a similar function to the chimeric protein. One such possible function would be a transcriptional activation or repression. Domains with these activities were characterized in a number of transcription factors and were found to be rich in particular amino acids such as serines, prolines, glutamines, acidic amino acids, alanines, or glycines (Mitchell et al., *Science* 1989 245, 371–378; Licht et al., *Nature* 1990, 346, 76–79; Shi et al., *Cell* 1991 67, 377–388; Madden et al., *Science* 1991 253, 1550–1553) While the AF-4, AF-6, and AF-17 polypeptides linked to the N-terminus of ALL-1, each contain stretches of one or more of those amino acids, the analogous polypeptide of AF-9 as well as its homologous C-terminal region in ENL are devoid of these amino acids. In addition, the AF-6 protein is probably located in the cytoplasm or the membrane of the cell, and therefore does not play a role in transcriptional regulation. Considering the above we find it less likely that the partner polypeptides of AF-6, AF-9 and ENL contribute domains involved in direct activation or repression of transcription.

The multiplicity and variance between the partner polypeptides which is unprecedented in leukemias associated with chromosome translocations suggests that the partner polypeptides play only a secondary role in 11q23 pathogenesis. This idea is consistent with the recent identification of several patients with AML in which ALL-1 is rearranged by tandem duplication of exons 2–6 with no involvement of partner genes. It is believed that the critical outcome of 11q23 abnormalities is the loss of function of ALL-1, and that the normal protein is directly involved in the differentiation of lymphoid and myeloid cells. Further, it is suggested that the chimeric protein would act in a dominant negative fashion to inactivate the normal ALL-1 protein encoded by the intact ALL-1 allele present in the leukemic cells. Inactivation could occur by nonproductive binding to the promoter of the normal target(s) for ALL-1 or by dimerization of the chimeric protein to the normal protein and sequestering the latter either to a complex with other proteins or into another cellular compartment. In this scenario the partner polypeptides could best play a role in the elimination of the normal protein activity through dimerization. They could make the dimer nonfunctional by virtue of their presence within, or by sequestering it through interaction with other cellular proteins. The leucine zipper dimerization motif in AF-17 and the GLGF motif in AF-6 could represent protein-protein interaction domains of partner polypeptides.

Postulating that the partner polypeptides play an accessory role in abolishing the activity of the ALL-1 protein relaxes the requirements demanded from such proteins and allows a larger variety of them to be involved in 11q23 aberrations. Although chromosome translocations are usually associated with overexpression or activation of oncogenes, there is a recent example for a translocation which apparently involve loss of function and a dominant negative effect. Thus, in the t(15;17) chromosome translocation associated with acute promyelocytic leukemia, the effect of the fusion protein PML/RAR is sequestering of the normal PML protein and inhibiting its organization into nuclear macromolecular organelles (Dyck et al., Cell 1994 76, 333–343 and Weiss et al., Cell 1994 76, 345–356).

EXAMPLE 5

Sequence Analysis of the ALL-1 Breakpoint Cluster Region in the ALL-1 Gene

Frozen bone marrow samples of patients diagnosed with acute leukemia were obtained from the Hospital of University of Pennsylvania, St. Jude Children's Research Hospital, and Roswell Park Cancer Institute. The cytogenetic analyses were performed at the time of diagnosis.

Genomic DNA was extracted from either bone marrow of leukemia patients or the cell lines. Aliquots (10 µg) of high molecular weight DNA were digested with BamHI, separated by electrophoreses on 0.7% agarose gels, and blotted onto nylon membrane. The probe was radiolabeled by using the Boehringer Mannheim random-primer kit.

An 859 bp BamHI fragment which spans exons 5–11 of the ALL-1 gene was isolated from the V26 cDNA clone (FIG. 21 and Gu et al., Cell 1992 71, 701–708) and subcloned into the pBluescript SK vector. This probe was named B859. The genomic region corresponding to B859, an 8.3 kb BamHI fragment, was included in the phage clone, mg 11.1 (Gu et al., Cell 1992 71, 701–708). For constructing a genomic library, patient or normal DNA was either partially digested with Sau3A or digested to completion with BamHI, and subsequently ligated with a phage vector, λEMBL3 (Stratagene) using standard techniques.

Sequencing reactions were performed by using an automatic sequencer (ABI). Sequences were reassembled and analyzed in the Genetic Computer Group system. Alu sequences were analyzed by the Pythia service.

Figure 21B:
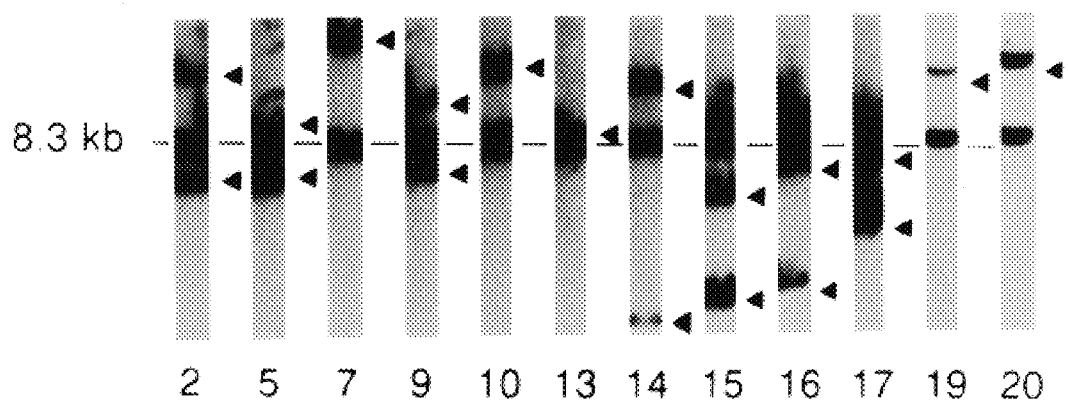

In previous studies, we have defined a breakpoint cluster region in the ALL-1 locus/gene disrupted in acute leukemia with 11q23 aberrations (Gu et al., Cell 1992 71, 701–708; Cimino et al., Cancer Res. 1992 52, 3811–3813 and Gu et al., Proc. Natl. Acad. Sci. USA 1992 89, 10464–10468). We have also noticed that exons within this region all started in the same phase within the open reading frame. We have now developed a new probe, a 859 bp cDNA that spans exons 5–11. The probe is supposed to detect two rearranged fragments in all reciprocal translocations. FIG. 21 shows DNA rearrangements detected by B859 probe in some of the various 11q23 aberrations studied in this report.

A phage clone, mg11.1, which spans the breakpoint cluster region in the ALL-1 gene (Gu et al., Cell 1992 71, 701–708), was subcloned into plasmids for sequencing. The complete sequence of the 8342 bp BamHI fragment is presented in FIG. 22. The exons included in this region are shown. The AF4 probe (Cimino et al., Cancer Res. 1992 52, 3811–3813 and Gu et al., Proc. Natl. Acad. Sci. USA 1992 89, 10464–10468), a modified DdeI fragment, spans nucleotides 3071 to 3261 and 3502 to 3754 (FIG. 22).

To search for the repetitive sequences in the breakpoint cluster region, the 8342 bp sequence was first screened for Alu repeats. Eight Alu repeats were identified and their positions are indicated in Table 1. The orientation of these Alu repeats is the same as that of the ALL-1 gene. Classification of these Alu repeats was based on recently published diagnostic criteria (Milosavljevic et al., J. Mol. Evol. 1991 32, 105–121). After the ALL-1 exons and Alu repeats were precisely identified, the rest of sequence was searched for other homologous sequence(s) in GenBank. A 130 bp fragment, encompassing nucleotides 7429 to 7559 in intron 9, shows around 80 percent sequence identity to genomic sequences in several genes such as TRE17, ApoA4, Factor VIII c subunit, Factor IX, a nuclear gene for mitochondrial ATP synthase c subunit, and G6PD gene (GenBank accessions: X63596, M14642, M88636, K02402, X69907, and Z29527, respectively). These similar sequences were located in 5' regulatory regions, or in 3' segments, or in introns, suggesting that they may represent a group of repetitive elements with low frequency in the genome.

Figure 23:
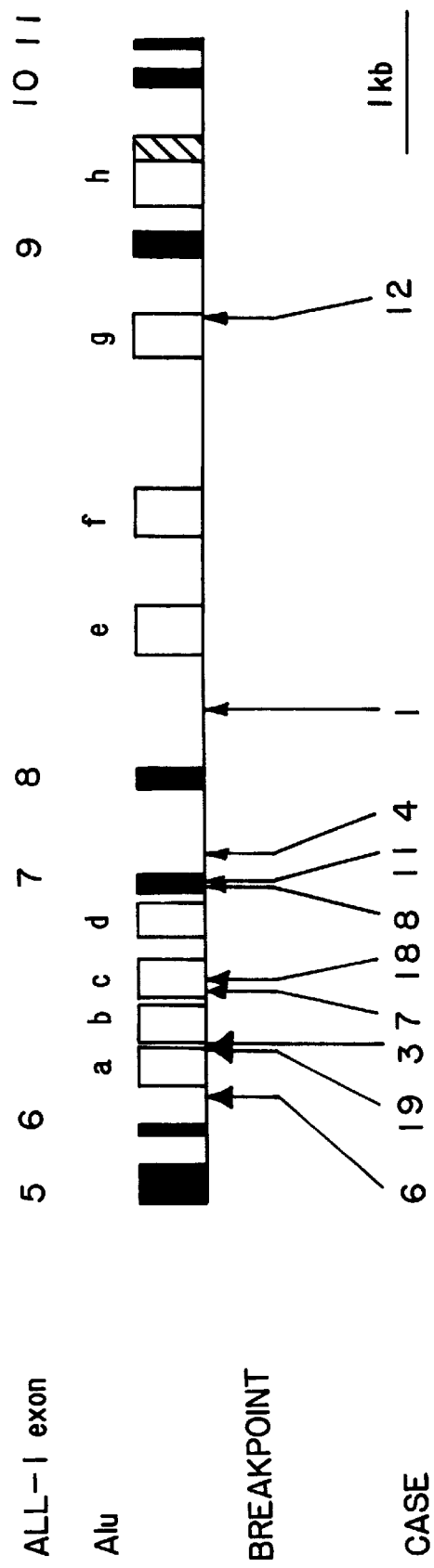
FIG. 23 is a schematic representation of the exons, Alu repeats, and the breakpoints in the breakpoint cluster region in the ALL-1 gene. Filled boxes are exons. Alu repeats are shown as open boxes. Arrows point to the positions of the breakpoints with their corresponding case numbers presented in Table 2. Hatched box represents a 130 bp novel repetitive sequence.

Ten out of twenty patient DNAs studied were analyzed by sequencing at the breakpoint junctions. The relevant sequences of the corresponding normal regions from chromosomes 1, 4, 6, 9, and intron 1 of the ALL-1 gene were also analyzed. Table 2 lists the results of cytogenetic and molecular studies from twenty patients, and the positions of the breakpoints from ten patients. Five of these breakpoints were located in three different Alu repeats, but none of the breaks on the partner chromosome is in the Alu sequence. Two breaks were located in exon 7 of the ALL-1 gene, and the last three were located in intron sequences (FIG. 23). All together, several of the breaks occurred in the Alu-rich region delineated by exons 6 and 7 (FIG. 23).

Using the B859 probe it was previously possible to detect rearrangements in DNAs of patients with therapy-related acute myeloid leukemia, or secondary leukemia (all with 11q23 aberrations) (Felix et al., Cancer Res. 1993 53, 2954–2956; Hunger et al., Blood 1993, 81, 3197–3203; Negrini et al., Cancer Res. 1993 53, 4489–4492). These secondary leukemias were linked to the treatment of the patients with inhibitors of topoisomerase II. One topoisomerase II recognition site which fits with the consensus 5' A/GNT/CNNCNNGT/CNGG/TTNT/CNT/C3' (Spitzner, et al., Nucleic Acids Res. 1988 16, 5533–5556) was found in exon 9 (FIG. 22). When one or two mismatches were allowed in the consuses, a total of 11 and 129 sites, respectively, were found within the two strands of the breakpoint cluster region. In patients 7 and 12 the breaks were located within the imperfect recognition sites on the minus strand after allowing two mismatches. When three mismatches were allowed, a total of 703 sites were found at the breakpoint in one additional patient, case 1, was located within such consensus sequence on the minus strand.

The DNA rearrangements in the ALL-1 gene involved in acute leukemia can be detected by a single probe, B859.

Digestion with BamHI is normally sufficient for the analysis. However, if only one or no rearranged fragments are detected, the sample DNA should be digested by other restriction enzymes such as HindIII, and probed with B859.

In order to search for features within the breakpoint cluster region of the ALL-1 gene which might predispose it to translocations, we have sequenced and analyzed the 8342 bp genomic BamHI fragment spanned by the B859 cDNA probe. The positions of the ALL-1 exons, Alu repeats and the breakpoints have been established as shown in FIG. 23. Breaks/mutations mediated by Alu sequences, particularly homologous recombination events, have been observed in a number of human diseases (Li et al, *Am. J. Hum. Genet.* 1993 53, 140–149). Five breakpoints were located within Alu sequences. If the Alu sequence mediate homologous recombination in these translocations, the germline sequence of the partner chromosome at the breakpoint should have been Alu. However, this is not the case in any of the five translocations. Nevertheless, the high concentration of the Alu sequences within the region, in particular, within the area spanned by exons 6 and 7, suggested a possible role for the Alu in the translocations. This indirect role might be destabilization of the region so as to make it more prone to breaks.

The previous detection of the ALL-1 rearrangements in therapy-related leukemia patients indicated that the consequences of the translocations in both de novo and secondary leukemia, inhibition of topoisomerase II apparently trigger the disease. We searched for topoisomerase II recognition sites in the region. Such sites were found in three out of ten cases when three mismatches were allowed in the consensus sequence. Thus, in the majority of the de novo All-1 rearrangements topoisomerase II recognition sites are not present at the breakpoints, and the enzyme is probably not involved. It will be necessary to sequence the breakpoint in secondary leukemias to determine whether in these cases topoisomerase II recognition sites are consistently associated with the breakpoints.

TABLE 1

POSITIONS OF ALL-1 EXONS AND ALU REPEATS WITHIN THE BREAKPOINT CLUSTER REGION AND CLASSIFICATION OF ALU REPEATS

| ALL-1/Exon | Position | Alu | Class[x] | Strand[y] |
|---|---|---|---|---|
| 5 | <1–263 | | | |
| 6 | 593–666 | | | |
| | 799–1108 | a | J | + |
| | 1119–1420 | b | Sx | |
| | 1432–1716 | c | SbO | + |
| | 1921–2216 | d | J | + |
| 7 | 2353–2484 | | | |
| 8 | 3032–3145 | | | |
| | 3973–4268 | e | Sbo | + |
| | 4764–5094 | f | J | + |
| | 6072–6362 | g | S | + |
| 9 | 6788–6934 | | | |
| | 7164–7427 | h | Sx | + |
| 10 | 7967–8062 | | | |
| 11 | 8304–>8342 | | | |

[x]Based on the diagnostic criteria in Negrine et al., Cancer Res. 1993 53, 4489–4492.
[y]"+" Strand corresponds to the coding strand of ALL-1.

TABLE 2

CLINICAL AND MOLECULAR DIAGNOSTIC DATA OF PATIENTS WITH ACUTE LEUKEMIA

| Case | Age/Sex | Karotype | B859[a] | Breakpoint[y] | Ref. |
|---|---|---|---|---|---|
| 1 | — | 46, — t(1;11) (p32–34;q23) | R | 3562/3563 | |
| 2 | 0.6/F | 46, XX, inv(1) (p34; q21), t(1;11) (p34;q23) | R | ND | |
| 3 | 10/M | 46, XY, t(4;11) (q21, q23) | R | 1161/1162 | |
| 4 | 32/F | 46, XY, t(4;11) (q21; q23) | R | 2530/2531 | i |
| 5 | 14/M | 45, XY, der(1)t(1;8) (p36;q13), −4, +6, −9, der(10)t(1;10) (q11;p15), der(11)t(4; 11) (q21, q23) | R | ND | |
| 6 | 47/F | 46, XX, t(6;11) (q27; q23) | R | 720/721 | ii |
| 7 | 5/M | 46, XY, del(11) (q23) | R | 1564/1565 | |
| 8 | 0.8/F | 46, XX, del(11) (q23) | R | 2415/2416 | |
| 9 | 0.5/M | 46, XY, t(9;11) (p21; q23)/47, XY, +6, t(9;11) (p21;q23) | R | ND | |
| 10 | 2/M | 46, XY, t(9;11) (p21; q23) | R | ND | |
| 11 | 5/F | 47, XX, X, t(9;11) (p21;q23) | R | 2437/2438 | iii |
| 12 | 0.6M | 46, XY, t(9;11) (p21; q23) | R | 6339/6340 | iii |
| 13 | adult/M | 46, XY, t(10;11) (p11; q23) | R | ND | |
| 14 | — | 46, —, t(11;17) (q23; q25) | R | ND | |
| 15 | 11/F | 46, XX, t(11;19) (q23; p13) | R | ND | |
| 16 | 1.5/F | 46, XX, t(11;19) (q23; p13) | R | ND | |
| 17 | 13.9/F | 47, XX, +8, t(11;19) (q23;p13) | R | ND | |
| 18 | 64/F | 47, XX, +11 | R | 1606/1607 | |
| 19 | 68/M | 47, XY, +11 | R | 1082/1083 | ii |
| 20 | 77/F | 46, XX | R | ND | |

[a]R is denoted for DNA rearrangements detected by B859 probe;
[b]The numbers correspond to nucleotide sequence in FIG. 22. ND = not determined.
i: Gu et al., Proc. Natl. Acad; Sci. USA 1992 89, 10464–10468
ii: Prasad et al., Cancer Res. 1993 53, 5581–5585
iii: Nakamura, et al., Proc. Natl. Acad. Sci. USA 1993 90, 4631–4635

EXAMPLE 6

Partial Duplication of ALL-1 in Acute Leukemia

Genomic DNA was extracted from bone marrow aspirates by a standard procedure (Gustincich et al., *BioTechniques* 1991, 11, 8–301). Approximately 8 µg of genomic DNA was digested to completion with BamHI or HindIII. Restriction enzyme digests were separated by electrophoresis on 0.7% agarose gels and blotted onto positively charged nylon membranes. Southern blotting, probe radiolabeling, and hybridization were performed by standard techniques. A single blot was prepared. After probing with SAS1, the blot was stripped, then probed again with B859.

Clones corresponding to the rearranged ALL-1 BamHI fragments were isolated from bacteriophage λEMBL3 libraries made from size-fractionated BamHI digests of patient DNA. Recombinants were identified in phage libraries by filter hybridization using the B859 probe. Construction of libraries, screening, phage purification, and restriction enzyme mapping were done by standard techniques. Subclones were constructed in the pBluescript II plasmid vector. DNA sequence of selected portions of subclones was determined by cycle sequencing using an Applied Biosystems 373A DNA sequencer. Programs from Genetics Computer Group (GCG) system (Devereux et al., *Nucl. Acids Res.* 1984, 12, 387–395) were used for data analysis.

Total cellular RNA was isolated using RNAzol™ (Biotecx Laboratories). Reverse transcriptase (RT) reaction and RNA-PCR amplification were performed with rTth DNA polymerase. Nested PCR amplification was performed with Taq DNA polymerase. oligonucleotide primers were used without further purification. Primers are 31.c (AGGAGAGAGTTTACCTGCTC) [SEQ ID NO:83] from exon 3, 5.3 (GGAAGTCAAGCAAGCAGGTC) [SEQ ID NO:84] from exon 5, 6.1 (GTCCAGAGCAGAGCAAACAG) [SEQ ID NO:85] from exon 6, and 3.2c (ACACAGATGGATCTGAGAGG) [SEQ ID NO:86] from exon 3. Primers used in reactions are as follows: 1) RT reaction—3.1c, 2) RNA-PCR amplication—5.3/3.1c, 3) nested PCR amplification—6.1/3.2c. RT reaction was performed for 15 minutes at 57° C. using 500 ng RNA. RNA-PCR amplification was performed for 35 cycles (95° C., 1 minutes; 53° C., 1 minutes; 72° C., 1 minute). Nested PCR amplification was performed using 0.5 μl of the RNA-PCR product for 30 cycles (95° C., 1 minute; 60° C. 1 minute; 72° C., 1 minute). PCR products were analyzed by 2% agarose gel electrophoresis.

FIG. 24 shows Southern blot rearrangements in the ALL-1 gene for three adult patients with acute myeloid leukemia (AML) lacking cytogenetic evidence of 11q23 translocations. The rearrangements were detected with a cDNA probe (B859) (Gu et al., *Cell* 1992 71, 701–708 and Caligiuri et al., *Cancer Res.* 1994 54, 370–373) which spans the ALL-1 breakpoint cluster region. Two of these patients (nos. 23 and 24) had trisomy 11 as a sole cytogenetic abnormality whereas one patient (no. 1) had a normal karyotype (Caligiuri et al., *Cancer Res.* 1994 54, 370–373). A single rearranged ALL-1 band is seen for each patient in both BamHI and HindIII restriction enzyme digests. Clones corresponding to the rearranged BamHI fragments from the two trisomy 11 patients were isolated and characterized. Each clone begins and ends with a portion of ALL-1 exon 5 delineated by the BamHI cloning site within this exon (FIG. 25A). The 5'-3' order of ALL-1 exons within each clone is 5-6-2-3-4-5. This novel exon structure indicates that the ALL-1 rearrangement in each patient is the result of a direct tandem duplication of a portion of the ALL-1 gene (FIG. 25B). The junction point of this duplication fuses the 5' portion of intron 6 to the 3' portion of intron 1. The precise junction points for the two clones are different. DNA sequence across the junctions (FIG. 25C) shows a 1 bp N-segment in one clone (λ24) and heptamer-like signal sequences (Akira et al., *Science* 1987 238, 1134–1138) near the junction points in both clones.

We next examined the genomic DNA of the three AML patients with a probe from intron 1 (SAS1) designed to detect specifically the rearrangement associates with the ALL-1 direct tandem duplication. The location of this probe is indicated in FIG. 25A. For all three patients, the SAS1 probe shows rearranged bands on Southern blot (FIG. 24B) that comigrate with the rearranged bands detected by the ALL-1 breakpoint cluster region probe (FIG. 24A). This result indicates that the ALL-1 partial duplication occurs in an AML patient (no. 1) with a normal karyotype, as well as in the two AML patients (nos. 23 and 24) with trisomy 11. Additional reported cases (Caligiuri et al., *Cancer Res.* 1994 54, 370–373) of ALL-1 rearrangements without 11q23 translocations lacked adequate material for study.

Figures 26A, 26B:
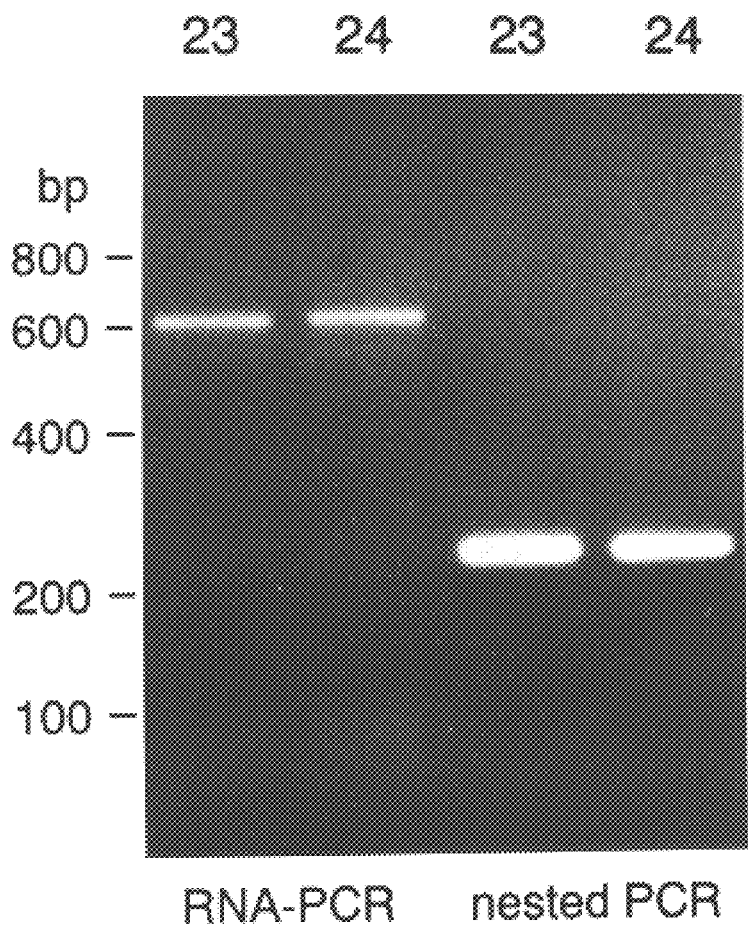
FIGS. 26A and B shows RNA-PCR analysis of trisomy 11 patient samples.
FIG. 26B: Sequence analysis of nested PCR products shows an in-frame fusion of ALL-1 exon 6 with exon 2 (SEQ ID NO: 77). Amino acid translation is shown beneath the DNA sequence.

To determine whether the partially duplicated ALL-1 gene is transcribed, RNA-PCR was performed using oligonucleotide primers specific for the ALL-1 duplication. Discrete bands of the predicted size were detected for the two patients with trisomy 11 (FIG. 26A). Sequence analysis of nested PCR products (FIG. 26B) shows an in-frame fusion of exon 6 with exon 2. These results demonstrate that the partially duplicated ALL-1 gene is transcribed into mRNA capable of encoding a partially duplicated protein.

The partial ALL-1 duplication creates a novel type of fusion protein in which a truncated polypeptide chain encoded by ALL-1 exons 1–6 is fused near the amino-terminus of the native ALL-1 protein. The partially duplicated protein may be involved in cellular transformation, as postulated for other ALL-1 fusions (Cimino et al., *Cancer Res.* 1991 51, 6712–6714; Gu et al., *Cell* 1992 71, 701–708; Tkachuk et al., *Cell* 1992 71, 691–700; Morrissey et al., *Blood* 1993 81, 1124–1131; Nakamura et al., *Proc. Natl. Acad. Sci. USA* 1993 90, 4631–4635; Prasad et al., *Cancer Res.* 1993 53, 5624–5628). The structure of the partial duplication suggests that dissociation of ALL-1 amino-terminal domains from their normal protein environments is the critical structural alteration leading to ALL-1 associated leukemogenesis. Because the ALL-1 gene is fused with itself, it follows that partner genes from other chromosomes are not necessary for involvement of ALL-1 in leukemia.

We have reported previously (Caligiuri et al., *Cancer Res.* 1994 54, 370–373) a high incidence (3 of 4 cases) of ALL-1 rearrangement associated with trisomy 11 as a sole chromosomal abnormality in AML. The ALL-1 partial duplications characterized in this report were cloned from two of these trisomy 11 cases. Trisomy 11 is a rare recurrent finding in AML, estimated to occur at a frequency of about 0.7% (CALGB AML cytogenetic data base). Trisomy of other chromosomes is reported frequently in hematologic malignancy, sometimes in association with disease progression (Heim et al., *Cancer Cytogenetics* 1987 (Liss, N.Y.)). Examples include trisomy 8 in AML and transformed chronic granulocytic leukemia (Mitelman et al., "Report of the Committee on Chromosome Changes in Neoplasia", *Chromosome Coordinating Meeting* 1992 pp. 700–726; Cuticchia et al. (eds.), *Genome Priority Reports*, vol. 1, 1993, Basel, Karger), trisomy 21 in AML, and trisomy 12 in chronic lymphocytic leukemia (Mitelman et al., "Report of the Committee on Chromosome Changes in Neoplasia", *Chromosome Coordinating Meeting* 1992 pp. 700–726; Cuticchia et al. (eds.), *Genome Priority Reports*, vol. 1, 1993 Basel, Karger). It has been postulated that trisomy, which occurs in somatic cells by nondisjunction, contributes to the neoplastic phenotype through a gene dosage effect (Mitelman, "Tumor Etiology and Chromosome Pattern: Evidence from Human and Experimental Neoplasms" in Arrighi et al. (eds.), *Genes, Chromosomes and Neoplasia* 1981 335–350, Raven Press, New York). Our findings suggest that, in many cases, the presence of trisomy in malignancy may indicate the partial duplication of a cellular protooncogene.

We claim:

1. A probe which identifies chromosomal abnormalities in the ALL-1 gene, said probe consisting of B859.

2. A probe comprising an oligonucleotide sequence of at least 15 nucleotides which identifies chromosome abnormalities within a gene, said gene selected from the group consisting of: the AF-4 gene of chromosome 4 (SEQ ID NOS. 25 and 27) and the AF-9 gene of chromosome 9 (SEQ ID NO 29).

3. A method of diagnosing acute lymphoblastic or non-lymphoblastic leukemia comprising:
   providing a tissue sample containing hematopoietic cells from a person suspected of having acute lymphoblastic or nonlymphoblastic leukemia; and detecting chromosome abnormalities within a gene in genetic material from the cells, said gene selected from the group consisting of: the AF-4 gene of chromosome 4 (SEQ ID NOS. 25 and 27) and the AF-9 gene of chromosome 9 (SEQ ID NO. 29).

4. The method of claim 3 wherein said gene is the AF-4 gene of chromosome 4 (SEQ ID NOS. 25 and 27).

5. The method of claim 3 wherein said gene is the AF-9 gene of chromosome 9 (SEQ ID NO. 29).

6. The method of claim 3 further comprising:
   digesting nucleic acid from the hematopoietic cells;
   subjecting the digested nucleic acid to Northern analysis using a probe selected from the group consisting of: a probe which identifies chromosome abnormalities within the AF-4 gene of chromosome 4 (SEQ ID NOS. 25 and 27), and a probe which identifies chromosome abnormalities within the AF-9 gene of chromosome 9 (SEQ ID NO 29); and
   detecting aberrant transcripts from the Northern analysis.

7. The method of claim 6 wherein said probe identifies chromosome abnormalities within the AF-4 gene of chromosome 4.

8. The method of claim 6 wherein said probe identifies chromosome abnormalities within the AF-9 gene of chromosome 9.

9. The method of claim 3 further comprising:
   digesting nucleic acid from the hematopoietic cells;
   subjecting the digested nucleic acid to Southern analysis using an ALL-1 probe which detects chromosome abnormalities in the ALL-1 breakpoint cluster region; and
   detecting chromosome abnormalities in said gene selected from the group consisting of: the AF-4 gene of chromosome 4 (SEQ ID NOS. 25 and 27) and the AF-9 gene of chromosome 9 (SEQ ID NO. 29).

10. The method of claim 9 wherein said gene is the AF-4 gene of chromosome 4 (SEQ ID NOS. 25 and 27).

11. The method of claim 9 wherein said gene is the AF-9 gene of chromosome 9 (SEQ ID NO. 29).

12. A method of diagnosing acute lymphoblastic or non-lymphoblastic leukemia involving translocations which generate a chimeric gene selected from the group consisting of: the chimeric ALL-1/AF-4 gene (SEQ ID NOS: 23 and 24) and the chimeric ALL-1/AF-9 gene (SEQ ID NOS: 32 and 34) comprising:
   providing a tissue sample containing hematopoietic cells from a person suspected of having acute lymphoblastic or nonlymphoblastic leukemia;
   isolating RNA from the sample;
   generating cDNA from said RNA;
   amplifying a chimeric gene sequence in said cDNA which is generated by said translocation using a set of PCR primers if a chimeric gene is present; and
   detecting the presence of amplified DNA.

* * * * *

UNITED STATES PATENT AND TRADEMARK OFFICE
CERTIFICATE OF CORRECTION

PATENT NO. : 6,040,140
DATED : March 21, 2000
INVENTOR(S) : Carlo Croce and Eli Canaani Page 1 of 1

It is certified that error appears in the above-identified patent and that said Letters Patent is hereby corrected as shown below:

Column 4,
Line 1, after "A" insert --I--

Column 34,
Line 51, "11,8-301" should be --11,298-301--

Signed and Sealed this

Third Day of July, 2001

Attest:

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 94

(2) INFORMATION FOR SEQ ID NO: 1:

(i) SEQUENCE CHARACTERISTICS:
      (A) LENGTH: 14255
      (B) TYPE: nucleic acid
      (C) STRANDEDNESS: single
      (D) TOPOLOGY: linear (iv) ANTI-SENSE: No (xi) SEQUENCE DESCRIPTION: SEQ ID NO: 1:

```
GCG GCG GCG GCG GCG GGA AGC AGC GGG GCT GGG GTT CCA GGG GGA      45
Ala Ala Ala Ala Ala Gly Ser Ser Gly Ala Gly Val Pro Gly Gly
                  5                  10                 15

GCG GCC GCC GCC TCA GCA GCC TCC TCG TCG TCC GCC TCG TCT TCG      90
Ala Ala Ala Ala Ser Ala Ala Ser Ser Ser Ser Ala Ser Ser Ser
                 20                  25                 30

TCT TCG TCA TCG TCC TCA GCC TCT TCA GGG CCG GCC CTG CTC CGG     135
Ser Ser Ser Ser Ser Ser Ala Ser Ser Gly Pro Ala Leu Leu Arg
                 35                  40                 45

GTG GGC CCG GGC TTC GAC GCG GCG CTG CAG GTC TCG GCC GCC ATC     180
Val Gly Pro Gly Phe Asp Ala Ala Leu Gln Val Ser Ala Ala Ile
                 50                  55                 60

GGC ACC AAC CTG CGC CGG TTC CGG GCC GTG TTT GGG GAG AGC GGC     225
Gly Thr Asn Leu Arg Arg Phe Arg Ala Val Phe Gly Glu Ser Gly
                 65                  70                 75

GGG GGA GGC GGC AGC GGA GAG GAT GAG CAA TTC TTA GGT TTT GGC     270
Gly Gly Gly Gly Ser Gly Glu Asp Glu Gln Phe Leu Gly Phe Gly
                 80                  85                 90

TCA GAT GAA GAA GTC AGA GTG CGA AGT CCC ACA AGG TCT CCT TCA     315
Ser Asp Glu Glu Val Arg Val Arg Ser Pro Thr Arg Ser Pro Ser
                 95                 100                105

GTT AAA ACT AGT CCT CGA AAA CCT CGT GGG AGA CCT AGA AGT GGC     360
Val Lys Thr Ser Pro Arg Lys Pro Arg Gly Arg Pro Arg Ser Gly
                110                 115                120

TCT GAC CGA AAT TCA GCT ATC CTC TCA GAT CCA TCT GTG TTT TCC     405
Ser Asp Arg Asn Ser Ala Ile Leu Ser Asp Pro Ser Val Phe Ser
                125                 130                135

CCT CTA AAT AAA TCA GAG ACC AAA TCT GGA GAT AAG ATC AAG AAG     450
Pro Leu Asn Lys Ser Glu Thr Lys Ser Gly Asp Lys Ile Lys Lys
                140                 145                150

AAA GAT TCT AAA AGT ATA GAA AAG AAG AGA GGA AGA CCT CCC ACC     495
Lys Asp Ser Lys Ser Ile Glu Lys Lys Arg Gly Arg Pro Pro Thr
                155                 160                165

TTC CCT GGA GTA AAA ATC AAA ATA ACA CAT GGA AAG GAC ATT TCA     540
Phe Pro Gly Val Lys Ile Lys Ile Thr His Gly Lys Asp Ile Ser
                170                 175                180

GAG TTA CCA AAG GGA AAC AAA GAA GAT AGC CTG AAA AAA ATT AAA     585
Glu Leu Pro Lys Gly Asn Lys Glu Asp Ser Leu Lys Lys Ile Lys
                185                 190                195

AGG ACA CCT TCT GCT ACG TTT CAG CAA GCC ACA AAG ATT AAA AAA     630
Arg Thr Pro Ser Ala Thr Phe Gln Gln Ala Thr Lys Ile Lys Lys
                200                 205                210

TTA AGA GCA GGT AAA CTC TCT CCT CTC AAG TCT AAG TTT AAG ACA     675
Leu Arg Ala Gly Lys Leu Ser Pro Leu Lys Ser Lys Phe Lys Thr
                215                 220                225
```

```
GGG AAG CTT CAA ATA GGA AGG AAG GGG GTA CAA ATT GTA CGA CGG        720
Gly Lys Leu Gln Ile Gly Arg Lys Gly Val Gln Ile Val Arg Arg
                230                 235                 240

AGA GGA AGG CCT CCA TCA ACA GAA AGG ATA AAG ACC CCT TCG GGT        765
Arg Gly Arg Pro Pro Ser Thr Glu Arg Ile Lys Thr Pro Ser Gly
                245                 250                 255

CTC CTC ATT AAT TCT GAA CTG GAA AAG CCC CAG AAA GTC CGG AAA        810
Leu Leu Ile Asn Ser Glu Leu Glu Lys Pro Gln Lys Val Arg Lys
                260                 265                 270

GAC AAG GAA GGA ACA CCT CCA CTT ACA AAA GAA GAT AAG ACA GTT        855
Asp Lys Glu Gly Thr Pro Pro Leu Thr Lys Glu Asp Lys Thr Val
                275                 280                 285

GTC AGA CAA AGC CCT CGA AGG ATT AAG CCA GTT AGG ATT ATT CCT        900
Val Arg Gln Ser Pro Arg Arg Ile Lys Pro Val Arg Ile Ile Pro
                290                 295                 300

TCT TCA AAA AGG ACA GAT GCA ACC ATT GCT AAG CAA CTC TTA CAG        945
Ser Ser Lys Arg Thr Asp Ala Thr Ile Ala Lys Gln Leu Leu Gln
                305                 310                 315

AGG GCA AAA AAG GGG GCT CAA AAG AAA ATT GAA AAA GAA GCA GCT        990
Arg Ala Lys Lys Gly Ala Gln Lys Lys Ile Glu Lys Glu Ala Ala
                320                 325                 330

CAG CTG CAG GGA AGA AAG GTG AAG ACA CAG GTC AAA AAT ATT CGA       1035
Gln Leu Gln Gly Arg Lys Val Lys Thr Gln Val Lys Asn Ile Arg
                335                 340                 345

CAG TTC ATC ATG CCT GTT GTC AGT GCT ATC TCC TCG CGG ATC ATT       1080
Gln Phe Ile Met Pro Val Val Ser Ala Ile Ser Ser Arg Ile Ile
                350                 355                 360

AAG ACC CCT CGG CGG TTT ATA GAG GAT GAG GAT TAT GAC CCT CCA       1125
Lys Thr Pro Arg Arg Phe Ile Glu Asp Glu Asp Tyr Asp Pro Pro
                365                 370                 375

ATT AAA ATT GCC CGA TTA GAG TCT ACA CCG AAT AGT AGA TTC AGT       1170
Ile Lys Ile Ala Arg Leu Glu Ser Thr Pro Asn Ser Arg Phe Ser
                380                 385                 390

GCC CCG TCC TGT GGA TCT TCT GAA AAA TCA AGT GCA GCT TCT CAG       1215
Ala Pro Ser Cys Gly Ser Ser Glu Lys Ser Ser Ala Ala Ser Gln
                395                 400                 405

CAC TCC TCT CAA ATG TCT TCA GAC TCC TCT CGA TCT AGT AGC CCC       1260
His Ser Ser Gln Met Ser Ser Asp Ser Ser Arg Ser Ser Ser Pro
                410                 415                 420

AGT GTT GAT ACC TCC ACA GAC TCT CAG GCT TCT GAG GAG ATT CAG       1305
Ser Val Asp Thr Ser Thr Asp Ser Gln Ala Ser Glu Glu Ile Gln
                425                 430                 435

GTA CTT CCT GAG GAG CGG AGC GAT ACC CCT GAA GTT CAT CCT CCA       1350
Val Leu Pro Glu Glu Arg Ser Asp Thr Pro Glu Val His Pro Pro
                440                 445                 450

CTG CCC ATT TCC CAG TCC CCA GAA AAT GAG AGT AAT GAT AGG AGA       1395
Leu Pro Ile Ser Gln Ser Pro Glu Asn Glu Ser Asn Asp Arg Arg
                455                 460                 465

AGC AGA AGG TAT TCA GTG TCG GAG AGA AGT TTT GGA TCT AGA ACG       1440
Ser Arg Arg Tyr Ser Val Ser Glu Arg Ser Phe Gly Ser Arg Thr
                470                 475                 480

ACG AAA AAA TTA TCA ACT CTA CAA AGT GCC CCC CAG CAG GAG ACC       1485
Thr Lys Lys Leu Ser Thr Leu Gln Ser Ala Pro Gln Gln Glu Thr
                485                 490                 495

TCC TCG TCT CCA CCT CCA CCT CTG CTG ACT CCA CCG CCA CCA CTG       1530
Ser Ser Ser Pro Pro Pro Pro Leu Leu Thr Pro Pro Pro Pro Leu
                500                 505                 510

CAG CCA GCC TCC AGT ATC TCT GAC CAC ACA CCT TGG CTT ATG CCT       1575
Gln Pro Ala Ser Ser Ile Ser Asp His Thr Pro Trp Leu Met Pro
                515                 520                 525
```

```
CCA ACA ATC CCC TTA GCA TCA CCA TTT TTG CCT GCT TCC ACT GCT       1620
Pro Thr Ile Pro Leu Ala Ser Pro Phe Leu Pro Ala Ser Thr Ala
                530                 535                 540

CCT ATG CAA GGG AAG CGA AAA TCT ATT TTG CGA GAA CCG ACA TTT       1665
Pro Met Gln Gly Lys Arg Lys Ser Ile Leu Arg Glu Pro Thr Phe
                545                 550                 555

AGG TGG ACT TCT TTA AAG CAT TCT AGG TCA GAG CCA CAA TAC TTT       1710
Arg Trp Thr Ser Leu Lys His Ser Arg Ser Glu Pro Gln Tyr Phe
                560                 565                 570

TCC TCA GCA AAG TAT GCC AAA GAA GGT CTT ATT CGC AAA CCA ATA       1755
Ser Ser Ala Lys Tyr Ala Lys Glu Gly Leu Ile Arg Lys Pro Ile
                575                 580                 585

TTT GAT AAT TTC CGA CCC CCT CCA CTA ACT CCC GAG GAC GTT GGC       1800
Phe Asp Asn Phe Arg Pro Pro Pro Leu Thr Pro Glu Asp Val Gly
                590                 595                 600

TTT GCA TCT GGT TTT TCT GCA TCT GGT ACC GCT GCT TCA GCC CGA       1845
Phe Ala Ser Gly Phe Ser Ala Ser Gly Thr Ala Ala Ser Ala Arg
                605                 610                 615

TTG TTT TCG CCA CTC CAT TCT GGA ACA AGG TTT GAT ATG CAC AAA       1890
Leu Phe Ser Pro Leu His Ser Gly Thr Arg Phe Asp Met His Lys
                620                 625                 630

AGG AGC CCT CTT CTG AGA GCT CCA AGA TTT ACT CCA AGT GAG GCT       1935
Arg Ser Pro Leu Leu Arg Ala Pro Arg Phe Thr Pro Ser Glu Ala
                635                 640                 645

CAC TCT AGA ATA TTT GAG TCT GTA ACC TTG CCT AGT AAT CGA ACT       1980
His Ser Arg Ile Phe Glu Ser Val Thr Leu Pro Ser Asn Arg Thr
                650                 655                 660

TCT GCT GGA ACA TCT TCT TCA GGA GTA TCC AAT AGA AAA AGG AAA       2025
Ser Ala Gly Thr Ser Ser Ser Gly Val Ser Asn Arg Lys Arg Lys
                665                 670                 675

AGA AAA GTG TTT AGT CCT ATT CGA TCT GAA CCA AGA TCT CCT TCT       2070
Arg Lys Val Phe Ser Pro Ile Arg Ser Glu Pro Arg Ser Pro Ser
                680                 685                 690

CAC TCC ATG AGG ACA AGA AGT GGA AGG CTT AGT AGT TCT GAG CTC       2115
His Ser Met Arg Thr Arg Ser Gly Arg Leu Ser Ser Ser Glu Leu
                695                 700                 705

TCA CCT CTC ACC CCC CCG TCT TCT GTC TCT TCC TCG TTA AGC ATT       2160
Ser Pro Leu Thr Pro Pro Ser Ser Val Ser Ser Ser Leu Ser Ile
                710                 715                 720

TCT GTT AGT CCT CTT GCC ACT AGT GCC TTA AAC CCA ACT TTT ACT       2205
Ser Val Ser Pro Leu Ala Thr Ser Ala Leu Asn Pro Thr Phe Thr
                725                 730                 735

TTT CCT TCT CAT TCC CTG ACT CAG TCT GGG GAA TCT GCA GAG AAA       2250
Phe Pro Ser His Ser Leu Thr Gln Ser Gly Glu Ser Ala Glu Lys
                740                 745                 750

AAT CAG AGA CCA AGG AAG CAG ACT AGT GCT CCG GCA GAG CCA TTT       2295
Asn Gln Arg Pro Arg Lys Gln Thr Ser Ala Pro Ala Glu Pro Phe
                755                 760                 765

TCA TCA AGT AGT CCT ACT CCT CTC TTC CCT TGG TTT ACC CCA GGC       2340
Ser Ser Ser Ser Pro Thr Pro Leu Phe Pro Trp Phe Thr Pro Gly
                770                 775                 780

TCT CAG ACT GAA AGA GGG AGA AAT AAA GAC AAG GCC CCC GAG GAG       2385
Ser Gln Thr Glu Arg Gly Arg Asn Lys Asp Lys Ala Pro Glu Glu
                785                 790                 795

CTG TCC AAA GAT CGA GAT GCT GAC AAG AGC GTG GAG AAG GAC AAG       2430
Leu Ser Lys Asp Arg Asp Ala Asp Lys Ser Val Glu Lys Asp Lys
                800                 805                 810

AGT AGA GAG AGA GAC CGG GAG AGA GAA AAG GAG AAT AAG CGG GAG       2475
Ser Arg Glu Arg Asp Arg Glu Arg Glu Lys Glu Asn Lys Arg Glu
```

```
                        815                 820                 825

TCA AGG AAA GAG AAA AGG AAA AAG GGA TCA GAA ATT CAG AGT AGT                    2520
Ser Arg Lys Glu Lys Arg Lys Lys Gly Ser Glu Ile Gln Ser Ser
            830                 835                 840

TCT GCT TTG TAT CCT GTG GGT AGG GTT TCC AAA GAG AAG GTT GTT                    2565
Ser Ala Leu Tyr Pro Val Gly Arg Val Ser Lys Glu Lys Val Val
            845                 850                 855

GGT GAA GAT GTT GCC ACT TCA TCT TCT GCC AAA AAA GCA ACA GGG                    2610
Gly Glu Asp Val Ala Thr Ser Ser Ser Ala Lys Lys Ala Thr Gly
            860                 865                 870

CGG AAG AAG TCT TCA TCA CAT GAT TCT GGG ACT GAT ATT ACT TCT                    2655
Arg Lys Lys Ser Ser Ser His Asp Ser Gly Thr Asp Ile Thr Ser
            875                 880                 885

GTG ACT CTT GGG GAT ACA ACA GCT GTC AAA ACC AAA ATA CTT ATA                    2700
Val Thr Leu Gly Asp Thr Thr Ala Val Lys Thr Lys Ile Leu Ile
            890                 895                 900

AAG AAA GGG AGA GGA AAT CTG GAA AAA ACC AAC TTG GAC CTC GGC                    2745
Lys Lys Gly Arg Gly Asn Leu Glu Lys Thr Asn Leu Asp Leu Gly
            905                 910                 915

CCA ACT GCC CCA TCC CTG GAG AAG GAG AAA ACC CTC TGC CTT TCC                    2790
Pro Thr Ala Pro Ser Leu Glu Lys Glu Lys Thr Leu Cys Leu Ser
            920                 925                 930

ACT CCT TCA TCT AGC ACT GTT AAA CAT TCC ACT TCC TCC ATA GGC                    2835
Thr Pro Ser Ser Ser Thr Val Lys His Ser Thr Ser Ser Ile Gly
            935                 940                 945

TCC ATG TTG GCT CAG GCA GAC AAG CTT CCA ATG ACT GAC AAG AGG                    2880
Ser Met Leu Ala Gln Ala Asp Lys Leu Pro Met Thr Asp Lys Arg
            950                 955                 960

GTT GCC AGC CTC CTA AAA AAG GCC AAA GCT CAG CTC TGC AAG ATT                    2925
Val Ala Ser Leu Leu Lys Lys Ala Lys Ala Gln Leu Cys Lys Ile
            965                 970                 975

GAG AAG AGT AAG AGT CTT AAA CAA ACC GAC CAG CCC AAA GCA CAG                    2970
Glu Lys Ser Lys Ser Leu Lys Gln Thr Asp Gln Pro Lys Ala Gln
            980                 985                 990

GGT CAA GAA AGT GAC TCA TCA GAG ACC TCT GTG CGA GGA CCC CGG                    3015
Gly Gln Glu Ser Asp Ser Ser Glu Thr Ser Val Arg Gly Pro Arg
            995                 1000                1005

ATT AAA CAT GTC TGC AGA AGA GCA GCT GTT GCC CTT GGC CGA AAA                    3060
Ile Lys His Val Cys Arg Arg Ala Ala Val Ala Leu Gly Arg Lys
            1010                1015                1020

CGA GCT GTG TTT CCT GAT GAC ATG CCC ACC CTG AGT GCC TTA CCA                    3105
Arg Ala Val Phe Pro Asp Asp Met Pro Thr Leu Ser Ala Leu Pro
            1025                1030                1035

TGG GAA GAA CGA GAA AAG ATT TTG TCT TCC ATG GGG AAT GAT GAC                    3150
Trp Glu Glu Arg Glu Lys Ile Leu Ser Ser Met Gly Asn Asp Asp
            1040                1045                1050

AAG TCA TCA ATT GCT GGC TCA GAA GAT GCT GAA CCT CTT GCT CCA                    3195
Lys Ser Ser Ile Ala Gly Ser Glu Asp Ala Glu Pro Leu Ala Pro
            1055                1060                1065

CCC ATC AAA CCA ATT AAA CCT GTC ACT AGA AAC AAG GCA CCC CAG                    3240
Pro Ile Lys Pro Ile Lys Pro Val Thr Arg Asn Lys Ala Pro Gln
            1070                1075                1080

GAA CCT CCA GTA AAG AAA GGA CGT CGA TCG AGG CGG TGT GGG CAG                    3285
Glu Pro Pro Val Lys Lys Gly Arg Arg Ser Arg Arg Cys Gly Gln
            1085                1090                1095

TGT CCC GGC TGC CAG GTG CCT GAG GAC TGT GGT GTT TGT ACT AAT                    3330
Cys Pro Gly Cys Gln Val Pro Glu Asp Cys Gly Val Cys Thr Asn
            1100                1105                1110

TGC TTA GAT AAG CCC AAG TTT GGT GGT CGC AAT ATA AAG AAG CAG                    3375
```

-continued

```
Cys Leu Asp Lys Pro Lys Phe Gly Gly Arg Asn Ile Lys Lys Gln
            1115                1120                1125
TGC TGC AAG ATG AGA AAA TGT CAG AAT CTA CAA TGG ATG CCT TCC        3420
Cys Cys Lys Met Arg Lys Cys Gln Asn Leu Gln Trp Met Pro Ser
            1130                1135                1140
AAA GCC TAC CTG CAG AAG CAA GCT AAA GCT GTG AAA AAG AAA GAG        3465
Lys Ala Tyr Leu Gln Lys Gln Ala Lys Ala Val Lys Lys Lys Glu
            1145                1150                1155
AAA AAG TCT AAG ACC AGT GAA AAG AAA GAC AGC AAA GAG AGC AGT        3510
Lys Lys Ser Lys Thr Ser Glu Lys Lys Asp Ser Lys Glu Ser Ser
            1160                1165                1170
GTT GTG AAG AAC GTG GTG GAC TCT AGT CAG AAA CCT ACC CCA TCA        3555
Val Val Lys Asn Val Val Asp Ser Ser Gln Lys Pro Thr Pro Ser
            1175                1180                1185
GCA AGA GAG GAT CCT GCC CCA AAG AAA AGC AGT AGT GAG CCT CCT        3600
Ala Arg Glu Asp Pro Ala Pro Lys Lys Ser Ser Ser Glu Pro Pro
            1190                1195                1200
CCA CGA AAG CCC GTC GAG GAA AAG AGT GAA GAA GGG AAT GTC TCG        3645
Pro Arg Lys Pro Val Glu Glu Lys Ser Glu Glu Gly Asn Val Ser
            1205                1210                1215
GCC CCT GGG CCT GAA TCC AAA CAG GCC ACC ACT CCA GCT TCC AGG        3690
Ala Pro Gly Pro Glu Ser Lys Gln Ala Thr Thr Pro Ala Ser Arg
            1220                1225                1230
AAG TCA AGC AAG CAG GTC TCC CAG CCA GCA CTG GTC ATC CCG CCT        3735
Lys Ser Ser Lys Gln Val Ser Gln Pro Ala Leu Val Ile Pro Pro
            1235                1240                1245
CAG CCA CCT ACT ACA GGA CCG CCA AGA AAA GAA GTT CCC AAA ACC        3780
Gln Pro Pro Thr Thr Gly Pro Pro Arg Lys Glu Val Pro Lys Thr
            1250                1255                1260
ACT CCT AGT GAG CCC AAG AAA AAG CAG CCT CCA CCA CCA GAA TCA        3825
Thr Pro Ser Glu Pro Lys Lys Lys Gln Pro Pro Pro Pro Glu Ser
            1265                1270                1275
GGT CCA GAG CAG AGC AAA CAG AAA AAA GTG GCT CCC CGC CCA AGT        3870
Gly Pro Glu Gln Ser Lys Gln Lys Lys Val Ala Pro Arg Pro Ser
            1280                1285                1290
ATC CCT GTA AAA CAA AAA CCA AAA GAA AAG GAA AAA CCA CCT CCG        3915
Ile Pro Val Lys Gln Lys Pro Lys Glu Lys Glu Lys Pro Pro Pro
            1295                1300                1305
GTC AAT AAG CAG GAG AAT GCA GGC ACT TTG AAC ATC CTC AGC ACT        3960
Val Asn Lys Gln Glu Asn Ala Gly Thr Leu Asn Ile Leu Ser Thr
            1310                1315                1320
CTC TCC AAT GGC AAT AGT TCT AAG CAA AAA ATT CCA GCA GAT GGA        4005
Leu Ser Asn Gly Asn Ser Ser Lys Gln Lys Ile Pro Ala Asp Gly
            1325                1330                1335
GTC CAC AGG ATC AGA GTG GAC TTT AAG GAG GAT TGT GAA GCA GAA        4050
Val His Arg Ile Arg Val Asp Phe Lys Glu Asp Cys Glu Ala Glu
            1340                1345                1350
AAT GTG TGG GAG ATG GGA GGC TTA GGA ATC TTG ACT TCT GTT CCT        4095
Asn Val Trp Glu Met Gly Gly Leu Gly Ile Leu Thr Ser Val Pro
            1355                1360                1365
ATA ACA CCC AGG GTG GTT TGC TTT CTC TGT GCC AGT AGT GGG CAT        4140
Ile Thr Pro Arg Val Val Cys Phe Leu Cys Ala Ser Ser Gly His
            1370                1375                1380
GTA GAG TTT GTG TAT TGC CAA GTC TGT TGT GAG CCC TTC CAC AAG        4185
Val Glu Phe Val Tyr Cys Gln Val Cys Cys Glu Pro Phe His Lys
            1385                1390                1395
TTT TGT TTA GAG GAG AAC GAG CGC CCT CTG GAG GAC CAG CTG GAA        4230
Phe Cys Leu Glu Glu Asn Glu Arg Pro Leu Glu Asp Gln Leu Glu
            1400                1405                1410
```

```
                                                    -continued

AAT TGG TGT TGT CGT CGT TGC AAA TTC TGT CAC GTT TGT GGA AGG        4275
Asn Trp Cys Cys Arg Arg Cys Lys Phe Cys His Val Cys Gly Arg
            1415                1420                1425

CAA CAT CAG GCT ACA AAG CAG CTG CTG GAG TGT AAT AAG TGC CGA        4320
Gln His Gln Ala Thr Lys Gln Leu Leu Glu Cys Asn Lys Cys Arg
            1430                1435                1440

AAC AGC TAT CAC CCT GAG TGC CTG GGA CCA AAC TAC CCC ACC AAA        4365
Asn Ser Tyr His Pro Glu Cys Leu Gly Pro Asn Tyr Pro Thr Lys
            1445                1450                1455

CCC ACA AAG AAG AAG AAA GTC TGG ATC TGT ACC AAG TGT GTT CGC        4410
Pro Thr Lys Lys Lys Lys Val Trp Ile Cys Thr Lys Cys Val Arg
            1460                1465                1470

TGT AAG AGC TGT GGA TCC ACA ACT CCA GGC AAA GGG TGG GAT GCA        4455
Cys Lys Ser Cys Gly Ser Thr Thr Pro Gly Lys Gly Trp Asp Ala
            1475                1480                1485

CAG TGG TCT CAT GAT TTC TCA CTG TGT CAT GAT TGC GCC AAG CTC        4500
Gln Trp Ser His Asp Phe Ser Leu Cys His Asp Cys Ala Lys Leu
            1490                1495                1500

TTT GCT AAA GGA AAC TTC TGC CCT CTC TGT GAC AAA TGT TAT GAT        4545
Phe Ala Lys Gly Asn Phe Cys Pro Leu Cys Asp Lys Cys Tyr Asp
            1505                1510                1515

GAT GAT GAC TAT GAG AGT AAG ATG ATG CAA TGT GGA AAG TGT GAT        4590
Asp Asp Asp Tyr Glu Ser Lys Met Met Gln Cys Gly Lys Cys Asp
            1520                1525                1530

CGC TGG GTC CAT TCC AAA TGT GAG AAT CTT TCA GGT ACA GAA GAT        4635
Arg Trp Val His Ser Lys Cys Glu Asn Leu Ser Gly Thr Glu Asp
            1535                1540                1545

GAG ATG TAT GAG ATT CTA TCT AAT CTG CCA GAA AGT GTG GCC TAC        4680
Glu Met Tyr Glu Ile Leu Ser Asn Leu Pro Glu Ser Val Ala Tyr
            1550                1555                1560

ACT TGT GTG AAC TGT ACT GAG CGG CAC CCT GCA GAG TGG CGA CTG        4725
Thr Cys Val Asn Cys Thr Glu Arg His Pro Ala Glu Trp Arg Leu
            1565                1570                1575

GCC CTT GAA AAA GAG CTG CAG ATT TCT CTG AAG CAA GTT CTG ACA        4770
Ala Leu Glu Lys Glu Leu Gln Ile Ser Leu Lys Gln Val Leu Thr
            1580                1585                1590

GCT TTG TTG AAT TCT CGG ACT ACC AGC CAT TTG CTA CGC TAC CGG        4815
Ala Leu Leu Asn Ser Arg Thr Thr Ser His Leu Leu Arg Tyr Arg
            1595                1600                1605

CAG GCT GCC AAG CCT CCA GAC TTA AAT CCC GAG ACA GAG GAG AGT        4860
Gln Ala Ala Lys Pro Pro Asp Leu Asn Pro Glu Thr Glu Glu Ser
            1610                1615                1620

ATA CCT TCC CGC AGC TCC CCC GAA GGA CCT GAT CCA CCA GTT CTT        4905
Ile Pro Ser Arg Ser Ser Pro Glu Gly Pro Asp Pro Pro Val Leu
            1625                1630                1635

ACT GAG GTC AGC AAA CAG GAT GAT CAG CAG CCT TTA GAT CTA GAA        4950
Thr Glu Val Ser Lys Gln Asp Asp Gln Gln Pro Leu Asp Leu Glu
            1640                1645                1650

GGA GTC AAG AGG AAG ATG GAC CAA GGG AAT TAC ACA TCT GTG TTG        4995
Gly Val Lys Arg Lys Met Asp Gln Gly Asn Tyr Thr Ser Val Leu
            1655                1660                1665

GAG TTC AGT GAT GAT ATT GTG AAG ATC ATT CAA GCA GCC ATT AAT        5040
Glu Phe Ser Asp Asp Ile Val Lys Ile Ile Gln Ala Ala Ile Asn
            1670                1675                1680

TCA GAT GGA GGA CAG CCA GAA ATT AAA AAA GCC AAC AGC ATG GTC        5085
Ser Asp Gly Gly Gln Pro Glu Ile Lys Lys Ala Asn Ser Met Val
            1685                1690                1695

AAG TCC TTC TTC ATT CGG CAA ATG GAA CGT GTT TTT CCA TGG TTC        5130
Lys Ser Phe Phe Ile Arg Gln Met Glu Arg Val Phe Pro Trp Phe
            1700                1705                1710
```

```
AGT GTC AAA AAG TCC AGG TTT TGG GAG CCA AAT AAA GTA TCA AGC       5175
Ser Val Lys Lys Ser Arg Phe Trp Glu Pro Asn Lys Val Ser Ser
            1715                1720                1725

AAC AGT GGG ATG TTA CCA AAC GCA GTG CTT CCA CCT TCA CTT GAC       5220
Asn Ser Gly Met Leu Pro Asn Ala Val Leu Pro Pro Ser Leu Asp
            1730                1735                1740

CAT AAT TAT GCT CAG TGG CAG GAG CGA GAG GAA AAC AGC CAC ACT       5265
His Asn Tyr Ala Gln Trp Gln Glu Arg Glu Glu Asn Ser His Thr
            1745                1750                1755

GAG CAG CCT CCT TTA ATG AAG AAA ATC ATT CCA GCT CCC AAA CCC       5310
Glu Gln Pro Pro Leu Met Lys Lys Ile Ile Pro Ala Pro Lys Pro
            1760                1765                1770

AAA GGT CCT GGA GAA CCA GAC TCA CCA ACT CCT CTG CAT CCT CCT       5355
Lys Gly Pro Gly Glu Pro Asp Ser Pro Thr Pro Leu His Pro Pro
            1775                1780                1785

ACA CCA CCA ATT TTG AGT ACT GAT AGG AGT CGA GAA GAC AGT CCA       5400
Thr Pro Pro Ile Leu Ser Thr Asp Arg Ser Arg Glu Asp Ser Pro
            1790                1795                1800

GAG CTG AAC CCA CCC CCA GGC ATA GAA GAC AAT AGA CAG TGT GCG       5445
Glu Leu Asn Pro Pro Pro Gly Ile Glu Asp Asn Arg Gln Cys Ala
            1805                1810                1815

TTA TGT TTG ACT TAT GGT GAT GAC AGT GCT AAT GAT GCT GGT CGT       5490
Leu Cys Leu Thr Tyr Gly Asp Asp Ser Ala Asn Asp Ala Gly Arg
            1820                1825                1830

TTA CTA TAT ATT GGC CAA AAT GAG TGG ACA CAT GTA AAT TGT GCT       5535
Leu Leu Tyr Ile Gly Gln Asn Glu Trp Thr His Val Asn Cys Ala
            1835                1840                1845

TTG TGG TCA GCG GAA GTG TTT GAA GAT GAT GAC GGA TCA CTA AAG       5580
Leu Trp Ser Ala Glu Val Phe Glu Asp Asp Asp Gly Ser Leu Lys
            1850                1855                1860

AAT GTG CAT ATG GCT GTG ATC AGG GGC AAG CAG CTG AGA TGT GAA       5625
Asn Val His Met Ala Val Ile Arg Gly Lys Gln Leu Arg Cys Glu
            1865                1870                1875

TTC TGC CAA AAG CCA GGA GCC ACC GTG GGT TGC TGT CTC ACA TCC       5670
Phe Cys Gln Lys Pro Gly Ala Thr Val Gly Cys Cys Leu Thr Ser
            1880                1885                1890

TGC ACC AGC AAC TAT CAC TTC ATG TGT TCC CGA GCC AAG AAC TGT       5715
Cys Thr Ser Asn Tyr His Phe Met Cys Ser Arg Ala Lys Asn Cys
            1895                1900                1905

GTC TTT CTG GAT GAT AAA AAA GTA TAT TGC CAA CGA CAT CGG GAT       5760
Val Phe Leu Asp Asp Lys Lys Val Tyr Cys Gln Arg His Arg Asp
            1910                1915                1920

TTG ATC AAA GGC GAA GTG GTT CCT GAG AAT GGA TTT GAA GTT TTC       5805
Leu Ile Lys Gly Glu Val Val Pro Glu Asn Gly Phe Glu Val Phe
            1925                1930                1935

AGA AGA GTG TTT GTG GAC TTT GAA GGA ATC AGC TTG AGA AGG AAG       5850
Arg Arg Val Phe Val Asp Phe Glu Gly Ile Ser Leu Arg Arg Lys
            1940                1945                1950

TTT CTC AAT GGC TTG GAA CCA GAA AAT ATC CAC ATG ATG ATT GGG       5895
Phe Leu Asn Gly Leu Glu Pro Glu Asn Ile His Met Met Ile Gly
            1955                1960                1965

TCT ATG ACA ATC GAC TGC TTA GGA ATT CTA AAT GAT CTC TCC GAC       5940
Ser Met Thr Ile Asp Cys Leu Gly Ile Leu Asn Asp Leu Ser Asp
            1970                1975                1980

TGT GAA GAT AAG CTC TTT CCT ATT GGA TAT CAG TGT TCC AGG GTA       5985
Cys Glu Asp Lys Leu Phe Pro Ile Gly Tyr Gln Cys Ser Arg Val
            1985                1990                1995

TAC TGG AGC ACC ACA GAT GCT CGC AAG CGC TGT GTA TAT ACA TGC       6030
Tyr Trp Ser Thr Thr Asp Ala Arg Lys Arg Cys Val Tyr Thr Cys
```

```
            2000              2005              2010
AAG ATA GTG GAG TGC CGT CCT CCA GTC GTA GAG CCG GAT ATC AAC      6075
Lys Ile Val Glu Cys Arg Pro Pro Val Val Glu Pro Asp Ile Asn
            2015              2020              2025

AGC ACT GTT GAA CAT GAT GAA AAC AGG ACC ATT GCC CAT AGT CCA      6120
Ser Thr Val Glu His Asp Glu Asn Arg Thr Ile Ala His Ser Pro
            2030              2035              2040

ACA TCT TTT ACA GAA AGT TCA TCA AAA GAG AGT CAA AAC ACA GCT      6165
Thr Ser Phe Thr Glu Ser Ser Ser Lys Glu Ser Gln Asn Thr Ala
            2045              2050              2055

GAA ATT ATA AGT CCT CCA TCA CCA GAC CGA CCT CCT CAT TCA CAA      6210
Glu Ile Ile Ser Pro Pro Ser Pro Asp Arg Pro Pro His Ser Gln
            2060              2065              2070

ACC TCT GGC TCC TGT TAT TAT CAT GTC ATC TCA AAG GTC CCC AGG      6255
Thr Ser Gly Ser Cys Tyr Tyr His Val Ile Ser Lys Val Pro Arg
            2075              2080              2085

ATT CGA ACA CCC AGT TAT TCT CCA ACA CAG AGA TCC CCT GGC TGT      6300
Ile Arg Thr Pro Ser Tyr Ser Pro Thr Gln Arg Ser Pro Gly Cys
            2090              2095              2100

CGA CCG TTG CCT TCT GCA GGA AGT CCT ACC CCA ACC ACT CAT GAA      6345
Arg Pro Leu Pro Ser Ala Gly Ser Pro Thr Pro Thr Thr His Glu
            2105              2110              2115

ATA GTC ACA GTA GGT GAT CCT TTA CTC TCC TCT GGA CTT CGA AGC      6390
Ile Val Thr Val Gly Asp Pro Leu Leu Ser Ser Gly Leu Arg Ser
            2120              2125              2130

ATT GGC TCC AGG CGT CAC AGT ACC TCT TCC TTA TCA CCC CAG CGG      6435
Ile Gly Ser Arg Arg His Ser Thr Ser Ser Leu Ser Pro Gln Arg
            2135              2140              2145

TCC AAA CTC CGG ATA ATG TCT CCA ATG AGA ACT GGG AAT ACT TAC      6480
Ser Lys Leu Arg Ile Met Ser Pro Met Arg Thr Gly Asn Thr Tyr
            2150              2155              2160

TCT AGG AAT AAT GTT TCC TCA GTC TCC ACC ACC GGG ACC GCT ACT      6525
Ser Arg Asn Asn Val Ser Ser Val Ser Thr Thr Gly Thr Ala Thr
            2165              2170              2175

GAT CTT GAA TCA AGT GCC AAA GTA GTT GAT CAT GTC TTA GGG CCA      6570
Asp Leu Glu Ser Ser Ala Lys Val Val Asp His Val Leu Gly Pro
            2180              2185              2190

CTG AAT TCA AGT ACT AGT TTA GGG CAA AAC ACT TCC ACC TCT TCA      6615
Leu Asn Ser Ser Thr Ser Leu Gly Gln Asn Thr Ser Thr Ser Ser
            2195              2200              2205

AAT TTG CAA AGG ACA GTG GTT ACT GTA GGC AAT AAA AAC AGT CAC      6660
Asn Leu Gln Arg Thr Val Val Thr Val Gly Asn Lys Asn Ser His
            2210              2215              2220

TTG GAT GGA TCT TCA TCT TCA GAA ATG AAG CAG TCC AGT GCT TCA      6705
Leu Asp Gly Ser Ser Ser Ser Glu Met Lys Gln Ser Ser Ala Ser
            2225              2230              2235

GAC TTG GTG TCC AAG AGC TCC TCT TTA AAG GGA GAG AAG ACC AAA      6750
Asp Leu Val Ser Lys Ser Ser Ser Leu Lys Gly Glu Lys Thr Lys
            2240              2245              2250

GTG CTG AGT TCC AAG AGC TCA GAG GGA TCT GCA CAT AAT GTG GCT      6795
Val Leu Ser Ser Lys Ser Ser Glu Gly Ser Ala His Asn Val Ala
            2255              2260              2265

TAC CCT GGA ATT CCT AAA CTG GCC CCA CAG GTT CAT AAC ACA ACA      6840
Tyr Pro Gly Ile Pro Lys Leu Ala Pro Gln Val His Asn Thr Thr
            2270              2275              2280

TCT AGA GAA CTG AAT GTT AGT AAA ATC GGC TCC TTT GCT GAA CCC      6885
Ser Arg Glu Leu Asn Val Ser Lys Ile Gly Ser Phe Ala Glu Pro
            2285              2290              2295

TCT TCA GTG TCG TTT TCT TCT AAA GAG GCC CTC TCC TTC CCA CAC      6930
```

```
Ser Ser Val Ser Phe Ser Ser Lys Glu Ala Leu Ser Phe Pro His
            2300                2305                2310

CTC CAT TTG AGA GGG CAA AGG AAT GAT CGA GAC CAA CAC ACA GAT          6975
Leu His Leu Arg Gly Gln Arg Asn Asp Arg Asp Gln His Thr Asp
            2315                2320                2325

TCT ACC CAA TCA GCA AAC TCC TCT CCA GAT GAA GAT ACT GAA GTC          7020
Ser Thr Gln Ser Ala Asn Ser Ser Pro Asp Glu Asp Thr Glu Val
            2330                2335                2340

AAA ACC TTG AAG CTA TCT GGA ATG AGC AAC AGA TCA TCC ATT ATC          7065
Lys Thr Leu Lys Leu Ser Gly Met Ser Asn Arg Ser Ser Ile Ile
            2345                2350                2355

AAC GAA CAT ATG GGA TCT AGT TCC AGA GAT AGG AGA CAG AAA GGG          7110
Asn Glu His Met Gly Ser Ser Ser Arg Asp Arg Arg Gln Lys Gly
            2360                2365                2370

AAA AAA TCC TGT AAA GAA ACT TTC AAA GAA AAG CAT TCC AGT AAA          7155
Lys Lys Ser Cys Lys Glu Thr Phe Lys Glu Lys His Ser Ser Lys
            2375                2380                2385

TCT TTT TTG GAA CCT GGT CAG GTG ACA ACT GGT GAG GAA GGA AAC          7200
Ser Phe Leu Glu Pro Gly Gln Val Thr Thr Gly Glu Glu Gly Asn
            2390                2395                2400

TTG AAG CCA GAG TTT ATG GAT GAG GTT TTG ACT CCT GAG TAT ATG          7245
Leu Lys Pro Glu Phe Met Asp Glu Val Leu Thr Pro Glu Tyr Met
            2405                2410                2415

GGC CAA CGA CCA TGT AAC AAT GTT TCT TCT GAT AAG ATT GGT GAT          7290
Gly Gln Arg Pro Cys Asn Asn Val Ser Ser Asp Lys Ile Gly Asp
            2420                2425                2430

AAA GGC CTT TCT ATG CCA GGA GTC CCC AAA GCT CCA CCC ATG CAA          7335
Lys Gly Leu Ser Met Pro Gly Val Pro Lys Ala Pro Pro Met Gln
            2435                2440                2445

GTA GAA GGA TCT GCC AAG GAA TTA CAG GCA CCA CGG AAA CGC ACA          7380
Val Glu Gly Ser Ala Lys Glu Leu Gln Ala Pro Arg Lys Arg Thr
            2450                2455                2460

GTC AAA GTG ACA CTG ACA CCT CTA AAA ATG GAA AAT GAG AGT CAA          7425
Val Lys Val Thr Leu Thr Pro Leu Lys Met Glu Asn Glu Ser Gln
            2465                2470                2475

TCC AAA AAT GCC CTG AAA GAA AGT AGT CCT GCT TCC CCT TTG CAA          7470
Ser Lys Asn Ala Leu Lys Glu Ser Ser Pro Ala Ser Pro Leu Gln
            2480                2485                2490

ATA GAG TCA ACA TCT CCC ACA GAA CCA ATT TCA GCC TCT GAA AAT          7515
Ile Glu Ser Thr Ser Pro Thr Glu Pro Ile Ser Ala Ser Glu Asn
            2495                2500                2505

CCA GGA GAT GGT CCA GTG GCC CAA CCA AGC CCC AAT AAT ACC TCA          7560
Pro Gly Asp Gly Pro Val Ala Gln Pro Ser Pro Asn Asn Thr Ser
            2510                2515                2520

TGC CAG GAT TCT CAA AGT AAC AAC TAT CAG AAT CTT CCA GTA CAG          7605
Cys Gln Asp Ser Gln Ser Asn Asn Tyr Gln Asn Leu Pro Val Gln
            2525                2530                2535

GAC AGA AAC CTA ATG CTT CCA GAT GGC CCC AAA CCT CAG GAG GAT          7650
Asp Arg Asn Leu Met Leu Pro Asp Gly Pro Lys Pro Gln Glu Asp
            2540                2545                2550

GGC TCT TTT AAA AGG AGG TAT CCC CGT CGC AGT GCC CGT GCA CGT          7695
Gly Ser Phe Lys Arg Arg Tyr Pro Arg Arg Ser Ala Arg Ala Arg
            2555                2560                2565

TCT AAC ATG TTT TTT GGG CTT ACC CCA CTC TAT GGA GTA AGA TCC          7740
Ser Asn Met Phe Phe Gly Leu Thr Pro Leu Tyr Gly Val Arg Ser
            2570                2575                2580

TAT GGT GAA GAA GAC ATT CCA TTC TAC AGC AGC TCA ACT GGG AAG          7785
Tyr Gly Glu Glu Asp Ile Pro Phe Tyr Ser Ser Ser Thr Gly Lys
            2585                2590                2595
```

```
AAG CGA GGC AAG AGA TCA GCT GAA GGA CAG GTG GAT GGG GCC GAT     7830
Lys Arg Gly Lys Arg Ser Ala Glu Gly Gln Val Asp Gly Ala Asp
            2600                2605                2610

GAC TTA AGC ACT TCA GAT GAA GAC GAC TTA TAC TAT TAC AAC TTC     7875
Asp Leu Ser Thr Ser Asp Glu Asp Asp Leu Tyr Tyr Tyr Asn Phe
            2615                2620                2625

ACT AGA ACA GTG ATT TCT TCA GGT GGA GAG GAA CGA CTG GCA TCC     7920
Thr Arg Thr Val Ile Ser Ser Gly Gly Glu Glu Arg Leu Ala Ser
            2630                2635                2640

CAT AAT TTA TTT CGG GAG GAG GAA CAG TGT GAT CTT CCA AAA ATC     7965
His Asn Leu Phe Arg Glu Glu Glu Gln Cys Asp Leu Pro Lys Ile
            2645                2650                2655

TCA CAG TTG GAT GGT GTT GAT GAT GGG ACA GAG AGT GAT ACT AGT     8010
Ser Gln Leu Asp Gly Val Asp Asp Gly Thr Glu Ser Asp Thr Ser
            2660                2665                2670

GTC ACA GCC ACA ACA AGG AAA AGC AGC CAG ATT CCA AAA AGA AAT     8055
Val Thr Ala Thr Thr Arg Lys Ser Ser Gln Ile Pro Lys Arg Asn
            2675                2680                2685

GGT AAA GAA AAT GGA ACA GAG AAC TTA AAG ATT GAT AGA CCT GAA     8100
Gly Lys Glu Asn Gly Thr Glu Asn Leu Lys Ile Asp Arg Pro Glu
            2690                2695                2700

GAT GCT GGG GAG AAA GAA CAT GTC ACT AAG AGT TCT GTT GGC CAC     8145
Asp Ala Gly Glu Lys Glu His Val Thr Lys Ser Ser Val Gly His
            2705                2710                2715

AAA AAT GAG CCA AAG ATG GAT AAC TGC CAT TCT GTA AGC AGA GTT     8190
Lys Asn Glu Pro Lys Met Asp Asn Cys His Ser Val Ser Arg Val
            2720                2725                2730

AAA ACA CAG GGA CAA GAT TCC TTG GAA GCT CAG CTC AGC TCA TTG     8235
Lys Thr Gln Gly Gln Asp Ser Leu Glu Ala Gln Leu Ser Ser Leu
            2735                2740                2745

GAG TCA AGC CGC AGA GTC CAC ACA AGT ACC CCC TCC GAC AAA AAT     8280
Glu Ser Ser Arg Arg Val His Thr Ser Thr Pro Ser Asp Lys Asn
            2750                2755                2760

TTA CTG GAC ACC TAT AAT ACT GAG CTC CTG AAA TCA GAT TCA GAC     8325
Leu Leu Asp Thr Tyr Asn Thr Glu Leu Leu Lys Ser Asp Ser Asp
            2765                2770                2775

AAT AAC AAC AGT GAT GAC TGT GGG AAT ATC CTG CCT TCA GAC ATT     8370
Asn Asn Asn Ser Asp Asp Cys Gly Asn Ile Leu Pro Ser Asp Ile
            2780                2785                2790

ATG GAC TTT GTA CTA AAG AAT ACT CCA TCC ATG CAG GCT TTG GGT     8415
Met Asp Phe Val Leu Lys Asn Thr Pro Ser Met Gln Ala Leu Gly
            2795                2800                2805

GAG AGC CCA GAG TCA TCT TCA TCA GAA CTC CTG AAT CTT GGT GAA     8460
Glu Ser Pro Glu Ser Ser Ser Ser Glu Leu Leu Asn Leu Gly Glu
            2810                2815                2820

GGA TTG GGT CTT GAC AGT AAT CGT GAA AAA GAC ATG GGT CTT TTT     8505
Gly Leu Gly Leu Asp Ser Asn Arg Glu Lys Asp Met Gly Leu Phe
            2825                2830                2835

GAA GTA TTT TCT CAG CAG CTG CCT ACA ACA GAA CCT GTG GAT AGT     8550
Glu Val Phe Ser Gln Gln Leu Pro Thr Thr Glu Pro Val Asp Ser
            2840                2845                2850

AGT GTC TCT TCC TCT ATC TCA GCA GAG GAA CAG TTT GAG TTG CCT     8595
Ser Val Ser Ser Ser Ile Ser Ala Glu Glu Gln Phe Glu Leu Pro
            2855                2860                2865

CTA GAG CTA CCA TCT GAT CTG TCT GTC TTG ACC ACC CGG AGT CCC     8640
Leu Glu Leu Pro Ser Asp Leu Ser Val Leu Thr Thr Arg Ser Pro
            2870                2875                2880

ACT GTC CCC AGC CAG AAT CCC AGT AGA CTA GCT GTT ATC TCA GAC     8685
Thr Val Pro Ser Gln Asn Pro Ser Arg Leu Ala Val Ile Ser Asp
            2885                2990                2895
```

```
TCA GGG GAG AAG AGA GTA ACC ATC ACA GAA AAA TCT GTA GCC TCC         8730
Ser Gly Glu Lys Arg Val Thr Ile Thr Glu Lys Ser Val Ala Ser
            2900                2905                2910

TCT GAA AGT GAC CCA GCA CTG CTG AGC CCA GGA GTA GAT CCA ACT         8775
Ser Glu Ser Asp Pro Ala Leu Leu Ser Pro Gly Val Asp Pro Thr
            2915                2920                2925

CCT GAA GGC CAC ATG ACT CCT GAT CAT TTT ATC CAA GGA CAC ATG         8820
Pro Glu Gly His Met Thr Pro Asp His Phe Ile Gln Gly His Met
            2930                2935                2940

GAT GCA GAC CAC ATC TCT AGC CCT CCT TGT GGT TCA GTA GAG CAA         8865
Asp Ala Asp His Ile Ser Ser Pro Pro Cys Gly Ser Val Glu Gln
            2945                2950                2955

GGT CAT GGC AAC AAT CAG GAT TTA ACT AGG AAC AGT AGC ACC CCT         8910
Gly His Gly Asn Asn Gln Asp Leu Thr Arg Asn Ser Ser Thr Pro
            2960                2965                2970

GGC CTT CAG GTA CCT GTT TCC CCA ACT GTT CCC ATC CAG AAC CAG         8955
Gly Leu Gln Val Pro Val Ser Pro Thr Val Pro Ile Gln Asn Gln
            2975                2980                2985

AAG TAT GTG CCC AAT TCT ACT GAT AGT CCT GGC CCG TCT CAG ATT         9000
Lys Tyr Val Pro Asn Ser Thr Asp Ser Pro Gly Pro Ser Gln Ile
            2990                2995                3000

TCC AAT GCA GCT GTC CAG ACC ACT CCA CCC CAC CTG AAG CCA GCC         9045
Ser Asn Ala Ala Val Gln Thr Thr Pro Pro His Leu Lys Pro Ala
            3005                3010                3015

ACT GAG AAA CTC ATA GTT GTT AAC CAG AAC ATG CAG CCA CTT TAT         9090
Thr Glu Lys Leu Ile Val Val Asn Gln Asn Met Gln Pro Leu Tyr
            3020                3025                3030

GTT CTC CAA ACT CTT CCA AAT GGA GTG ACC CAA AAA ATC CAA TTG         9135
Val Leu Gln Thr Leu Pro Asn Gly Val Thr Gln Lys Ile Gln Leu
            3035                3040                3045

ACC TCT TCT GTT AGT TCT ACA CCC AGT GTG ATG GAG ACA AAT ACT         9180
Thr Ser Ser Val Ser Ser Thr Pro Ser Val Met Glu Thr Asn Thr
            3050                3055                3060

TCA GTA TTG GGA CCC ATG GGA GGT GGT CTC ACC CTT ACC ACA GGA         9225
Ser Val Leu Gly Pro Met Gly Gly Gly Leu Thr Leu Thr Thr Gly
            3065                3070                3075

CTA AAT CCA AGC TTG CCA ACT TCT CAA TCT TTG TTC CCT TCT GCT         9270
Leu Asn Pro Ser Leu Pro Thr Ser Gln Ser Leu Phe Pro Ser Ala
            3080                3085                3090

AGC AAA GGA TTG CTA CCC ATG TCT CAT CAC CAG CAC TTA CAT TCC         9315
Ser Lys Gly Leu Leu Pro Met Ser His His Gln His Leu His Ser
            3095                3100                3105

TTC CCT GCA GCT ACT CAA AGT AGT TTC CCA CCA AAC ATC AGC AAT         9360
Phe Pro Ala Ala Thr Gln Ser Ser Phe Pro Pro Asn Ile Ser Asn
            3110                3115                3120

CCT CCT TCA GGC CTG CTT ATT GGG GTT CAG CCT CCT CCG GAT CCC         9405
Pro Pro Ser Gly Leu Leu Ile Gly Val Gln Pro Pro Pro Asp Pro
            3125                3130                3135

CAA CTT TTG GTT TCA GAA TCC AGC CAG AGG ACA GAC CTC AGT ACC         9450
Gln Leu Leu Val Ser Glu Ser Ser Gln Arg Thr Asp Leu Ser Thr
            3140                3145                3150

ACA GTA GCC ACT CCA TCC TCT GGA CTC AAG AAA AGA CCC ATA TCT         9495
Thr Val Ala Thr Pro Ser Ser Gly Leu Lys Lys Arg Pro Ile Ser
            3155                3160                3165

CGT CTA CAG ACC CGA AAG AAT AAA AAA CTT GCT CCC TCT AGT ACC         9540
Arg Leu Gln Thr Arg Lys Asn Lys Lys Leu Ala Pro Ser Ser Thr
            3170                3175                3180

CCT TCA AAC ATT GCC CCT TCT GAT GTG GTT TCT AAT ATG ACA TTG         9585
Pro Ser Asn Ile Ala Pro Ser Asp Val Val Ser Asn Met Thr Leu
```

|  |  |  |  |
|---|---|---|---|
| | 3185 | 3190 | 3195 |

ATT AAC TTC ACA CCC TCC CAG CTT CCT AAT CAT CCA AGT CTG TTA        9630
Ile Asn Phe Thr Pro Ser Gln Leu Pro Asn His Pro Ser Leu Leu
        3200            3205            3210

GAT TTG GGG TCA CTT AAT ACT TCA TCT CAC CGA ACT GTC CCC AAC        9675
Asp Leu Gly Ser Leu Asn Thr Ser Ser His Arg Thr Val Pro Asn
        3215            3220            3225

ATC ATA AAA AGA TCT AAA TCT AGC ATC ATG TAT TTT GAA CCG GCA        9720
Ile Ile Lys Arg Ser Lys Ser Ser Ile Met Tyr Phe Glu Pro Ala
        3230            3235            3240

CCC CTG TTA CCA CAG AGT GTG GGA GGA ACT GCT GCC ACA GCG GCA        9765
Pro Leu Leu Pro Gln Ser Val Gly Gly Thr Ala Ala Thr Ala Ala
        3245            3250            3255

GGC ACA TCA ACA ATA AGC CAG GAT ACT AGC CAC CTC ACA TCA GGG        9810
Gly Thr Ser Thr Ile Ser Gln Asp Thr Ser His Leu Thr Ser Gly
        3260            3265            3270

TCT GTG TCT GGC TTG GCA TCC AGT TCC TCT GTC TTG AAT GTT GTA        9855
Ser Val Ser Gly Leu Ala Ser Ser Ser Ser Val Leu Asn Val Val
        3275            3280            3285

TCC ATG CAA ACT ACC ACA ACC CCT ACA AGT AGT GCG TCA GTT CCA        9900
Ser Met Gln Thr Thr Thr Thr Pro Thr Ser Ser Ala Ser Val Pro
        3290            3295            3300

GGA CAC GTC ACC TTA ACC AAC CCA AGG TTG CTT GGT ACC CCA GAT        9945
Gly His Val Thr Leu Thr Asn Pro Arg Leu Leu Gly Thr Pro Asp
        3305            3310            3315

ATT GGC TCA ATA AGC AAT CTT TTA ATC AAA GCT AGC CAG CAG AGC        9990
Ile Gly Ser Ile Ser Asn Leu Leu Ile Lys Ala Ser Gln Gln Ser
        3320            3325            3330

CTG GGG ATT CAG GAC CAG CCT GTG GCT TTA CCG CCA AGT TCA GGA        10035
Leu Gly Ile Gln Asp Gln Pro Val Ala Leu Pro Pro Ser Ser Gly
        3335            3340            3345

ATG TTT CCA CAA CTG GGG ACA TCA CAG ACC CCC TCT ACT GCT GCA        10080
Met Phe Pro Gln Leu Gly Thr Ser Gln Thr Pro Ser Thr Ala Ala
        3350            3355            3360

ATA ACA GCG GCA TCT AGC ATC TGT GTG CTC CCC TCC ACT CAG ACT        10125
Ile Thr Ala Ala Ser Ser Ile Cys Val Leu Pro Ser Thr Gln Thr
        3365            3370            3375

ACG GGC ATA ACA GCC GCT TCA CCT TCT GGG GAA GCA GAC GAA CAC        10170
Thr Gly Ile Thr Ala Ala Ser Pro Ser Gly Glu Ala Asp Glu His
        3380            3385            3390

TAT CAG CTT CAG CAT GTG AAC CAG CTC CTT GCC AGC AAA ACT GGG        10215
Tyr Gln Leu Gln His Val Asn Gln Leu Leu Ala Ser Lys Thr Gly
        3395            3400            3405

ATT CAT TCT TCC CAG CGT GAT CTT GAT TCT GCT TCA GGG CCC CAG        10260
Ile His Ser Ser Gln Arg Asp Leu Asp Ser Ala Ser Gly Pro Gln
        3410            3415            3420

GTA TCC AAC TTT ACC CAG ACG GTA GAC GCT CCT AAT AGC ATG GGA        10305
Val Ser Asn Phe Thr Gln Thr Val Asp Ala Pro Asn Ser Met Gly
        3425            3430            3435

CTG GAG CAG AAC AAG GCT TTA TCC TCA GCT GTG CAA GCC AGC CCC        10350
Leu Glu Gln Asn Lys Ala Leu Ser Ser Ala Val Gln Ala Ser Pro
        3440            3445            3450

ACC TCT CCT GGG GGT TCT CCA TCC TCT CCA TCT TCT GGA CAG CGG        10395
Thr Ser Pro Gly Gly Ser Pro Ser Ser Pro Ser Ser Gly Gln Arg
        3455            3460            3465

TCA GCA AGC CCT TCA GTG CCG GGT CCC ACT AAA CCC AAA CCA AAA        10440
Ser Ala Ser Pro Ser Val Pro Gly Pro Thr Lys Pro Lys Pro Lys
        3470            3475            3480

ACC AAA CGG TTT CAG CTG CCT CTA GAC AAA GGG AAT GGC AAG AAG        10485

-continued

```
Thr Lys Arg Phe Gln Leu Pro Leu Asp Lys Gly Asn Gly Lys Lys
              3485                3490                3495

CAC AAT GTT TCC CAT TTG CGG ACC AGT TCT TCT GAA GCA CAC ATT         10530
His Asn Val Ser His Leu Arg Thr Ser Ser Ser Glu Ala His Ile
              3500                3505                3510

CCA GAC CAA GAA ACG ACA TCC CTG ACC TCA GGC ACA GGG ACT CCA         10575
Pro Asp Gln Glu Thr Thr Ser Leu Thr Ser Gly Thr Gly Thr Pro
              3515                3520                3525

GGA GCA GAG GCT GAG CAG CAG GAT ACA GCT AGC GTG GAG CAG TCC         10620
Gly Ala Glu Ala Glu Gln Gln Asp Thr Ala Ser Val Glu Gln Ser
              3530                3535                3540

TCC CAG AAG GAG TGT GGG CAA CCT GCA GGG CAA GTC GCT GTT CTT         10665
Ser Gln Lys Glu Cys Gly Gln Pro Ala Gly Gln Val Ala Val Leu
              3545                3550                3555

CCG GAA GTT CAG GTG ACC CAA AAT CCA GCA AAT GAA CAA GAA AGT         10710
Pro Glu Val Gln Val Thr Gln Asn Pro Ala Asn Glu Gln Glu Ser
              3560                3565                3570

GCA GAA CCT AAA ACA GTG GAA GAA GAG GAA AGT AAT TTC AGC TCC         10755
Ala Glu Pro Lys Thr Val Glu Glu Glu Glu Ser Asn Phe Ser Ser
              3575                3580                3585

CCA CTG ATG CTT TGG CTT CAG CAA GAA CAA AAG CGG AAG GAA AGC         10800
Pro Leu Met Leu Trp Leu Gln Gln Glu Gln Lys Arg Lys Glu Ser
              3590                3595                3600

ATT ACT GAG AAA AAA CCC AAG AAA GGA CTT GTT TTT GAA ATT TCC         10845
Ile Thr Glu Lys Lys Pro Lys Lys Gly Leu Val Phe Glu Ile Ser
              3605                3610                3615

AGT GAT GAT GGC TTT CAG ATC TGT GCA GAA AGT ATT GAA GAT GCC         10890
Ser Asp Asp Gly Phe Gln Ile Cys Ala Glu Ser Ile Glu Asp Ala
              3620                3625                3530

TGG AAG TCA TTG ACA GAT AAA GTC CAG GAA GCT CGA TCA AAT GCC         10935
Trp Lys Ser Leu Thr Asp Lys Val Gln Glu Ala Arg Ser Asn Ala
              3535                3540                3545

CGC CTA AAG CAG CTC TCA TTT GCA GGT GTT AAC GGT TTG AGG ATG         10980
Arg Leu Lys Gln Leu Ser Phe Ala Gly Val Asn Gly Leu Arg Met
              3550                3555                3560

CTG GGG ATT CTC CAT GAT GCA GTT GTG TTC CTC ATT GAG CAG CTG         11025
Leu Gly Ile Leu His Asp Ala Val Val Phe Leu Ile Glu Gln Leu
              3565                3570                3575

TCT GGT GCC AAG CAC TGT CGA AAT TAC AAA TTC CGT TTC CAC AAG         11070
Ser Gly Ala Lys His Cys Arg Asn Tyr Lys Phe Arg Phe His Lys
              3580                3585                3590

CCA GAG GAG GCC AAT GAA CCC CCC TTG AAC CCT CAC GGC TCA GCC         11115
Pro Glu Glu Ala Asn Glu Pro Pro Leu Asn Pro His Gly Ser Ala
              3595                3600                3605

AGG GCT GAA GTC CAC CTC AGG AAG TCA GCA TTT GAC ATG TTT AAC         11160
Arg Ala Glu Val His Leu Arg Lys Ser Ala Phe Asp Met Phe Asn
              3610                3615                3620

TTC CTG GCT TCT AAA CAT CGT CAG CCT CCT GAA TAC AAC CCC AAT         11205
Phe Leu Ala Ser Lys His Arg Gln Pro Pro Glu Tyr Asn Pro Asn
              3625                3630                3635

GAT GAA GAA GAG GAG GAG GTA CAG CTG AAG TCA GCT CGG AGG GCA         11250
Asp Glu Glu Glu Glu Glu Val Gln Leu Lys Ser Ala Arg Arg Ala
              3640                3645                3650

ACT AGC ATG GAT CTG CCA ATG CCC ATG CGC TTC CGG CAC TTA AAA         11295
Thr Ser Met Asp Leu Pro Met Pro Met Arg Phe Arg His Leu Lys
              3655                3660                3665

AAG ACT TCT AAG GAG GCA GTT GGT GTC TAC AGG TCT CCC ATC CAT         11340
Lys Thr Ser Lys Glu Ala Val Gly Val Tyr Arg Ser Pro Ile His
              3670                3675                3680
```

```
GGC CGG GGT CTT TTC TGT AAG AGA AAC ATT GAT GCA GGT GAG ATG        11385
Gly Arg Gly Leu Phe Cys Lys Arg Asn Ile Asp Ala Gly Glu Met
            3685                3690                3695

GTG ATT GAG TAT GCC GGC AAC GTC ATC CGC TCC ATC CAG ACT GAC        11430
Val Ile Glu Tyr Ala Gly Asn Val Ile Arg Ser Ile Gln Thr Asp
            3700                3705                3710

AAG CGG GAA AAG TAT TAC GAC AGC AAG GGC ATT GGT TGC TAT ATG        11475
Lys Arg Glu Lys Tyr Tyr Asp Ser Lys Gly Ile Gly Cys Tyr Met
            3715                3720                3725

TTC CGA ATT GAT GAC TCA GAG GTA GTG GAT GCC ACC ATG CAT GGA        11520
Phe Arg Ile Asp Asp Ser Glu Val Val Asp Ala Thr Met His Gly
            3730                3735                3740

AAT GCT GCA CGC TTC ATC AAT CAC TCG TGT GAG CCT AAC TGC TAT        11565
Asn Ala Ala Arg Phe Ile Asn His Ser Cys Glu Pro Asn Cys Tyr
            3745                3750                3755

TCT CGG GTC ATC AAT ATT GAT GGG CAG AAG CAC ATT GTC ATC TTT        11610
Ser Arg Val Ile Asn Ile Asp Gly Gln Lys His Ile Val Ile Phe
            3760                3765                3770

GCC ATG CGT AAG ATC TAC CGA GGA GAG GAA CTC ACT TAC GAC TAT        11655
Ala Met Arg Lys Ile Tyr Arg Gly Glu Glu Leu Thr Tyr Asp Tyr
            3775                3780                3785

AAG TTC CCC ATT GAG GAT GCC AGC AAC AAG CTG CCC TGC AAC TGT        11700
Lys Phe Pro Ile Glu Asp Ala Ser Asn Lys Leu Pro Cys Asn Cys
            3790                3795                3800

GGC GCC AAG AAA TGC CGG AAG TTC CTA AAC TAA AGC TGC TCT TCT        11745
Gly Ala Lys Lys Cys Arg Lys Phe Leu Asn
            3805                3810

CCCCCAGTGT TGGAGTGCAA GGAGGCGGGG CCATCCAAAG CAACG                  11790

CTGAAGGCCT TTTCCAGCAG CTGGGAGCTC CCGGATTGCG TGGCACAGCT             11840

GAGGGGCCTC TGTGATGGCT GAGCTCTCTT ATGTCCTATA CTCACATCAG             11890

ACATGTGATC ATAGTCCCAG AGACAGAGTT GAGGTCTCGA AGAAAAGATC             11940

CATGATCGGC TTTCTCCTGG GGCCCCTCCA ATTGTTTACT GTTAGAAAGT             11990

GGGAATGGGG TCCCTAGCAG ACTTGCCTGG AAGGAGCCTA TTATAGAGGG             12040

TTGGTTATGT TGGGAGATTG GGCCTGAATT TCTCCACAGA AATAAGTTGC             12090

CATCCTCAGG TTGGCCCTTT CCCAAGCACT GTAAGTGAGT GGGTCAGCCA             12140

AAGCCCCAAA TGGAGGGTTG GTTAGATTCC TGACAGTTTG CCAGCCAGCC             12190

GCCACCTACA GCGTCTGTCG AACAAACAGA GGTCTGGTGG TTTTCCCTAC             12240

TGTCCTCCCA CTCGAGAGTT CACTTCTGGT TGGGAGACAG GATTCCTAGC             12290

ACCTCCGGTG TCAAAAGGCT GTCATGGGGT TGTGCCAATT AATTACCAAA             12340

CATTGAGCCT GCAGGCTTTG AGTGGGAGTG TTGCCCCCAG GAGCCTTATC             12390

TCAGCCAATT ACCTTTCTTG ACAGTAGGAG CGGCTTCCCT CTCCCATTCC             12440

CTCTTCACTC CCTTTTCTTC CTTTCCCCTG TCTTCATGCC ACTGCTTTCC             12490

CATGCTTCTT TCGGTTGTAG GGGAGACTGA CTGCCTGCTC AAGGACACTC             12540

CCTGCTGGGC ATAGGATGTG CCTGCAAAAA GTTCCCTGAG CCTGTAAGCA             12590

CTCCAGGTGG GGAAGTGGAC AGGAGCCATT GGTCATAACC AGACAGAATT             12640

TGGAAACATT TTCATAAAGC TCCATGGAGA GTTTTAAAGA AACATATGTA             12690

GCATGATTTT GTAGGAGAGG AAAAAGATTA TTTAAATAGG ATTTAAATCA             12740

TGCAACAACG AGAGTATCAC AGCCAGGATG ACCCTTGGGT CCCATTCCTA             12790

AGACATGGTT ACTTTATTTT CCCCTTGTTA AGACATAGGA AGACTTAATT             12840
```

-continued

| | |
|---|---|
| TTTAAACGGT CAGTGTCCAG TTGAAGGCAG AACACTAATC AGATTTCAAG | 12890 |
| GCCCACAACT TGGGGACTAG ACCACCTTAT GTTGAGGGAA CTCTGCCACC | 12940 |
| TGCGTGCAAC CCACAGCTAA AGTAAATTCA ATGACACTAC TGCCCTGATT | 12990 |
| ACTCCTTAGG ATGTGGTCAA AACAGCATCA AATGTTTCTT CTCTTCCTTT | 13040 |
| CCCCAAGACA GAGTCCTGAA CCTGTTAAAT TAAGTCATTG GATTTTACTC | 13090 |
| TGTTCTGTTT ACAGTTTACT ATTTAAGGTT TTATAAATGT AAATATATTT | 13140 |
| TGTATATTTT TCTATGAGAA GCACTTCATA GGGAGAAGCA CTTATGACAA | 13190 |
| GGCTATTTTT TAAACCGCGG TATTATCCTA ATTTAAAAGA AGATCGGTTT | 13240 |
| TTAATAATTT TTTATTTTCA TAGGATGAAG TTAGAGAAAA TATTCAGCTG | 13290 |
| TACACACAAA GTCTGGTTTT TCCTGCCCAA CTTCCCCCTG GAAGGTGTAC | 13340 |
| TTTTTGTTGT TTAATGTGTA GCTTGTTTGT GCCCTGTTGA CATAAATGTT | 13390 |
| TCCTGGGTTT GCTCTTTGAC AATAAATGGA GAAGGAAGGT CACCCAACTC | 13440 |
| CATTGGGCCA CTCCCCTCCT TCCCCTATTG AAGCTCCTCA AAAGGCTACA | 13490 |
| GTAATATCTT GATACAACAG ATTCTCTTCT TTCCCGCCTC TCTCCTTTCC | 13540 |
| GGCGCAACTT CCAGAGTGGT GGGAGACGGC AATCTTTACA TTTCCCTCAT | 13590 |
| CTTTCTTACT TCAGAGTTAG CAAACAACAA GTTGAATGGC AACTTGACAT | 13640 |
| TTTTGCATCA CCATCTGCCT CATAGGCCAC TCTTTCCTTT CCCTCTGCCC | 13690 |
| ACCAAGTCCT CATATCTGCA GAGAACCCAT TGATCACCTT GTGCCCTCTT | 13740 |
| TTGGGGCAGC CTGTTGAAAC TGAAGCACAG TCTGACCACT CACGATAAAG | 13790 |
| CAGATTTTCT CTGCCTCTGC CACAAGGTTT CAGAGTAGTG TAGTCCAAGT | 13840 |
| AGAGGGTGGG GCACCCTTTT CTCGCCGCAA GAAGCCCATT CCTATGGAAG | 13890 |
| TCTAGCAAAG CAATACGACT CAGCCCAGCA CTCTCTGCCC CAGGACTCAT | 13940 |
| GGCTCTGCTG TGCCTTCCAT CCTGGGCTCC CTTCTCTCCT GTGACCTTAA | 13990 |
| GAACTTTGTC TGGTGGCTTT GCTGGAACAT TGTCACTGTT TTCACTGTCA | 14040 |
| TGCAGGGAGC CCAGCACTGT GGCCAGGATG GCAGAGACTT CCTTGTCATC | 14090 |
| ATGGAGAAGT GCCAGCAGGG GACTGGGAAA AGCACTCTAC CCAGACCTCA | 14140 |
| CCTCCCTTCC TCCTTTTGCC CATGAACAAG ATGCAGTGGC CCTAGGGGTT | 14190 |
| CCACTAGTGT CTGCTTTCCT TTATTATTGC ACTGTGTGAG GTTTTTTTGT | 14240 |
| AAATCCTTGT ATTCC | 14255 |

(2) INFORMATION FOR SEQ ID NO: 2:

(i) SEQUENCE CHARACTERISTICS:
        (A) LENGTH: 218
        (B) TYPE: amino acid
        (D) TOPOLOGY: linear (xi) SEQUENCE DESCRIPTION: SEQ ID NO: 2:

```
Arg Ala Leu Cys Phe Leu Cys Gly Ser Thr Gly Leu Asp Pro Leu
              5                  10                  15

Ile Phe Cys Ala Cys Cys Glu Pro Tyr His Gln Tyr Cys Val
             20                  25                  30

Gln Asp Glu Tyr Asn Leu Lys His Gly Ser Phe Glu Asp Thr Thr
             35                  40                  45

Leu Met Gly Ser Leu Leu Glu Thr Thr Val Asn Ala Ser Thr Gly
```

```
                    50                  55                  60
Pro Ser Ser Ser Leu Asn Gln Leu Thr Gln Arg Leu Asn Trp Leu
                65                  70                  75

Cys Pro Arg Cys Thr Val Cys Tyr Thr Cys Asn Met Ser Ser Gly
                80                  85                  90

Ser Lys Val Lys Cys Gln Lys Cys Gln Lys Asn Tyr His Ser Thr
                95                 100                 105

Cys Leu Gly Thr Ser Lys Arg Leu Leu Gly Ala Asp Arg Pro Leu
               110                 115                 120

Ile Cys Val Asn Cys Leu Lys Cys Lys Ser Cys Ser Thr Thr Lys
               125                 130                 135

Val Ser Lys Phe Val Gly Asn Leu Pro Met Cys Thr Gly Cys Phe
               140                 145                 150

Lys Leu Arg Lys Lys Gly Asn Phe Cys Pro Ile Cys Gln Arg Cys
               155                 160                 165

Tyr Asp Asp Asn Asp Phe Asp Leu Lys Met Met Glu Cys Gly Asp
               170                 175                 180

Cys Gly Gln Trp Val His Ser Lys Cys Glu Gly Leu Ser Asp Glu
               185                 190                 195

Gln Tyr Asn Leu Leu Ser Thr Leu Pro Glu Ser Ile Glu Phe Ile
               200                 205                 210

Cys Lys Lys Cys Ala Arg Arg Asn
               215

(2) INFORMATION FOR SEQ ID NO: 3:

(i) SEQUENCE CHARACTERISTICS:
        (A) LENGTH: 109
        (B) TYPE: amino acid
        (D) TOPOLOGY: linear (xi) SEQUENCE DESCRIPTION: SEQ ID NO: 3:

Asp Thr Arg Met Cys Leu Phe Cys Arg Lys Ser Gly Glu Gly Leu
                 5                  10                  15

Ser Gly Glu Glu Ala Arg Leu Leu Tyr Cys Gly His Asp Cys Trp
                20                  25                  30

Val His Thr Asn Cys Ala Met Trp Ser Ala Glu Val Phe Glu Glu
                35                  40                  45

Ile Asp Gly Ser Leu Gln Asn Val His Ser Ala Val Ala Arg Gly
                50                  55                  60

Arg Met Ile Lys Cys Thr Val Cys Gly Asn Arg Gly Ala Thr Val
                65                  70                  75

Gly Cys Asn Val Arg Ser Cys Gly Glu His Tyr His Tyr Pro Cys
                80                  85                  90

Ala Arg Ser Ile Asp Cys Ala Phe Leu Thr Asp Lys Ser Met Tyr
                95                 100                 105

Cys Pro Ala His
           109

(2) INFORMATION FOR SEQ ID NO: 4:

(i) SEQUENCE CHARACTERISTICS:
        (A) LENGTH: 210
        (B) TYPE: amino acid
        (D) TOPOLOGY: linear (xi) SEQUENCE DESCRIPTION: SEQ ID NO: 4:
```

```
Glu Leu Glu Glu Asn Ala Tyr Asp Cys Ala Arg Cys Glu Pro Tyr
                  5                  10                 15

Ser Asn Arg Ser Glu Tyr Asp Met Phe Ser Trp Leu Ala Ser Arg
                 20                  25                 30

His Arg Lys Gln Pro Ile Gln Val Phe Val Gln Pro Ser Asp Asn
                 35                  40                 45

Glu Leu Val Pro Arg Arg Gly Thr Gly Ser Asn Leu Pro Met Ala
                 50                  55                 60

Met Lys Tyr Arg Thr Leu Lys Glu Thr Tyr Lys Asp Tyr Val Gly
                 65                  70                 75

Val Phe Arg Ser His Ile His Gly Arg Gly Leu Tyr Cys Thr Lys
                 80                  85                 90

Asp Ile Glu Ala Gly Glu Met Val Ile Glu Tyr Ala Gly Glu Leu
                 95                 100                105

Ile Arg Ser Thr Leu Thr Asp Lys Arg Glu Arg Tyr Tyr Asp Ser
                110                 115                120

Arg Gly Ile Gly Cys Tyr Met Phe Lys Ile Asp Asp Asn Leu Val
                125                 130                135

Val Asp Ala Thr Met Arg Gly Asn Ala Ala Arg Phe Ile Asn His
                140                 145                150

Cys Cys Glu Pro Asn Cys Tyr Ser Lys Val Val Asp Ile Leu Gly
                155                 160                165

His Lys His Ile Ile Ile Phe Ala Val Arg Arg Ile Val Gln Gly
                170                 175                180

Glu Glu Leu Thr Tyr Asp Tyr Lys Phe Pro Phe Glu Asp Glu Lys
                185                 190                195

Ile Pro Cys Ser Cys Gly Ser Lys Arg Cys Arg Lys Tyr Leu Asn
                200                 205                210

(2) INFORMATION FOR SEQ ID NO: 5:

(i) SEQUENCE CHARACTERISTICS:
        (A) LENGTH: 17
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 5:

TGAATTTTTT AGGTCCA                                                     17

(2) INFORMATION FOR SEQ ID NO: 6:

(i) SEQUENCE CHARACTERISTICS:
        (A) LENGTH: 16
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 6:

GAAAAGGTGA GGAGAG                                                      16

(2) INFORMATION FOR SEQ ID NO: 7:

(i) SEQUENCE CHARACTERISTICS:
        (A) LENGTH: 18
        (B) TYPE: nucleic acid
        (C) STRANDEDNESS: single
```

(D) TOPOLOGY: linear (iv) ANTI-SENSE: No (xi) SEQUENCE DESCRIPTION: SEQ ID NO: 7:

TTGGCTCCTT CGGAAAAA                                                18

(2) INFORMATION FOR SEQ ID NO: 8:

(i) SEQUENCE CHARACTERISTICS:
        (A) LENGTH: 16
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 8:

TTTAAGGTAA AGGTGT                                                  16

(2) INFORMATION FOR SEQ ID NO: 9:

(i) SEQUENCE CHARACTERISTICS:
        (A) LENGTH: 18
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 9:

CTCTCTCCAC AGGAGGAT                                                18

(2) INFORMATION FOR SEQ ID NO: 10:

(i) SEQUENCE CHARACTERISTICS:
        (A) LENGTH: 16
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 10:

ATAGAGGTAA GGCATC                                                  16

(2) INFORMATION FOR SEQ ID NO: 11:

(i) SEQUENCE CHARACTERISTICS:
        (A) LENGTH: 18
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 11:

TTCTTACTAT AGTTTGTG                                                18

(2) INFORMATION FOR SEQ ID NO: 12:

(i) SEQUENCE CHARACTERISTICS:
        (A) LENGTH: 16
        (B) TYPE: nucleic acid
        (C) STRANDEDNESS: single
        (D) TOPOLOGY: linear (iv) ANTI-SENSE: No

```
        (xi) SEQUENCE DESCRIPTION:  SEQ ID NO: 12:

ACAAAGGTAC AAAACT                                                16

(2) INFORMATION FOR SEQ ID NO: 13:

(i) SEQUENCE CHARACTERISTICS:
         (A) LENGTH: 18
         (B) TYPE: nucleic acid
         (C) STRANDEDNESS: single
         (D) TOPOLOGY: linear (iv) ANTI-SENSE:  No (xi) SEQUENCE DESCRIPTION:  SEQ ID NO: 13:

ATTTTCTTAC AGCAGCTG                                              18

(2) INFORMATION FOR SEQ ID NO: 14:

(i) SEQUENCE CHARACTERISTICS:
         (A) LENGTH: 16
         (B) TYPE: nucleic acid
         (C) STRANDEDNESS: single
         (D) TOPOLOGY: linear (iv) ANTI-SENSE:  No (xi) SEQUENCE DESCRIPTION:  SEQ ID NO: 14:

GTCTGGGTGA GTTATA                                                16

(2) INFORMATION FOR SEQ ID NO: 15:

(i) SEQUENCE CHARACTERISTICS:
         (A) LENGTH: 18
         (B) TYPE: nucleic acid
         (C) STRANDEDNESS: single
         (D) TOPOLOGY: linear (iv) ANTI-SENSE:  No (xi) SEQUENCE DESCRIPTION:  SEQ ID NO: 15:

CTTCTTTTCT AGATCTGT                                              18

(2) INFORMATION FOR SEQ ID NO: 16:

(i) SEQUENCE CHARACTERISTICS:
         (A) LENGTH: 14
         (B) TYPE: nucleic acid
         (C) STRANDEDNESS: single
         (D) TOPOLOGY: linear (iv) ANTI-SENSE:  No (xi) SEQUENCE DESCRIPTION:  SEQ ID NO: 16:

AAAGGTACCC AAAA                                                  14

(2) INFORMATION FOR SEQ ID NO: 17:

(i) SEQUENCE CHARACTERISTICS:
         (A) LENGTH: 17
         (B) TYPE: nucleic acid
         (C) STRANDEDNESS: single
         (D) TOPOLOGY: linear (iv) ANTI-SENSE:  No (xi) SEQUENCE DESCRIPTION:  SEQ ID NO: 17:

CTTTGCTTTC AGGAAAC                                               17
```

(2) INFORMATION FOR SEQ ID NO: 18:

(i) SEQUENCE CHARACTERISTICS:
        (A) LENGTH: 14
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 18:

```
GAAGGTTGGA GTCT                                                         14
```

(2) INFORMATION FOR SEQ ID NO: 19:

(i) SEQUENCE CHARACTERISTICS:
        (A) LENGTH: 189
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 19:

```
GTT GCA ATG CAG CAG AAG CCC ACG GCT TAT GTC CGG CCC ATG GAT             45
Val Ala Met Gln Gln Lys Pro Thr Ala Tyr Val Arg Pro Met Asp
              5                  10                  15

GGT CAA GAT CAG GCC CCT AGT GAA TCC CCT GAA CTG AAA CCA CTG             90
Gly Gln Asp Gln Ala Pro Ser Glu Ser Pro Glu Leu Lys Pro Leu
             20                  25                  30

CCG GAG GAC TAT CGA CAG CAG ACC TTT GAA AAA ACA GAC TTG AAA            135
Pro Glu Asp Tyr Arg Gln Gln Thr Phe Glu Lys Thr Asp Leu Lys
             35                  40                  45

GTG CCT GCC AAA GCC AAG CTC ACC AAA CTG AAG ATG CCT TCT CAG            180
Val Pro Ala Lys Ala Lys Leu Thr Lys Leu Lys Met Pro Ser Gln
             50                  55                  60

TCA GTT GAG                                                            189
Ser Val Glu
        63
```

(2) INFORMATION FOR SEQ ID NO: 20:

(i) SEQUENCE CHARACTERISTICS:
        (A) LENGTH: 147
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 20:

```
TTT GTG TAT TGC CAA GTC TGT TGT GAG CCC TTC CAC AAG TTT TGT             45
Phe Val Tyr Cys Gln Val Cys Cys Glu Pro Phe His Lys Phe Cys
              5                  10                  15

TTA GAG GAG AAC GAG CGC CCT CTG GAG GAC CAG CTG GAA AAT TGG             90
Leu Glu Glu Asn Glu Arg Pro Leu Glu Asp Gln Leu Glu Asn Trp
             20                  25                  30

TGT TGT CGT CGT TGC AAA TTC TGT CAC GTT TGT GGA AGG CAA CAT            135
Cys Cys Arg Arg Cys Lys Phe Cys His Val Cys Gly Arg Gln His
             35                  40                  45

CAG GCT ACA AAG                                                        147
Gln Ala Thr Lys
        49
```

(2) INFORMATION FOR SEQ ID NO: 21:

(i) SEQUENCE CHARACTERISTICS:
            (A) LENGTH: 132
            (B) TYPE: nucleic acid
            (C) STRANDEDNESS: single
            (D) TOPOLOGY: linear (iv) ANTI-SENSE: No (xi) SEQUENCE DESCRIPTION: SEQ ID NO: 21:

GAA AAA CCA CCT CCG GTC AAT AAG CAG GAG AAT GCA GGC ACT TTG            45
Glu Lys Pro Pro Pro Val Asn Lys Gln Glu Asn Ala Gly Thr Leu
                 5                  10                  15

AAC ATC TTC AGC ACT CTC TCC AAT GGC AAT AGT TCT AAG CAA AAA            90
Asn Ile Phe Ser Thr Leu Ser Asn Gly Asn Ser Ser Lys Gln Lys
                20                  25                  30

ATT CCA GCA GAT GGA GTC CAC AGG ATC AGA GTG GAC TTT AAG               132
Ile Pro Ala Asp Gly Val His Arg Ile Arg Val Asp Phe Lys
                35                  40

(2) INFORMATION FOR SEQ ID NO: 22:

(i) SEQUENCE CHARACTERISTICS:
            (A) LENGTH: 270
            (B) TYPE: nucleic acid
            (C) STRANDEDNESS: single
            (D) TOPOLOGY: linear (iv) ANTI-SENSE: No (xi) SEQUENCE DESCRIPTION: SEQ ID NO: 22:

ACC TAC TCC AAT GAA GTC CAT TGT GTT GAA GAG ATT CTG AAG GAA            45
Thr Tyr Ser Asn Glu Val His Cys Val Glu Glu Ile Leu Lys Glu
                 5                  10                  15

ATG ACC CAT TCA TGG CCG CCT CCT TTG ACA GCA ATA CAT ACG CCT            90
Met Thr His Ser Trp Pro Pro Pro Leu Thr Ala Ile His Thr Pro
                20                  25                  30

AGT ACA GCT GAG CCA TCC AAG TTT CCT TTC CCT ACA AAG GAC TCT           135
Ser Thr Ala Glu Pro Ser Lys Phe Pro Phe Pro Thr Lys Asp Ser
                35                  40                  45

CAG CAT GTC AGT TCT GTA ACC CAA AAC CAA AAA CAA TAT GAT ACA           180
Gln His Val Ser Ser Val Thr Gln Asn Gln Lys Gln Tyr Asp Thr
                50                  55                  60

TCT TCA AAA ACT CAC TCA AAT TCT CAG CAA GGA ACG TCA TCC ATG           225
Ser Ser Lys Thr His Ser Asn Ser Gln Gln Gly Thr Ser Ser Met
                65                  70                  75

CTC GAA GAC GAC CTT CAG CTC AGT GAC AGT GAG GAC AGT GAC AGT           270
Leu Glu Asp Asp Leu Gln Leu Ser Asp Ser Glu Asp Ser Asp Ser
                80                  85                  90

(2) INFORMATION FOR SEQ ID NO: 23:

(i) SEQUENCE CHARACTERISTICS:
            (A) LENGTH: 336
            (B) TYPE: nucleic acid
            (C) STRANDEDNESS: single
            (D) TOPOLOGY: linear (iv) ANTI-SENSE: No (xi) SEQUENCE DESCRIPTION: SEQ ID NO: 23:

GTT GCA ATG CAG CAG AAG CCC ACG GCT TAT GTC CGG CCC ATG GAT            45
Val Ala Met Gln Gln Lys Pro Thr Ala Tyr Val Arg Pro Met Asp
                 5                  10                  15

GGT CAA GAT CAG GCC CCT AGT GAA TCC CCT GAA CTG AAA CCA CTG            90
Gly Gln Asp Gln Ala Pro Ser Glu Ser Pro Glu Leu Lys Pro Leu
                20                  25                  30

```
CCG GAG GAC TAT CGA CAG CAG ACC TTT GAA AAA ACA GAC TTG AAA          135
Pro Glu Asp Tyr Arg Gln Gln Thr Phe Glu Lys Thr Asp Leu Lys
                35                  40                  45

GTG CCT GCC AAA GCC AAG CTC ACC AAA CTG AAG ATG CCT TCT CAG          180
Val Pro Ala Lys Ala Lys Leu Thr Lys Leu Lys Met Pro Ser Gln
            50                  55                  60

TCA GTT GAG TTT GTG TAT TGC CAA GTC TGT TGT GAG CCC TTC CAC          225
Ser Val Glu Phe Val Tyr Cys Gln Val Cys Cys Glu Pro Phe His
                65                  70                  75

AAG TTT TGT TTA GAG GAG AAC GAG CGC CCT CTG GAG GAC CAG CTG          270
Lys Phe Cys Leu Glu Glu Asn Glu Arg Pro Leu Glu Asp Gln Leu
            80                  85                  90

GAA AAT TGG TGT TGT CGT CGT TGC AAA TTC TGT CAC GTT TGT GGA          315
Glu Asn Trp Cys Cys Arg Arg Cys Lys Phe Cys His Val Cys Gly
                95                  100                 105

AGG CAA CAT CAG GCT ACA AAG                                          336
Arg Gln His Gln Ala Thr Lys
            110

(2) INFORMATION FOR SEQ ID NO: 24:

(i) SEQUENCE CHARACTERISTICS:
        (A) LENGTH: 402
        (B) TYPE: nucleic acid
        (C) STRANDEDNESS: single
        (D) TOPOLOGY: linear (iv) ANTI-SENSE: No (xi) SEQUENCE DESCRIPTION: SEQ ID NO: 24:

GAA AAA CCA CCT CCG GTC AAT AAG CAG GAG AAT GCA GGC ACT TTG           45
Glu Lys Pro Pro Pro Val Asn Lys Gln Glu Asn Ala Gly Thr Leu
                5                   10                  15

AAC ATC TTC AGC ACT CTC TCC AAT GGC AAT AGT TCT AAG CAA AAA           90
Asn Ile Phe Ser Thr Leu Ser Asn Gly Asn Ser Ser Lys Gln Lys
            20                  25                  30

ATT CCA GCA GAT GGA GTC CAC AGG ATC AGA GTG GAC TTT AAG ACC          135
Ile Pro Ala Asp Gly Val His Arg Ile Arg Val Asp Phe Lys Thr
                35                  40                  45

TAC TCC AAT GAA GTC CAT TGT GTT GAA GAG ATT CTG AAG GAA ATG          180
Tyr Ser Asn Glu Val His Cys Val Glu Glu Ile Leu Lys Glu Met
            50                  55                  60

ACC CAT TCA TGG CCG CCT CCT TTG ACA GCA ATA CAT ACG CCT AGT          225
Thr His Ser Trp Pro Pro Pro Leu Thr Ala Ile His Thr Pro Ser
                65                  70                  75

ACA GCT GAG CCA TCC AAG TTT CCT TTC CCT ACA AAG GAC TCT CAG          270
Thr Ala Glu Pro Ser Lys Phe Pro Phe Pro Thr Lys Asp Ser Gln
            80                  85                  90

CAT GTC AGT TCT GTA ACC CAA AAC CAA AAA CAA TAT GAT ACA TCT          315
His Val Ser Ser Val Thr Gln Asn Gln Lys Gln Tyr Asp Thr Ser
                95                  100                 105

TCA AAA ACT CAC TCA AAT TCT CAG CAA GGA ACG TCA TCC ATG CTC          360
Ser Lys Thr His Ser Asn Ser Gln Gln Gly Thr Ser Ser Met Leu
            110                 115                 120

GAA GAC GAC CTT CAG CTC AGT GAC AGT GAG GAC AGT GAC AGT              402
Glu Asp Asp Leu Gln Leu Ser Asp Ser Glu Asp Ser Asp Ser
                125                 130

(2) INFORMATION FOR SEQ ID NO:25:

(i) SEQUENCE CHARACTERISTICS:
        (A) LENGTH: 9391 base pairs
```

-continued (B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 421..4053

(xi) SEQUENCE DESCRIPTION: SEQ ID NO:25:

```
GGCAATTTCT TTTCCTTTCT AACTGTGGCC CGCGTTGTGC TGTTGCTGGG CAGGCGTTGG      60

GCGCCGGCGG TCTTCGAGCG TGGGGGCCCG CTGGCTTTCC CTTCTCAGAA ACTGCGCCGG     120

GGGCGCTCGC TTGCCCCGGA TTCGGACGCG GCGCTCCCCG GGCTCGTCTG AAGTGCAGAT     180

CGCCGCAGAG GCCCCAGTGC CCGGATGTCC ATCAGGATTA GCGCGAGCCA ATACGGGCCG     240

AGCCCGGGGC TGCGCCGAGG ACGCCCGGGG CTCGAGAGCA GGTAGTCCCG TAACATCGGG     300

GCGCCGCGCC GGGACGCGTC CCCGCCCGGC TCCGCCAAAT GGTGAGCGCG GCGCTGGCAG     360

CAGGGCCCGC GGGGTGAAGG CGCTCATGGA CGGAAGACCC CTGGCTCTAT AAGCTGAATT     420

ATG GCA GCC CAG TCA AGT TTG TAC AAT GAC GAC AGA AAC CTG CTT CGA      468
Met Ala Ala Gln Ser Ser Leu Tyr Asn Asp Asp Arg Asn Leu Leu Arg
  1               5                  10                  15

ATT AGA GAG AAG GAA AGA CGC AAC CAG GAA GCC CAC CAA GAG AAA GAG      516
Ile Arg Glu Lys Glu Arg Arg Asn Gln Glu Ala His Gln Glu Lys Glu
             20                  25                  30

GCA TTT CCT GAA AAG ATT CCC CTT TTT GGA GAG CCC TAC AAG ACA GCA      564
Ala Phe Pro Glu Lys Ile Pro Leu Phe Gly Glu Pro Tyr Lys Thr Ala
         35                  40                  45

AAA GGT GAT GAG CTG TCT AGT CGA ATA CAG AAC ATG TTG GGA AAC TAC      612
Lys Gly Asp Glu Leu Ser Ser Arg Ile Gln Asn Met Leu Gly Asn Tyr
     50                  55                  60

GAA GAA GTG AAG GAG TTC CTT AGT ACT AAG TCT CAC ACT CAT CGC CTG      660
Glu Glu Val Lys Glu Phe Leu Ser Thr Lys Ser His Thr His Arg Leu
 65                  70                  75                  80

GAT GCT TCT GAA AAT AGG TTG GGA AAG CCG AAA TAT CCT TTA ATT CCT      708
Asp Ala Ser Glu Asn Arg Leu Gly Lys Pro Lys Tyr Pro Leu Ile Pro
                 85                  90                  95

GAC AAA GGG AGC AGC ATT CCA TCC AGC TCC TTC CAC ACT AGT GTC CAC      756
Asp Lys Gly Ser Ser Ile Pro Ser Ser Ser Phe His Thr Ser Val His
            100                 105                 110

CAC CAG TCC ATT CAC ACT CCT GCG TCT GGA CCA CTT TCT GTT GGC AAC      804
His Gln Ser Ile His Thr Pro Ala Ser Gly Pro Leu Ser Val Gly Asn
        115                 120                 125

ATT AGC CAC AAT CCA AAG ATG GCG CAG CCA AGA ACT GAA CCA ATG CCA      852
Ile Ser His Asn Pro Lys Met Ala Gln Pro Arg Thr Glu Pro Met Pro
    130                 135                 140

AGT CTC CAT GCC AAA AGC TGC GGC CCA CCG GAC AGC CAG CAC CTG ACC      900
Ser Leu His Ala Lys Ser Cys Gly Pro Pro Asp Ser Gln His Leu Thr
145                 150                 155                 160

CAG GAT CGC CTT GGT CAG GAG GGG TTC GGC TCT AGT CAT CAC AAG AAA      948
Gln Asp Arg Leu Gly Gln Glu Gly Phe Gly Ser Ser His His Lys Lys
                165                 170                 175

GGT GAC CGA AGA GCT GAC GGA GAC CAC TGT GCT TCG GTG ACA GAT TCG      996
Gly Asp Arg Arg Ala Asp Gly Asp His Cys Ala Ser Val Thr Asp Ser
            180                 185                 190

GCT CCA GAG AGG GAG CTT TCT CCC TTA ATC TCT TTG CCT TCC CCA GTT     1044
Ala Pro Glu Arg Glu Leu Ser Pro Leu Ile Ser Leu Pro Ser Pro Val
        195                 200                 205

CCC CCT TTG TCA CCT ATA CAT TCC AAC CAG CAA ACT CTT CCC CGG ACG     1092
```

```
                                              -continued

Pro Pro Leu Ser Pro Ile His Ser Asn Gln Gln Thr Leu Pro Arg Thr
    210                 215                 220

CAA GGA AGC AGC AAG GTT CAT GGC AGC AGC AAT AAC AGT AAA GGC TAT     1140
Gln Gly Ser Ser Lys Val His Gly Ser Ser Asn Asn Ser Lys Gly Tyr
225                 230                 235                 240

TGC CCA GCC AAA TCT CCC AAG GAC CTA GCA GTG AAA GTC CAT GAT AAA     1188
Cys Pro Ala Lys Ser Pro Lys Asp Leu Ala Val Lys Val His Asp Lys
                245                 250                 255

GAG ACC CCT CAA GAC AGT TTG GTG GCC CCT GCC CAG CCG CCT TCT CAG     1236
Glu Thr Pro Gln Asp Ser Leu Val Ala Pro Ala Gln Pro Pro Ser Gln
                260                 265                 270

ACA TTT CCA CCT CCC TCC CTC CCC TCA AAA AGT GTT GCA ATG CAG CAG     1284
Thr Phe Pro Pro Pro Ser Leu Pro Ser Lys Ser Val Ala Met Gln Gln
            275                 280                 285

AAG CCC ACG GCT TAT GTC CGG CCC ATG GAT GGT CAA GAT CAG GCC CCT     1332
Lys Pro Thr Ala Tyr Val Arg Pro Met Asp Gly Gln Asp Gln Ala Pro
        290                 295                 300

AGT GAA TCC CCT GAA CTG AAA CCA CTG CCG GAG GAC TAT CGA CAG CAG     1380
Ser Glu Ser Pro Glu Leu Lys Pro Leu Pro Glu Asp Tyr Arg Gln Gln
305                 310                 315                 320

ACC TTT GAA AAA ACA GAC TTG AAA GTG CCT GCC AAA GCC AAG CTC ACC     1428
Thr Phe Glu Lys Thr Asp Leu Lys Val Pro Ala Lys Ala Lys Leu Thr
                325                 330                 335

AAA CTG AAG ATG CCT TCT CAG TCA GTT GAG CAG ACC TAC TCC AAT GAA     1476
Lys Leu Lys Met Pro Ser Gln Ser Val Glu Gln Thr Tyr Ser Asn Glu
                340                 345                 350

GTC CAT TGT GTT GAA GAG ATT CTG AAG GAA ATG ACC CAT TCA TGG CCG     1524
Val His Cys Val Glu Glu Ile Leu Lys Glu Met Thr His Ser Trp Pro
            355                 360                 365

CCT CCT TTG ACA GCA ATA CAT ACG CCT AGT ACA GCT GAG CCA TCC AAG     1572
Pro Pro Leu Thr Ala Ile His Thr Pro Ser Thr Ala Glu Pro Ser Lys
        370                 375                 380

TTT CCT TTC CCT ACA AAG GAC TCT CAG CAT GTC AGT TCT GTA ACC CAA     1620
Phe Pro Phe Pro Thr Lys Asp Ser Gln His Val Ser Ser Val Thr Gln
385                 390                 395                 400

AAC CAA AAA CAA TAT GAT ACA TCT TCA AAA ACT CAC TCA AAT TCT CAG     1668
Asn Gln Lys Gln Tyr Asp Thr Ser Ser Lys Thr His Ser Asn Ser Gln
                405                 410                 415

CAA GGA ACG TCA TCC ATG CTC GAA GAC GAC CTT CAG CTC AGT GAC AGT     1716
Gln Gly Thr Ser Ser Met Leu Glu Asp Asp Leu Gln Leu Ser Asp Ser
                420                 425                 430

GAG GAC AGT GAC AGT GAA CAA ACC CCA GAG AAG CCT CCC TCC TCA TCT     1764
Glu Asp Ser Asp Ser Glu Gln Thr Pro Glu Lys Pro Pro Ser Ser Ser
            435                 440                 445

GCA CCT CCA AGT GCT CCA CAG TCC CTT CCA GAA CCA GTG GCA TCA GCA     1812
Ala Pro Pro Ser Ala Pro Gln Ser Leu Pro Glu Pro Val Ala Ser Ala
        450                 455                 460

CAT TCC AGC AGT GCA GAG TCA GAA AGC ACC AGT GAC TCA GAC AGT TCC     1860
His Ser Ser Ser Ala Glu Ser Glu Ser Thr Ser Asp Ser Asp Ser Ser
465                 470                 475                 480

TCA GAC TCA GAG AGC GAG AGC AGT TCA AGT GAC AGC GAA GAA AAT GAG     1908
Ser Asp Ser Glu Ser Glu Ser Ser Ser Asp Ser Glu Glu Asn Glu
                485                 490                 495

CCC CTA GAA ACC CCA GCT CCG GAG CCT GAG CCT CCA ACA ACA AAC AAA     1956
Pro Leu Glu Thr Pro Ala Pro Glu Pro Glu Pro Pro Thr Thr Asn Lys
                500                 505                 510

TGG CAG CTG GAC AAC TGG CTG ACC AAA GTC AGC CAG CCA GCT GCG CCA     2004
Trp Gln Leu Asp Asn Trp Leu Thr Lys Val Ser Gln Pro Ala Ala Pro
            515                 520                 525
```

```
CCA GAG GGC CCC AGG AGC ACA GAG CCC CCA CGG CGG CAC CCA GAG AGT       2052
Pro Glu Gly Pro Arg Ser Thr Glu Pro Pro Arg Arg His Pro Glu Ser
        530                 535                 540

AAG GGC AGC AGC GAC AGT GCC ACG AGT CAG GAG CAT TCT GAA TCC AAA       2100
Lys Gly Ser Ser Asp Ser Ala Thr Ser Gln Glu His Ser Glu Ser Lys
545                 550                 555                 560

GAT CCT CCC CCT AAA AGC TCC AGC AAA GCC CCC CGG GCC CCA CCC GAA       2148
Asp Pro Pro Pro Lys Ser Ser Ser Lys Ala Pro Arg Ala Pro Pro Glu
                565                 570                 575

GCC CCC CAC CCC GGA AAG AGG AGC TGT CAG AAG TCT CCG GCA CAG CAG       2196
Ala Pro His Pro Gly Lys Arg Ser Cys Gln Lys Ser Pro Ala Gln Gln
            580                 585                 590

GAG CCC CCA CAA AGG CAA ACC GTT GGA ACC AAA CAA CCC AAA AAA CCT       2244
Glu Pro Pro Gln Arg Gln Thr Val Gly Thr Lys Gln Pro Lys Lys Pro
        595                 600                 605

GTC AAG GCC TCT GCC CGG GCA GGT TCA CGG ACC AGC CTG CAG GGG GAA       2292
Val Lys Ala Ser Ala Arg Ala Gly Ser Arg Thr Ser Leu Gln Gly Glu
    610                 615                 620

AGG GAG CCA GGG CTT CTT CCC TAT GGC TCC CGA GAC CAG ACT TCC AAA       2340
Arg Glu Pro Gly Leu Leu Pro Tyr Gly Ser Arg Asp Gln Thr Ser Lys
625                 630                 635                 640

GAC AAG CCC AAG GTG AAG ACG AAA GGA CGG CCC CGG GCC GCA GCA AGC       2388
Asp Lys Pro Lys Val Lys Thr Lys Gly Arg Pro Arg Ala Ala Ala Ser
                645                 650                 655

AAC GAA CCC AAG CCA GCA GTG CCC CCC TCC AGT GAG AAG AAG AAG CAC       2436
Asn Glu Pro Lys Pro Ala Val Pro Pro Ser Ser Glu Lys Lys Lys His
            660                 665                 670

AAG AGC TCC CTC CCT GCC CCC TCT AAG GCT CTC TCA GGC CCA GAA CCC       2484
Lys Ser Ser Leu Pro Ala Pro Ser Lys Ala Leu Ser Gly Pro Glu Pro
        675                 680                 685

GCG AAG GAC AAT GTG GAG GAC AGG ACC CCT GAG CAC TTT GCT CTT GTT       2532
Ala Lys Asp Asn Val Glu Asp Arg Thr Pro Glu His Phe Ala Leu Val
    690                 695                 700

CCC CTG ACT GAG AGC CAG GGC CCA CCC CAC AGT GGC AGC GGC AGC AGG       2580
Pro Leu Thr Glu Ser Gln Gly Pro Pro His Ser Gly Ser Gly Ser Arg
705                 710                 715                 720

ACT AGT GGC TGC CGC CAA GCC GTG GTG GTC CAG GAG GAC AGC CGC AAA       2628
Thr Ser Gly Cys Arg Gln Ala Val Val Val Gln Glu Asp Ser Arg Lys
                725                 730                 735

GAC AGA CTC CCA TTG CCT TTG AGA GAC ACC AAG CTG CTC TCA CCG CTC       2676
Asp Arg Leu Pro Leu Pro Leu Arg Asp Thr Lys Leu Leu Ser Pro Leu
            740                 745                 750

AGG GAC ACT CCT CCC CCA CAA AGC TTG ATG GTG AAG ATC ACC CTA GAC       2724
Arg Asp Thr Pro Pro Pro Gln Ser Leu Met Val Lys Ile Thr Leu Asp
        755                 760                 765

CTG CTC TCT CGG ATA CCC CAG CCT CCC GGG AAG GGG AGC CGC CAG AGG       2772
Leu Leu Ser Arg Ile Pro Gln Pro Pro Gly Lys Gly Ser Arg Gln Arg
    770                 775                 780

AAA GCA GAA GAT AAA CAG CCG CCC GCA GGG AAG AAG CAC AGC TCT GAG       2820
Lys Ala Glu Asp Lys Gln Pro Pro Ala Gly Lys Lys His Ser Ser Glu
785                 790                 795                 800

AAG AGG AGC TCA GAC AGC TCA AGC AAG TTG GCC AAA AAG AGA AAG GGT       2868
Lys Arg Ser Ser Asp Ser Ser Ser Lys Leu Ala Lys Lys Arg Lys Gly
                805                 810                 815

GAA GCA GAA AGA GAC TGT GAT AAC AAG AAA ATC AGA CTG GAG AAG GAA       2916
Glu Ala Glu Arg Asp Cys Asp Asn Lys Lys Ile Arg Leu Glu Lys Glu
            820                 825                 830

ATC AAA TCA CAG TCA TCT TCA TCT TCC TCC CAC AAA GAA TCT TCT           2964
Ile Lys Ser Gln Ser Ser Ser Ser Ser Ser His Lys Glu Ser Ser
        835                 840                 845
```

```
AAA ACA AAG CCC TCC AGG CCC TCC TCA CAG TCC TCA AAG AAG GAA ATG    3012
Lys Thr Lys Pro Ser Arg Pro Ser Ser Gln Ser Ser Lys Lys Glu Met
    850                 855                 860

CTC CCC CCG CCA CCC GTG TCC TCG TCC TCC CAG AAG CCA GCC AAG CCT    3060
Leu Pro Pro Pro Pro Val Ser Ser Ser Ser Gln Lys Pro Ala Lys Pro
865                 870                 875                 880

GCA CTT AAG AGG TCA AGG CGG GAA GCA GAC ACC TGT GGC CAG GAC CCT    3108
Ala Leu Lys Arg Ser Arg Arg Glu Ala Asp Thr Cys Gly Gln Asp Pro
                885                 890                 895

CCC AAA AGT GCC AGC AGT ACC AAG AGC AAC CAC AAA GAC TCT TCC ATT    3156
Pro Lys Ser Ala Ser Ser Thr Lys Ser Asn His Lys Asp Ser Ser Ile
            900                 905                 910

CCC AAG CAG AGA AGA GTA GAG GGG AAG GGC TCC AGA AGC TCC TCG GAG    3204
Pro Lys Gln Arg Arg Val Glu Gly Lys Gly Ser Arg Ser Ser Ser Glu
        915                 920                 925

CAC AAG GGT TCT TCC GGA GAT ACT GCA AAT CCT TTT CCA GTG CCT TCT    3252
His Lys Gly Ser Ser Gly Asp Thr Ala Asn Pro Phe Pro Val Pro Ser
    930                 935                 940

TTG CCA AAT GGT AAC TCT AAA CCA GGG AAG CCT CAA GTG AAG TTT GAC    3300
Leu Pro Asn Gly Asn Ser Lys Pro Gly Lys Pro Gln Val Lys Phe Asp
945                 950                 955                 960

AAA CAA CAA GCA GAC CTT CAC ATG AGG GAG GCA AAA AAG ATG AAG CAG    3348
Lys Gln Gln Ala Asp Leu His Met Arg Glu Ala Lys Lys Met Lys Gln
                965                 970                 975

AAA GCA GAG TTA ATG ACG GAC AGG GTT GGA AAG GCT TTT AAG TAC CTG    3396
Lys Ala Glu Leu Met Thr Asp Arg Val Gly Lys Ala Phe Lys Tyr Leu
            980                 985                 990

GAA GCC GTC TTG TCC TTC ATT GAG TGC GGA ATT GCC ACA GAG TCT GAA    3444
Glu Ala Val Leu Ser Phe Ile Glu Cys Gly Ile Ala Thr Glu Ser Glu
        995                 1000                1005

AGC CAG TCA TCC AAG TCA GCT TAC TCT GTC TAC TCA GAA ACT GTA GAT    3492
Ser Gln Ser Ser Lys Ser Ala Tyr Ser Val Tyr Ser Glu Thr Val Asp
    1010                1015                1020

CTC ATT AAA TTC ATA ATG TCA TTA AAA TCC TTC TCA GAT GCC ACA GCG    3540
Leu Ile Lys Phe Ile Met Ser Leu Lys Ser Phe Ser Asp Ala Thr Ala
1025                1030                1035                1040

CCA ACA CAA GAG AAA ATA TTT GCT GTT TTA TGC ATG CGT TGC CAG TCC    3588
Pro Thr Gln Glu Lys Ile Phe Ala Val Leu Cys Met Arg Cys Gln Ser
                1045                1050                1055

ATT TTG AAC ATG GCG ATG TTT CGT TGT AAA AAA GAC ATA GCA ATA AAG    3636
Ile Leu Asn Met Ala Met Phe Arg Cys Lys Lys Asp Ile Ala Ile Lys
            1060                1065                1070

TAT TCT CGT ACT CTT AAT AAA CAC TTC GAG AGT TCT TCC AAA GTC GCC    3684
Tyr Ser Arg Thr Leu Asn Lys His Phe Glu Ser Ser Ser Lys Val Ala
        1075                1080                1085

CAG GCA CCT TCT CCA TGC ATT GCA AGC ACA GGC ACA CCA TCC CCT CTT    3732
Gln Ala Pro Ser Pro Cys Ile Ala Ser Thr Gly Thr Pro Ser Pro Leu
    1090                1095                1100

TCC CCA ATG CCT TCT CCT GCC AGC TCC GTA GGG TCC CAG TCA AGT GCT    3780
Ser Pro Met Pro Ser Pro Ala Ser Ser Val Gly Ser Gln Ser Ser Ala
1105                1110                1115                1120

GGC AGT GTG GGG AGC AGT GGG GTG GCT GCC ACT ATC AGC ACC CCA GTC    3828
Gly Ser Val Gly Ser Ser Gly Val Ala Ala Thr Ile Ser Thr Pro Val
                1125                1130                1135

ACC ATC CAG AAT ATG ACA TCT TCC TAT GTC ACC ATC ACA TCC CAT GTT    3876
Thr Ile Gln Asn Met Thr Ser Ser Tyr Val Thr Ile Thr Ser His Val
            1140                1145                1150

CTT ACC GCC TTT GAC CTT TGG GAA CAG GCC GAG GCC CTC ACG AGG AAG    3924
Leu Thr Ala Phe Asp Leu Trp Glu Gln Ala Glu Ala Leu Thr Arg Lys
```

-continued

```
         1155                1160                1165
AAT AAA GAA TTC TTT GCT CGG CTC AGC ACA AAT GTG TGC ACC TTG GCC      3972
Asn Lys Glu Phe Phe Ala Arg Leu Ser Thr Asn Val Cys Thr Leu Ala
    1170                1175                1180

CTC AAC AGC AGT TTG GTG GAC CTG GTG CAC TAT ACA CGA CAG GGT TTT      4020
Leu Asn Ser Ser Leu Val Asp Leu Val His Tyr Thr Arg Gln Gly Phe
1185                1190                1195                1200

CAG CAG CTA CAA GAA TTA ACC AAA ACA CCT TAATGGAGCC CCAGGTTGAT        4070
Gln Gln Leu Gln Glu Leu Thr Lys Thr Pro
                1205                1210

TCAATGCCTT GGGAACTATT TTTGCACATT GGAAGCCTCA AAAACAGTCC AGACGTTTGT    4130

TTCATCAGGA CACCAAACTC TAAAAAAGAA GCACCACGAG ATGGCCAGGA CATTTGTCCA    4190

CTTAAACTCT CAACAACAGT GTGATCATTG GTTGGACACT GTGGTTATGC AGAAGCAGAG    4250

ATGAGGAGGC TGGCCCCAGA GATGATCTTG CCCTTCCTAA CTAAAGGACA GAAGTGCAAT    4310

TTAGCTTAAA TGGGTGTATG AATGGTCTAG AAACATTTCT ATTTTTTTTT TAAACCAGCA    4370

GGATACAAGT TGCAAATGAA ATGAGGAGAA ACAGTTTCAA CTCTGAAAGT GAATTTCACG    4430

TCATCTCAGT AGCCACGCTA GTCCATTCCC AGAAGGAAAT TTTTTTTTTT AACAATGACT    4490

TTTGGTAAAG GGTTTTGTGG ATGATTTTTT TTCTTTTGAG TTTGGGAGA AATATTTGTT     4550

TAATAACTTC TAATGGCCAT CTGTAAACCA TAAGTAATGA AGGACTCCAC TGTGCCCCAC    4610

TTTCTGCCAA TGAACAGTGG CTTGATAATA CCAAGTATTG TTGTAATTTA TAAAATTGAA    4670

GGCAACCCCC GCTCCTGCCG CCCCCAATCT CCCCATTGCC TAGAGCGCTG CACATTGACC    4730

CCAGCTCTGA CTTCTCATTA CTGTGCTGAA AGTCAGCCCA CGTCGGAGCG GTGAGGAGGA    4790

GCCACAGCAC ATGGGGTGCC ACCTCGAGGT CTGCACAGGA GGACTTGGCG CTGCCATTTC    4850

CTACCCCTGC CATTTCCCAC CCCTGCTTCA GCGAAAGGGA CTCTCTAACA GGGCAGTCAC    4910

TGTTGACTCT ATTCTGAATT TCCTCCCTTG GGAAGAAGG GAACCAACAT TTATACCTGA     4970

CCAGATGGCT AAAGTGCTTT TAAAGTTTTG TTTAAGTAGA GCTGGAATTT GAGGTGCTGA    5030

TCTGTGGTCT ACAGTTATGT GGTAACTCAT GTTGTCCAGC CAACTCAGAG TTTCGTCAGT    5090

GAACAAGAAA CATGAAATCT GCTTCTTAGA GAGGCTATAT TTTTCTGCTA CAAATATTTT    5150

ATATTTATAG CAAAACTAGA CTTTCAGAGT CCTTGATTGT CTAGGGGAAG TTAACTCCCT    5210

GAGAGGATGT AGAGATTTGG GGTGGTTGAT TAGACTTTTG AAAAACTCAT CACCACATGC    5270

CTTCACTCCA GAGTGTTCTC AGCTAGATTT GATTTGGTTG AGGAGGAACT GTGGCCCTCC    5330

GTAAGTTATT GCCATAGTGT ATGCATTAAA CCAAGTCCAT TTTGAATGAC CTAAAATGAA    5390

GTAACACAAT CAGAAATCCC ATGTGCCCAT AAGCACAGAT TTTTCTTTTT CATTGAAACT    5450

TTAAAGGTTA TTATTGGAAA CATTACTTTG AGTGCAGTGT TTTTAAAAGC CAATTCTTTT    5510

TTATCCCTTT TAGAAGTAGA ATTTCACAC TTACTACAAT TGAGGAGTGT CATCTCTATA     5570

ACTTTTTCTC CGCCTTTGTC CCATTCTGCC CCTGGACATG TTTCCTACCA AGCATGTTTC    5630

ACATTTTCCT ATTAGTGGAG GAGGGAGAAC CATATTTATT TATAATGAAG ACATCTAAGA    5690

TCCCTATGAT GAATGCAGGA ACTCTCTTGG TAGTTTGTAA ATACACAAAG GGATGTGTCG    5750

AGGGATGGGA GCGATGCTTA TCTCTCACAG TGTGAGTGG CTGTGTGAGG CTGTTCCTTC     5810

AGTTCTTCTC CAGACTGTTC TTTGGTTGTC ACTTAAGTCA GAGGTCTGGT CCCTCATGTT    5870

TAGGTGAAAG CCAGAGAATG ACAGCTGTAG TCATATCTGA GCATAAGACC TTGATGTGTG    5930

ATTCCTGATG ACCGGTTTCA TTTATTCATG TAATAAAGCA AAGGCCCTGG TCCTTTTTAA    5990

ACTACTAGTT TTAAAAACCT GTGTTAAATG AACAGTAATT GCCTGGTAGG TTTGGTGTGT    6050
```

```
GTGTAGCATT GTGTGTCCAT CTGTTATATG TAAAGGACAA GGCACCAGAA TCAGGCTTTA     6110

TTTCGATATT GAAGATGTTA TTTAACATCT TTCTTTTTTC CTTACTCCCT TAGCCATCCC     6170

CTCCCCTTTT GTCCTATCAT TCCCTAGAAC AAGCCACCTG TCAATTGTGA AGGGTTGTGT     6230

TCTTTATGGC AGGTTCTATG CAGATTGTGC CAGAGCATGT GCGTGTTCTG TTGGCAAGCC     6290

ACAGTGCTCC CTTGACTGAA GACATTTCCA GGTAGATTTC TCAGCCAGCT CTAAAACAGA     6350

TTGCTTTTTC AGTGGCCTTA CTCTTTGTGG GTTTTTTTTT TTCTCTGAAC TTGATATAAA     6410

GATTTTATTT GTCCCTTGAA AAAGTAACAA ATGTGCATAG ATCAATTTGT ACTACTTTGG     6470

TCATTGGATA TTTCTGATCC TTATTGCATT GTACCTAAAG GAGAGTAACT AATGGTAACC     6530

TTTTTAATAG AGTATGTGAA AGGTAGTGGC TGATGAATCC TTAACGTTCA TAGGGTCTTT     6590

TTGCTGTTAC GGTTGTATAT AGAGGTCTGA AGGATTTTTA AAATGATTTG CACTTTTTCA     6650

CTGCATGCTT ACAATTCCCA AAGGCAAAAT CTGTACTGAG GTAGATCATT TGAAAGGGCT     6710

AGATTATAAA ATTAAGCCTT AGAGTATGGA AAGTTCTTAT AACAATAATA GTACACACTT     6770

CAGAGTAAGA CAAATGCAAA GCATCTTAAG GAGTGAAAAT AGAGTCTAAA TCTTGCCTTT     6830

GGCACTACAA GGTGTGTGTG TGTGTGTGTG TTGTGTGTCT TTAGTAGGAA ATGGAAGAAC     6890

ACTGTTTTAT TTTTTAAAGT GTTTAATGTT CTGTCCTTT CTGTGAATTA TTGAATTTAA     6950

GAGCCCTGCT AAATAATGAA AAAACACTTT ACTAAAATTT ATCAAATTAT ACTGGGTTCG     7010

GATTGTGAAA ACATTGGCCA CCTAGTAGCA GTGGTGAGGA GTGGGAGGGC CCAGCAAGCA     7070

TTTATCAGAA ATAGAATCAC AATAGGAGGA GAATTTGGCT GTCTGATATT ATGATTTGAT     7130

TACAATACTG AATGGGAAAA GTATCTAATA TTTTGTAACA AAAAGACCTT CATATTATCT     7190

GTTTTGACCA AAATATGTAG CTATTTCCCT TACACAGATT GGACCGCACT TATCTCCCTT     7250

GTCCTGTATC CTTTAATTTC AGGTCTCAGG ATGTTTAGAA AGCTAAAACC CCCTACCCCT     7310

TTCTGGCTGA AAACTTGCCT TATTTGGTAT CTTACACATT AATGTTACTA GCATCAGGAG     7370

CTTACTGTTT TATTATGATT CATCTTCAGT AATTTTTAGA AGCAAGAAGA AAGCCATTGT     7430

GTCCTCTACA AATTAACAAA ACTTATCTCT GATATACAAA GGGATATAAA TATATACACT     7490

TAAATAGAGA AAAAGAGGTT GATTGAATTG TGCCTTTGAG TGAACCCAGT TTTTAAATAC     7550

CGCTGTGTTT GTTTCGCCAT GGCTTCAGGG ATGCTACATG GCTCTTGCAC CTTTTACTCC     7610

TCTGCTTTAT GAAGTTTGAG TTGTATTTGT GCATCTTAAA GTAGGTTGAG GCTTGAGGCT     7670

GGGCTTTCGG GTTTTTTTGT TTTTTGTTTT GTTTTGTTTT GTTTTGTTTT CTTGTACTTA     7730

AACCTGCTTG CTTCCTACCA CAGATTCTTT ATTTTCCCAA ACACTACAAA AAAACTTTTA     7790

AAACTTTGCC ATTTCATCTG TTTACACTCT TTGCCACTGA TTAGCAGTAT TTAAATCTTG     7850

CAAGAATATT TTGTGCTTTC TTTAGAAACA CAAGAGTAGA GATTTTTCTC ACTGAAAAGT     7910

GAGAGTTACG CATTGCAGCC ATGAAGGGAT GCTAGGATCA ATTATGGCAG TACCTTTTTT     7970

CCCCTCCTGT TCTTGAGCCA GTTGTCTCTT TTGTGTTGGG TCCCACTTAG GATTAACGGA     8030

TGTAAGGTAT TTTCCTGTGC CTTTATTTTG TGTCATTCTA TTGGAAGGAG GTGTAACGGC     8090

AGAATAGCAT CGTGTTGGGG GTTTTCCTTC AAACACTGCA AGTGATATTG CCACCATGTG     8150

AACCTCAAAT ATGCAATCCA GTTGTGTTGG TTTCTCGGTG ACTTGGAGTG TTCATCTCTT     8210

CATGAATTGT GAGCACTGAC CATGTTCTTC AGTTCTTAAT TATGGTGAGT TGACAAATAC     8270

CAACTACTGC TTTTCTTTAG GTGGCTATAA ATTTCTTACT GTCAGGAGGA AATGACATTA     8330

TATTCTGTTC CACTGAACGT CAGAGATCAG CAGGCACTGT ACTGGGTAGA GAAGTGCCTA     8390
```

```
                                  -continued

TACTTCTCTA CCTAAGAGGG CAGGAGGGAA ACCCTACAGC TCCTTGTGAG CCTATATATT    8450

AGTATATCGG CCTGGAGAGG ACAAGGGAAT AAGACCACTC ATAGTGAGGC TGGCCAAGCT    8510

GCACTGGTCG GACCAGGCAG TGGCTGACCT AAGGAAGGCA ACTTGCTTTG CTTAAAAGTA    8570

GATTTTTTAA GCAATGCTTA ACACAGGCAG CATTCACCTT TGTTCAGGCC ATCGACATGT    8630

ATTGTTAAAA TTACTGCATA TCCCCCTCAG ATATCAAGTA TACACTGTTC ATGTTGGGGT    8690

TGTGTGTGTG TATGTGTGTA TGTACGCACG CATGTGTCCC AAATCTTGTT TTAATTTTTT    8750

TTTTCTGAAT GTGATCATGT TTTGGATAAT ACCTGAGCAG GGTTGCCTTT TTTTTATTTA    8810

TTACCATTAT ATATTATATT ATATTATATA TTTTTTGCTT TCTTATAACT TGGAGGAAA    8870

GTCAAATCTT GGTATTATTA AAATTGTTTT AAAAAGGAGT AAATTTTCCA GTTGATAAAT    8930

GAAAATCACT GGCCTATGTT TAATAAGTTT TTCTTTAATT ACTGTGGAAT AACGTGCCAG    8990

CTATCATCAA CACAATGATT TTGTACATAG GGTAGGGAAG CAGTGATGCT CTCAATGGGA    9050

AGATGTGCAA CACAAATTAA GGGGAACTCC ATGTATTTTA CCTACTTCAG CAATGGAACT    9110

GCAACTTGGG GCTTTGTGAA TAAAATTTAG CTGCCTTGTA TAGTCGTTTG AAAGAATATG    9170

TGATCTGTGA GAGAATTATA GTTTTTTTTT AGAAGAAAAA TCTGCAAAAG ATCTTTCCAA    9230

AGACAATGTG CCACAGATCT TTTGTTCTCT GTAATGAGGA TTAATTGCTG TTTAAACAAA    9290

AATGTAATTG TTCATCTTTA AATTCTTTCC TTTTCATAAG AGGATCAAGC TGTAAAAAAA    9350

CAAAAAAATT AATAAAAATT TCGAGAAATC AAAAAAAAA A                        9391

(2) INFORMATION FOR SEQ ID NO:26:

(i) SEQUENCE CHARACTERISTICS:
        (A) LENGTH: 1210 amino acids
        (B) TYPE: amino acid
        (D) TOPOLOGY: linear (ii) MOLECULE TYPE: protein (xi) SEQUENCE DESCRIPTION: SEQ ID NO:26:

Met Ala Ala Gln Ser Ser Leu Tyr Asn Asp Asp Arg Asn Leu Leu Arg
  1               5                  10                  15

Ile Arg Glu Lys Glu Arg Arg Asn Gln Glu Ala His Gln Glu Lys Glu
                 20                  25                  30

Ala Phe Pro Glu Lys Ile Pro Leu Phe Gly Glu Pro Tyr Lys Thr Ala
             35                  40                  45

Lys Gly Asp Glu Leu Ser Ser Arg Ile Gln Asn Met Leu Gly Asn Tyr
         50                  55                  60

Glu Glu Val Lys Glu Phe Leu Ser Thr Lys Ser His Thr His Arg Leu
 65                  70                  75                  80

Asp Ala Ser Glu Asn Arg Leu Gly Lys Pro Lys Tyr Pro Leu Ile Pro
                 85                  90                  95

Asp Lys Gly Ser Ser Ile Pro Ser Ser Phe His Thr Ser Val His
                100                 105                 110

His Gln Ser Ile His Thr Pro Ala Ser Gly Pro Leu Ser Val Gly Asn
            115                 120                 125

Ile Ser His Asn Pro Lys Met Ala Gln Pro Arg Thr Glu Pro Met Pro
        130                 135                 140

Ser Leu His Ala Lys Ser Cys Gly Pro Pro Asp Ser Gln His Leu Thr
145                 150                 155                 160

Gln Asp Arg Leu Gly Gln Glu Gly Phe Gly Ser Ser His His Lys Lys
                165                 170                 175
```

-continued

```
Gly Asp Arg Arg Ala Asp Gly Asp His Cys Ala Ser Val Thr Asp Ser
            180                 185                 190

Ala Pro Glu Arg Glu Leu Ser Pro Leu Ile Ser Leu Pro Ser Pro Val
            195                 200                 205

Pro Pro Leu Ser Pro Ile His Ser Asn Gln Gln Thr Leu Pro Arg Thr
            210                 215                 220

Gln Gly Ser Ser Lys Val His Gly Ser Ser Asn Asn Ser Lys Gly Tyr
225                 230                 235                 240

Cys Pro Ala Lys Ser Pro Lys Asp Leu Ala Val Lys Val His Asp Lys
                    245                 250                 255

Glu Thr Pro Gln Asp Ser Leu Val Ala Pro Ala Gln Pro Pro Ser Gln
                260                 265                 270

Thr Phe Pro Pro Ser Leu Pro Ser Lys Ser Val Ala Met Gln Gln
            275                 280                 285

Lys Pro Thr Ala Tyr Val Arg Pro Met Asp Gly Gln Asp Gln Ala Pro
            290                 295                 300

Ser Glu Ser Pro Glu Leu Lys Pro Leu Pro Glu Asp Tyr Arg Gln Gln
305                 310                 315                 320

Thr Phe Glu Lys Thr Asp Leu Lys Val Pro Ala Lys Ala Lys Leu Thr
                325                 330                 335

Lys Leu Lys Met Pro Ser Gln Ser Val Glu Gln Thr Tyr Ser Asn Glu
            340                 345                 350

Val His Cys Val Glu Glu Ile Leu Lys Glu Met Thr His Ser Trp Pro
            355                 360                 365

Pro Pro Leu Thr Ala Ile His Thr Pro Ser Thr Ala Glu Pro Ser Lys
            370                 375                 380

Phe Pro Phe Pro Thr Lys Asp Ser Gln His Val Ser Ser Val Thr Gln
385                 390                 395                 400

Asn Gln Lys Gln Tyr Asp Thr Ser Ser Lys Thr His Ser Asn Ser Gln
                405                 410                 415

Gln Gly Thr Ser Ser Met Leu Glu Asp Asp Leu Gln Leu Ser Asp Ser
            420                 425                 430

Glu Asp Ser Asp Ser Glu Gln Thr Pro Glu Lys Pro Pro Ser Ser Ser
            435                 440                 445

Ala Pro Pro Ser Ala Pro Gln Ser Leu Pro Glu Pro Val Ala Ser Ala
            450                 455                 460

His Ser Ser Ser Ala Glu Ser Glu Ser Thr Ser Asp Ser Asp Ser Ser
465                 470                 475                 480

Ser Asp Ser Glu Ser Glu Ser Ser Ser Asp Ser Glu Glu Asn Glu
                    485                 490                 495

Pro Leu Glu Thr Pro Ala Pro Glu Pro Glu Pro Thr Thr Asn Lys
            500                 505                 510

Trp Gln Leu Asp Asn Trp Leu Thr Lys Val Ser Gln Pro Ala Ala Pro
            515                 520                 525

Pro Glu Gly Pro Arg Ser Thr Glu Pro Pro Arg Arg His Pro Glu Ser
            530                 535                 540

Lys Gly Ser Ser Asp Ser Ala Thr Ser Gln Glu His Ser Glu Ser Lys
545                 550                 555                 560

Asp Pro Pro Pro Lys Ser Ser Lys Ala Pro Arg Ala Pro Pro Glu
                    565                 570                 575

Ala Pro His Pro Gly Lys Arg Ser Cys Gln Lys Ser Pro Ala Gln Gln
            580                 585                 590

Glu Pro Pro Gln Arg Gln Thr Val Gly Thr Lys Gln Pro Lys Lys Pro
```

-continued

```
            595                 600                 605
Val Lys Ala Ser Ala Arg Ala Gly Ser Arg Thr Ser Leu Gln Gly Glu
        610                 615                 620

Arg Glu Pro Gly Leu Leu Pro Tyr Gly Ser Arg Asp Gln Thr Ser Lys
625                 630                 635                 640

Asp Lys Pro Lys Val Lys Thr Lys Gly Arg Pro Arg Ala Ala Ala Ser
                645                 650                 655

Asn Glu Pro Lys Pro Ala Val Pro Pro Ser Glu Lys Lys Lys His
            660                 665                 670

Lys Ser Ser Leu Pro Ala Pro Ser Lys Ala Leu Ser Gly Pro Glu Pro
        675                 680                 685

Ala Lys Asp Asn Val Glu Asp Arg Thr Pro Glu His Phe Ala Leu Val
    690                 695                 700

Pro Leu Thr Glu Ser Gln Gly Pro Pro His Ser Gly Ser Gly Ser Arg
705                 710                 715                 720

Thr Ser Gly Cys Arg Gln Ala Val Val Gln Glu Asp Ser Arg Lys
                725                 730                 735

Asp Arg Leu Pro Leu Pro Leu Arg Asp Thr Lys Leu Leu Ser Pro Leu
            740                 745                 750

Arg Asp Thr Pro Pro Gln Ser Leu Met Val Lys Ile Thr Leu Asp
        755                 760                 765

Leu Leu Ser Arg Ile Pro Gln Pro Gly Lys Gly Ser Arg Gln Arg
770                 775                 780

Lys Ala Glu Asp Lys Gln Pro Pro Ala Gly Lys Lys His Ser Ser Glu
785                 790                 795                 800

Lys Arg Ser Ser Asp Ser Ser Lys Leu Ala Lys Arg Lys Gly
                805                 810                 815

Glu Ala Glu Arg Asp Cys Asp Asn Lys Lys Ile Arg Leu Glu Lys Glu
            820                 825                 830

Ile Lys Ser Gln Ser Ser Ser Ser Ser His Lys Glu Ser Ser
        835                 840                 845

Lys Thr Lys Pro Ser Arg Pro Ser Ser Gln Ser Ser Lys Lys Glu Met
    850                 855                 860

Leu Pro Pro Pro Val Ser Ser Ser Gln Lys Pro Ala Lys Pro
865                 870                 875                 880

Ala Leu Lys Arg Ser Arg Arg Glu Ala Asp Thr Cys Gly Gln Asp Pro
                885                 890                 895

Pro Lys Ser Ala Ser Ser Thr Lys Ser Asn His Lys Asp Ser Ser Ile
            900                 905                 910

Pro Lys Gln Arg Arg Val Glu Gly Lys Gly Ser Arg Ser Ser Ser Glu
        915                 920                 925

His Lys Gly Ser Ser Gly Asp Thr Ala Asn Pro Phe Pro Val Pro Ser
    930                 935                 940

Leu Pro Asn Gly Asn Ser Lys Pro Gly Lys Pro Gln Val Lys Phe Asp
945                 950                 955                 960

Lys Gln Gln Ala Asp Leu His Met Arg Glu Ala Lys Lys Met Lys Gln
                965                 970                 975

Lys Ala Glu Leu Met Thr Asp Arg Val Gly Lys Ala Phe Lys Tyr Leu
            980                 985                 990

Glu Ala Val Leu Ser Phe Ile Glu Cys Gly Ile Ala Thr Glu Ser Glu
        995                 1000                1005

Ser Gln Ser Ser Lys Ser Ala Tyr Ser Val Tyr Ser Glu Thr Val Asp
    1010                1015                1020
```

-continued

```
Leu Ile Lys Phe Ile Met Ser Leu Lys Ser Phe Ser Asp Ala Thr Ala
1025                1030                1035                1040

Pro Thr Gln Glu Lys Ile Phe Ala Val Leu Cys Met Arg Cys Gln Ser
                1045                1050                1055

Ile Leu Asn Met Ala Met Phe Arg Cys Lys Lys Asp Ile Ala Ile Lys
            1060                1065                1070

Tyr Ser Arg Thr Leu Asn Lys His Phe Glu Ser Ser Ser Lys Val Ala
        1075                1080                1085

Gln Ala Pro Ser Pro Cys Ile Ala Ser Thr Gly Thr Pro Ser Pro Leu
    1090                1095                1100

Ser Pro Met Pro Ser Pro Ala Ser Ser Val Gly Ser Gln Ser Ser Ala
1105                1110                1115                1120

Gly Ser Val Gly Ser Ser Gly Val Ala Ala Thr Ile Ser Thr Pro Val
                1125                1130                1135

Thr Ile Gln Asn Met Thr Ser Ser Tyr Val Thr Ile Thr Ser His Val
                1140                1145                1150

Leu Thr Ala Phe Asp Leu Trp Glu Gln Ala Glu Ala Leu Thr Arg Lys
            1155                1160                1165

Asn Lys Glu Phe Phe Ala Arg Leu Ser Thr Asn Val Cys Thr Leu Ala
1170                1175                1180

Leu Asn Ser Ser Leu Val Asp Leu Val His Tyr Thr Arg Gln Gly Phe
1185                1190                1195                1200

Gln Gln Leu Gln Glu Leu Thr Lys Thr Pro
                1205                1210

(2) INFORMATION FOR SEQ ID NO:27:

(i) SEQUENCE CHARACTERISTICS:
        (A) LENGTH: 9370 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 469..4032

(xi) SEQUENCE DESCRIPTION: SEQ ID NO:27:

GGCAATTTCT TTTCCTTTCT AACTGTGGCC CGCGTTGTGC TGTTGCTGGG CAGGCGTTGG      60

GCGCCGGCGG TCTTCGAGCG TGGGGGCCCG CTGGCTTTCC CTTCTCAGAA ACTGCGCCGG     120

GGGCGCTCGC TTGCCCCGGA TTCGGACGCG GCGCTCCCCG GCTCGTCTG AAGTGCAGAT      180

CGCCGCAGAG GCCCCAGTGC CCGGATGTCC ATCAGGATTA GCGCGAGCCA ATACGGGCCG    240

AGCCCGGGGC TGCGCCGAGG ACGCCCGGGG AGTCTGAGAG GCGTGGAGAA TTTTGCTTGT    300

GCAAGATTAT TTCAGAGCAA GGTCGTGCGG TGTGTGTAGA AGATGAACAG ACTAGCCACT    360

TTGCATTGAC TGGAAACAAT GGCATTTACA GAAAGAGTCA ACAGCAGTGG CAACAGTTTG    420

TACAATGACG ACAGAAACCT GCTTCGAATT AGAGAGAAGG AAAGACGC AAC CAG GAA    477
                                                   Asn Gln Glu
                                                     1

GCC CAC CAA GAG AAA GAG GCA TTT CCT GAA AAG ATT CCC CTT TTT GGA      525
Ala His Gln Glu Lys Glu Ala Phe Pro Glu Lys Ile Pro Leu Phe Gly
      5                  10                  15

GAG CCC TAC AAG ACA GCA AAA GGT GAT GAG CTG TCT AGT CGA ATA CAG      573
Glu Pro Tyr Lys Thr Ala Lys Gly Asp Glu Leu Ser Ser Arg Ile Gln
 20                  25                  30                  35
```

```
AAC ATG TTG GGA AAC TAC GAA GAA GTG AAG GAG TTC CTT AGT ACT AAG      621
Asn Met Leu Gly Asn Tyr Glu Glu Val Lys Glu Phe Leu Ser Thr Lys
                40                  45                  50

TCT CAC ACT CAT CGC CTG GAT GCT TCT GAA AAT AGG TTG GGA AAG CCG      669
Ser His Thr His Arg Leu Asp Ala Ser Glu Asn Arg Leu Gly Lys Pro
                55                  60                  65

AAA TAT CCT TTA ATT CCT GAC AAA GGG AGC AGC ATT CCA TCC AGC TCC      717
Lys Tyr Pro Leu Ile Pro Asp Lys Gly Ser Ser Ile Pro Ser Ser Ser
                70                  75                  80

TTC CAC ACT AGT GTC CAC CAC CAG TCC ATT CAC ACT CCT GCG TCT GGA      765
Phe His Thr Ser Val His His Gln Ser Ile His Thr Pro Ala Ser Gly
        85                  90                  95

CCA CTT TCT GTT GGC AAC ATT AGC CAC AAT CCA AAG ATG GCG CAG CCA      813
Pro Leu Ser Val Gly Asn Ile Ser His Asn Pro Lys Met Ala Gln Pro
100                 105                 110                 115

AGA ACT GAA CCA ATG CCA AGT CTC CAT GCC AAA AGC TGC GGC CCA CCG      861
Arg Thr Glu Pro Met Pro Ser Leu His Ala Lys Ser Cys Gly Pro Pro
                120                 125                 130

GAC AGC CAG CAC CTG ACC CAG GAT CGC CTT GGT CAG GAG GGG TTC GGC      909
Asp Ser Gln His Leu Thr Gln Asp Arg Leu Gly Gln Glu Gly Phe Gly
                135                 140                 145

TCT AGT CAT CAC AAG AAA GGT GAC CGA AGA GCT GAC GGA GAC CAC TGT      957
Ser Ser His His Lys Lys Gly Asp Arg Arg Ala Asp Gly Asp His Cys
                150                 155                 160

GCT TCG GTG ACA GAT TCG GCT CCA GAG AGG GAG CTT TCT CCC TTA ATC     1005
Ala Ser Val Thr Asp Ser Ala Pro Glu Arg Glu Leu Ser Pro Leu Ile
        165                 170                 175

TCT TTG CCT TCC CCA GTT CCC CCT TTG TCA CCT ATA CAT TCC AAC CAG     1053
Ser Leu Pro Ser Pro Val Pro Pro Leu Ser Pro Ile His Ser Asn Gln
180                 185                 190                 195

CAA ACT CTT CCC CGG ACG CAA GGA AGC AGC AAG GTT CAT GGC AGC AGC     1101
Gln Thr Leu Pro Arg Thr Gln Gly Ser Ser Lys Val His Gly Ser Ser
                200                 205                 210

AAT AAC AGT AAA GGC TAT TGC CCA GCC AAA TCT CCC AAG GAC CTA GCA     1149
Asn Asn Ser Lys Gly Tyr Cys Pro Ala Lys Ser Pro Lys Asp Leu Ala
                215                 220                 225

GTG AAA GTC CAT GAT AAA GAG ACC CCT CAA GAC AGT TTG GTG GCC CCT     1197
Val Lys Val His Asp Lys Glu Thr Pro Gln Asp Ser Leu Val Ala Pro
                230                 235                 240

GCC CAG CCG CCT TCT CAG ACA TTT CCA CCT CCC TCC CTC CCC TCA AAA     1245
Ala Gln Pro Pro Ser Gln Thr Phe Pro Pro Pro Ser Leu Pro Ser Lys
245                 250                 255

AGT GTT GCA ATG CAG CAG AAG CCC ACG GCT TAT GTC CGG CCC ATG GAT     1293
Ser Val Ala Met Gln Gln Lys Pro Thr Ala Tyr Val Arg Pro Met Asp
260                 265                 270                 275

GGT CAA GAT CAG GCC CCT AGT GAA TCC CCT GAA CTG AAA CCA CTG CCG     1341
Gly Gln Asp Gln Ala Pro Ser Glu Ser Pro Glu Leu Lys Pro Leu Pro
                280                 285                 290

GAG GAC TAT CGA CAG CAG ACC TTT GAA AAA ACA GAC TTG AAA GTG CCT     1389
Glu Asp Tyr Arg Gln Gln Thr Phe Glu Lys Thr Asp Leu Lys Val Pro
                295                 300                 305

GCC AAA GCC AAG CTC ACC AAA CTG AAG ATG CCT TCT CAG TCA GTT GAG     1437
Ala Lys Ala Lys Leu Thr Lys Leu Lys Met Pro Ser Gln Ser Val Glu
                310                 315                 320

CAG ACC TAC TCC AAT GAA GTC CAT TGT GTT GAA GAG ATT CTG AAG GAA     1485
Gln Thr Tyr Ser Asn Glu Val His Cys Val Glu Glu Ile Leu Lys Glu
                325                 330                 335

ATG ACC CAT TCA TGG CCG CCT CCT TTG ACA GCA ATA CAT ACG CCT AGT     1533
Met Thr His Ser Trp Pro Pro Pro Leu Thr Ala Ile His Thr Pro Ser
```

-continued

```
340                     345                     350                     355

ACA GCT GAG CCA TCC AAG TTT CCT TTC CCT ACA AAG GAC TCT CAG CAT     1581
Thr Ala Glu Pro Ser Lys Phe Pro Phe Pro Thr Lys Asp Ser Gln His
                        360                     365                     370

GTC AGT TCT GTA ACC CAA AAC CAA AAA CAA TAT GAT ACA TCT TCA AAA     1629
Val Ser Ser Val Thr Gln Asn Gln Lys Gln Tyr Asp Thr Ser Ser Lys
                375                     380                     385

ACT CAC TCA AAT TCT CAG CAA GGA ACG TCA TCC ATG CTC GAA GAC GAC     1677
Thr His Ser Asn Ser Gln Gln Gly Thr Ser Ser Met Leu Glu Asp Asp
            390                     395                     400

CTT CAG CTC AGT GAC AGT GAG GAC AGT GAC AGT GAA CAA ACC CCA GAG     1725
Leu Gln Leu Ser Asp Ser Glu Asp Ser Asp Ser Glu Gln Thr Pro Glu
        405                     410                     415

AAG CCT CCC TCC TCA TCT GCA CCT CCA AGT GCT CCA CAG TCC CTT CCA     1773
Lys Pro Pro Ser Ser Ser Ala Pro Pro Ser Ala Pro Gln Ser Leu Pro
420                     425                     430                     435

GAA CCA GTG GCA TCA GCA CAT TCC AGC AGT GCA GAG TCA GAA AGC ACC     1821
Glu Pro Val Ala Ser Ala His Ser Ser Ser Ala Glu Ser Glu Ser Thr
                    440                     445                     450

AGT GAC TCA GAC AGT TCC TCA GAC TCA GAG AGC GAG AGC AGT TCA AGT     1869
Ser Asp Ser Asp Ser Ser Ser Asp Ser Glu Ser Glu Ser Ser Ser Ser
                455                     460                     465

GAC AGC GAA GAA AAT GAG CCC CTA GAA ACC CCA GCT CCG GAG CCT GAG     1917
Asp Ser Glu Glu Asn Glu Pro Leu Glu Thr Pro Ala Pro Glu Pro Glu
            470                     475                     480

CCT CCA ACA ACA AAC AAA TGG CAG CTG GAC AAC TGG CTG ACC AAA GTC     1965
Pro Pro Thr Thr Asn Lys Trp Gln Leu Asp Asn Trp Leu Thr Lys Val
        485                     490                     495

AGC CAG CCA GCT GCG CCA CCA GAG GGC CCC AGG AGC ACA GAG CCC CCA     2013
Ser Gln Pro Ala Ala Pro Pro Glu Gly Pro Arg Ser Thr Glu Pro Pro
500                     505                     510                     515

CGG CGG CAC CCA GAG AGT AAG GGC AGC AGC GAC AGT GCC ACG AGT CAG     2061
Arg Arg His Pro Glu Ser Lys Gly Ser Ser Asp Ser Ala Thr Ser Gln
                    520                     525                     530

GAG CAT TCT GAA TCC AAA GAT CCT CCC CCT AAA AGC TCC AGC AAA GCC     2109
Glu His Ser Glu Ser Lys Asp Pro Pro Pro Lys Ser Ser Ser Lys Ala
                535                     540                     545

CCC CGG GCC CCA CCC GAA GCC CCC CAC CCC GGA AAG AGG AGC TGT CAG     2157
Pro Arg Ala Pro Pro Glu Ala Pro His Pro Gly Lys Arg Ser Cys Gln
            550                     555                     560

AAG TCT CCG GCA CAG CAG GAG CCC CCA CAA AGG CAA ACC GTT GGA ACC     2205
Lys Ser Pro Ala Gln Gln Glu Pro Pro Gln Arg Gln Thr Val Gly Thr
        565                     570                     575

AAA CAA CCC AAA AAA CCT GTC AAG GCC TCT GCC CGG GCA GGT TCA CGG     2253
Lys Gln Pro Lys Lys Pro Val Lys Ala Ser Ala Arg Ala Gly Ser Arg
580                     585                     590                     595

ACC AGC CTG CAG GGG GAA AGG GAG CCA GGG CTT CTT CCC TAT GGC TCC     2301
Thr Ser Leu Gln Gly Glu Arg Glu Pro Gly Leu Leu Pro Tyr Gly Ser
                    600                     605                     610

CGA GAC CAG ACT TCC AAA GAC AAG CCC AAG GTG AAG ACG AAA GGA CGG     2349
Arg Asp Gln Thr Ser Lys Asp Lys Pro Lys Val Lys Thr Lys Gly Arg
                615                     620                     625

CCC CGG GCC GCA GCA AGC AAC GAA CCC AAG CCA GCA GTG CCC CCC TCC     2397
Pro Arg Ala Ala Ala Ser Asn Glu Pro Lys Pro Ala Val Pro Pro Ser
            630                     635                     640

AGT GAG AAG AAG AAG CAC AAG AGC TCC CTC CCT GCC CCC TCT AAG GCT     2445
Ser Glu Lys Lys Lys His Lys Ser Ser Leu Pro Ala Pro Ser Lys Ala
        645                     650                     655

CTC TCA GGC CCA GAA CCC GCG AAG GAC AAT GTG GAG GAC AGG ACC CCT     2493
```

```
Leu Ser Gly Pro Glu Pro Ala Lys Asp Asn Val Glu Asp Arg Thr Pro
660             665                 670                 675

GAG CAC TTT GCT CTT GTT CCC CTG ACT GAG AGC CAG GGC CCA CCC CAC    2541
Glu His Phe Ala Leu Val Pro Leu Thr Glu Ser Gln Gly Pro Pro His
                680                 685                 690

AGT GGC AGC GGC AGC AGG ACT AGT GGC TGC CGC CAA GCC GTG GTG GTC    2589
Ser Gly Ser Gly Ser Arg Thr Ser Gly Cys Arg Gln Ala Val Val Val
            695                 700                 705

CAG GAG GAC AGC CGC AAA GAC AGA CTC CCA TTG CCT TTG AGA GAC ACC    2637
Gln Glu Asp Ser Arg Lys Asp Arg Leu Pro Leu Pro Leu Arg Asp Thr
        710                 715                 720

AAG CTG CTC TCA CCG CTC AGG GAC ACT CCT CCC CCA CAA AGC TTG ATG    2685
Lys Leu Leu Ser Pro Leu Arg Asp Thr Pro Pro Pro Gln Ser Leu Met
    725                 730                 735

GTG AAG ATC ACC CTA GAC CTG CTC TCT CGG ATA CCC CAG CCT CCC GGG    2733
Val Lys Ile Thr Leu Asp Leu Leu Ser Arg Ile Pro Gln Pro Pro Gly
740                 745                 750                 755

AAG GGG AGC CGC CAG AGG AAA GCA GAA GAT AAA CAG CCG CCC GCA GGG    2781
Lys Gly Ser Arg Gln Arg Lys Ala Glu Asp Lys Gln Pro Pro Ala Gly
                760                 765                 770

AAG AAG CAC AGC TCT GAG AAG AGG AGC TCA GAC AGC TCA AGC AAG TTG    2829
Lys Lys His Ser Ser Glu Lys Arg Ser Ser Asp Ser Ser Ser Lys Leu
            775                 780                 785

GCC AAA AAG AGA AAG GGT GAA GCA GAA AGA GAC TGT GAT AAC AAG AAA    2877
Ala Lys Lys Arg Lys Gly Glu Ala Glu Arg Asp Cys Asp Asn Lys Lys
        790                 795                 800

ATC AGA CTG GAG AAG GAA ATC AAA TCA CAG TCA TCT TCA TCT TCA TCC    2925
Ile Arg Leu Glu Lys Glu Ile Lys Ser Gln Ser Ser Ser Ser Ser Ser
    805                 810                 815

TCC CAC AAA GAA TCT TCT AAA ACA AAG CCC TCC AGG CCC TCC TCA CAG    2973
Ser His Lys Glu Ser Ser Lys Thr Lys Pro Ser Arg Pro Ser Ser Gln
820                 825                 830                 835

TCC TCA AAG AAG GAA ATG CTC CCC CCG CCA CCC GTG TCC TCG TCC TCC    3021
Ser Ser Lys Lys Glu Met Leu Pro Pro Pro Val Ser Ser Ser Ser
                840                 845                 850

CAG AAG CCA GCC AAG CCT GCA CTT AAG AGG TCA AGG CGG GAA GCA GAC    3069
Gln Lys Pro Ala Lys Pro Ala Leu Lys Arg Ser Arg Arg Glu Ala Asp
            855                 860                 865

ACC TGT GGC CAG GAC CCT CCC AAA AGT GCC AGC AGT ACC AAG AGC AAC    3117
Thr Cys Gly Gln Asp Pro Pro Lys Ser Ala Ser Ser Thr Lys Ser Asn
        870                 875                 880

CAC AAA GAC TCT TCC ATT CCC AAG CAG AGA AGA GTA GAG GGG AAG GGC    3165
His Lys Asp Ser Ser Ile Pro Lys Gln Arg Arg Val Glu Gly Lys Gly
    885                 890                 895

TCC AGA AGC TCC TCG GAG CAC AAG GGT TCT TCC GGA GAT ACT GCA AAT    3213
Ser Arg Ser Ser Ser Glu His Lys Gly Ser Ser Gly Asp Thr Ala Asn
900                 905                 910                 915

CCT TTT CCA GTG CCT TCT TTG CCA AAT GGT AAC TCT AAA CCA GGG AAG    3261
Pro Phe Pro Val Pro Ser Leu Pro Asn Gly Asn Ser Lys Pro Gly Lys
                920                 925                 930

CCT CAA GTG AAG TTT GAC AAA CAA CAA GCA GAC CTT CAC ATG AGG GAG    3309
Pro Gln Val Lys Phe Asp Lys Gln Gln Ala Asp Leu His Met Arg Glu
            935                 940                 945

GCA AAA AAG ATG AAG CAG AAA GCA GAG TTA ATG ACG GAC AGG GTT GGA    3357
Ala Lys Lys Met Lys Gln Lys Ala Glu Leu Met Thr Asp Arg Val Gly
        950                 955                 960

AAG GCT TTT AAG TAC CTG GAA GCC GTC TTG TCC TTC ATT GAG TGC GGA    3405
Lys Ala Phe Lys Tyr Leu Glu Ala Val Leu Ser Phe Ile Glu Cys Gly
    965                 970                 975
```

-continued

| | |
|---|---|
| ATT GCC ACA GAG TCT GAA AGC CAG TCA TCC AAG TCA GCT TAC TCT GTC<br>Ile Ala Thr Glu Ser Glu Ser Gln Ser Ser Lys Ser Ala Tyr Ser Val<br>980     985     990     995 | 3453 |
| TAC TCA GAA ACT GTA GAT CTC ATT AAA TTC ATA ATG TCA TTA AAA TCC<br>Tyr Ser Glu Thr Val Asp Leu Ile Lys Phe Ile Met Ser Leu Lys Ser<br>    1000     1005     1010 | 3501 |
| TTC TCA GAT GCC ACA GCG CCA ACA CAA GAG AAA ATA TTT GCT GTT TTA<br>Phe Ser Asp Ala Thr Ala Pro Thr Gln Glu Lys Ile Phe Ala Val Leu<br>1015     1020     1025 | 3549 |
| TGC ATG CGT TGC CAG TCC ATT TTG AAC ATG GCG ATG TTT CGT TGT AAA<br>Cys Met Arg Cys Gln Ser Ile Leu Asn Met Ala Met Phe Arg Cys Lys<br>  1030     1035     1040 | 3597 |
| AAA GAC ATA GCA ATA AAG TAT TCT CGT ACT CTT AAT AAA CAC TTC GAG<br>Lys Asp Ile Ala Ile Lys Tyr Ser Arg Thr Leu Asn Lys His Phe Glu<br>1045     1050     1055 | 3645 |
| AGT TCT TCC AAA GTC GCC CAG GCA CCT TCT CCA TGC ATT GCA AGC ACA<br>Ser Ser Ser Lys Val Ala Gln Ala Pro Ser Pro Cys Ile Ala Ser Thr<br>1060     1065     1070     1075 | 3693 |
| GGC ACA CCA TCC CCT CTT TCC CCA ATG CCT TCT CCT GCC AGC TCC GTA<br>Gly Thr Pro Ser Pro Leu Ser Pro Met Pro Ser Pro Ala Ser Ser Val<br>    1080     1085     1090 | 3741 |
| GGG TCC CAG TCA AGT GCT GGC AGT GTG GGG AGC AGT GGG GTG GCT GCC<br>Gly Ser Gln Ser Ser Ala Gly Ser Val Gly Ser Ser Gly Val Ala Ala<br>    1095     1100     1105 | 3789 |
| ACT ATC AGC ACC CCA GTC ACC ATC CAG AAT ATG ACA TCT TCC TAT GTC<br>Thr Ile Ser Thr Pro Val Thr Ile Gln Asn Met Thr Ser Ser Tyr Val<br>    1110     1115     1120 | 3837 |
| ACC ATC ACA TCC CAT GTT CTT ACC GCC TTT GAC CTT TGG GAA CAG GCC<br>Thr Ile Thr Ser His Val Leu Thr Ala Phe Asp Leu Trp Glu Gln Ala<br>1125     1130     1135 | 3885 |
| GAG GCC CTC ACG AGG AAG AAT AAA GAA TTC TTT GCT CGG CTC AGC ACA<br>Glu Ala Leu Thr Arg Lys Asn Lys Glu Phe Phe Ala Arg Leu Ser Thr<br>1140     1145     1150     1155 | 3933 |
| AAT GTG TGC ACC TTG GCC CTC AAC AGC AGT TTG GTG GAC CTG GTG CAC<br>Asn Val Cys Thr Leu Ala Leu Asn Ser Ser Leu Val Asp Leu Val His<br>    1160     1165     1170 | 3981 |
| TAT ACA CGA CAG GGT TTT CAG CAG CTA CAA GAA TTA ACC AAA ACA CCT<br>Tyr Thr Arg Gln Gly Phe Gln Gln Leu Gln Glu Leu Thr Lys Thr Pro<br>1175     1180     1185 | 4029 |
| TAATGGAGCC CCAGGTTGAT TCAATGCCTT GGGAACTATT TTTGCACATT GGAAGCCTCA | 4089 |
| AAAACAGTCC AGACGTTTGT TCATCAGGA CACCAAACTC TAAAAAAGAA GCACCACGAG | 4149 |
| ATGGCCAGGA CATTTGTCCA CTTAAACTCT CAACAACAGT GTGATCATTG GTTGGACACT | 4209 |
| GTGGTTATGC AGAAGCAGAG ATGAGGAGGC TGGCCCCAGA GATGATCTTG CCCTTCCTAA | 4269 |
| CTAAAGGACA GAAGTGCAAT TTAGCTTAAA TGGGTGTATG AATGGTCTAG AAACATTTCT | 4329 |
| ATTTTTTTTT TAAACCAGCA GGATACAAGT TGCAAATGAA ATGAGGAGAA ACAGTTTCAA | 4389 |
| CTCTGAAAGT GAATTTCACG TCATCTCAGT AGCCACGCTA GTCCATTCCC AGAAGGAAAT | 4449 |
| TTTTTTTTTT AACAATGACT TTTGGTAAAG GGTTTTGTGG ATGATTTTTT TTCTTTTGAG | 4509 |
| TTTTGGGAGA AATATTTGTT TAATAACTTC TAATGGCCAT CTGTAAACCA TAAGTAATGA | 4569 |
| AGGACTCCAC TGTGCCCCAC TTTCTGCCAA TGAACAGTGG CTTGATAATA CCAAGTATTG | 4629 |
| TTGTAATTTA TAAAATTGAA GGCAACCCCC GCTCCTGCCG CCCCAATCT CCCCATTGCC | 4689 |
| TAGAGCGCTG CACATTGACC CCAGCTCTGA CTTCTCATTA CTGTGCTGAA AGTCAGCCCA | 4749 |
| CGTCGGAGCG GTGAGGAGGA GCCACAGCAC ATGGGGTGCC ACCTCGAGGT CTGCACAGGA | 4809 |
| GGACTTGGCG CTGCCATTTC CTACCCCTGC CATTTCCCAC CCTGCTTCA GCGAAAGGGA | 4869 |

```
CTCTCTAACA GGGCAGTCAC TGTTGACTCT ATTCTGAATT TCCTCCCTTG GGGAAGAAGG    4929

GAACCAACAT TTATACCTGA CCAGATGGCT AAAGTGCTTT TAAAGTTTTG TTTAAGTAGA    4989

GCTGGAATTT GAGGTGCTGA TCTGTGGTCT ACAGTTATGT GGTAACTCAT GTTGTCCAGC    5049

CAACTCAGAG TTTCGTCAGT GAACAAGAAA CATGAAATCT GCTTCTTAGA GAGGCTATAT    5109

TTTTCTGCTA CAAATATTTT ATATTTATAG CAAAACTAGA CTTTCAGAGT CCTTGATTGT    5169

CTAGGGGAAG TTAACTCCCT GAGAGGATGT AGAGATTTGG GGTGGTTGAT TAGACTTTTG    5229

AAAAACTCAT CACCACATGC CTTCACTCCA GAGTGTTCTC AGCTAGATTT GATTTGGTTG    5289

AGGAGGAACT GTGGCCCTCC GTAAGTTATT GCCATAGTGT ATGCATTAAA CCAAGTCCAT    5349

TTTGAATGAC CTAAAATGAA GTAACACAAT CAGAAATCCC ATGTGCCCAT AAGCACAGAT    5409

TTTTCTTTTT CATTGAAACT TTAAAGGTTA TTATTGGAAA CATTACTTTG AGTGCAGTGT    5469

TTTTAAAAGC CAATTCTTTT TTATCCCTTT TAGAAGTAGA ATTTGCACAC TTACTACAAT    5529

TGAGGAGTGT CATCTCTATA ACTTTTTCTC CGCCTTTGTC CCATTCTGCC CCTGGACATG    5589

TTTCCTACCA AGCATGTTTC ACATTTTCCT ATTAGTGGAG GAGGGAGAAC CATATTTATT    5649

TATAATGAAG ACATCTAAGA TCCCTATGAT GAATGCAGGA ACTCTCTTGG TAGTTTGTAA    5709

ATACACAAAG GGATGTGTCG AGGGATGGGA GCGATGCTTA TCTCTCACAG TGTGAGTGGT    5769

CTGTGTGAGG CTGTTCCTTC AGTTCTTCTC CAGACTGTTC TTTGGTTGTC ACTTAAGTCA    5829

GAGGTCTGGT CCCTCATGTT TAGGTGAAAG CCAGAGAATG ACAGCTGTAG TCATATCTGA    5889

GCATAAGACC TTGATGTGTG ATTCCTGATG ACCGGTTTCA TTTATTCATG TAATAAAGCA    5949

AAGGCCCTGG TCCTTTTTAA ACTACTAGTT TTAAAAACCT GTGTTAAATG AACAGTAATT    6009

GCCTGGTAGG TTTGGTGTGT GTGTAGCATT GTGTGTCCAT CTGTTATATG TAAAGGACAA    6069

GGCACCAGAA TCAGGCTTTA TTTCGATATT GAAGATGTTA TTTAACATCT TTCTTTTTTC    6129

CTTACTCCCT TAGCCATCCC CTCCCCTTTT GTCCTATCAT TCCCTAGAAC AAGCCACCTG    6189

TCAATTGTGA AGGGTTGTGT TCTTTATGGC AGGTTCTATG CAGATTGTGC CAGAGCATGT    6249

GCGTGTTCTG TTGGCAAGCC ACAGTGCTCC CTTGACTGAA GACATTTCCA GGTAGATTTC    6309

TCAGCCAGCT CTAAAACAGA TTGCTTTTTC AGTGGCCTTA CTCTTTGTGG GTTTTTTTTT    6369

TTCTCTGAAC TTGATATAAA GATTTTATTT GTCCCTTGAA AAAGTAACAA ATGTGCATAG    6429

ATCAATTTGT ACTACTTTGG TCATTGGATA TTTCTGATCC TTATTGCATT GTACCTAAAG    6489

GAGAGTAACT AATGGTAACC TTTTTAATAG AGTATGTGAA AGGTAGTGGC TGATGAATCC    6549

TTAACGTTCA TAGGGTCTTT TTGCTGTTAC GGTTGTATAT AGAGGTCTGA AGGATTTTTA    6609

AAATGATTTG CACTTTTTCA CTGCATGCTT ACAATTCCCA AAGGCAAAAT CTGTACTGAG    6669

GTAGATCATT TGAAAGGGCT AGATTATAAA ATTAAGCCTT AGAGTATGGA AAGTTCTTAT    6729

AACAATAATA GTACACACTT CAGAGTAAGA CAAATGCAAA GCATCTTAAG GAGTGAAAAT    6789

AGAGTCTAAA TCTTGCCTTT GGCACTACAA GGTGTGTGTG TGTGTGTGTG TTGTGTGTCT    6849

TTAGTAGGAA ATGGAAGAAC ACTGTTTTAT TTTTTAAAGT GTTTAATGTT TCTGTCCTTT    6909

CTGTGAATTA TTGAATTTAA GAGCCCTGCT AAATAATGAA AAAACACTTT ACTAAAATTT    6969

ATCAAATTAT ACTGGGTTCG GATTGTGAAA ACATTGGCCA CCTAGTAGCA GTGGTGAGGA    7029

GTGGGAGGGC CCAGCAAGCA TTTATCAGAA ATAGAATCAC AATAGGAGGA GAATTTGGCT    7089

GTCTGATATT ATGATTTGAT TACAATACTG AATGGGAAAA GTATCTAATA TTTTGTAACA    7149

AAAAGACCTT CATATTATCT GTTTTGACCA AAATATGTAG CTATTTCCCT TACACAGATT    7209
```

```
GGACCGCACT TATCTCCCTT GTCCTGTATC CTTTAATTTC AGGTCTCAGG ATGTTTAGAA      7269

AGCTAAAACC CCCTACCCCT TTCTGGCTGA AAACTTGCCT TATTTGGTAT CTTACACATT      7329

AATGTTACTA GCATCAGGAG CTTACTGTTT TATTATGATT CATCTTCAGT AATTTTTAGA      7389

AGCAAGAAGA AAGCCATTGT GTCCTCTACA AATTAACAAA ACTTATCTCT GATATACAAA      7449

GGGATATAAA TATATACACT TAAATAGAGA AAAAGAGGTT GATTGAATTG TGCCTTTGAG      7509

TGAACCCAGT TTTTAAATAC CGCTGTGTTT GTTTCGCCAT GGCTTCAGGG ATGCTACATG      7569

GCTCTTGCAC CTTTTACTCC TCTGCTTTAT GAAGTTTGAG TTGTATTTGT GCATCTTAAA      7629

GTAGGTTGAG GCTTGAGGCT GGGCTTTCGG GTTTTTTTGT TTTTTGTTTT GTTTTGTTTT      7689

GTTTTGTTTT CTTGTACTTA AACCTGCTTG CTTCCTACCA CAGATTCTTT ATTTTCCCAA      7749

ACACTACAAA AAAACTTTTA AAACTTTGCC ATTTCATCTG TTTACACTCT TTGCCACTGA      7809

TTAGCAGTAT TTAAATCTTG CAAGAATATT TTGTGCTTTC TTTAGAAACA CAAGAGTAGA      7869

GATTTTTCTC ACTGAAAAGT GAGAGTTACG CATTGCAGCC ATGAAGGGAT GCTAGGATCA      7929

ATTATGGCAG TACCTTTTTT CCCCTCCTGT TCTTGAGCCA GTTGTCTCTT TTGTGTTGGG      7989

TCCCACTTAG GATTAACGGA TGTAAGGTAT TTTCCTGTGC CTTTATTTTG TGTCATTCTA      8049

TTGGAAGGAG GTGTAACGGC AGAATAGCAT CGTGTTGGGG GTTTTCCTTC AAACACTGCA      8109

AGTGATATTG CCACCATGTG AACCTCAAAT ATGCAATCCA GTTGTGTTGG TTTCTCGGTG      8169

ACTTGGAGTG TTCATCTCTT CATGAATTGT GAGCACTGAC CATGTTCTTC AGTTCTTAAT      8229

TATGGTGAGT TGACAAATAC CAACTACTGC TTTTCTTTAG GTGGCTATAA ATTTCTTACT      8289

GTCAGGAGGA AATGACATTA TATTCTGTTC CACTGAACGT CAGAGATCAG CAGGCACTGT      8349

ACTGGGTAGA GAAGTGCCTA TACTTCTCTA CCTAAGAGGG CAGGAGGGAA ACCCTACAGC      8409

TCCTTGTGAG CCTATATATT AGTATATCGG CCTGGAGAGG ACAAGGGAAT AAGACCACTC      8469

ATAGTGAGGC TGGCCAAGCT GCACTGGTCG GACCAGGCAG TGGCTGACCT AAGGAAGGCA      8529

ACTTGCTTTG CTTAAAAGTA GATTTTTTAA GCAATGCTTA ACACAGGCAG CATTCACCTT      8589

TGTTCAGGCC ATCGACATGT ATTGTTAAAA TTACTGCATA TCCCCCTCAG ATATCAAGTA      8649

TACACTGTTC ATGTTGGGGT TGTGTGTGTG TATGTGTGTA TGTACGCACG CATGTGTCCC      8709

AAATCTTGTT TTAATTTTTT TTTTCTGAAT GTGATCATGT TTTGGATAAT ACCTGAGCAG      8769

GGTTGCCTTT TTTTTATTTA TTACCATTAT ATATTATATT ATATTATATA TTTTTTGCTT      8829

TCTTATAACT TTGGAGGAAA GTCAAATCTT GGTATTATTA AAATTGTTTT AAAAAGGAGT      8889

AAATTTTCCA GTTGATAAAT GAAAATCACT GGCCTATGTT TAATAAGTTT TTCTTTAATT      8949

ACTGTGGAAT AACGTGCCAG CTATCATCAA CACAATGATT TTGTACATAG GGTAGGGAAG      9009

CAGTGATGCT CTCAATGGGA AGATGTGCAA CACAAATTAA GGGGAACTCC ATGTATTTTA      9069

CCTACTTCAG CAATGGAACT GCAACTTGGG GCTTTGTGAA TAAAATTTAG CTGCCTTGTA      9129

TAGTCGTTTG AAAGAATATG TGATCTGTGA GAGAATTATA GTTTTTTTTT AGAAGAAAAA      9189

TCTGCAAAAG ATCTTTCCAA AGACAATGTG CCACAGATCT TTTGTTCTCT GTAATGAGGA      9249

TTAATTGCTG TTTAAACAAA AATGTAATTG TTCATCTTTA AATTCTTTCC TTTTCATAAG      9309

AGGATCAAGC TGTAAAAAAA CAAAAAAATT AATAAAAATT TCGAGAAATC AAAAAAAAAA      9369

A                                                                    9370
```

(2) INFORMATION FOR SEQ ID NO:28:

(i) SEQUENCE CHARACTERISTICS:
        (A) LENGTH: 1187 amino acids (B) TYPE: amino acid
(D) TOPOLOGY: linear (ii) MOLECULE TYPE: protein (xi) SEQUENCE DESCRIPTION: SEQ ID NO:28:

```
Asn Gln Glu Ala His Gln Glu Lys Glu Ala Phe Pro Glu Lys Ile Pro
 1               5                  10                  15

Leu Phe Gly Glu Pro Tyr Lys Thr Ala Lys Gly Asp Glu Leu Ser Ser
                20                  25                  30

Arg Ile Gln Asn Met Leu Gly Asn Tyr Glu Glu Val Lys Glu Phe Leu
             35                  40                  45

Ser Thr Lys Ser His Thr His Arg Leu Asp Ala Ser Glu Asn Arg Leu
         50                  55                  60

Gly Lys Pro Lys Tyr Pro Leu Ile Pro Asp Lys Gly Ser Ser Ile Pro
 65                  70                  75                  80

Ser Ser Ser Phe His Thr Ser Val His His Gln Ser Ile His Thr Pro
                 85                  90                  95

Ala Ser Gly Pro Leu Ser Val Gly Asn Ile Ser His Asn Pro Lys Met
                100                 105                 110

Ala Gln Pro Arg Thr Glu Pro Met Pro Ser Leu His Ala Lys Ser Cys
            115                 120                 125

Gly Pro Pro Asp Ser Gln His Leu Thr Gln Asp Arg Leu Gly Gln Glu
130                 135                 140

Gly Phe Gly Ser Ser His His Lys Lys Gly Asp Arg Arg Ala Asp Gly
145                 150                 155                 160

Asp His Cys Ala Ser Val Thr Asp Ser Ala Pro Glu Arg Glu Leu Ser
                165                 170                 175

Pro Leu Ile Ser Leu Pro Ser Pro Val Pro Pro Leu Ser Pro Ile His
                180                 185                 190

Ser Asn Gln Gln Thr Leu Pro Arg Thr Gln Gly Ser Ser Lys Val His
            195                 200                 205

Gly Ser Ser Asn Asn Ser Lys Gly Tyr Cys Pro Ala Lys Ser Pro Lys
210                 215                 220

Asp Leu Ala Val Lys Val His Asp Lys Glu Thr Pro Gln Asp Ser Leu
225                 230                 235                 240

Val Ala Pro Ala Gln Pro Pro Ser Gln Thr Phe Pro Pro Pro Ser Leu
                245                 250                 255

Pro Ser Lys Ser Val Ala Met Gln Gln Lys Pro Thr Ala Tyr Val Arg
            260                 265                 270

Pro Met Asp Gly Gln Asp Gln Ala Pro Ser Glu Ser Pro Glu Leu Lys
        275                 280                 285

Pro Leu Pro Glu Asp Tyr Arg Gln Gln Thr Phe Glu Lys Thr Asp Leu
    290                 295                 300

Lys Val Pro Ala Lys Ala Lys Leu Thr Lys Leu Lys Met Pro Ser Gln
305                 310                 315                 320

Ser Val Glu Gln Thr Tyr Ser Asn Glu Val His Cys Val Glu Glu Ile
                325                 330                 335

Leu Lys Glu Met Thr His Ser Trp Pro Pro Leu Thr Ala Ile His
            340                 345                 350

Thr Pro Ser Thr Ala Glu Pro Ser Lys Phe Pro Phe Pro Thr Lys Asp
        355                 360                 365

Ser Gln His Val Ser Ser Val Thr Gln Asn Gln Lys Gln Tyr Asp Thr
370                 375                 380
```

-continued

```
Ser Ser Lys Thr His Ser Asn Ser Gln Gln Gly Thr Ser Ser Met Leu
385                 390                 395                 400

Glu Asp Asp Leu Gln Leu Ser Asp Ser Glu Asp Ser Asp Ser Glu Gln
                405                 410                 415

Thr Pro Glu Lys Pro Pro Ser Ser Ala Pro Pro Ser Ala Pro Gln
            420                 425                 430

Ser Leu Pro Glu Pro Val Ala Ser Ala His Ser Ser Ala Glu Ser
        435                 440                 445

Glu Ser Thr Ser Asp Ser Asp Ser Ser Asp Ser Glu Ser Glu Ser
    450                 455                 460

Ser Ser Ser Asp Ser Glu Glu Asn Glu Pro Leu Glu Thr Pro Ala Pro
465                 470                 475                 480

Glu Pro Glu Pro Pro Thr Thr Asn Lys Trp Gln Leu Asp Asn Trp Leu
                485                 490                 495

Thr Lys Val Ser Gln Pro Ala Ala Pro Pro Glu Gly Pro Arg Ser Thr
                500                 505                 510

Glu Pro Pro Arg Arg His Pro Glu Ser Lys Gly Ser Ser Asp Ser Ala
            515                 520                 525

Thr Ser Gln Glu His Ser Glu Ser Lys Asp Pro Pro Lys Ser Ser
    530                 535                 540

Ser Lys Ala Pro Arg Ala Pro Glu Ala Pro His Pro Gly Lys Arg
545                 550                 555                 560

Ser Cys Gln Lys Ser Pro Ala Gln Gln Glu Pro Pro Gln Arg Gln Thr
                565                 570                 575

Val Gly Thr Lys Gln Pro Lys Lys Pro Val Lys Ala Ser Ala Arg Ala
                580                 585                 590

Gly Ser Arg Thr Ser Leu Gln Gly Glu Arg Glu Pro Gly Leu Leu Pro
            595                 600                 605

Tyr Gly Ser Arg Asp Gln Thr Ser Lys Asp Lys Pro Lys Val Lys Thr
            610                 615                 620

Lys Gly Arg Pro Arg Ala Ala Ala Ser Asn Glu Pro Lys Pro Ala Val
625                 630                 635                 640

Pro Pro Ser Ser Glu Lys Lys His Lys Ser Ser Leu Pro Ala Pro
                645                 650                 655

Ser Lys Ala Leu Ser Gly Pro Glu Pro Ala Lys Asp Asn Val Glu Asp
                660                 665                 670

Arg Thr Pro Glu His Phe Ala Leu Val Pro Leu Thr Glu Ser Gln Gly
            675                 680                 685

Pro Pro His Ser Gly Ser Gly Ser Arg Thr Ser Gly Cys Arg Gln Ala
            690                 695                 700

Val Val Val Gln Glu Asp Ser Arg Lys Asp Arg Leu Pro Leu Pro Leu
705                 710                 715                 720

Arg Asp Thr Lys Leu Leu Ser Pro Leu Arg Asp Thr Pro Pro Gln
            725                 730                 735

Ser Leu Met Val Lys Ile Thr Leu Asp Leu Leu Ser Arg Ile Pro Gln
                740                 745                 750

Pro Pro Gly Lys Gly Ser Arg Gln Arg Lys Ala Glu Asp Lys Gln Pro
            755                 760                 765

Pro Ala Gly Lys Lys His Ser Glu Lys Ser Arg Ser Ser Asp Ser Ser
        770                 775                 780

Ser Lys Leu Ala Lys Lys Arg Lys Gly Glu Ala Glu Arg Asp Cys Asp
785                 790                 795                 800

Asn Lys Lys Ile Arg Leu Glu Lys Glu Ile Lys Ser Gln Ser Ser Ser
```

```
                805                 810                 815
Ser Ser Ser Ser His Lys Glu Ser Ser Lys Thr Lys Pro Ser Arg Pro
            820                 825                 830

Ser Ser Gln Ser Ser Lys Lys Glu Met Leu Pro Pro Pro Val Ser
            835                 840                 845

Ser Ser Ser Gln Lys Pro Ala Lys Pro Ala Leu Lys Arg Ser Arg Arg
    850                 855                 860

Glu Ala Asp Thr Cys Gly Gln Asp Pro Pro Lys Ser Ala Ser Ser Thr
865                 870                 875                 880

Lys Ser Asn His Lys Asp Ser Ser Ile Pro Lys Gln Arg Arg Val Glu
                885                 890                 895

Gly Lys Gly Ser Arg Ser Ser Glu His Lys Gly Ser Ser Gly Asp
            900                 905                 910

Thr Ala Asn Pro Phe Pro Val Pro Ser Leu Pro Asn Gly Asn Ser Lys
            915                 920                 925

Pro Gly Lys Pro Gln Val Lys Phe Asp Lys Gln Gln Ala Asp Leu His
        930                 935                 940

Met Arg Glu Ala Lys Lys Met Lys Gln Lys Ala Glu Leu Met Thr Asp
945                 950                 955                 960

Arg Val Gly Lys Ala Phe Lys Tyr Leu Glu Ala Val Leu Ser Phe Ile
                965                 970                 975

Glu Cys Gly Ile Ala Thr Glu Ser Ser Gln Ser Ser Lys Ser Ala
            980                 985                 990

Tyr Ser Val Tyr Ser Glu Thr Val Asp Leu Ile Lys Phe Ile Met Ser
                995                 1000                1005

Leu Lys Ser Phe Ser Asp Ala Thr Ala Pro Thr Gln Glu Lys Ile Phe
    1010                1015                1020

Ala Val Leu Cys Met Arg Cys Gln Ser Ile Leu Asn Met Ala Met Phe
1025                1030                1035                1040

Arg Cys Lys Lys Asp Ile Ala Ile Lys Tyr Ser Arg Thr Leu Asn Lys
                1045                1050                1055

His Phe Glu Ser Ser Lys Val Ala Gln Ala Pro Ser Pro Cys Ile
            1060                1065                1070

Ala Ser Thr Gly Thr Pro Ser Pro Leu Ser Pro Met Pro Ser Pro Ala
        1075                1080                1085

Ser Ser Val Gly Ser Gln Ser Ser Ala Gly Ser Val Gly Ser Ser Gly
    1090                1095                1100

Val Ala Ala Thr Ile Ser Thr Pro Val Thr Ile Gln Asn Met Thr Ser
1105                1110                1115                1120

Ser Tyr Val Thr Ile Thr Ser His Val Leu Thr Ala Phe Asp Leu Trp
            1125                1130                1135

Glu Gln Ala Glu Ala Leu Thr Arg Lys Asn Lys Glu Phe Phe Ala Arg
                1140                1145                1150

Leu Ser Thr Asn Val Cys Thr Leu Ala Leu Asn Ser Ser Leu Val Asp
            1155                1160                1165

Leu Val His Tyr Thr Arg Gln Gly Phe Gln Gln Leu Gln Glu Leu Thr
        1170                1175                1180

Lys Thr Pro
1185
```

(2) INFORMATION FOR SEQ ID NO:29:

(i) SEQUENCE CHARACTERISTICS:
        (A) LENGTH: 3376 base pairs (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 196..1902

(xi) SEQUENCE DESCRIPTION: SEQ ID NO:29:

```
TTTGGGGCTG AGTTTAATAA GCGAGCGAGC GAGCAAGCGA GCGCGGGGGG AAAAAGGCAG      60

AGAATGTCCG CCATCTACCC TCCGCTCCTG GGCGCGCTCT CATTCATAGC AGCCTCTTCA     120

TGAATTACAG CTGAGGGGGG GCGGAGGAGG GGGGGGTACC ACACAACACC CCAGCAAACC     180

TCCGGGCCCC CAGGC ATG GCT AGC TCG TGT TCC GTG CAG GTG AAG CTG GAG     231
              Met Ala Ser Ser Cys Ser Val Gln Val Lys Leu Glu
                1               5                  10

CTG GGG CAC CGC GCC CAG GTG AGG AAA AAA CCC ACC GTG GAG GGC TTC     279
Leu Gly His Arg Ala Gln Val Arg Lys Lys Pro Thr Val Glu Gly Phe
         15                  20                  25

ACC CAC GAC TGG ATG GTG TTC GTA CGC GGT CCG GAG CAC AGT AAC ATA     327
Thr His Asp Trp Met Val Phe Val Arg Gly Pro Glu His Ser Asn Ile
 30                  35                  40

CAG CAC TTT GTG GAG AAA GTC GTC TTC CAC TTG CAC GAA AGC TTT CCT     375
Gln His Phe Val Glu Lys Val Val Phe His Leu His Glu Ser Phe Pro
 45                  50                  55                  60

AGG CCA AAA AGA GTG TGC AAA GAT CCA CCT TAC AAA GTA GAA GAA TCT     423
Arg Pro Lys Arg Val Cys Lys Asp Pro Pro Tyr Lys Val Glu Glu Ser
                 65                  70                  75

GGG TAT GCT GGT TTC ATT TTG CCA ATT GAA GTT TAT TTT AAA AAC AAG     471
Gly Tyr Ala Gly Phe Ile Leu Pro Ile Glu Val Tyr Phe Lys Asn Lys
             80                  85                  90

GAA GAA CCT AGG AAA GTC CGC TTT GAT TAT GAC TTA TTC CTG CAT CTT     519
Glu Glu Pro Arg Lys Val Arg Phe Asp Tyr Asp Leu Phe Leu His Leu
         95                 100                 105

GAA GGC CAT CCA CCA GTG AAT CAC CTC CGC TGT GAA AAG CTA ACT TTC     567
Glu Gly His Pro Pro Val Asn His Leu Arg Cys Glu Lys Leu Thr Phe
110                 115                 120

AAC AAC CCC ACA GAG GAC TTT AGG AGA AAG TTG CTG AAG GCA GGA GGG     615
Asn Asn Pro Thr Glu Asp Phe Arg Arg Lys Leu Leu Lys Ala Gly Gly
125                 130                 135                 140

GAC CCT AAT AGG AGT ATT CAT ACC AGC AGC AGC AGC AGC AGC AGC AGT     663
Asp Pro Asn Arg Ser Ile His Thr Ser Ser Ser Ser Ser Ser Ser Ser
                145                 150                 155

AGC AGC AGC AGC AGC AGC AGC AGC AGC AGT AGC AGC AGC AGC AGC         711
Ser Ser Ser Ser Ser Ser Ser Ser Ser Ser Ser Ser Ser Ser Ser
            160                 165                 170

AGC AGC AGC AGC AGC AGT AGC AGC AGC AGT AGC AGC AGC AGC AGC         759
Ser Ser Ser Ser Ser Ser Ser Ser Ser Ser Ser Ser Ser Ser Ser
        175                 180                 185

AGT AGT ACC AGT TTT TCA AAG CCT CAC AAA TTA ATG AAG GAG CAC AAG     807
Ser Ser Thr Ser Phe Ser Lys Pro His Lys Leu Met Lys Glu His Lys
    190                 195                 200

GAA AAA CCT TCT AAA GAC TCC AGA GAA CAT AAA AGT GCC TTC AAA GAA     855
Glu Lys Pro Ser Lys Asp Ser Arg Glu His Lys Ser Ala Phe Lys Glu
205                 210                 215                 220

CCT TCC AGG GAT CAC AAC AAA TCT TCC AAA GAA TCC TCT AAG AAA CCC     903
Pro Ser Arg Asp His Asn Lys Ser Ser Lys Glu Ser Ser Lys Lys Pro
                225                 230                 235

AAA GAA AAT AAA CCA CTG AAA GAA GAG AAA ATA GTT CCT AAG ATG GCC     951
```

```
                Lys Glu Asn Lys Pro Leu Lys Glu Lys Ile Val Pro Lys Met Ala
                                240                 245                 250

TTC AAG GAA CCT AAA CCC ATG TCA AAA GAG CCA AAA CCA GAT AGT AAC              999
Phe Lys Glu Pro Lys Pro Met Ser Lys Glu Pro Lys Pro Asp Ser Asn
                255                 260                 265

TTA CTC ACC ATC ACC AGT GGA CAA GAT AAG AAG GCT CCT AGT AAA AGG             1047
Leu Leu Thr Ile Thr Ser Gly Gln Asp Lys Lys Ala Pro Ser Lys Arg
    270                 275                 280

CCG CCC ATT TCA GAT TCT GAA GAA CTC TCA GCC AAA AAA AGG AAA AAG             1095
Pro Pro Ile Ser Asp Ser Glu Glu Leu Ser Ala Lys Lys Arg Lys Lys
285                 290                 295                 300

AGT AGC TCA GAG GCT TTA TTT AAA AGT TTT TCT AGC GCA CCA CCA CTG             1143
Ser Ser Ser Glu Ala Leu Phe Lys Ser Phe Ser Ser Ala Pro Pro Leu
                305                 310                 315

ATA CTC ACT TGT TCT GCT GAC AAA AAA CAG ATA AAA GAT AAA TCT CAT             1191
Ile Leu Thr Cys Ser Ala Asp Lys Lys Gln Ile Lys Asp Lys Ser His
                320                 325                 330

GTC AAG ATG GGA AAG GTC AAA ATT GAA AGT GAG ACA TCA GAG AAG AAG             1239
Val Lys Met Gly Lys Val Lys Ile Glu Ser Glu Thr Ser Glu Lys Lys
                335                 340                 345

AAA TCA ACG TTA CCG CCA TTT GAT GAT ATT GTG GAT CCC AAT GAT TCA             1287
Lys Ser Thr Leu Pro Pro Phe Asp Asp Ile Val Asp Pro Asn Asp Ser
    350                 355                 360

GAT GTG GAG GAG AAT ATA TCC TCT AAA TCT GAT TCT GAA CAA CCC AGT             1335
Asp Val Glu Glu Asn Ile Ser Ser Lys Ser Asp Ser Glu Gln Pro Ser
365                 370                 375                 380

CCT GCC AGC TCC AGC TCC AGC TCC AGC TCC AGC TTC ACA CCA TCC CAG             1383
Pro Ala Ser Ser Ser Ser Ser Ser Ser Ser Ser Phe Thr Pro Ser Gln
                385                 390                 395

ACC AGG CAA CAA GGT CCT TTG AGG TCT ATA ATG AAA GAT CTG CAT TCT             1431
Thr Arg Gln Gln Gly Pro Leu Arg Ser Ile Met Lys Asp Leu His Ser
                400                 405                 410

GAT GAC AAT GAG GAG GAA TCA GAT GAA GTG GAG GAT AAC GAC AAT GAC             1479
Asp Asp Asn Glu Glu Glu Ser Asp Glu Val Glu Asp Asn Asp Asn Asp
                415                 420                 425

TCT GAA ATG GAG AGG CCT GTA AAT AGA GGA GGC AGC CGA AGT CGC AGA             1527
Ser Glu Met Glu Arg Pro Val Asn Arg Gly Gly Ser Arg Ser Arg Arg
    430                 435                 440

GTT AGC TTA AGT GAT GGC AGC GAT AGT GAA AGC AGT TCT GCT TCT TCA             1575
Val Ser Leu Ser Asp Gly Ser Asp Ser Glu Ser Ser Ser Ala Ser Ser
445                 450                 455                 460

CCC CTA CAT CAC GAA CCT CCA CCA CCC TTA CTA AAA ACC AAC AAC AAC             1623
Pro Leu His His Glu Pro Pro Pro Pro Leu Leu Lys Thr Asn Asn Asn
                465                 470                 475

CAG ATT CTT GAA GTG AAA AGT CCA ATA AAG CAA AGC AAA TCA GAT AAG             1671
Gln Ile Leu Glu Val Lys Ser Pro Ile Lys Gln Ser Lys Ser Asp Lys
                480                 485                 490

CAA ATA AAG AAT GGT GAA TGT GAC AAG GCA TAC CTA GAT GAA CTG GTA             1719
Gln Ile Lys Asn Gly Glu Cys Asp Lys Ala Tyr Leu Asp Glu Leu Val
                495                 500                 505

GAG CTT CAC AGA AGG TTA ATG ACA TTG AGA GAA AGA CAC ATT CTG CAG             1767
Glu Leu His Arg Arg Leu Met Thr Leu Arg Glu Arg His Ile Leu Gln
    510                 515                 520

CAG ATC GTG AAC CTT ATA GAA GAA ACT GGA CAC TTT CAT ATC ACA AAC             1815
Gln Ile Val Asn Leu Ile Glu Glu Thr Gly His Phe His Ile Thr Asn
525                 530                 535                 540

ACA ACA TTT GAT TTT GAT CTT TGC TCG CTG GAC AAA ACC ACA GTC CGT             1863
Thr Thr Phe Asp Phe Asp Leu Cys Ser Leu Asp Lys Thr Thr Val Arg
                545                 550                 555
```

```
AAA CTA CAG AGT TAC CTG GAA ACA TCT GGA ACA TCC TGAGGATATA          1909
Lys Leu Gln Ser Tyr Leu Glu Thr Ser Gly Thr Ser
            560                 565

ACAACTGGAT GCATCAAGAA CTATTGTGTT TTTTTTTTTT GGTTTTTTTT TTTTTTGGTT   1969

GTGATTTTTT GTTCTTGTTG TTTATATGAA AACACTCAAA ATGATGCAAC CAAAAGGGAA   2029

AAAATAAAAA TCAAACAACC TTCAGCTTTA TTTTTCTTTA AAGCCAGTCA TCATCTCTTG   2089

ATAAAGGAGA GGTTAAAGCA AACCAGCCTC AGCGGACCAC TCTTCTCTCC AAGGAAATCC   2149

CCGGGAAGAG TTAGCCTGGA TAGCCTTGAA ACAAACAAA TCAAACACAA CACAAGAAAA    2209

CTCAAAGAAT GTGTATGGTA TCATGTATCT CTCTGTGGTG GTTCATTCCA CAGGACGAAT   2269

GCATATTCAA CACACTGCCT TATTACATAA CTGATCTATT TATTATCGCA TACAGATATT   2329

CTAAGTCGTT GAGGGAATGA CACCATCAGA CATTATAAGT ACTTGGTCCC GTGGATGCTC   2389

TTTCAATGCA GCACCCTTGC CATCCCAAGC CCAGTGACCT TACTCGTATA CCGTGCCACT   2449

TTCCACCAAC TTTTTCCAAG TCCTTTAACT CGTTGCAGTC TGTATTTTCC ACCTTTTGTT   2509

TTTCCAGTTC CAGGACACAG ATTATCAACT GGGGGGACCA ATAGCCACC TTGATTTTCT    2569

TCTTTGTGGT CTTTTTCCTG AAAGTTGGGG CCCAGTCCTT GGCTGTATCC ATGTAATGAT   2629

CTTGGACCAT GGTAGAAAAT GCACCAAATA GGATCATATG AATTGCTGTC TAGCCTTAGT   2689

CAATAAACTT GTAGGACTTT TAAACAAAAG TGTACCTGTA AATGTCCTGA ATCCAGCATT   2749

GTTGAGCTGT CATCAACATT CTTGTGTCTG TTTTACTGTT ACAATATTAG GTGAATATGG   2809

AAGTAAAGGC ATTCCACAGG ATCATCATTT AAAAAAAAAG AATTCTGGTC CTGTTTTCTA   2869

AAAAAAAAAA ACTGTTGTAG AAATTCTTAA TTTGGATCTA TTTATTAGTC AGAGTTTCAG   2929

CTTTCTTCAG CTGCCAGTGT GTTACTCATC TTTATCCTAA AAATCTGGAA TCAGAGATTT   2989

TTGTTTGTTC ACATATGATT CTCTTAGACA CTTTTATATT TGAAAAAATT AAAATCTTTC   3049

TTTGGGGAAA AATTCTTGGT TATTCTGCCA TAACAGATTA TGTATTAACT TGTAGATTCA   3109

GTGGTTCAAT ACCTGTTTAG TTGCTTGCTA ATATTTCCAG AAGGATTCT TGTATTGGTG    3169

AAAGACGGTT GGGGATGGGG GGATTTTTTT GTTCTTGTTG TACCCTTGTT TTGAAACTAG   3229

AAATCTGTCC TGTGGCATGC AAAAGAAAGC AAATTATTTT TAAAAGAAAA AAACCAAAGT   3289

ACTTTTGGTG TCATTATTCC ATCTTCTCCA TAAGTGGAGA ATGAAAAGT AAGAACAGCT    3349

CATCTTCAAA GTTTTTACTA GAAATTC                                      3376

(2) INFORMATION FOR SEQ ID NO:30:

(i) SEQUENCE CHARACTERISTICS:
        (A) LENGTH: 568 amino acids
        (B) TYPE: amino acid
        (D) TOPOLOGY: linear (ii) MOLECULE TYPE: protein (xi) SEQUENCE DESCRIPTION: SEQ ID NO:30:

Met Ala Ser Ser Cys Ser Val Gln Val Lys Leu Glu Leu Gly His Arg
 1               5                  10                  15

Ala Gln Val Arg Lys Lys Pro Thr Val Glu Gly Phe Thr His Asp Trp
            20                  25                  30

Met Val Phe Val Arg Gly Pro Glu His Ser Asn Ile Gln His Phe Val
        35                  40                  45

Glu Lys Val Val Phe His Leu His Glu Ser Phe Pro Arg Pro Lys Arg
    50                  55                  60

Val Cys Lys Asp Pro Pro Tyr Lys Val Glu Glu Ser Gly Tyr Ala Gly
```

-continued

```
                65                  70                  75                  80
            Phe Ile Leu Pro Ile Glu Val Tyr Phe Lys Asn Lys Glu Pro Arg
                            85                  90                  95
            Lys Val Arg Phe Asp Tyr Asp Leu Phe Leu His Leu Glu Gly His Pro
                        100                 105                 110
            Pro Val Asn His Leu Arg Cys Glu Lys Leu Thr Phe Asn Asn Pro Thr
                        115                 120                 125
            Glu Asp Phe Arg Arg Lys Leu Leu Lys Ala Gly Asp Pro Asn Arg
                        130                 135                 140
            Ser Ile His Thr Ser Ser Ser Ser Ser Ser Ser Ser Ser Ser Ser Ser
            145                 150                 155                 160
            Ser Ser Ser Ser Ser Ser Ser Ser Ser Ser Ser Ser Ser Ser Ser Ser
                        165                 170                 175
            Ser Ser Ser Ser Ser Ser Ser Ser Ser Ser Ser Ser Ser Thr Ser
                        180                 185                 190
            Phe Ser Lys Pro His Lys Leu Met Lys Glu His Lys Glu Lys Pro Ser
                        195                 200                 205
            Lys Asp Ser Arg Glu His Lys Ser Ala Phe Lys Glu Pro Ser Arg Asp
                        210                 215                 220
            His Asn Lys Ser Ser Lys Glu Ser Ser Lys Lys Pro Lys Glu Asn Lys
            225                 230                 235                 240
            Pro Leu Lys Glu Glu Lys Ile Val Pro Lys Met Ala Phe Lys Glu Pro
                        245                 250                 255
            Lys Pro Met Ser Lys Glu Pro Lys Pro Asp Ser Asn Leu Leu Thr Ile
                        260                 265                 270
            Thr Ser Gly Gln Asp Lys Lys Ala Pro Ser Lys Arg Pro Pro Ile Ser
                        275                 280                 285
            Asp Ser Glu Glu Leu Ser Ala Lys Lys Arg Lys Lys Ser Ser Ser Glu
                        290                 295                 300
            Ala Leu Phe Lys Ser Phe Ser Ser Ala Pro Pro Leu Ile Leu Thr Cys
            305                 310                 315                 320
            Ser Ala Asp Lys Lys Gln Ile Lys Asp Lys Ser His Val Lys Met Gly
                        325                 330                 335
            Lys Val Lys Ile Glu Ser Glu Thr Ser Glu Lys Lys Lys Ser Thr Leu
                        340                 345                 350
            Pro Pro Phe Asp Asp Ile Val Asp Pro Asn Asp Ser Asp Val Glu Glu
                        355                 360                 365
            Asn Ile Ser Ser Lys Ser Asp Ser Glu Gln Pro Ser Pro Ala Ser Ser
                        370                 375                 380
            Ser Ser Ser Ser Ser Ser Phe Thr Pro Ser Gln Thr Arg Gln Gln
            385                 390                 395                 400
            Gly Pro Leu Arg Ser Ile Met Lys Asp Leu His Ser Asp Asn Glu
                        405                 410                 415
            Glu Glu Ser Asp Glu Val Glu Asp Asn Asp Asn Asp Ser Glu Met Glu
                        420                 425                 430
            Arg Pro Val Asn Arg Gly Gly Ser Arg Ser Arg Val Ser Leu Ser
                        435                 440                 445
            Asp Gly Ser Asp Ser Glu Ser Ser Ala Ser Ser Pro Leu His His
                        450                 455                 460
            Glu Pro Pro Pro Leu Leu Lys Thr Asn Asn Asn Gln Ile Leu Glu
            465                 470                 475                 480
            Val Lys Ser Pro Ile Lys Gln Ser Lys Ser Asp Lys Gln Ile Lys Asn
                        485                 490                 495
```

-continued

```
Gly Glu Cys Asp Lys Ala Tyr Leu Asp Glu Leu Val Glu Leu His Arg
            500                 505                 510

Arg Leu Met Thr Leu Arg Glu Arg His Ile Leu Gln Gln Ile Val Asn
            515                 520                 525

Leu Ile Glu Glu Thr Gly His Phe His Ile Thr Asn Thr Thr Phe Asp
            530                 535                 540

Phe Asp Leu Cys Ser Leu Asp Lys Thr Thr Val Arg Lys Leu Gln Ser
545                 550                 555                 560

Tyr Leu Glu Thr Ser Gly Thr Ser
            565
```

(2) INFORMATION FOR SEQ ID NO:31:

(i) SEQUENCE CHARACTERISTICS:
        (A) LENGTH: 559 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Met Asp Asn Gln Cys Thr Val Gln Val Arg Leu Glu Leu Gly His Arg
1               5                   10                  15

Ala Gln Leu Arg Lys Lys Pro Thr Thr Glu Gly Phe Thr His Asp Trp
            20                  25                  30

Met Val Phe Val Arg Gly Pro Glu Gln Cys Asp Ile Gln His Phe Val
            35                  40                  45

Glu Lys Val Val Phe Trp Leu His Asp Ser Phe Pro Lys Pro Arg Arg
50                  55                  60

Val Cys Lys Glu Pro Pro Tyr Lys Val Glu Glu Ser Gly Tyr Ala Gly
65                  70                  75                  80

Phe Ile Met Pro Ile Glu Val His Phe Lys Asn Lys Glu Glu Pro Arg
            85                  90                  95

Lys Val Cys Phe Thr Tyr Asp Leu Phe Leu Asn Leu Glu Gly Asn Pro
            100                 105                 110

Pro Val Asn His Leu Arg Cys Glu Lys Leu Thr Phe Asn Asn Pro Thr
            115                 120                 125

Thr Glu Phe Arg Tyr Lys Leu Leu Arg Ala Gly Gly Val Met Val Met
            130                 135                 140

Pro Glu Gly Ala Asp Thr Val Ser Arg Pro Ser Pro Asp Tyr Pro Met
145                 150                 155                 160

Leu Pro Thr Ile Pro Leu Ser Ala Phe Ser Asp Pro Lys Lys Thr Lys
            165                 170                 175

Pro Ser His Gly Ser Lys Asp Ala Asn Lys Glu Ser Ser Lys Thr Ser
            180                 185                 190

Lys Pro His Lys Val Thr Lys Glu His Arg Glu Arg Pro Arg Lys Asp
            195                 200                 205

Ser Glu Ser Lys Ser Ser Ser Lys Glu Leu Glu Arg Glu Gln Ala Lys
            210                 215                 220

Ser Ser Lys Asp Thr Ser Arg Lys Leu Gly Glu Gly Arg Leu Pro Lys
225                 230                 235                 240

Glu Glu Lys Ala Pro Pro Lys Ala Ala Phe Lys Glu Pro Lys Met
            245                 250                 255

Ala Leu Lys Glu Thr Lys Leu Glu Ser Thr Ser Pro Asn Pro Gly Pro
            260                 265                 270
```

```
Pro Pro Pro Pro Pro Pro Arg Ala Ser Ser Lys Arg Pro Ala
        275                 280                 285

Thr Ala Asp Ser Pro Lys Pro Ser Ala Lys Lys Gln Lys Lys Ser Ser
    290                 295                 300

Ser Lys Gly Ser Arg Ser Ala Pro Gly Thr Ser Pro Arg Thr Ser Ser
305                 310                 315                 320

Ser Ser Ser Phe Ser Asp Lys Lys Pro Ala Lys Asp Lys Ser Ser Thr
                325                 330                 335

Arg Gly Glu Lys Val Lys Ala Glu Ser Glu Pro Arg Glu Ala Lys Lys
                340                 345                 350

Ala Leu Glu Val Glu Glu Ser Asn Ser Glu Asp Glu Ala Ser Phe Lys
                355                 360                 365

Ser Glu Ser Ala Gln Ser Ser Pro Ser Asn Ser Ser Ser Ser Ser Asp
                370                 375                 380

Ser Ser Ser Asp Ser Asp Phe Glu Pro Ser Gln Asn His Ser Gln Gly
385                 390                 395                 400

Pro Leu Arg Ser Met Val Glu Asp Leu Gln Ser Glu Glu Ser Asp Glu
                405                 410                 415

Asp Asp Ser Ser Ser Gly Glu Glu Ala Ala Gly Lys Thr Asn Pro Gly
                420                 425                 430

Arg Asp Ser Arg Leu Ser Phe Ser Asp Ser Glu Ser Asp Asn Ser Ala
                435                 440                 445

Asp Ser Ser Leu Pro Ser Arg Glu Pro Pro Pro Gln Lys Pro Pro
                450                 455                 460

Pro Pro Asn Ser Lys Val Ser Gly Arg Arg Ser Pro Glu Ser Cys Ser
465                 470                 475                 480

Lys Pro Glu Lys Ile Leu Lys Lys Gly Thr Tyr Asp Lys Ala Tyr Thr
                485                 490                 495

Asp Glu Leu Val Glu Leu His Arg Arg Leu Met Ala Leu Arg Glu Arg
                500                 505                 510

Asn Val Leu Gln Gln Ile Val Asn Leu Ile Glu Glu Thr Gly His Phe
                515                 520                 525

Asn Val Thr Asn Thr Thr Phe Asp Phe Asp Leu Phe Ser Leu Asp Glu
                530                 535                 540

Thr Thr Val Arg Lys Leu Gln Ser Cys Leu Glu Ala Val Ala Thr
545                 550                 555

(2) INFORMATION FOR SEQ ID NO:32:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..260

(xi) SEQUENCE DESCRIPTION: SEQ ID NO:32:

CA GAT GAA GTG GAG GAT AAC GAC AAT GAC TCT GAA ATG GAG AGG CCT        47
   Asp Glu Val Glu Asp Asn Asp Asn Asp Ser Glu Met Glu Arg Pro
   1               5                  10                  15

GTA AAT AGA GGA GGC AGC CGA AGT CGC AGA GTT AGC TTA AGT GAT GGC        95
Val Asn Arg Gly Gly Ser Arg Ser Arg Arg Val Ser Leu Ser Asp Gly
                20                  25                  30
```

```
AGC GAT AGT GAA AGC AGT TCT GCT TCT TCA CCC CTA CAT CAC GAA CCT      143
Ser Asp Ser Glu Ser Ser Ser Ala Ser Ser Pro Leu His His Glu Pro
            35                  40                  45

CCA CCA CCC TTA CTA AAA ACC AAC AAC AAC CAG ATT CTT GAA GTA AAA      191
Pro Pro Pro Leu Leu Lys Thr Asn Asn Asn Gln Ile Leu Glu Val Lys
        50                  55                  60

ATT CCA GCA GAT GGA GTC CAC AGG ATC AGA GTG GAC TTT AAG TTT GTG      239
Ile Pro Ala Asp Gly Val His Arg Ile Arg Val Asp Phe Lys Phe Val
    65                  70                  75

TAT TGC CAA GTC TGT TGT GAG CC                                       262
Tyr Cys Gln Val Cys Cys Glu
80                  85

(2) INFORMATION FOR SEQ ID NO:33:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO:33:

Asp Glu Val Glu Asp Asn Asp Asn Asp Ser Glu Met Glu Arg Pro Val
 1               5                  10                  15

Asn Arg Gly Gly Ser Arg Ser Arg Arg Val Ser Leu Ser Asp Gly Ser
            20                  25                  30

Asp Ser Glu Ser Ser Ser Ala Ser Ser Pro Leu His His Glu Pro Pro
            35                  40                  45

Pro Pro Leu Leu Lys Thr Asn Asn Asn Gln Ile Leu Glu Val Lys Ile
        50                  55                  60

Pro Ala Asp Gly Val His Arg Ile Arg Val Asp Phe Lys Phe Val Tyr
65                  70                  75                  80

Cys Gln Val Cys Cys Glu
                85

(2) INFORMATION FOR SEQ ID NO:34:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..436

(xi) SEQUENCE DESCRIPTION: SEQ ID NO:34:

A CCT ACT ACA GGA CCG CCA AGA AAA GAA GTT CCC AAA ACC ACT CCT         46
  Pro Thr Thr Gly Pro Pro Arg Lys Glu Val Pro Lys Thr Thr Pro
  1               5                  10                  15

AGT GAG CCC AAG AAA AAG CAG CCT CCA CCA CCA GAA TCA GGT CCA GAG       94
Ser Glu Pro Lys Lys Lys Gln Pro Pro Pro Pro Glu Ser Gly Pro Glu
            20                  25                  30

CAG AGC AAA CAG AAA AAA GTG GCT CCC CGC CCA AGT ATC CCT GTA AAA      142
Gln Ser Lys Gln Lys Lys Val Ala Pro Arg Pro Ser Ile Pro Val Lys
            35                  40                  45

CAA AAA CCA AAA GAA AAG ATT CTT GAA GTG AAA AGT CCA ATA AAG CAA      190
Gln Lys Pro Lys Glu Lys Ile Leu Glu Val Lys Ser Pro Ile Lys Gln
        50                  55                  60
```

```
AGC AAA TCA GAT AAG CAA ATA AAG AAT GGT GAA TGT GAC AAG GCA TAC        238
Ser Lys Ser Asp Lys Gln Ile Lys Asn Gly Glu Cys Asp Lys Ala Tyr
    65                  70                  75

CTA GAT GAA CTG GTA GAG CTT CAC AGA AGG TTA ATG ACA TTG AGA GAA        286
Leu Asp Glu Leu Val Glu Leu His Arg Arg Leu Met Thr Leu Arg Glu
80                  85                  90                  95

AGA CAC ATT CTG CAG CAG ATC GTG AAC CTT ATA GAA GAA ACT GGA CAC        334
Arg His Ile Leu Gln Gln Ile Val Asn Leu Ile Glu Glu Thr Gly His
                100                 105                 110

TTT CAT ATC ACA AAC ACA ACA CTT GAT TTT GAT CTT TGC TCG CTG GAC        382
Phe His Ile Thr Asn Thr Thr Leu Asp Phe Asp Leu Cys Ser Leu Asp
            115                 120                 125

AAA ACC ACA GTC CGT AAA CTA CAG AGT TAC CTG GAA ACA TCT GGA ACA        430
Lys Thr Thr Val Arg Lys Leu Gln Ser Tyr Leu Glu Thr Ser Gly Thr
        130                 135                 140

TCC TGAGGA                                                             439
Ser
    145

(2) INFORMATION FOR SEQ ID NO:35:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:35:

Pro Thr Thr Gly Pro Pro Arg Lys Glu Val Pro Lys Thr Thr Pro Ser
1               5                   10                  15

Glu Pro Lys Lys Lys Gln Pro Pro Pro Glu Ser Gly Pro Glu Gln
            20                  25                  30

Ser Lys Gln Lys Lys Val Ala Pro Arg Pro Ser Ile Pro Val Lys Gln
        35                  40                  45

Lys Pro Lys Glu Lys Ile Leu Glu Val Lys Ser Pro Ile Lys Gln Ser
    50                  55                  60

Lys Ser Asp Lys Gln Ile Lys Asn Gly Glu Cys Asp Lys Ala Tyr Leu
65                  70                  75                  80

Asp Glu Leu Val Glu Leu His Arg Arg Leu Met Thr Leu Arg Glu Arg
                85                  90                  95

His Ile Leu Gln Gln Ile Val Asn Leu Ile Glu Glu Thr Gly His Phe
            100                 105                 110

His Ile Thr Asn Thr Thr Leu Asp Phe Asp Leu Cys Ser Leu Asp Lys
        115                 120                 125

Thr Thr Val Arg Lys Leu Gln Ser Tyr Leu Glu Thr Ser Gly Thr Ser
    130                 135                 140

(2) INFORMATION FOR SEQ ID NO:36:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..341
```

(xi) SEQUENCE DESCRIPTION: SEQ ID NO:36:

```
CA ACG TTA CCG CCA TTT GAT GAT ATT GTG GAT CCC AAT GAT TCA GAT        47
   Thr Leu Pro Pro Phe Asp Asp Ile Val Asp Pro Asn Asp Ser Asp
    1               5                  10                  15

GTG GAG GAG AAT ATA TCC TCT AAA TCT GAT TTT GTG TAT TGC CAA GTC        95
Val Glu Glu Asn Ile Ser Ser Lys Ser Asp Phe Val Tyr Cys Gln Val
                20                  25                  30

TGT TGT GAG CCC TTC CAC AAG TTT TGT TTA GAG GAG AAC GAG CGC CCT       143
Cys Cys Glu Pro Phe His Lys Phe Cys Leu Glu Glu Asn Glu Arg Pro
            35                  40                  45

CTG GAG GAC CAG CTG GAA AAT TGG TGT TGT CGT CGT TGC AAA TTC TGT       191
Leu Glu Asp Gln Leu Glu Asn Trp Cys Cys Arg Arg Cys Lys Phe Cys
        50                  55                  60

CAC GTT TGT GGA AGG CAA CAT CAG GCT ACA AAG CAG CTG CTG GAG TGT       239
His Val Cys Gly Arg Gln His Gln Ala Thr Lys Gln Leu Leu Glu Cys
    65                  70                  75

AAT AAG TGC CGA AAC AGC TAT CAC CCT GAG TGC CTG GGA CCA AAC TAC       287
Asn Lys Cys Arg Asn Ser Tyr His Pro Glu Cys Leu Gly Pro Asn Tyr
 80                  85                  90                  95

CCC ACC AAA CCC ACA AAG AAG AAG AAA GTC TGG ATC TGT ACC AAG TGT       335
Pro Thr Lys Pro Thr Lys Lys Lys Lys Val Trp Ile Cys Thr Lys Cys
                100                 105                 110

GTT CGC TG                                                            343
Val Arg
```

(2) INFORMATION FOR SEQ ID NO:37:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:37:

```
Thr Leu Pro Pro Phe Asp Asp Ile Val Asp Pro Asn Asp Ser Asp Val
 1               5                  10                  15

Glu Glu Asn Ile Ser Ser Lys Ser Asp Phe Val Tyr Cys Gln Val Cys
                20                  25                  30

Cys Glu Pro Phe His Lys Phe Cys Leu Glu Glu Asn Glu Arg Pro Leu
            35                  40                  45

Glu Asp Gln Leu Glu Asn Trp Cys Cys Arg Arg Cys Lys Phe Cys His
        50                  55                  60

Val Cys Gly Arg Gln His Gln Ala Thr Lys Gln Leu Leu Glu Cys Asn
 65                  70                  75                  80

Lys Cys Arg Asn Ser Tyr His Pro Glu Cys Leu Gly Pro Asn Tyr Pro
                85                  90                  95

Thr Lys Pro Thr Lys Lys Lys Val Trp Ile Cys Thr Lys Cys Val
            100                 105                 110

Arg
```

(2) INFORMATION FOR SEQ ID NO:38:

(i) SEQUENCE CHARACTERISTICS:
        (A) LENGTH: 11
        (B) TYPE: nucleic acid
        (C) STRANDEDNESS: single
        (D) TOPOLOGY: linear (xi) SEQUENCE DESCRIPTION: SEQ ID NO:38:

```
ATTCTTGAAG T                                                              11

(2) INFORMATION FOR SEQ ID NO:39:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO:39:

TCCTCAGGAT GTTCCAGATG T                                                   21

(2) INFORMATION FOR SEQ ID NO:40:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO:40:

GGCTCACAAC AGACTTGGCA A                                                   21

(2) INFORMATION FOR SEQ ID NO:41:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO:41:

ACCTACTACA GGACCGCCAA G                                                   21

(2) INFORMATION FOR SEQ ID NO:42:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO:42:

CAGATGAAGT GGAGGATAAC G                                                   21

(2) INFORMATION FOR SEQ ID NO:43:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO:43:

CAGCGAACAC ACTTGGTACA G                                                   21

(2) INFORMATION FOR SEQ ID NO:44:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:44:

CAACGTTACC GCCATTTGAT                                                     20
```

(2) INFORMATION FOR SEQ ID NO:45:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:45:

```
TGAGGAGAGA TTTGTTTCTC TGCCATTTCT CAGGGATGTA TTCTATTTTG TAGGGAAAAG        60
CCTTATCCTT GACTTCTATG TAGATGGCAG TGGAATTTCT TAAAATTAAG AAA             113
```

(2) INFORMATION FOR SEQ ID NO:46:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:46:

```
TTCCTCATAG GAAATAAAAT CTTTTAAATT AGCTTGTTTA GTTCCAGGAA AAAGGAAAAG        60
CCTTATCCTT GACTTCTATG TAGATGGCAG TGGAATTTCT TAAAATTAAG AAA             113
```

(2) INFORMATION FOR SEQ ID NO:47:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:47:

```
TTCCTCATAG GAAATAAAAT CTTTTAAATT AGCTTGTTTA GTTCCAGGAA AAAAAGAAAA        60
CCCAACAAAA CCATTGTATT TTTAGTTACT GTTTTCTTAA ATTTATAAAT TAA             113
```

(2) INFORMATION FOR SEQ ID NO:48:

(i) SEQUENCE CHARACTERISTICS:
        (A) LENGTH: 1612 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:48:

```
Met Ser Ala Gly Gly Arg Asp Glu Glu Arg Arg Lys Leu Ala Asp Ile
1               5                   10                  15

Ile His His Trp Asn Ala Asn Arg Leu Asp Leu Phe Glu Ile Ser Gln
            20                  25                  30

Pro Thr Glu Asp Leu Glu Phe His Gly Val Met Arg Phe Tyr Phe Gln
        35                  40                  45

Asp Lys Ala Ala Gly Asn Phe Ala Thr Lys Cys Ile Arg Val Ser Ser
    50                  55                  60

Thr Ala Thr Thr Gln Asp Val Ile Glu Thr Leu Ala Glu Lys Phe Arg
65                  70                  75                  80

Pro Asp Met Arg Met Leu Ser Ser Pro Lys Tyr Ser Leu Tyr Glu Val
                85                  90                  95

His Val Ser Gly Glu Arg Arg Leu Asp Ile Asp Glu Lys Pro Leu Val
            100                 105                 110

Val Gln Leu Asn Trp Asn Lys Asp Asp Arg Glu Gly Arg Phe Val Leu
        115                 120                 125

Lys Asn Glu Asn Asp Ala Ile Pro Pro Lys Ala Gln Ser Asn Gly Pro
130                 135                 140

Glu Lys Gln Glu Lys Glu Gly Val Ile Gln Asn Phe Lys Arg Thr Leu
145                 150                 155                 160

Ser Lys Lys Glu Lys Lys Glu Lys Lys Arg Glu Lys Glu Ala Leu
                165                 170                 175

Arg Gln Ala Ser Asp Lys Asp Arg Pro Phe Gln Gly Glu Asp Val
                180                 185                 190

Glu Asn Ser Arg Leu Ala Ala Glu Val Tyr Lys Asp Met Pro Glu Thr
            195                 200                 205

Ser Phe Thr Arg Thr Ile Ser Asn Pro Glu Val Val Met Lys Arg Arg
    210                 215                 220

Arg Gln Gln Lys Leu Glu Lys Arg Met Gln Glu Phe Arg Ser Ser Asp
225                 230                 235                 240

Gly Arg Pro Asp Ser Gly Gly Thr Leu Arg Ile Tyr Ala Asp Ser Leu
                245                 250                 255

Lys Pro Asn Ile Pro Tyr Lys Thr Ile Leu Leu Ser Thr Thr Asp Pro
            260                 265                 270

Ala Asp Phe Ala Val Ala Glu Ala Leu Glu Lys Tyr Gly Leu Glu Lys
        275                 280                 285

Glu Asn Pro Lys Asp Tyr Cys Ile Ala Arg Val Met Leu Pro Pro Gly
290                 295                 300

Ala Gln His Ser Asp Glu Lys Gly Ala Lys Glu Ile Ile Leu Asp Asp
305                 310                 315                 320

Asp Glu Cys Pro Leu Gln Ile Phe Arg Glu Trp Pro Ser Asp Lys Gly
                325                 330                 335

Ile Leu Val Phe Gln Leu Lys Arg Arg Pro Asp His Ile Pro Lys
            340                 345                 350

Lys Thr Lys Lys His Leu Glu Gly Lys Thr Pro Lys Gly Lys Glu Arg
        355                 360                 365

Ala Asp Gly Ser Val Tyr Gly Ser Thr Leu Pro Pro Glu Lys Leu Pro
370                 375                 380

Tyr Leu Val Glu Leu Ser Pro Asp Gly Ser Asp Ser Arg Asp Lys Pro
385                 390                 395                 400

Lys Leu Tyr Arg Leu Gln Leu Ser Val Thr Glu Val Gly Thr Glu Lys
                405                 410                 415
```

-continued

```
Leu Asp Asp Asn Ser Ile Gln Leu Phe Gly Pro Gly Ile Gln Pro His
            420                 425                 430

His Cys Asp Leu Thr Asn Met Asp Gly Val Val Thr Val Thr Pro Arg
            435                 440                 445

Ser Met Asp Ala Glu Thr Tyr Val Glu Gly Gln Arg Ile Ser Glu Thr
450                 455                 460

Thr Met Leu Gln Ser Gly Met Lys Val Gln Phe Gly Ala Ser His Val
465                 470                 475                 480

Phe Lys Phe Val Asp Pro Ser Gln Asp His Ala Leu Ala Lys Arg Ser
                485                 490                 495

Val Asp Gly Gly Leu Met Val Lys Gly Pro Arg His Lys Pro Gly Ile
            500                 505                 510

Val Gln Glu Thr Thr Phe Asp Leu Gly Gly Asp Ile His Ser Gly Thr
            515                 520                 525

Ala Leu Pro Thr Ser Lys Ser Thr Thr Arg Leu Asp Ser Asp Arg Val
            530                 535                 540

Ser Ser Ala Ser Ser Thr Ala Glu Arg Gly Met Val Lys Pro Met Ile
545                 550                 555                 560

Arg Val Glu Gln Gln Pro Asp Tyr Arg Arg Gln Glu Ser Arg Thr Gln
                565                 570                 575

Asp Ala Ser Gly Pro Glu Leu Ile Leu Pro Ala Ser Ile Glu Phe Arg
            580                 585                 590

Glu Ser Ser Glu Asp Ser Phe Leu Ser Ala Ile Ile Asn Tyr Thr Asn
            595                 600                 605

Ser Ser Thr Val His Phe Lys Leu Ser Pro Thr Tyr Val Leu Tyr Met
610                 615                 620

Ala Cys Arg Tyr Val Leu Ser Asn Gln Tyr Arg Pro Asp Ile Ser Pro
625                 630                 635                 640

Thr Glu Arg Thr His Lys Val Ile Ala Val Asn Lys Met Val Ser
                645                 650                 655

Met Met Glu Gly Val Ile Gln Lys Gln Lys Asn Ile Ala Gly Ala Leu
            660                 665                 670

Ala Phe Trp Met Ala Asn Ala Ser Glu Leu Leu Asn Phe Ile Lys Gln
            675                 680                 685

Asp Arg Asp Leu Ser Arg Ile Thr Leu Asp Ala Gln Asp Val Leu Ala
            690                 695                 700

His Leu Val Gln Met Ala Phe Lys Tyr Leu Val His Cys Leu Gln Ser
705                 710                 715                 720

Glu Leu Asn Asn Tyr Met Pro Ala Phe Leu Asp Asp Pro Glu Glu Asn
                725                 730                 735

Ser Leu Gln Arg Pro Lys Ile Asp Asp Val Leu His Thr Leu Thr Gly
            740                 745                 750

Ala Met Ser Leu Leu Arg Arg Cys Arg Val Asn Ala Ala Leu Thr Ile
            755                 760                 765

Gln Leu Phe Ser Gln Leu Phe His Phe Ile Asn Met Trp Leu Phe Asn
            770                 775                 780

Arg Leu Val Thr Asp Pro Asp Ser Gly Leu Cys Ser His Tyr Trp Gly
785                 790                 795                 800

Ala Ile Ile Arg Gln Gln Leu Gly His Ile Glu Ala Trp Ala Glu Lys
                805                 810                 815

Gln Gly Leu Glu Leu Ala Ala Asp Cys His Leu Ser Arg Ile Val Gln
            820                 825                 830
```

-continued

```
Ala Thr Thr Leu Leu Thr Met Asp Lys Tyr Ala Pro Asp Asp Ile Pro
            835                 840                 845

Asn Ile Asn Ser Thr Cys Phe Lys Leu Asn Ser Leu Gln Leu Gln Ala
        850                 855                 860

Leu Leu Gln Asn Tyr His Cys Ala Pro Asp Glu Pro Phe Ile Pro Thr
865                 870                 875                 880

Asp Leu Ile Glu Asn Val Val Thr Val Ala Glu Asn Thr Ala Asp Glu
                885                 890                 895

Leu Ala Arg Ser Asp Gly Arg Glu Val Gln Leu Glu Glu Asp Pro Asp
            900                 905                 910

Leu Gln Leu Pro Phe Leu Leu Pro Glu Asp Gly Tyr Ser Cys Asp Val
        915                 920                 925

Val Arg Asn Ile Pro Asn Gly Leu Gln Glu Phe Leu Asp Pro Leu Cys
    930                 935                 940

Gln Arg Gly Phe Cys Arg Leu Ile Pro His Thr Arg Ser Pro Gly Thr
945                 950                 955                 960

Trp Thr Ile Tyr Phe Glu Gly Ala Asp Tyr Glu Ser His Leu Leu Arg
                965                 970                 975

Glu Asn Thr Glu Leu Ala Gln Pro Leu Arg Lys Glu Pro Glu Ile Ile
            980                 985                 990

Thr Val Thr Leu Lys Lys Gln Asn Gly Met Gly Leu Ser Ile Val Ala
        995                 1000                1005

Ala Lys Gly Ala Gly Gln Asp Lys Leu Gly Ile Tyr Val Lys Ser Val
    1010                1015                1020

Val Lys Gly Gly Ala Ala Asp Val Asp Gly Arg Leu Ala Ala Gly Asp
1025                1030                1035                1040

Gln Leu Leu Ser Val Asp Gly Arg Ser Leu Val Gly Leu Ser Gln Glu
                1045                1050                1055

Arg Ala Ala Glu Leu Met Thr Arg Thr Ser Ser Val Val Thr Leu Glu
            1060                1065                1070

Val Ala Lys Gln Gly Ala Ile Tyr His Gly Leu Ala Thr Leu Leu Asn
        1075                1080                1085

Gln Pro Ser Pro Met Met Gln Arg Ile Ser Asp Arg Arg Gly Ser Gly
    1090                1095                1100

Lys Pro Arg Pro Lys Ser Glu Gly Phe Glu Leu Tyr Asn Asn Ser Thr
1105                1110                1115                1120

Gln Asn Gly Ser Pro Glu Ser Pro Gln Leu Pro Trp Ala Glu Tyr Ser
                1125                1130                1135

Glu Pro Lys Lys Leu Pro Gly Asp Asp Arg Leu Met Lys Asn Arg Ala
            1140                1145                1150

Asp His Arg Ser Ser Pro Asn Val Ala Asn Gln Pro Ser Pro Gly
        1155                1160                1165

Gly Lys Ser Ala Tyr Ala Ser Gly Thr Thr Ala Lys Ile Thr Ser Val
    1170                1175                1180

Ser Thr Gly Asn Leu Cys Thr Glu Glu Gln Thr Pro Pro Arg Pro
1185                1190                1195                1200

Glu Ala Tyr Pro Ile Pro Thr Gln Thr Tyr Thr Arg Glu Tyr Phe Thr
                1205                1210                1215

Phe Pro Ala Ser Lys Ser Gln Asp Arg Met Ala Pro Pro Gln Asn Gln
            1220                1225                1230

Trp Pro Asn Tyr Glu Glu Lys Pro His Met His Thr Asp Ser Asn His
        1235                1240                1245

Ser Ser Ile Ala Ile Gln Arg Val Thr Arg Ser Gln Glu Glu Leu Arg
```

```
            1250                1255                1260
Glu Asp Lys Ala Tyr Gln Leu Glu Arg His Arg Ile Glu Ala Ala Met
1265                1270                1275                1280
Asp Arg Lys Ser Asp Ser Asp Met Trp Ile Asn Gln Ser Ser Ser Leu
                1285                1290                1295
Asp Ser Ser Thr Ser Ser Gln Glu His Leu Asn His Ser Ser Lys Ser
            1300                1305                1310
Val Thr Pro Ala Ser Thr Leu Thr Lys Ser Gly Pro Gly Arg Trp Lys
        1315                1320                1325
Thr Pro Ala Ala Ile Pro Ala Thr Pro Val Ala Val Ser Gln Pro Ile
1330                1335                1340
Arg Thr Asp Leu Pro Pro Pro Pro Pro Pro Val His Tyr Ala
1345                1350                1355                1360
Gly Asp Phe Asp Gly Met Ser Met Asp Leu Pro Leu Pro Pro Pro Pro
            1365                1370                1375
Ser Ala Asn Gln Ile Gly Leu Pro Ser Ala Gln Val Ala Ala Ala Glu
        1380                1385                1390
Arg Arg Lys Arg Glu Glu His Gln Arg Trp Tyr Glu Lys Glu Lys Ala
    1395                1400                1405
Pro Leu Glu Glu Glu Arg Glu Arg Lys Arg Glu Gln Glu Arg Lys
    1410                1415                1420
Leu Gly Gln Met Arg Thr Gln Ser Leu Asn Pro Ala Pro Phe Ser Pro
1425                1430                1435                1440
Leu Thr Ala Gln Gln Met Lys Pro Glu Lys Pro Ser Thr Leu Gln Arg
                1445                1450                1455
Pro Gln Glu Thr Val Ile Arg Glu Leu Gln Pro Gln Gln Pro Arg
            1460                1465                1470
Thr Ile Glu Arg Arg Asp Leu Gln Tyr Ile Thr Val Ser Lys Glu Glu
        1475                1480                1485
Leu Ser Ser Gly Asp Ser Leu Ser Pro Asp Pro Trp Lys Arg Asp Ala
    1490                1495                1500
Lys Glu Lys Leu Glu Lys Gln Gln Gln Met His Ile Val Asp Met Leu
1505                1510                1515                1520
Ser Lys Glu Ile Gln Glu Leu Gln Ser Lys Pro Asp Arg Ser Ala Glu
                1525                1530                1535
Glu Ser Asp Arg Leu Arg Lys Leu Met Leu Glu Trp Gln Phe Gln Lys
            1540                1545                1550
Arg Leu Gln Glu Ser Lys Gln Lys Asp Glu Asp Glu Glu Glu
        1555                1560                1565
Asp Asp Asp Val Asp Thr Met Leu Ile Met Gln Arg Leu Glu Ala Glu
    1570                1575                1580
Arg Arg Ala Arg Val Lys Gly Gly Val Leu Trp Leu Cys Pro Ser Val
1585                1590                1595                1600
Val Pro Ile Leu Ala Ser Ala Cys Phe Pro Trp Gly
            1605                1610

(2) INFORMATION FOR SEQ ID NO:49:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (ix) FEATURE:
            (A) NAME/KEY: CDS
            (B) LOCATION: 3..269

(xi) SEQUENCE DESCRIPTION: SEQ ID NO:49:

| GT | CCA | GAG | CAG | AGC | AAA | CAG | AAA | AAA | GTG | GCT | CCC | CGC | CCA | AGT | ATC | 47 |
|    | Pro | Glu | Gln | Ser | Lys | Gln | Lys | Lys | Val | Ala | Pro | Arg | Pro | Ser | Ile |    |
|    | 1   |     |     |     | 5   |     |     |     |     | 10  |     |     |     |     | 15  |    |

| CCT | GTA | AAA | CAA | AAA | CCA | AAA | GAA | AAG | GAT | TTG | GAG | TTC | CAT | GGA | GTG | 95 |
| Pro | Val | Lys | Gln | Lys | Pro | Lys | Glu | Lys | Asp | Leu | Glu | Phe | His | Gly | Val |    |
|     |     |     |     | 20  |     |     |     |     | 25  |     |     |     |     | 30  |     |    |

| ATG | AGA | TTT | TAT | TTT | CAA | GAT | AAA | GCT | GCT | GGA | AAC | TTT | GCA | ACA | AAA | 143 |
| Met | Arg | Phe | Tyr | Phe | Gln | Asp | Lys | Ala | Ala | Gly | Asn | Phe | Ala | Thr | Lys |     |
|     |     |     |     | 35  |     |     |     |     | 40  |     |     |     |     | 45  |     |     |

| TGT | ATT | CGG | GTC | TCT | AGT | ACT | GCC | ACC | ACT | CAA | GAT | GTA | ATC | GAA | ACG | 191 |
| Cys | Ile | Arg | Val | Ser | Ser | Thr | Ala | Thr | Thr | Gln | Asp | Val | Ile | Glu | Thr |     |
|     |     |     | 50  |     |     |     |     | 55  |     |     |     |     | 60  |     |     |     |

| CTC | GCG | GAG | AAA | TTT | CGA | CCT | GAT | ATG | CGA | ATG | CTG | TCC | TCT | CCC | AAG | 239 |
| Leu | Ala | Glu | Lys | Phe | Arg | Pro | Asp | Met | Arg | Met | Leu | Ser | Ser | Pro | Lys |     |
|     | 65  |     |     |     |     | 70  |     |     |     |     | 75  |     |     |     |     |     |

| TAT | TCA | CTC | TAT | GAA | GTG | CAT | GTC | AGC | GGA | G | 270 |
| Tyr | Ser | Leu | Tyr | Glu | Val | His | Val | Ser | Gly |   |     |
| 80  |     |     |     |     | 85  |     |     |     |     |   |     |

(2) INFORMATION FOR SEQ ID NO:50:

(i) SEQUENCE CHARACTERISTICS:
            (A) LENGTH: 89 amino acids
            (B) TYPE: amino acid
            (D) TOPOLOGY: linear (ii) MOLECULE TYPE: protein (xi) SEQUENCE DESCRIPTION: SEQ ID NO:50:

Pro Glu Gln Ser Lys Gln Lys Lys Val Ala Pro Arg Pro Ser Ile Pro
1               5                   10                  15

Val Lys Gln Lys Pro Lys Glu Lys Asp Leu Glu Phe His Gly Val Met
            20                  25                  30

Arg Phe Tyr Phe Gln Asp Lys Ala Ala Gly Asn Phe Ala Thr Lys Cys
            35                  40                  45

Ile Arg Val Ser Ser Thr Ala Thr Thr Gln Asp Val Ile Glu Thr Leu
        50                  55                  60

Ala Glu Lys Phe Arg Pro Asp Met Arg Met Leu Ser Ser Pro Lys Tyr
65                  70                  75                  80

Ser Leu Tyr Glu Val His Val Ser Gly
                85

(2) INFORMATION FOR SEQ ID NO:51:

(i) SEQUENCE CHARACTERISTICS:
            (A) LENGTH: 84 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:51:

Lys Lys Gln Asn Gly Met Gly Leu Ser Ile Val Ala Ala Lys Gly Ala
1               5                   10                  15

Gly Gln Asp Lys Leu Gly Ile Tyr Val Lys Ser Val Val Lys Gly Gly
            20                  25                  30

Ala Ala Asp Val Asp Gly Arg Leu Ala Ala Gly Asp Gln Leu Leu Ser
            35                  40                  45

Val Asp Gly Arg Ser Leu Val Gly Leu Ser Gln Glu Arg Ala Ala Glu
        50                  55                  60

Leu Met Thr Arg Thr Ser Ser Val Val Thr Leu Glu Val Ala Lys Gln
65                  70                  75                  80

Gly Ala Ile Tyr (2) INFORMATION FOR SEQ ID NO:52:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:52:

Arg Lys Gly Asp Ser Val Gly Leu Arg Leu Ala Gly Gly Asn Asp Val
1               5                   10                  15

Gly Ile Phe Val Ala Gly Val Leu Glu Asp Ser Pro Ala Ala Lys Glu
            20                  25                  30

Gly Leu Glu Glu Gly Asp Gln Ile Leu Arg Val Asn Asn Val Asp Phe
            35                  40                  45

Thr Asn Ile Ile Arg Glu Glu Ala Val Leu Phe Leu Leu Asp Leu Pro
        50                  55                  60

Lys Gly Glu Glu Val Thr Ile Leu Ala Gln Lys Lys Lys Asp Val Tyr
65                  70                  75                  80

(2) INFORMATION FOR SEQ ID NO:53:

(i) SEQUENCE CHARACTERISTICS:
        (A) LENGTH: 86 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

Lys Gly Pro Lys Gly Leu Gly Phe Ser Ile Ala Gly Gly Val Gly Asn
1               5                   10                  15

Gln His Ile Pro Gly Asp Asn Ser Ile Tyr Val Thr Lys Ile Ile Glu
            20                  25                  30

Gly Gly Ala Ala His Lys Asp Gly Arg Leu Gln Ile Gly Asp Lys Ile
            35                  40                  45

Leu Ala Val Asn Ser Val Gly Leu Glu Asp Val Met His Glu Asp Ala
        50                  55                  60

Val Ala Ala Leu Lys Asn Thr Tyr Asp Val Val Tyr Leu Lys Val Ala
65                  70                  75                  80

Lys Pro Ser Asn Ala Tyr
                85

(2) INFORMATION FOR SEQ ID NO:54:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:54:

Lys Gly Pro Gln Gly Leu Gly Phe Asn Ile Val Gly Gly Glu Asp Gly
1               5                   10                  15

Gln Gly Ile Tyr Val Ser Phe Ile Leu Ala Gly Gly Pro Ala Asp Leu
            20                  25                  30

Gly Ser Glu Leu Lys Arg Gly Asp Gln Leu Leu Ser Val Asn Asn Val
        35                  40                  45

Asn Leu Thr His Ala Thr His Glu Glu Ala Ala Gln Ala Leu Lys Thr
    50                  55                  60

Ser Gly Gly Val Val Thr Leu Leu Ala Gln Tyr Arg Pro Glu Glu Tyr
65                  70                  75                  80

(2) INFORMATION FOR SEQ ID NO:55:

(i) SEQUENCE CHARACTERISTICS:
        (A) LENGTH: 1093 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:55:

Met Lys Glu Met Val Gly Gly Cys Cys Val Cys Ser Asp Glu Arg Gly
1               5                   10                  15

Trp Ala Glu Asn Pro Leu Val Tyr Cys Asp Gly His Ala Cys Ser Val
            20                  25                  30

Ala Val His Gln Ala Cys Tyr Gly Ile Val Gln Val Pro Thr Gly Pro
        35                  40                  45

Trp Phe Cys Arg Lys Cys Glu Ser Gln Glu Arg Ala Ala Arg Val Arg
    50                  55                  60

Cys Glu Leu Cys Pro His Lys Asp Gly Ala Leu Lys Arg Thr Asp Asn
65                  70                  75                  80

Gly Gly Trp Ala His Val Val Cys Ala Leu Tyr Ile Pro Glu Val Gln
            85                  90                  95

Phe Ala Asn Val Leu Thr Met Glu Pro Ile Val Leu Gln Tyr Val Pro
            100                 105                 110

His Asp Arg Phe Asn Lys Thr Cys Tyr Ile Cys Glu Glu Thr Gly Arg
            115                 120                 125

Glu Ser Lys Ala Ala Ser Gly Ala Cys Met Thr Cys Asn Arg His Gly
            130                 135                 140

-continued

```
Cys Arg Gln Ala Phe His Val Thr Cys Ala Gln Met Ala Gly Leu Leu
145                 150                 155                 160

Cys Glu Glu Val Leu Glu Val Asp Asn Val Lys Tyr Cys Gly Tyr
            165                 170                 175

Cys Lys Tyr His Phe Ser Lys Met Lys Thr Ser Arg His Ser Ser Gly
            180                 185                 190

Gly Gly Gly Gly Ala Gly Gly Gly Ser Met Gly Gly Gly
        195                 200             205

Gly Ser Gly Phe Ile Ser Gly Arg Arg Ser Arg Ser Ala Ser Pro Ser
        210                 215                 220

Thr Gln Gln Glu Lys His Pro Thr His Glu Arg Gly Gln Lys Lys
225                 230                 235                 240

Ser Arg Lys Asp Lys Glu Arg Leu Lys Gln Lys His Lys Lys Arg Pro
            245                 250                 255

Glu Ser Pro Pro Ser Ile Leu Thr Pro Pro Val Val Pro Thr Ala Asp
            260                 265                 270

Lys Val Ser Ser Ser Ala Ser Ser Ser His His Glu Ala Ser Thr
        275                 280                 285

Gln Glu Thr Ser Glu Ser Ser Arg Glu Ser Lys Gly Lys Lys Ser Ser
    290                 295                 300

Ser His Ser Leu Ser His Lys Gly Lys Lys Leu Ser Ser Gly Lys Gly
305                 310                 315                 320

Val Ser Ser Phe Thr Ser Ala Ser Ser Ser Ser Ser Ser Ser Ser
            325                 330                 335

Ser Ser Gly Gly Pro Phe Gln Pro Ala Val Ser Ser Leu Gln Ser Ser
        340                 345                 350

Pro Asp Phe Ser Ala Phe Pro Lys Leu Glu Gln Pro Glu Asp Lys
    355                 360                 365

Tyr Ser Lys Pro Thr Ala Pro Ala Pro Ser Ala Pro Pro Ser Pro Ser
    370                 375                 380

Ala Pro Glu Pro Pro Lys Ala Asp Leu Phe Glu Gln Lys Val Val Phe
385                 390                 395                 400

Ser Gly Phe Gly Pro Ile Met Arg Phe Ser Thr Thr Ser Ser Ser
            405                 410                 415

Gly Arg Ala Arg Ala Pro Ser Pro Gly Asp Tyr Lys Ser Pro His Val
        420                 425                 430

Thr Gly Ser Gly Ala Ser Ala Gly Thr His Lys Arg Met Pro Ala Leu
        435                 440                 445

Ser Ala Thr Pro Val Pro Ala Asp Glu Thr Pro Glu Thr Gly Leu Lys
450                 455                 460

Glu Lys Lys His Lys Ala Ser Lys Arg Ser Arg His Gly Pro Gly Arg
465                 470                 475                 480

Pro Lys Gly Ser Arg Asn Lys Glu Gly Thr Gly Gly Pro Ala Ala Pro
            485                 490                 495

Ser Leu Pro Ser Ala Gln Leu Ala Gly Phe Thr Ala Thr Ala Ala Ser
        500                 505                 510

Pro Phe Ser Gly Gly Ser Leu Val Ser Ser Gly Leu Gly Gly Leu Ser
        515                 520                 525

Ser Arg Thr Phe Gly Pro Ser Gly Ser Leu Pro Ser Leu Ser Leu Glu
        530                 535                 540

Ser Pro Leu Leu Gly Ala Gly Ile Tyr Thr Ser Asn Lys Asp Pro Ile
545                 550                 555                 560

Ser His Ser Gly Gly Met Leu Arg Ala Val Cys Ser Thr Pro Leu Ser
```

```
                565                 570                 575
Ser Ser Leu Leu Gly Pro Pro Gly Thr Ser Ala Leu Pro Arg Leu Ser
            580                 585                 590

Arg Ser Pro Phe Thr Ser Thr Leu Pro Ser Ser Ala Ser Ile Ser
            595                 600                 605

Thr Thr Gln Val Phe Ser Leu Ala Gly Ser Thr Phe Ser Leu Pro Ser
610                 615                 620

Thr His Ile Phe Gly Thr Pro Met Gly Ala Val Asn Pro Leu Leu Ser
625                 630                 635                 640

Gln Ala Glu Ser Ser His Thr Glu Pro Asp Leu Glu Asp Cys Ser Phe
            645                 650                 655

Arg Cys Arg Gly Thr Ser Pro Gln Glu Ser Leu Ser Ser Met Ser Pro
            660                 665                 670

Ile Ser Ser Leu Pro Ala Leu Phe Asp Gln Thr Ala Ser Ala Pro Cys
            675                 680                 685

Gly Gly Gly Gln Leu Asp Pro Ala Ala Pro Gly Thr Thr Asn Met Glu
            690                 695                 700

Gln Leu Leu Glu Lys Gln Gly Asp Gly Glu Ala Gly Val Asn Ile Val
705                 710                 715                 720

Glu Met Leu Lys Ala Leu His Ala Leu Gln Lys Glu Asn Gln Arg Leu
            725                 730                 735

Gln Glu Gln Ile Leu Ser Leu Thr Ala Lys Lys Glu Arg Leu Gln Ile
            740                 745                 750

Leu Asn Val Gln Leu Ser Val Pro Phe Pro Ala Leu Pro Ala Ala Leu
            755                 760                 765

Pro Ala Ala Asn Gly Pro Val Pro Gly Pro Tyr Gly Leu Pro Pro Gln
770                 775                 780

Ala Gly Ser Ser Asp Ser Leu Ser Thr Ser Lys Ser Pro Pro Gly Lys
785                 790                 795                 800

Ser Ser Leu Gly Leu Asp Asn Ser Leu Ser Thr Ser Glu Asp Pro
            805                 810                 815

His Ser Gly Cys Pro Ser Arg Ser Ser Ser Leu Ser Phe His Ser
            820                 825                 830

Thr Pro Pro Pro Leu Pro Leu Leu Gln Gln Ser Pro Ala Thr Leu Pro
            835                 840                 845

Leu Ala Leu Pro Gly Ala Pro Ala Pro Leu Pro Pro Gln Pro Gln Asn
850                 855                 860

Gly Leu Gly Arg Ala Pro Gly Ala Ala Gly Leu Gly Ala Met Pro Met
865                 870                 875                 880

Ala Glu Gly Leu Leu Gly Gly Leu Ala Gly Ser Gly Gly Leu Pro Leu
            885                 890                 895

Asn Gly Leu Leu Gly Gly Leu Asn Gly Ala Ala Ala Pro Asn Pro Ala
            900                 905                 910

Ser Leu Ser Gln Ala Gly Gly Ala Pro Thr Leu Gln Leu Pro Gly Cys
            915                 920                 925

Leu Asn Ser Leu Thr Glu Gln Gln Arg His Leu Leu Gln Gln Gln Glu
            930                 935                 940

Gln Gln Leu Gln Gln Leu Gln Leu Leu Ala Ser Pro Gln Leu Thr
945                 950                 955                 960

Pro Glu His Gln Thr Val Val Tyr Gln Met Ile Gln Gln Ile Gln Gln
            965                 970                 975

Lys Arg Glu Leu Gln Arg Leu Gln Met Ala Gly Gly Ser Gln Leu Pro
            980                 985                 990
```

```
Met Ala Ser Leu Leu Ala Gly Ser Ser Thr Pro Leu Leu Ser Ala Gly
    995                1000                1005

Thr Pro Gly Leu Leu Pro Thr Ala Ser Ala Pro Pro Leu Leu Pro Ala
    1010                1015                1020

Gly Ala Leu Val Ala Pro Ser Leu Gly Asn Asn Thr Ser Leu Met Ala
1025                1030                1035                1040

Ala Ala Ala Ala Ala Ala Val Ala Ala Gly Gly Pro Pro Val
                1045                1050                1055

Leu Thr Ala Gln Thr Asn Pro Phe Leu Ser Leu Ser Gly Ala Glu Gly
                1060                1065                1070

Ser Gly Gly Pro Lys Gly Gly Thr Ala Asp Lys Gly Ala Ser Ala
        1075                1080                1085

Asn Gln Glu Lys Gly
    1090
```

(2) INFORMATION FOR SEQ ID NO:56:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..228

(xi) SEQUENCE DESCRIPTION: SEQ ID NO:56:

```
CCA CCT ACT ACA GGA CCG CCA AGA AAA GAA GTT CCC AAA ACC ACT CCT      48
Pro Pro Thr Thr Gly Pro Pro Arg Lys Glu Val Pro Lys Thr Thr Pro
 1               5                  10                  15

AGT GAG CCC AAG AAA AAG CAG CCT CCA CCA CCA GAA TCA GGC ATC TAC      96
Ser Glu Pro Lys Lys Lys Gln Pro Pro Pro Glu Ser Gly Ile Tyr
             20                  25                  30

ACC AGT AAT AAG GAC CCC ATC TCC CAC AGT GGC GGG ATG CTG CGG GCT    144
Thr Ser Asn Lys Asp Pro Ile Ser His Ser Gly Gly Met Leu Arg Ala
         35                  40                  45

GTC TGC AGC ACC CCT CTC TCC TCC AGC CTC CTG GGG CCC CCA GGG ACC    192
Val Cys Ser Thr Pro Leu Ser Ser Ser Leu Leu Gly Pro Pro Gly Thr
 50                  55                  60

TCG GCC CTG CCC CGC CTC AGC CGC TCC CCG TTC ACC                      228
Ser Ala Leu Pro Arg Leu Ser Arg Ser Pro Phe Thr
 65                  70                  75
```

(2) INFORMATION FOR SEQ ID NO:57:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO:57:

```
Pro Pro Thr Thr Gly Pro Pro Arg Lys Glu Val Pro Lys Thr Thr Pro
 1               5                  10                  15

Ser Glu Pro Lys Lys Lys Gln Pro Pro Pro Glu Ser Gly Ile Tyr
```

```
                    20                  25                  30
Thr Ser Asn Lys Asp Pro Ile Ser His Ser Gly Gly Met Leu Arg Ala
            35                  40                  45

Val Cys Ser Thr Pro Leu Ser Ser Ser Leu Leu Gly Pro Pro Gly Thr
    50                  55                  60

Ser Ala Leu Pro Arg Leu Ser Arg Ser Pro Phe Thr
65                  70                  75
```

(2) INFORMATION FOR SEQ ID NO:58:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:58:

```
Met Lys Glu Met Val Gly Gly Cys Cys Val Cys Ser Asp Glu Arg Gly
1               5                   10                  15

Trp Ala Glu Asn Pro Leu Val Tyr Cys Asp Gly His Ala Cys Ser Val
            20                  25                  30

Ala Val His Gln Ala Cys Tyr Gly Ile Val Gln Val Pro Thr Gly Pro
        35                  40                  45

Trp Phe Cys Arg Lys Cys Glu Ser Gln Glu Arg Ala Ala Arg Val Arg
    50                  55                  60

Cys Glu Leu Cys Pro His Lys Asp Gly Ala Leu Lys Arg Thr Asp Asn
65                  70                  75                  80

Gly Gly Trp Ala His Val Val Cys Ala Leu Tyr Ile Pro Glu Val Gln
                85                  90                  95

Phe Ala Asn Val Leu Thr Met Glu Pro Ile Val Leu Gln Tyr Val Pro
            100                 105                 110

His Asp Arg Phe Asn Lys Thr Cys Tyr Ile Cys Glu Glu Thr Gly Arg
        115                 120                 125

Glu Ser Lys Ala Ala Ser Gly Ala Cys Met Thr Cys Asn Arg His Gly
    130                 135                 140

Cys Arg Gln Ala Phe His Val Thr Cys Ala Gln Met Ala Gly Leu Leu
145                 150                 155                 160

Cys Glu Glu Glu Val Leu Glu Val Asp Asn Val Lys Tyr Cys Gly Tyr
                165                 170                 175

Cys Lys Tyr His Phe Ser Lys Met Lys Thr Ser Arg
            180                 185
```

(2) INFORMATION FOR SEQ ID NO:59:

(i) SEQUENCE CHARACTERISTICS:
        (A) LENGTH: 187 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO -continued (xi) SEQUENCE DESCRIPTION: SEQ ID NO:59:

Leu Val Asp Glu Asp Ala Val Cys Cys Ile Cys Asn Asp Gly Glu Cys
1               5                   10                  15

Gln Asn Ser Asn Val Ile Leu Phe Cys Asp Met Cys Asn Leu Glu Val
            20                  25                  30

His Gln Glu Cys Tyr Gly Val Pro Tyr Ile Pro Glu Gly Gln Trp Leu
        35                  40                  45

Cys Arg Arg Cys Leu Gln Ser Pro Ser Arg Ala Val Asp Cys Ala Leu
    50                  55                  60

Cys Pro Asn Lys Gly Gly Ala Phe Lys Gln Thr Asp Asp Gly Arg Trp
65                  70                  75                  80

Ala His Val Val Cys Ala Leu Trp Ile Pro Glu Val Cys Phe Ala Asn
                85                  90                  95

Thr Val Phe Leu Glu Pro Ile Asp Ser Ile Glu His Ile Pro Pro Ala
            100                 105                 110

Arg Trp Lys Leu Thr Cys Tyr Ile Cys Lys Gln Arg Gly Ser Gly Ala
        115                 120                 125

Cys Ile Gln Cys His Lys Ala Asn Cys Tyr Thr Ala Phe His Val Thr
130                 135                 140

Cys Ala Gln Gln Ala Gly Leu Tyr Met Lys Met Glu Pro Val Arg Glu
145                 150                 155                 160

Thr Gly Ala Asn Gly Thr Ser Phe Ser Val Arg Lys Thr Ala Tyr Cys
                165                 170                 175

Asp Ile His Thr Pro Pro Gly Ser Ala Arg Arg
            180                 185

(2) INFORMATION FOR SEQ ID NO:60:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:60:

Cys Val Asp Glu Arg Gly Trp Ala Glu Asn Pro Leu Val Tyr Asp Gly
1               5                   10                  15

His Ala (2) INFORMATION FOR SEQ ID NO:61:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:61:

Arg Lys Glu Ser Gln Glu Arg Ala Ala Arg Val Arg Glu Leu
1               5                   10

6,040,140

165                                                                              166

-continued (2) INFORMATION FOR SEQ ID NO:62:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:62:

Tyr Ile Glu Glu Thr Gly Arg Glu Ser Lys Ala Ala Ser Gly Ala Met
1               5                   10                  15

Thr (2) INFORMATION FOR SEQ ID NO:63:

(i) SEQUENCE CHARACTERISTICS:
        (A) LENGTH: 8342 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..265

(ix) FEATURE:
        (A) NAME/KEY: CDS
        (B) LOCATION: 595..666

(ix) FEATURE:
        (A) NAME/KEY: CDS
        (B) LOCATION: 2353..2484

(ix) FEATURE:
        (A) NAME/KEY: CDS
        (B) LOCATION: 3032..3145

(ix) FEATURE:
        (A) NAME/KEY: CDS
        (B) LOCATION: 6788..6934

(ix) FEATURE:
        (A) NAME/KEY: CDS
        (B) LOCATION: 7967..8062

(ix) FEATURE:
        (A) NAME/KEY: CDS
        (B) LOCATION: 8304..8342

(xi) SEQUENCE DESCRIPTION: SEQ ID NO:63:

```
G GAT CCT GCC CCA AAG AAA AGC AGT AGT GAG CCT CCT CCA CGA AAG              46
  Asp Pro Ala Pro Lys Lys Ser Ser Ser Glu Pro Pro Pro Arg Lys
  1               5                   10                  15

CCC GTC GAG GAA AAG AGT GAA GAA GGG AAT GTC TCG GCC CCT GGG CCT            94
Pro Val Glu Glu Lys Ser Glu Glu Gly Asn Val Ser Ala Pro Gly Pro
                20                  25                  30

GAA TCC AAA CAG GCC ACC ACT CCA GCT TCC AGG AAG TCA AGC AAG CAG           142
Glu Ser Lys Gln Ala Thr Thr Pro Ala Ser Arg Lys Ser Ser Lys Gln
            35                  40                  45
```

```
GTC TCC CAG CCA GCA CTG GTC ATC CCG CCT CAG CCA CCT ACT ACA GGA       190
Val Ser Gln Pro Ala Leu Val Ile Pro Pro Gln Pro Pro Thr Thr Gly
         50                  55                  60

CCG CCA AGA AAA GAA GTT CCC AAA ACC ACT CCT AGT GAG CCC AAG AAA       238
Pro Pro Arg Lys Glu Val Pro Lys Thr Thr Pro Ser Glu Pro Lys Lys
 65                  70                  75

AAG CAG CCT CCA CCA CCA GAA TCA GGT GAGTGAGGAG GGCAAGAA GG            285
Lys Gln Pro Pro Pro Pro Glu Ser Gly
 80                  85

AATTGCTGAC CCACAAGTAC TAACAAAAAA GCACTGATGT CTCAAACAGC ATTTGAAAGC     345

AGGAAATGTA TGATTTGAAG TCTTCAGTTC AAGAAAATCA GCTCTCTTTC TAACTATTAT     405

GTTTAATAAT AAAGAAACAG AAACAAAAAA AACAGTTAAA TTGGAGGTAT TGTTTTAATT     465

TCCTGTTCGA AGCCTAGAGT TTAAATAGTT TTTTTTTTTT TTTTCTAATG GCCCTTTCTT     525

CACAGGTCAG TCAGTACTAA AGTAGTCGTT GCCAGCATCT GACTGCAATT TATTCTGAAT     585

TTTTTAGGT CCA GAG CAG AGC AAA CAG AAA AAA GTG GCT CCC CGC CCA         633
          Pro Glu Gln Ser Lys Gln Lys Lys Val Ala Pro Arg Pro
           1               5                  10

AGT ATC CCT GTA AAA CAA AAA CCA AAA GAA AAG GTGAGGAGAG ATTTGTTTCT     686
Ser Ile Pro Val Lys Gln Lys Pro Lys Glu Lys
         15                  20

CTGCCATTTC TCAGGGATGT ATTCTATTTT GTAGGGAAAA GCCTTATCCT TGACTTCTAT     746

GTAGATGGCA GTGAATTTC TTAAAATTAA GAAACTTCAA GTTTAGGCTT TTAGCTGGGC      806

ACGGTGGCTC ACGCTGGTAA TCCCAACACT TAGTGAGGCT GAGGTGGGAG GATTGCTTGA     866

GGCCAGCAGT TCAAGACCAG CCTGGGCAAC ATAGCAAGAC CCTGTCTTTA TTTAAACCAA     926

AAAAAAAAAA AGAAGAAGAA GAAGTTAGCC AGGCATGGTG GCAGTTGCGT GTAGTCCCAG     986

GTACTCAGGA GGCTGAGATA GAAGGATTGT CTTGAGCCCA GGAATTCAAG GCTGTAGTGA    1046

GCTATGATTG TACCACTGCA GTCCAGCCTG GGTGACAAAG CAAAACACTG TCTCCAAAAA    1106

AAATTTAGGC TTGGCAAGGC GCAGCGGCTC ACGCCTGTGA TCCCAGCACT TTGGGAAGCC    1166

GAAGCAGGCA GATCACTTGA GGTCAGGAGT TGGAGACCAG CCTGGCCAAC ATGGTGAAAC    1226

CCTGTCTCTA CTGAAAATAC AAAAAATTAGC CGGTTGTGGT AGTGGGTGCT TGGTAATCCT   1286

AGCTACTTGG GAGGCTGAGG CAGGGGAAT TGCCTGAAAC CTGCGAGGCG GAGGCTGCAG     1346

TGAGCCGAGA TTGCATCATT GCACTCTAGC CTGGACAACA GAGCTAGACT CCATCCCAAA    1406

AAAAAAAAAA AAAAGTAGCC GGGCACGGTG GCTCACGCCT GTAATCCCAG CACTTTGGGA    1466

GGCCGAGGCG GCGGATCAT GAGGGCAGGA GATCGAGACC ATCCTGGCTA ACACGGTGAA     1526

ACCCTGTCTC TACTAAAAAT ACAAAAAATT AGCCCGGCGA GGTGGCGGGC GCCTGTAGTC    1586

CCAGCTACTC AGGAGAGTGA GCCAGGAGAA TGGCGTGAAC CCGGGGGCG GAGCCTGCAG     1646

TGAGCCGAGA TCGCGCCACT GCACTCCAGC TTGGGTGACA CCGAGACTCC GTCTCAAAAA    1706

AAAATAAAAA GTTTAGGCTT TAGCCTGTTT CTTTTTTGGT TTCTTCCTTG TTGCTTTTCC    1766

CTTCTTTGTG GCCCCACATG TTCTAGCCTA GGAATCTGCT TATTCTAAAG GCCATTTGGC    1826

GTAATTATTT TTTGACCCCA ACATCCTTTA GCAATTATTT GTCTGTAAAA ATCACCCTTC    1886

CCTGTATTCA CTATTTTTAT TTATTATGGA TAAAGAGATA GTGTGGTGGC TCACATCTAT    1946

AATCCCAGCA CTTTGGGGGC CCAAGGCGGG AGGATCACTT GAGGGCAGGA GCTGGAGACC    2006

AGCCTGGGCA GCACAGTGAC ACACAGTTGC TATAAAAAAT TTAAACCCA ACTAGGCATG     2066

GTGGCATGCA CCTGTAGTCC CAGCTACTCT TGAGAAGCTG AGGCAGGAGG ATCACGAGCC    2126
```

```
CACAAGGTCT AGGCTGCAGT GAGCTGTGAC TGTGCCACTG TATTGCAGCC TAGGCAACAA         2186

AGCAAGACCC AGTCTCTTTT AAAAAAAAAT TCAAAGATTA TTGTTTATGT TGGAAACATG         2246

TTTTTTAGAT CTATTAATAA AATTTGTCAT TTGCATTATT ATCTGTTGCA AATGTGAAGG         2306

CAAATAGGGT GTGATTTTGT TCTATATTCA TCTTTTGTCT CCTTAG GAA AAA CCA           2361
                                                  Glu Lys Pro
                                                   1

CCT CCG GTC AAT AAG CAG GAG AAT GCA GGC ACT TTG AAC ATC CTC AGC          2409
Pro Pro Val Asn Lys Gln Glu Asn Ala Gly Thr Leu Asn Ile Leu Ser
    5               10                  15

ACT CTC TCC AAT GGC AAT AGT TCT AAG CAA AAA ATT CCA GCA GAT GGA          2457
Thr Leu Ser Asn Gly Asn Ser Ser Lys Gln Lys Ile Pro Ala Asp Gly
 20              25              30                  35

GTC CAC AGG ATC AGA GTG GAC TTT AAG GTAAAGGTGT TCAGTGATCA                2504
Val His Arg Ile Arg Val Asp Phe Lys
                40

TAAAGTATAT TGAGTGTCAA AGACTTTAAA TAAAGAAAAT GCTACTACCA AAGGTGTTGA         2564

AAGAGGAAAT CAGCACCAAC TGGGGGAATG AATAAGAACT CCCATTAGCA GGTGGGTTTA         2624

GCGCTGGGAG AGCTTTGGAC AGTGTTGTTA GGTCACTGTT TGTGAACTGA CTGCAGAACA         2684

TACATAATGA AACATTCCTA TCCATCCTGA GGAGTATCAG AGGAAGTAAT TCCTTCACAT         2744

GGAAAGTATC AAACCATGAT GATTCCTTGA GTCAGCAAAA CTGTAAGAGA AATTCAATCC         2804

CAGTGTATTT TCGCAATATC TTCACTATGA ATTGAACAAC TAGGTGAGCC TTTTAATAGT         2864

CCGTGTCTGA GATTAAAACT TTTTAAAGCA GCAGTTATTT TTGGACTCAT TGAAATGAAA         2924

TACTCTGACA TTGTGATGTC ACACTAATTT TATGCTTTTC ATCCTTATTT TCCATCCAAA         2984

GTTGTGTAAT TGTAAAACTT TCCTAAGTGA CCTTTCTCTC TCCACAG GAG GAT TGT          3040
                                                  Glu Asp Cys
                                                   1

GAA GCA GAA AAT GTG TGG GAG ATG GGA GGC TTA GGA ATC TTG ACT TCT          3088
Glu Ala Glu Asn Val Trp Glu Met Gly Gly Leu Gly Ile Leu Thr Ser
    5               10                  15

GTT CCT ATA ACA CCC AGG GTG GTT TGC TTT CTC TGT GCC AGT AGT GGG          3136
Val Pro Ile Thr Pro Arg Val Val Cys Phe Leu Cys Ala Ser Ser Gly
 20              25              30                  35

CAT GTA GAG GTAAGGCATC CTGCTTCTTT GTACCCCAGG AAGTACATA A                 3185
His Val Glu

ATGATTGATC TGGGGATGAG ATTACTATAG TCTGTTTTGT TGGTATTTAG CAGGTACTAT         3245

TCCCTGTTTA AACCAGCTAA AGAAATGTTT TGAAGTATTT TAGAGATTTT AGGAAGGAAT         3305

CTGCTATTAG AGTAGCAAAG TTATTGAGAG TGAAAAGATC AATAATCCCA TCTCTCTTAA         3365

ATTCAGTCTT TATTAGAGTT CTGATCTTTC TGTTAGATGT CTAAATAAGA GAAAAAATTA         3425

TACAGTGGTC TATTAAAAGG GATGCTATTG ATGGTTATTT TATATTGTAT ATCAAAGCCT         3485

CTTCATCTAT AAGGAGCTCT TACCAATTAA TAAGAAAAAG GAATGACATC CAGAAAAAAA         3545

AATAGGCAAA AGACAGAAAT AGATAATTCA CAAAATTAGA ATAAATACA TGTTGGGTGG         3605

CAGGGGGAGG TGAAGGGAGG GTGTCTGTTT TTTAGCCCTC TAGTGACCAA AAACTGGAAA         3665

TTAAAGCATG ATAAAAAAAG AATCCTGAAT AAATGGGAC TTTCTGTTGG TGGAAAGAAA         3725

TATAGATTAG TTACAATCTT TCTTTCTGAG GGAATTATTT GGAAATATAT ATATCTATCT         3785

TTAAAATAGG TATATCCTCT AACATAGCAA TTGCACTTCA AACACTTATG GATATAATTA         3845

GATAAATTGG CAAATCTGTA GATATAAAGA AGTGTTCATT TCAATATTGC TCATAATAAT         3905

AAAAAACTGG AAACAACCCG AAAGTCCATC TATAGGGAGC ATGGGTTAAA ATAAGCATAG         3965
```

```
GGCATATAGC TGGGCACGGT GGCTCACGCC TGTAATCCCA GCACTTTGGG AGGCCAAGGC    4025

AGGCGGATCA CAAGGTCAGG AGATCCAGAC CATCCTGGCT AACACAGTGA AACCCCGTCT    4085

CTATTAAAAA TACAAAAAAA TTAGCCGGGT GTGGTGGCGG GCGCCTGTAG TCCCAGCTAC    4145

TCGAGAGGCT GAGGCAGGAG AACGGCATGA ACCCGGGAGG TGGAGCTTGC AGTGAGCCGA    4205

GATCGCCCCA CTGCACTCCC GCCTGGGCGA CAGAGCAAGA CTCCGTCTCA AAAAAAAATA    4265

AAAGTGTAGG GCATATATAA TGCCAAATAT GAAGTCCTAA AGATAATATA TATTAATATT    4325

ATTAGGTTGG TCCAAAAGTA ATTGCAGTAA TAACATGGAA AGATGTCCAT GACATATCAC    4385

TGAGTGAAAA GAGCAGGTTA CAAGATAATA TATAAAGCAC AATCCCATCT TAGTTTGGAA    4445

AAGTGTTTTT AAAGTATATA TCTAGAAAAC AATCTGGAAG GATTCACACC AAAATATTAA    4505

GAGTGTGGTT GGATTATGGG TGACCTTTAT TTGTTTCTCT GGTTTTTTTT TTTTTAATCT    4565

TTCTGAGTTT TTTGGAGTAT GTACCACCTT TACAATGAGG AAGGAAAAAG TAGCACAATT    4625

TTAAATAGGA AGCAGTAGTT TGTCATTTAT AAGGGACATA TCCTACATCC TTTACAGTTC    4685

TTAAATTCCT GGCAGATACC TCTTTGGCTT ATTACTTACC ACATAAGATA TGTATTCAAA    4745

GGTGGTAAAG AAAATCCACG TCGGGTGCAG TGGCTCACGC CTGTAATCCC AGTACTTTGG    4805

GAGGCTGACG CAGGAGGACC GCTTGAGCTC AGGAGTTCAA GACCAGCCTG AGCACCATAG    4865

TGAGACCTCA TCTCTACTAA AAAAAAAATA AAATACCAGG CATGGTAGCA TGTGCCTGTA    4925

GTCCCAGCTA CTCTAGTCCC AGCTACTTGG GAGGCTGAGG TGAGAGGATC ACTTGAGCCC    4985

AGGAGATCGA GGCTGCAGTG AGCCATTATC ACGCCACTGC ACTCCAGCCT GGGCAACTAA    5045

GCAAGACCCT GTCTCAAAAA AATTTTAAAA AATTTAAAAA ATAAGAAAAT CCAAGCTAGG    5105

TTGAAATCTG AATGTTGAGC AGTCAGTGAG ACACAAACTA GCTAAGAAAG TCAACCCTGC    5165

CCACTTGCCA TTTGAAGTTA TTACTAGCAA AATTACAAAT TATTGCCTAC TATTCATTTA    5225

CTAAGCAAAT ATTCTCTTAG TCCCTATTAC GAACAACTTA TTGTTCTAAG TGCAGAAGTT    5285

CAGATATCAT TGAGACTGAG AATATTCAGT CTACAAGTGC CAGGGGTCTA CTGTATCCTC    5345

TTTTCCGTCT TAATACAGTG CTTTGCACCC ATATATATGC CACCCACAGG AATAACTTTT    5405

TTTATAGCAC CAGTCCTTCA ACTTCTGGGA TTAAACAGAT TTTTTTTCAG GGTATAATTG    5465

TTCTGATCTA AATTCTTTAT AGTTGTACAT AGCAATCTCA CAGGGTTCCT AAAATATAAA    5525

ATAGAGAATA GCATGCTGCC TGCACTGCAC TCCTAAAGCA TGACCAGTGC TTGATAAACT    5585

CTCCTCCATG CGAATTTTTT AAACTTTTTA TGTTGACATG ATTTCAGACT TACAAAAAAA    5645

CTATGAGTTG TACAGAGAAT TCTAAGTACC CCTCACCCAA ATTCCCTAAG TGTTAATATG    5705

TTTCTCTGTG TGTATATATT TTACAAAATA ACAAATAAAA TACATATACA CATTTTACCT    5765

GTAGATACAC ATGTATCTAA AAATTTGAGA ACAAGTTGGA GACATAAACC ATTTTACCTC    5825

TAAATATTTT AGTGTATATT TTTAAAAATC AAGGACGTTC TCGTATTTAA CCATGGTATA    5885

ATTACCAAAT CAGGAAATTA ACACACTGGG ACATTACTAT TATCTGATCT ATAGGCCTTA    5945

TTTAGGTTTG ACCAATTGTC CCAATAATTC CTTTATGGCA AAAGAAAATT CTGGATTATC    6005

CTAGTTAGTA TTTTTGAAAA TCCTATATCA ATATGAAAAT AACTTATTTC TAAAATTAGA    6065

AATGGAGGCT GGGCGTGGTG GCTCACGCCT ATAATCCCAG CACTTTGGGA GGCCGAGGCA    6125

GGCAGATCAC AAGGTCAGGA GATTGAGACC ATCCTCGCTA ACACAGTGAA ACCCCATCTC    6185

TACTAAAAAT ACAAAAAATT AGCCAGGTGT GGTGGGACGC GCCTGTGATC CCAGCTACTC    6245

AGGAGACTGA GGCTGGAGAA TCGCTTGAAC CCAACAGGCG GAGGGTTGCA GTGAGTCGAG    6305

ATCGCACCAC TGCACCCCAG CCTGGGCGAC AGCGAGACTC CGTCTCAAAA AAATAAATAA    6365
```

```
ATAAAAATTA AAACAATTAA AAAAATAAAA TTACAAATGG AAAGGACAAA CCAGACCTTA         6425

CAACTGTTTC GTATATTACA GAAAACGTTT AAACCCTCCC TATTTCCCCC ACCCCACTCC         6485

TTTATATTCC CATAGCTCTT TGTTTATACC ACTCTTAGGT CACTTAGCAT GTTCTGTTAA         6545

ATCTTGTATT ATATTTATTT TGTTACTTTC TATTTCCACT GGTATTACCA CTTTAGTACT         6605

CTGAATCTCC CGCAATGTCC AATACTGTAC TTTTTTACAT AGTCATTGCT TAATGAATAT         6665

GTATTGAATT AAATATATGC CAGTGGACTA CTAAAACCCA AAGTATATAA GAAGGGTATG         6725

GTTGATTATG TTTTTCTACA TATTATTTGA CATACTTCTA TCTTCCCATG TTCTTACTAT         6785

AG TTT GTG TAT TGC CAA GTC TGT TGT GAG CCC TTC CAC AAG TTT TGT            6832
   Phe Val Tyr Cys Gln Val Cys Cys Glu Pro Phe His Lys Phe Cys
    1               5                  10                  15

TTA GAG GAG AAC GAG CGC CCT CTG GAG GAC CAG CTG GAA AAT TGG TGT           6880
Leu Glu Glu Asn Glu Arg Pro Leu Glu Asp Gln Leu Glu Asn Trp Cys
             20                  25                  30

TGT CGT CGC TGC AAA TTC TGT CAC GTT TGT GGA GGG CAA CAT CAG GCT           6928
Cys Arg Arg Cys Lys Phe Cys His Val Cys Gly Gly Gln His Gln Ala
         35                  40                  45

ACA AAG GTACAAAACT TGGTAATAGA ACTACAGCTG GGCCTCTGTA TCAGTGGGTT            6984
Thr Lys
CTGTATCCCT GGACTCAACC AACCTTGGAT TGAATGTATC TGGGAAAAAA TGAGTAGTTG         7044

CCTCTGTACT CTATGTGAAC AGACTTTTTC TTGTCATTAT TTCCTAAACA ATACAGTATA         7104

ACAACTATTT ACATTGTATT AGGTATGATA AGTAATCTAG ATAATTTTA AAGTATATGG          7164

TGGGCGGATC ACTTGAAGCC AGGAGTTCGA GACCAGCCTG AGCCAACATG GTGAAACCCC         7224

ATCTCTACTA AAAATACAAA AAATTAGCCA GGTGTGGTGG TGGGCACCTG TAGTCCCAGC         7284

TACTTGGGAG GCTGAGGGAG GAAAATCGCT TGAACTTTGG AGGCAGAGGT TGCAGTGAGC         7344

CACTCCAGCC TGTGGTGCAG TCTGTCACTC CAGCCTGGGT GACACAGTGA GACTCCATCT         7404

CAAAAAAAAA AAAAAAAAAA AAACTATATG GGAGGATGTG CATTTTGTTA TATGCAAATG         7464

CTGCACCATT TTGTCTAGGG ACTTGGGCAT CCATGGACTT TGGTATCCTC TGGGGGTCCT         7524

GGAACCAATC CCCCATGGAA ACCAAGGATG ACTGTGCTTA GAGTATTGCT TTCTTTCTTG         7584

ATTTGTATTT CTGTCTTCCA GTTAAGATTT TGTATCTATA TTATTTCTCT TTTTACTTAG         7644

TCTGTCTTTA GCATTTAATT GGGTGTAATC AGTTGCCTAT TTTGTGTTTT AATTTTGGGA         7704

CTATAGCAGA AAACATGATG TTGAATAAAA TTCCAAAAAT AAGTCAAATC TACCTAATAT         7764

GAATACTCAT CACTGAGTGC CTTTGGCAGG AAATAAATCT ATCTCAATGC GTTAATTGGG         7824

AGTAAATAAT GCATGAGGAA ATTTAAACTC ATAATTGTGT GCTGTACTTA CTTGCCAGTA         7884

AATGTGAAAT GGGGTACTAA GTAATAGGTG TTGGGTGAAG GTAATATGAT GCTTATCTTT         7944

TTGCCATTAT ATTTTCTTAC AG CAG CTG CTG GAG TGT AAT AAG TGC CGA AAC          7996
                          Gln Leu Leu Glu Cys Asn Lys Cys Arg Asn
                           1               5                  10

AGC TAT CAC CCT GAG TGC CTG GGA CCA AAC TAC CCC ACC AAA CCC ACA           8044
Ser Tyr His Pro Glu Cys Leu Gly Pro Asn Tyr Pro Thr Lys Pro Thr
             15                  20                  25

AAG AAG AAG AAA GTC TGG GTGAGTTATA CACATGATGC TCTTTTATAG                  8092
Lys Lys Lys Lys Val Trp
             30

AGAACCACCA TGTGACTATT GGACTTATGT AACTTGTATT ACAAATATCT ATGCATGAGG         8152

ATGTCAGTAT GACAATCTTT TTCCCTCATT ACTAGGAAAT CATCTCAGGA GAGAAATTAA         8212

ATCTATAAAT GGATGCATTT AAGATCTTTT TAGTTAAGTA AAGATATTAA AAACAAGAAA         8272
```

```
TTCCTATTGA ATTTCTTTTC TTCTTTTCTA G ATC TGT ACC AAG TGT GTT CGC                8324
                                   Ile Cys Thr Lys Cys Val Arg
                                     1               5

TGT AAG AGC TGT GGA TCC                                                        8342
Cys Lys Ser Cys Gly Ser
         10
```

(2) INFORMATION FOR SEQ ID NO:64:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO:64:

```
Asp Pro Ala Pro Lys Lys Ser Ser Glu Pro Pro Arg Lys Pro
 1               5                  10                  15

Val Glu Glu Lys Ser Glu Gly Asn Val Ser Ala Pro Gly Pro Glu
                20                  25                  30

Ser Lys Gln Ala Thr Thr Pro Ala Ser Arg Lys Ser Ser Lys Gln Val
            35                  40                  45

Ser Gln Pro Ala Leu Val Ile Pro Pro Gln Pro Thr Thr Gly Pro
        50                  55                  60

Pro Arg Lys Glu Val Pro Lys Thr Thr Pro Ser Glu Pro Lys Lys Lys
65                  70                  75                  80

Gln Pro Pro Pro Pro Glu Ser Gly
                85
```

(2) INFORMATION FOR SEQ ID NO:65:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO:65:

```
Pro Glu Gln Ser Lys Gln Lys Lys Val Ala Pro Arg Pro Ser Ile Pro
 1               5                  10                  15

Val Lys Gln Lys Pro Lys Glu Lys
                20
```

(2) INFORMATION FOR SEQ ID NO:66:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:66:

```
Glu Lys Pro Pro Pro Val Asn Lys Gln Glu Asn Ala Gly Thr Leu Asn
 1               5                  10                  15

Ile Leu Ser Thr Leu Ser Asn Gly Asn Ser Ser Lys Gln Lys Ile Pro
                20                  25                  30

Ala Asp Gly Val His Arg Ile Arg Val Asp Phe Lys
            35                  40
```

(2) INFORMATION FOR SEQ ID NO:67:

(i) SEQUENCE CHARACTERISTICS:
            (A) LENGTH: 38 amino acids
            (B) TYPE: amino acid
            (D) TOPOLOGY: linear (ii) MOLECULE TYPE: protein (xi) SEQUENCE DESCRIPTION: SEQ ID NO:67:

Glu Asp Cys Glu Ala Glu Asn Val Trp Glu Met Gly Gly Leu Gly Ile
 1               5                  10                  15

Leu Thr Ser Val Pro Ile Thr Pro Arg Val Val Cys Phe Leu Cys Ala
            20                  25                  30

Ser Ser Gly His Val Glu
            35

(2) INFORMATION FOR SEQ ID NO:68:

(i) SEQUENCE CHARACTERISTICS:
            (A) LENGTH: 49 amino acids
            (B) TYPE: amino acid
            (D) TOPOLOGY: linear (ii) MOLECULE TYPE: protein (xi) SEQUENCE DESCRIPTION: SEQ ID NO:68:

Phe Val Tyr Cys Gln Val Cys Cys Glu Pro Phe His Lys Phe Cys Leu
 1               5                  10                  15

Glu Glu Asn Glu Arg Pro Leu Glu Asp Gln Leu Glu Asn Trp Cys Cys
            20                  25                  30

Arg Arg Cys Lys Phe Cys His Val Cys Gly Gly Gln His Gln Ala Thr
            35                  40                  45

Lys (2) INFORMATION FOR SEQ ID NO:69:

(i) SEQUENCE CHARACTERISTICS:
            (A) LENGTH: 32 amino acids
            (B) TYPE: amino acid
            (D) TOPOLOGY: linear (ii) MOLECULE TYPE: protein (xi) SEQUENCE DESCRIPTION: SEQ ID NO:69:

Gln Leu Leu Glu Cys Asn Lys Cys Arg Asn Ser Tyr His Pro Glu Cys
 1               5                  10                  15

Leu Gly Pro Asn Tyr Pro Thr Lys Pro Thr Lys Lys Lys Val Trp
            20                  25                  30

(2) INFORMATION FOR SEQ ID NO:70:

(i) SEQUENCE CHARACTERISTICS:
            (A) LENGTH: 13 amino acids
            (B) TYPE: amino acid
            (D) TOPOLOGY: linear (ii) MOLECULE TYPE: protein (xi) SEQUENCE DESCRIPTION: SEQ ID NO:70:

Ile Cys Thr Lys Cys Val Arg Cys Lys Ser Cys Gly Ser
 1               5                  10

(2) INFORMATION FOR SEQ ID NO:71:

(i) SEQUENCE CHARACTERISTICS:

(A) LENGTH: 60 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:71:

GCCTGTAGTC CCAGCTACTC AGGAGAGTGA GCCAGGAGAA TGGCGTGAAC CCGGGGGGCG    60

(2) INFORMATION FOR SEQ ID NO:72:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:72:

GCCTGTAGTC CCAGCTACTC AGGAGAGTGA GTCCTAAAAG TTATATATGT CTTTTAATAT    60

(2) INFORMATION FOR SEQ ID NO:73:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:73:

TTTAAATTTA AGAGATGAAC CTGCTAATTT GTCCTAAAAG TTATATATGT CTTTTAATAT    60

(2) INFORMATION FOR SEQ ID NO:74:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:74:

TTGTACCACT GCAGTCCAGC CTGGGTGACA AAGCAAAACA CTGTCTCCAA AAAAAATTTA    60

(2) INFORMATION FOR SEQ ID NO:75:

(i) SEQUENCE CHARACTERISTICS:
        (A) LENGTH: 60 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:75:

TTGTACCACT GCAGTCCAGC CTGGGTGACT GCATCCAGCA CTCTCCTCAC TGGCATCACG     60

(2) INFORMATION FOR SEQ ID NO:76:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:76:

CTGAGACCCT AAACCAACCC TTCTCTCCCC ACATCCAGCA CTCTCCTCAC TGGCATCACG     60

(2) INFORMATION FOR SEQ ID NO:77:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: CDS
            (B) LOCATION: 1..30

(xi) SEQUENCE DESCRIPTION: SEQ ID NO:77:

AAA CCA AAA GAA AAG GAT GAG CAA TTC TTA                              30
Lys Pro Lys Glu Lys Asp Glu Gln Phe Leu
1               5                   10

(2) INFORMATION FOR SEQ ID NO:78:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO:78:

Lys Pro Lys Glu Lys Asp Glu Gln Phe Leu
1               5                   10

(2) INFORMATION FOR SEQ ID NO:79:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:79:

ATCTGAATTC TCCGCTGACA TGCACTTCAT AG                                      32

(2) INFORMATION FOR SEQ ID NO:80:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:80:

ATCTGAATTC TCCGCTGACA TGCACTTCAT AG                                      32

(2) INFORMATION FOR SEQ ID NO:81:

(i) SEQUENCE CHARACTERISTICS:
              (A) LENGTH: 31 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:81:

CGGGATCCCG ACCTACTACA GGACCGCCAA G                                       31

(2) INFORMATION FOR SEQ ID NO:82:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:82:

ATCTGAATTC TGGTGGAGAT AGAAGCAGAA                                         30

(2) INFORMATION FOR SEQ ID NO:83:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:83:

AGGAGAGAGT TTACCTGCTC                                                  20

(2) INFORMATION FOR SEQ ID NO:84:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:84:

GGAAGTCAAG CAAGCAGGTC                                                  20

(2) INFORMATION FOR SEQ ID NO:85:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:85:

GTCCAGAGCA GAGCAAACAG                                                  20

(2) INFORMATION FOR SEQ ID NO:86:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:86:

ACACAGATGG ATCTGAGAGG                                                  20

(2) INFORMATION FOR SEQ ID NO:87:

(i) SEQUENCE CHARACTERISTICS:
           (A) LENGTH: 279 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:87:

```
GTCCAGAGCA GAGCAAACAG AAAAAAGTGG CTCCCGCCCA AGTATCCCTG TAAAACAAAA      60

ACCAAAAGAA AAGGATTTGG AGTTCCATGG AGTGATGAGA TTTTATTTTC AAGATAAAGC     120

TGCTGGAAAC TTTGCAACAA AATGTATTCG GGTCTCTAGT ACTGCCACCA CTCAAGATGT     180

AATCGAAACG CTCGCGGAGA AATTTCGACC TGATATGCGA ATGCTGTCCT CTCCCAAGTA     240

TTCACTCTAT GAAGTGCATG TCAGCGGAGA TCTGAGAGG                            279
```

(2) INFORMATION FOR SEQ ID NO:88:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:88:

```
Pro Glu Gln Ser Lys Gln Lys Val Ala Pro Arg Pro Ser Ile Pro
 1               5                  10                  15

Val Lys Gln Lys Pro Lys Glu Lys Asp Glu Phe Phe His Gly Val Met
                20                  25                  30

Arg Phe Tyr Phe Gln Asp Lys Ala Ala Gly Asn Phe Ala Thr Lys Cys
             35                  40                  45

Ile Arg Val Ser Ser Thr Ala Thr Thr Gln Asp Val Ile Glu Thr Leu
         50                  55                  60

Ala Glu Lys Phe Arg Pro Asp Met Arg Met Ile Ser Ser Pro Lys Tyr
     65                  70                  75

Ser Leu Tyr Glu Val His Val Ser Gly
 80                  85
```

(2) INFORMATION FOR SEQ ID NO:89:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:89:

```
GTCCAGAGCA GAGCAAACAG AAAAAAGTGG CTCCCGCCCA AGTATCCCTG TAAAACAAAA      60

ACCAAAAGAA AAG                                                        73
```

(2) INFORMATION FOR SEQ ID NO:90:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:90:

```
GATTTGGAGT TCCATGGAGT GATGAGATTT TATTTTCAAG ATAAAGCTGC TGGAAACTTT        60

GCAACAAAAT GTATTCGGGT CTCTAGTACT GCCACCACTC AAGATGTAAT CGAAACGCTC       120

GCGGAGAAAT TTCGACCTGA TATGCGAATG CTGTCCTCTC CCAAGTATTC ACTCTATGAA       180

GTGCATGTCA GCGGAG                                                      196
```

(2) INFORMATION FOR SEQ ID NO:91:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:91:

```
CCACCTACTA CAGGACCGCC AAGAAAAGAA GTTCCCAAAA CCACTCCTAG TGAGCCCAAG        60

AAAAAGCAGC CTCCACCACC AGAATCAGGC ATCTACACCA GTAATAAGGA CCCCATCTCC       120

CACAGTGGCG GGATGCGGGC TGTCTGCAGC ACCCCTCTCT CCTCCAGCCT CCTGGGGCCC       180

CCAGGGACCT CGGCCCTGCC CCGCCTCAGC CGCTCCCCGT TCACC                      225
```

(2) INFORMATION FOR SEQ ID NO:92:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO:92:

```
Pro Pro Thr Thr Gly Pro Pro Arg Lys Glu Val Pro Lys Thr Thr Pro
1               5                   10                  15

Ser Glu Pro Lys Lys Lys Gln Pro Pro Pro Glu Ser Gly Ile Tyr
            20                  25                  30

Thr Ser Asn Lys Asp Pro Ile Ser His Ser Gly Gly Met Leu Arg Ala
            35                  40                  45

Val Cys Ser Thr Pro Leu Ser Ser Ser Leu Leu Gly Pro Pro Gly Thr
        50                  55                  60

Ser Ala Leu Pro Arg Leu Ser Arg Ser Pro Phe Thr
65                  70                  75
```

(2) INFORMATION FOR SEQ ID NO:93:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:93:

-continued

```
CCACCTACTA CAGGACCGCC AAGAAAAGAA GTTCCCAAAA CCACTCCTAG TGAGCCCAAG      60

AAAAAGCAGC CTCCACCACC AGAATCAG                                        88

(2) INFORMATION FOR SEQ ID NO:94:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:94:

GCATCTACAC CAGTAATAAG GACCCCATCT CCCACAGTGG CGGGATGCGG GCTGTCTGCA      60

GCACCCCTCT CTCCTCCAGC CTCCTGGGGC CCCCAGGGAC CTCGGCCCTG CCCCGCCTCA     120

GCCGCTCCCC GTTCACC                                                   137
```